US012486230B2

(12) United States Patent
Anémian et al.

(10) Patent No.: US 12,486,230 B2
(45) Date of Patent: Dec. 2, 2025

(54) MATERIALS FOR ORGANIC ELECTROLUMINESCENT DEVICES

(71) Applicant: Merck Patent GmbH, Darmstadt (DE)

(72) Inventors: Rémi Anémian, Seoul (KR); Teresa Mujica-Fernaud, Darmstadt (DE); Myoung-Gi Jo, Anyang-si (KR); Hyeon-Hui Kang, Uiwang-Si (KR); Jochen Pfister, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 13 days.

(21) Appl. No.: 16/306,634

(22) PCT Filed: May 31, 2017

(86) PCT No.: PCT/EP2017/063081
§ 371 (c)(1),
(2) Date: Dec. 3, 2018

(87) PCT Pub. No.: WO2017/207596
PCT Pub. Date: Dec. 7, 2017

(65) Prior Publication Data

US 2019/0312203 A1 Oct. 10, 2019

(30) Foreign Application Priority Data

Jun. 3, 2016 (EP) .................................... 16172772

(51) Int. Cl.

| | |
|---|---|
| ***C07D 209/86*** | (2006.01) |
| ***C07C 209/10*** | (2006.01) |
| ***C07C 211/00*** | (2006.01) |
| ***C07C 211/61*** | (2006.01) |
| ***C07D 219/02*** | (2006.01) |
| ***C07D 307/91*** | (2006.01) |
| ***C07D 333/76*** | (2006.01) |
| ***C07D 405/04*** | (2006.01) |
| ***C07D 417/04*** | (2006.01) |
| ***H10K 50/11*** | (2023.01) |
| ***H10K 50/15*** | (2023.01) |
| ***H10K 85/60*** | (2023.01) |

(52) U.S. Cl.
CPC .......... *C07D 209/86* (2013.01); *C07C 209/10* (2013.01); *C07C 211/00* (2013.01); *C07C 211/61* (2013.01); *C07D 219/02* (2013.01); *C07D 307/91* (2013.01); *C07D 333/76* (2013.01); *C07D 405/04* (2013.01); *C07D 417/04* (2013.01); *H10K 85/633* (2023.02); *H10K 85/6572* (2023.02); *H10K 85/6574* (2023.02); *H10K 85/6576* (2023.02); *C07C 2603/18* (2017.05); *C07C 2603/94* (2017.05); *H10K 50/11* (2023.02); *H10K 50/15* (2023.02)

(58) Field of Classification Search
None
See application file for complete search history.

(56) References Cited

U.S. PATENT DOCUMENTS

| | | | | |
|---|---|---|---|---|
| 4,539,507 | A | 9/1985 | VanSlyke et al. | |
| 5,840,217 | A | 11/1998 | Lupo et al. | |
| 9,837,617 | B2 | 12/2017 | Pfister et al. | |
| 10,283,716 | B2 | 5/2019 | Park et al. | |
| 2015/0065730 | A1* | 3/2015 | Montenegro | H01L 51/0058 548/440 |
| 2016/0225993 | A1* | 8/2016 | Huh | H01L 51/006 |
| 2018/0033966 | A1* | 2/2018 | Park | H01L 51/006 |
| 2018/0145272 | A1* | 5/2018 | Cha | H01L 51/508 |

(Continued)

FOREIGN PATENT DOCUMENTS

| | | | |
|---|---|---|---|
| CN | 105481811 | A | 4/2016 |
| CN | 105492574 | A | 4/2016 |
| EP | 676461 | A2 | 10/1995 |

(Continued)

OTHER PUBLICATIONS

English translation of WO 2015/022051 A1 and original WO 2015/022051 A1, Pfister Jochen, Feb. 19, 2015 (Year: 2015).*
English translation of KR 10/1614740 B1 and original KR 10/1614740 B1, Dae Sung Kim, Apr. 22, 2016 (Year: 2016).*
International Search Report for PCT/EP2017/063081 mailed Oct. 2, 2017.
Written Opinion of the International Searching Authority for PCT/EP2017/063081 mailed Oct. 2, 2017.

(Continued)

*Primary Examiner* — Seokmin Jeon
(74) *Attorney, Agent, or Firm* — Faegre Drinker Biddle & Reath LLP

(57) ABSTRACT

The present invention relates to compounds of the formula (1) which are suitable for use in electronic devices, in particular organic electroluminescent devices, and to electronic devices, which comprise these compounds.

formula (1)

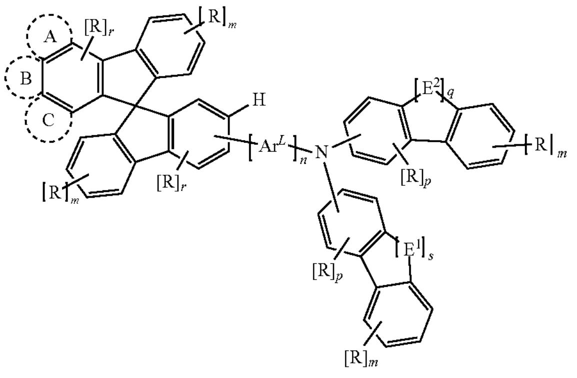

3 Claims, No Drawings

(56) References Cited

U.S. PATENT DOCUMENTS

2019/0067576 A1 2/2019 Voges et al.

FOREIGN PATENT DOCUMENTS

| | | | |
|---|---|---|---|
| JP | 2016-530367 | A | 9/2016 |
| JP | 2018-511572 | A | 4/2018 |
| JP | 2019-512466 | A | 5/2019 |
| KR | 10-1530886 | B1 | 6/2015 |
| KR | 101520955 | B1 | 6/2015 |
| KR | 101614740 | B1 | 4/2016 |
| TW | 201527292 | A | 7/2015 |
| WO | 2014/129846 | A1 | 8/2014 |
| WO | 2014/171779 | A1 | 10/2014 |
| WO | WO-2015022051 | A1 | 2/2015 |
| WO | 2016/078738 | A1 | 5/2016 |
| WO | 2016/102048 | A1 | 6/2016 |
| WO | 2017/105078 | | 6/2017 |
| WO | 2017/144150 | A2 | 8/2017 |

OTHER PUBLICATIONS

Baldo, M., et al., "Very high-efficiency green organic light-emitting devices based on electrophosphorescence", Applied Physics Letters, 1999, vol. 75, No. 1, pp. 4-6.

International Preliminary Report on Patentability received for PCT Patent Application No. PCT/EP2017/063081, mailed on Dec. 13, 2018, 10 pages.

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2017/063081, filed May 31, 2017, which claims benefit of European Application No. 16172772.2, filed Jun. 3, 2016, both of which are incorporated herein by reference in their entirety.

The present invention relates to materials for use in electronic devices, in particular in organic electroluminescent devices, and to electronic devices comprising these materials.

BACKGROUND OF THE INVENTION

The structure of organic electroluminescent devices (OLEDs) in which organic semiconductors are employed as functional materials is described, for example in U.S. Pat. No. 4,539,507. The emitting materials employed here are increasingly organometallic complexes which exhibit phosphorescence instead of fluorescence (M. A. Baldo et al., *Appl. Phys. Lett.* 1999, 75, 4-6).

In accordance with the prior art, the hole-transport materials used in the hole-transport layer or in the hole-injection layer are, in particular, triarylamine derivatives which frequently contain at least two triarylamino groups or at least one triarylamino group and at least one carbazole group. These compounds are frequently derived from diarylamino-substituted triphenylamines (TPA type), from diarylamino-substituted biphenyl derivatives (TAD type) or combinations of these base compounds. Furthermore, for example, use is made of spirobifluorene derivatives, which are substituted by one to four diarylamino groups (for example in accordance with EP 676461). More recently, benzospirobifluorene derivatives have been employed as hole-transport materials in OLEDs (for example in accordance with KR-10-1520955). In the case of these compounds, there is still a need for improvement both in the case of fluorescent and in the case of phosphorescent OLEDs, in particular with respect to efficiency, lifetime and operating voltage on use in an organic electroluminescent device.

At the same time, it is important that the compounds processed by vacuum evaporation exhibit a high temperature stability, in order to obtain OLEDs with reproducible properties. The compounds used in OLEDs should also exhibit a low crystallinity and a high glass transition temperature, in order to obtain OLEDs with a satisfying lifetime.

BRIEF SUMMARY OF THE INVENTION

The object of the present invention is to provide compounds which are suitable for use in a fluorescent or phosphorescent OLED, in particular a phosphorescent OLED, for example as hole-transport material in a hole-transport or exciton-blocking layer or as matrix material in an emitting layer.

It has now been found that certain compounds described below in greater detail achieve this object and result in significant improvements in the organic electroluminescent device, in particular with respect to the lifetime, the efficiency and the operating voltage. This applies to phosphorescent and fluorescent electroluminescent devices, especially on use of the compounds according to the invention as hole-transport material or as matrix material. Furthermore, the compounds described below contain a rigid planar Spiro unit and flexible structure elements in the outer periphery, whereby the flexibility of the molecule center is reduced and the solubility is increased by the substituents, which leads to an easier cleaning and an easier handling of these compounds. Finally, the compounds of the present invention generally have high thermal stability and can therefore be sublimed without decomposition and without a residue. The present invention therefore relates to these compounds and to electronic devices which comprise compounds of this type.

DETAILED DESCRIPTION OF THE INVENTION

The present invention therefore relates to a compound of the following formula (1):

formula (1)

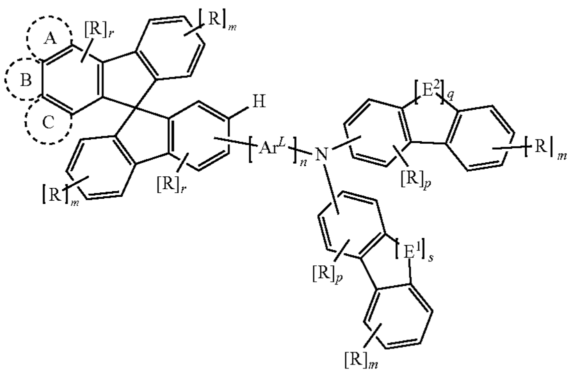

where exactly one ring A, B, or C as depicted in formula (1) is present, and where the following applies to the symbols and indices used:

A, B and C stand for a condensed aryl or a condensed heteroaryl group having 6 to 18 aromatic ring atoms, which may be substituted at each free position with a substituent R;

$E^1$, $E^2$ are identically or differently on each occurrence, selected from $B(R^0)$, $C(R^0)_2$, $Si(R^0)_2$, C═O, $C{=}NR^0$, $C{=}C(R^0)_2$, O, S, S═O, $SO_2$, $N(R^0)$, $P(R^0)$ and $P({=}O)R^0$;

$Ar^L$ is an aromatic or heteroaromatic ring system having 5 to 40 aromatic ring atoms, which may in each case be substituted by one or more radicals R;

R, $R^0$ stand on each occurrence, identically or differently, for H, D, F, Cl, Br, I, CHO, CN, $C({=}O)Ar^3$, $P({=}O)(Ar^3)_2$, $S({=}O)Ar^3$, $S({=}O)_2Ar^3$, $N(Ar^3)_2$, $NO_2$, $Si(R^1)_3$, $B(OR^1)_2$, $OSO_2R^1$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^1$, where in each case one or more non-adjacent $CH_2$ groups may be replaced by $R^1C{=}CR^1$, C≡C, $Si(R^1)_2$, $Ge(R^1)_2$, $Sn(R^1)_2$, C═O, C═S, C═Se, $P({=}O)(R^1)$, SO, $SO_2$, O, S or $CONR^1$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^1$, or an aryloxy groups having 5 to 40 aromatic ring atoms, which may be substituted by one or more radicals $R^1$, where two adjacent substituents R and/or two adjacent substituents $R^0$ may form a mono- or polycyclic, aliphatic ring system or aromatic ring system, which may be substituted by one or more radicals $R^1$;

$R^1$ stands on each occurrence, identically or differently, for H, D, F, Cl, Br, I, CHO, CN, $C(=O)Ar^3$, $P(=O)(Ar^3)_2$, $S(=O)Ar^3$, $S(=O)_2Ar^3$, $N(Ar_3)_2$, $NO_2$, $Si(R^2)_3$, $B(OR^2)_2$, $OSO_2R^2$, a straight-chain alkyl, alkoxy or thioalkyl groups having 1 to 40 C atoms or branched or cyclic alkyl, alkoxy or thioalkyl groups having 3 to 40 C atoms, each of which may be substituted by one or more radicals $R^2$ where in each case one or more non-adjacent $CH_2$ groups may be replaced by $R^2C{=}CR^2$, C≡C, $Si(R^2)_2$, $Ge(R^2)_2$, $Sn(R^2)_2$, C═O, C═S, C═Se, $P(=O)(R^2)$, SO, $SO_2$, O, S or $CONR^2$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^2$, or an aryloxy group having 5 to 60 aromatic ring atoms, which may be substituted by one or more radicals $R^2$, where two adjacent substituents $R^1$ may form a mono- or polycyclic, aliphatic ring system or aromatic ring system, which may be substituted by one or more radicals $R^2$;

$R^2$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 C atoms;

$Ar^3$ is an aromatic or heteroaromatic ring system having 5 to 24 aromatic ring atoms, which may in each case also be substituted by one or more radicals $R^3$;

n is 0, 1, 2 or 3;

m is on each occurrence, identically or differently, 0, 1, 2, 3 or 4;

p is on each occurrence, identically or differently, 0, 1, 2 or 3;

q, s are on each occurrence, identically or differently, 0 or 1;

r is on each occurrence, identically or differently, 0, 1 or 2.

Adjacent substituents in the sense of the present invention are substituents, which are bonded to carbon atoms which are linked directly to one another or which are bonded to the same carbon atom.

When n is 0, then the group $Ar^L$ is absent and the nitrogen of the diarylamine group is directly bonded to the phenyl ring of the spirobifluorene derivative depicted in formula (1).

Furthermore, the following definitions of chemical groups apply for the purposes of the present application:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzo-pyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spiro-truxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzo-pyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cyclo-heptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyl-oxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two radicals may form a ring with one another is, for the purposes of the present application, intended to be taken to mean, inter alia, that the two radicals are linked to one another by a chemical bond. This is illustrated by the following schemes:

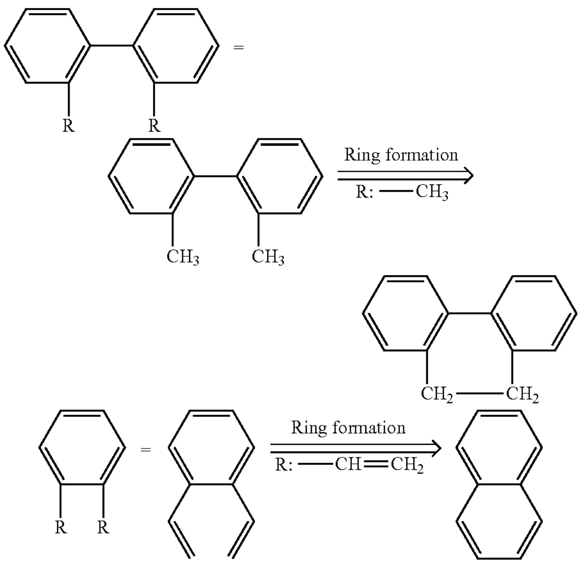

Furthermore, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

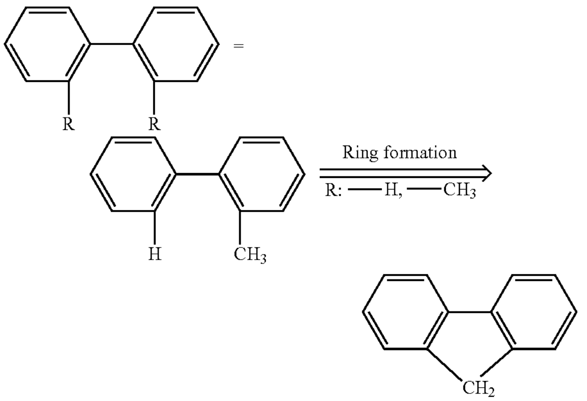

In accordance with a preferred embodiment, n is equal to 0.

In accordance with another preferred embodiment, q is equal to 1 and/or s is equal to 1. More preferably, q=s=1.

In accordance with a preferred embodiment, the rings A, B and C stand for a benzene, a naphthalene, a pyridine, a pyrimidine, or a pyrazine group, which may be substituted at each free position with a substituent R. It is very preferred that the rings A, B and C stand for a benzene ring, which may be substituted at each free position with a substituent R.

Thus, the compounds of formula (1) are preferably selected from the compounds of the following formulae (1A), (1B) and (1C), formula (1A)
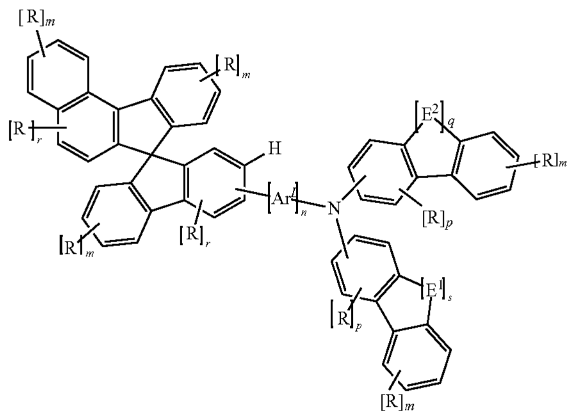
formula (1B)
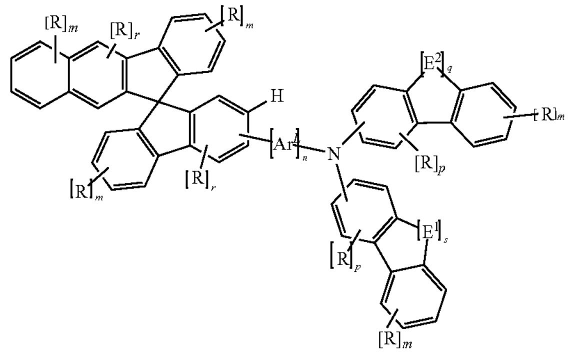
formula (1C)
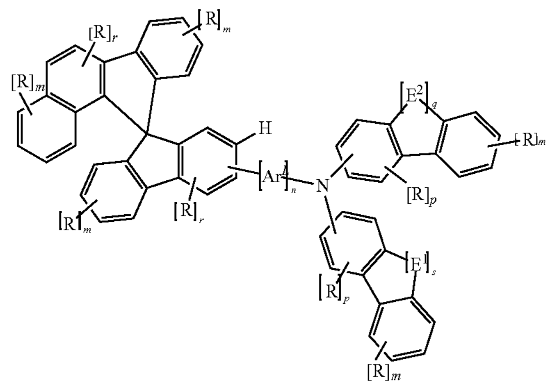
where the symbols and indices have the same meaning as above.
It is even more preferred that the compounds of formula (1), (1A), (1B) and (1C) are selected from the compounds of following formulae (1A-1) to (1C-1) and (1A-2) to (1C-2),
formula (1A-1)
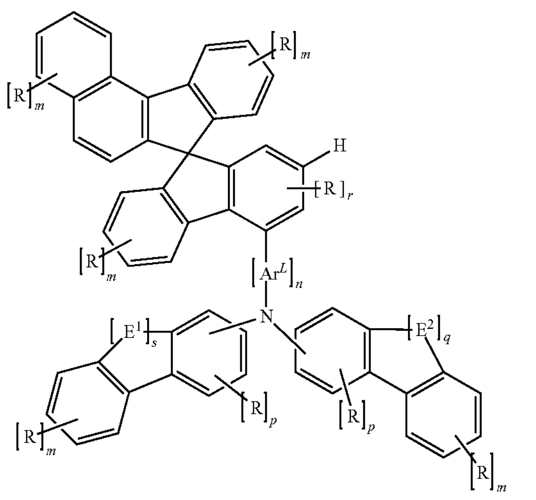
formula (1A-2)
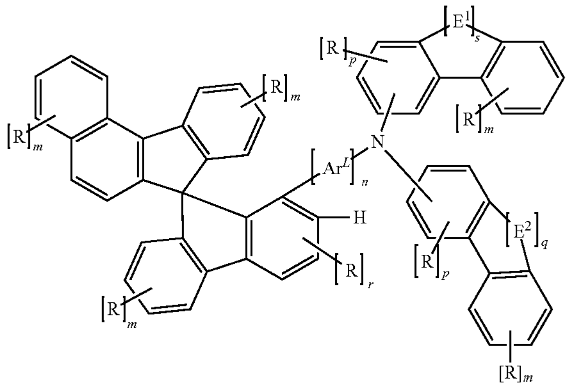
formula (1B-1)
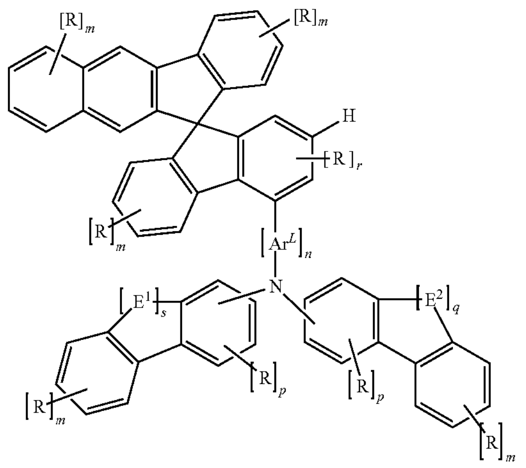

-continued
formula (1B-2)
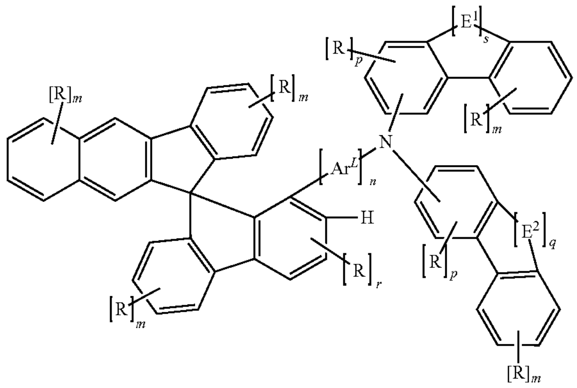
formula (1C-1)
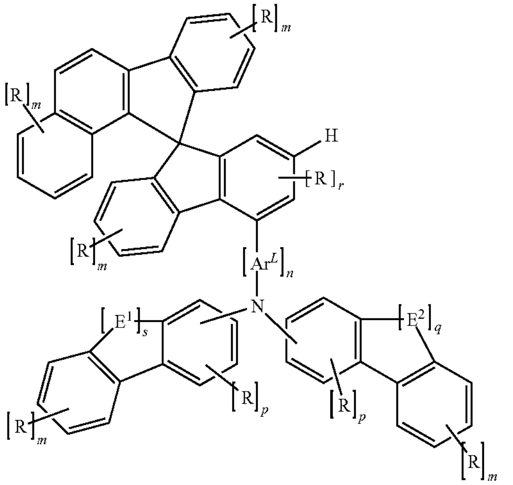
formula (1C-2)
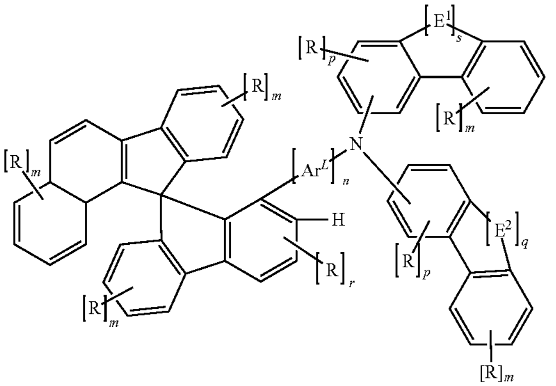
where the symbols and indices have the same meaning as above.
It is particularly preferred that the compounds of formula (1), (1A) to (1C), (1A-1) to (1C-1) and (1A-2) to (1C-2) are selected from the compounds of the following formulae (1A-1-1) to (1C-1-1) and (1A-2-1) to (1C-2-1).
formula (1A-1-1)
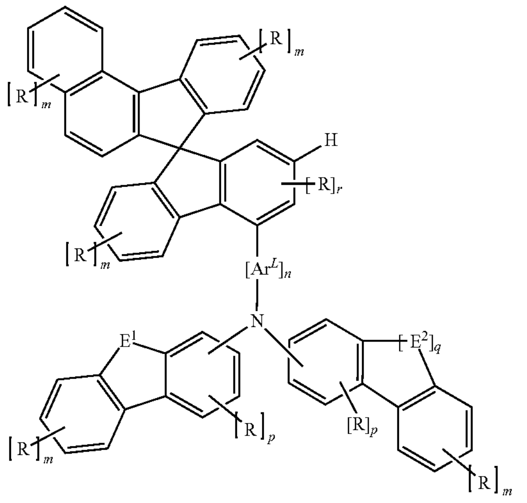
formula (1A-2-1)
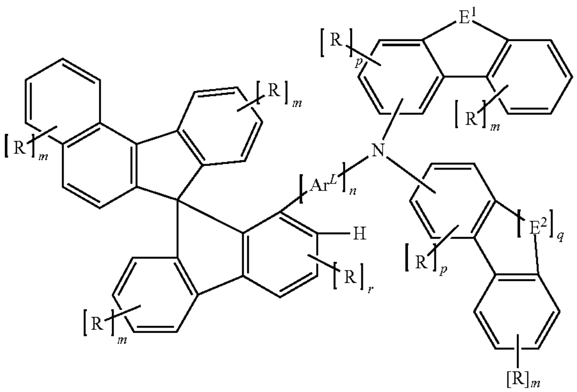
formula (1B-1-1)
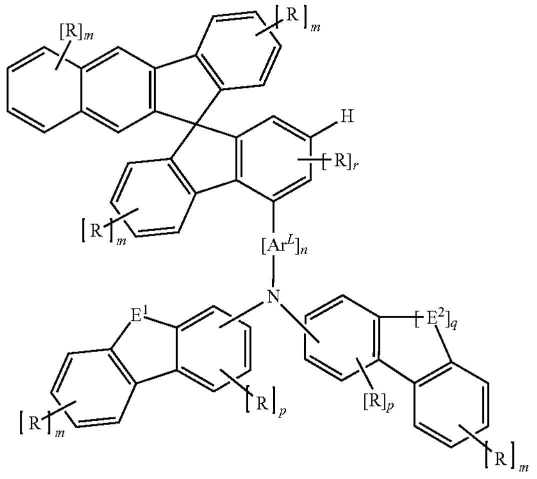

-continued
formula (1B-2-1)
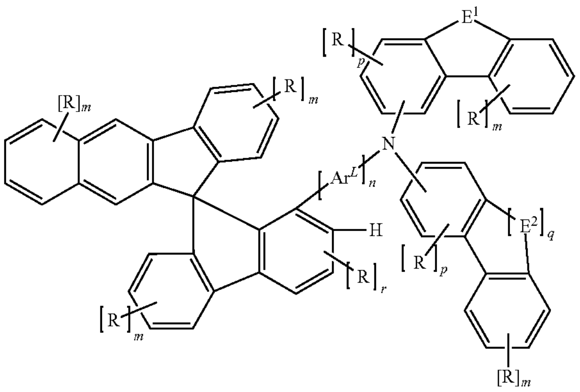
formula (1C-1-1)
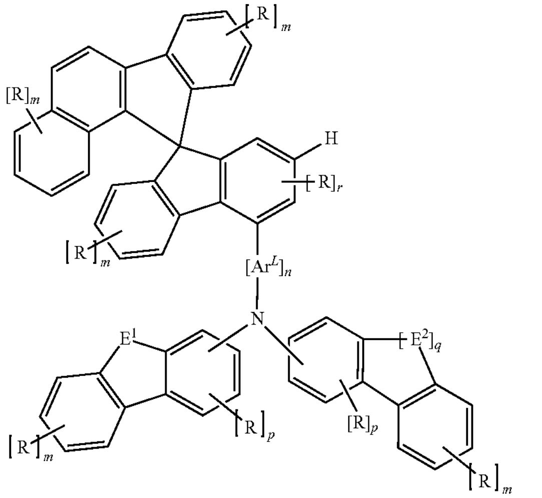
formula (1C-2-1)
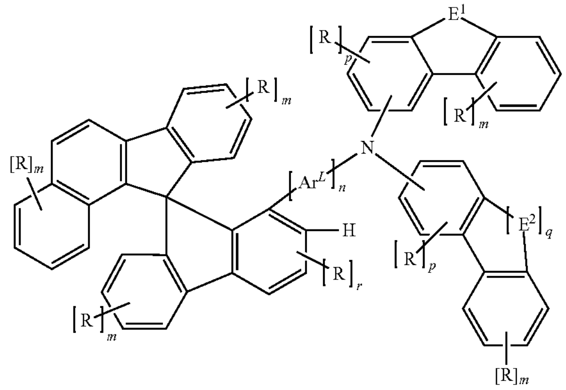
where the symbols and indices have the same meaning as above
It is even more particularly preferred that the compounds of formula (1), (1A) to (1C), (1A-1) to (1C-1), (1A-2) to (1C-2), (1A-1-1) to (1C-1-1) and (1A-2-1) to (1C-2-1) are selected from the compounds of the following formulae (1A-1-2) to (1A-1-5), (1B-1-2) to (1B-1-5), (1C-1-2) to (1C-1-5), (1A-2-2) to (1A-2-5), (1B-2-2) to (1B-2-5) and (1C-2-2) to (1C-2-5),
formula (1A-1-2)
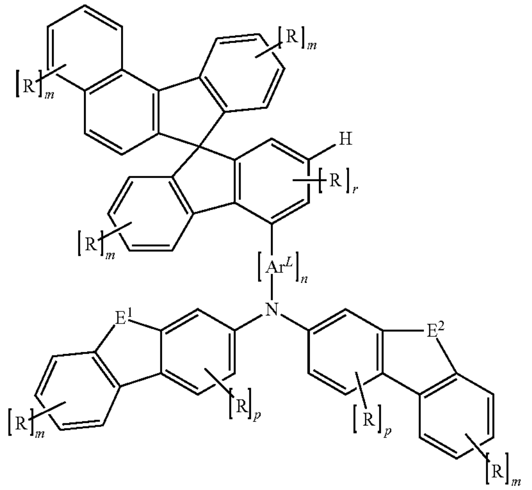
formula (1A-1-3)
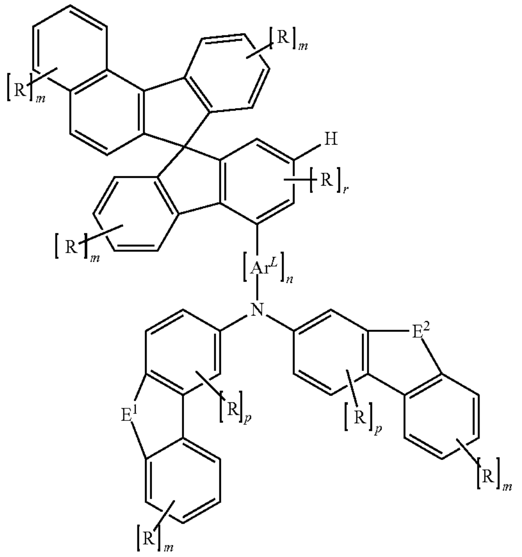
formula (1A-1-4)
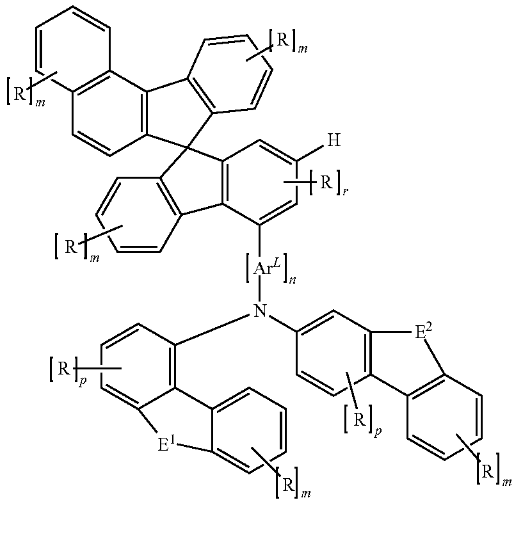

-continued
formula (1A-1-5)
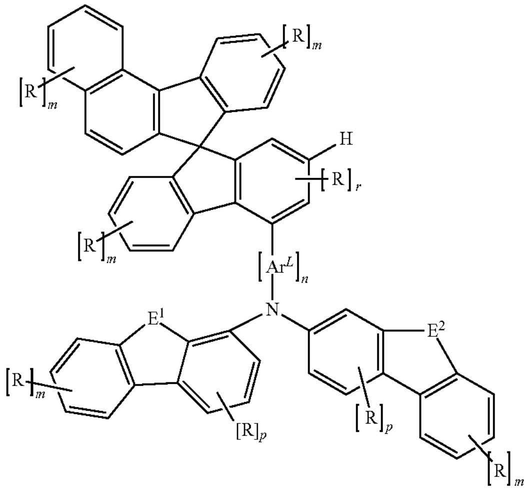
formula (1B-1-2)
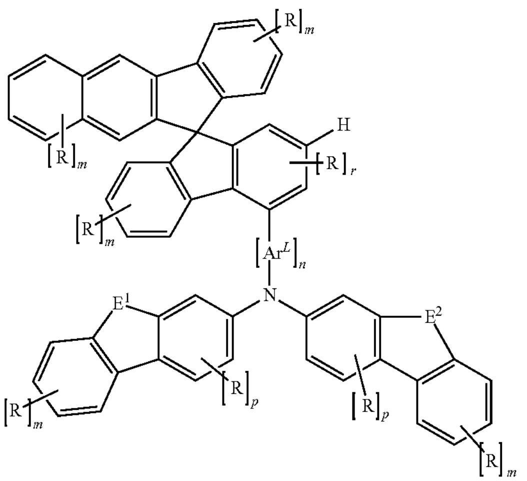
formula (1B-1-3)
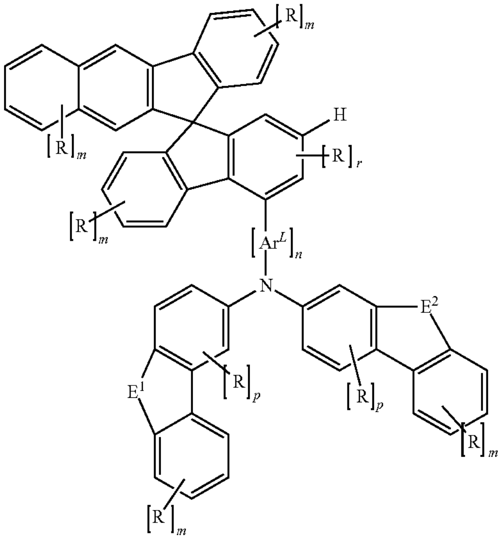
-continued
formula (1B-1-4)
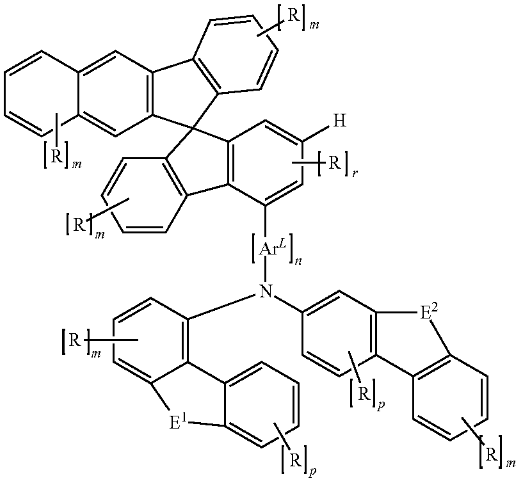
formula (1B-1-5)
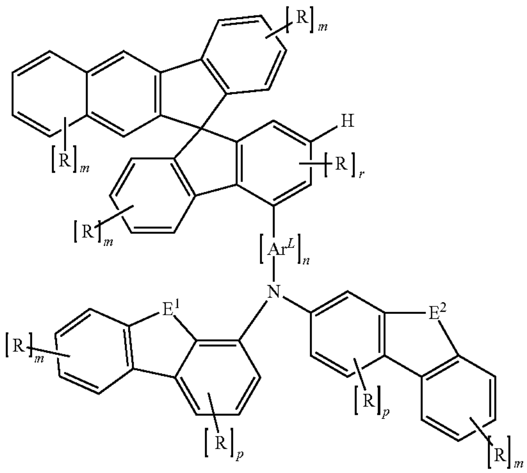
formula (1C-1-2)
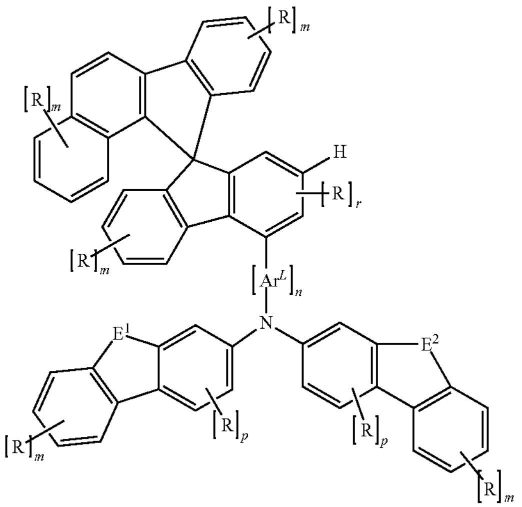

-continued
formula (1C-1-3)
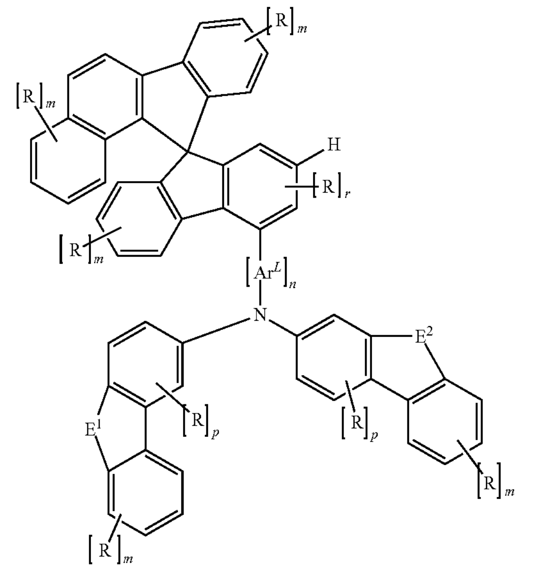
formula (1C-1-4)
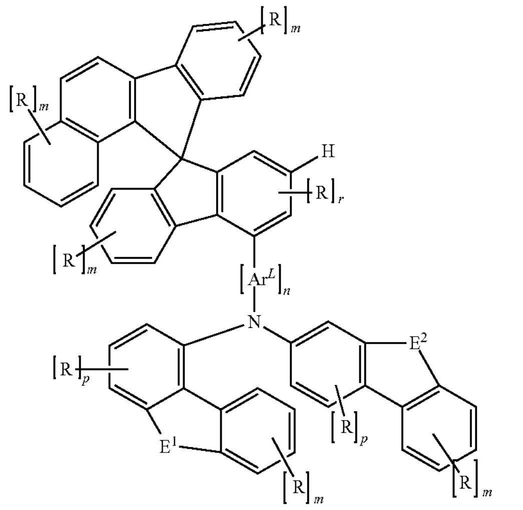
formula (1C-1-5)
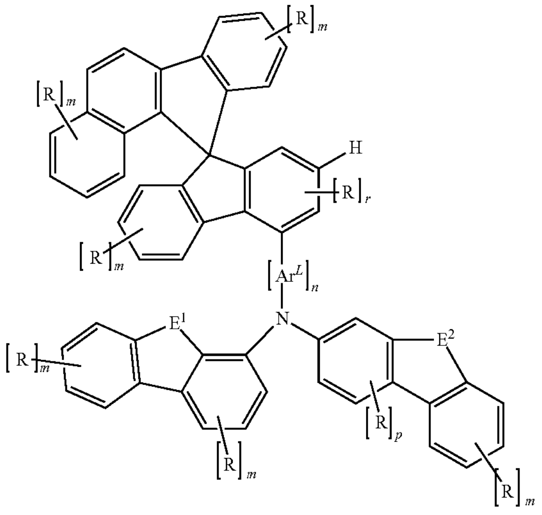
-continued
formula (1A-2-2)
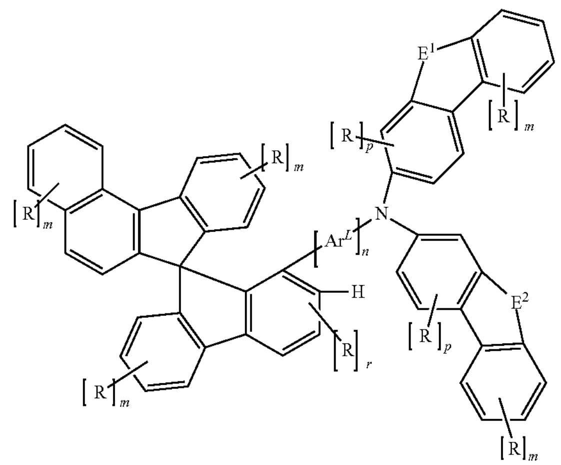
formula (1A-2-3)
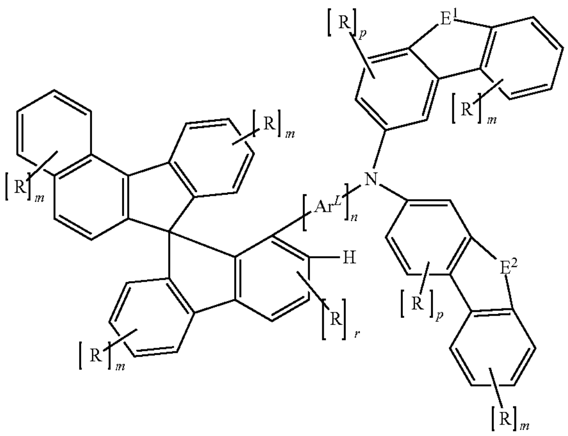
formula (1A-2-4)
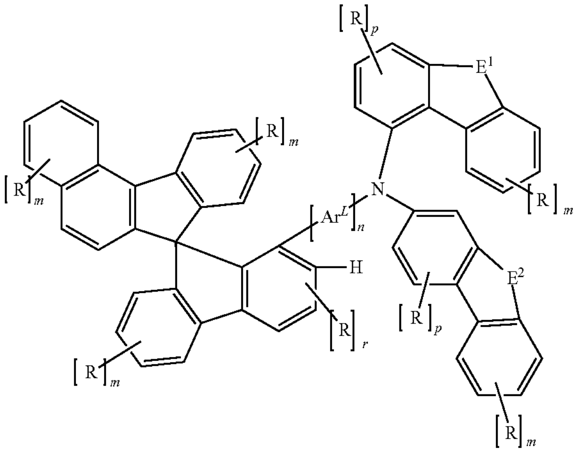

-continued
formula (1A-2-5)
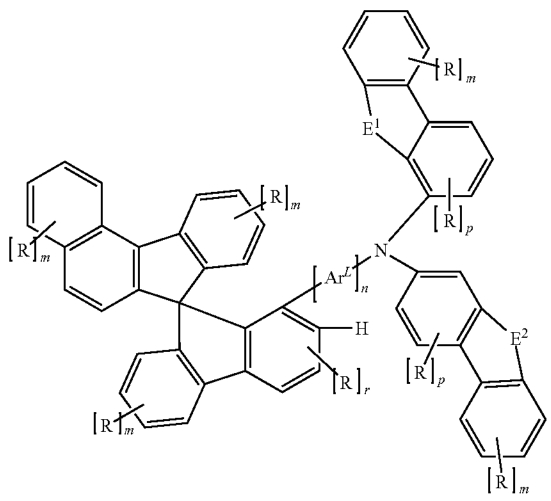
formula (1B-2-2)
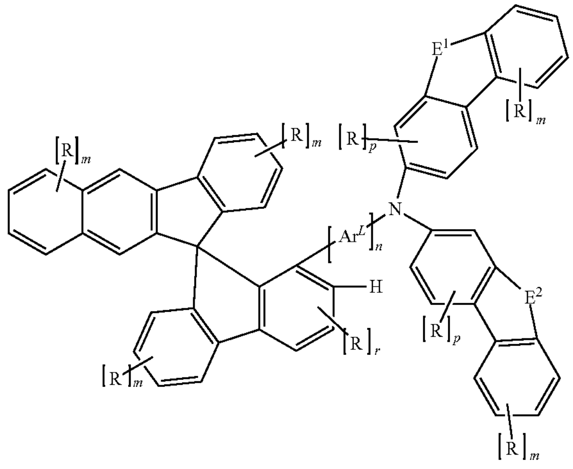
formula (1B-2-3)
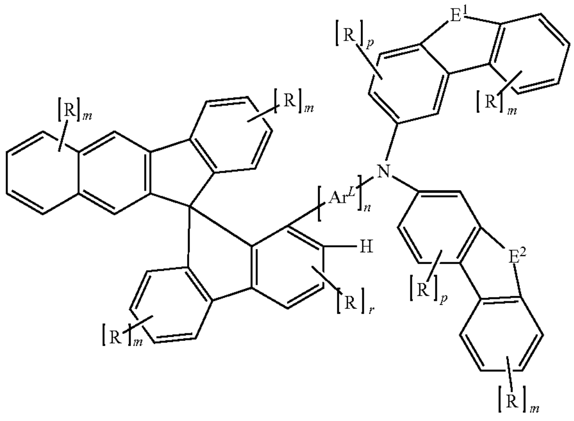
-continued
formula (1B-2-4)
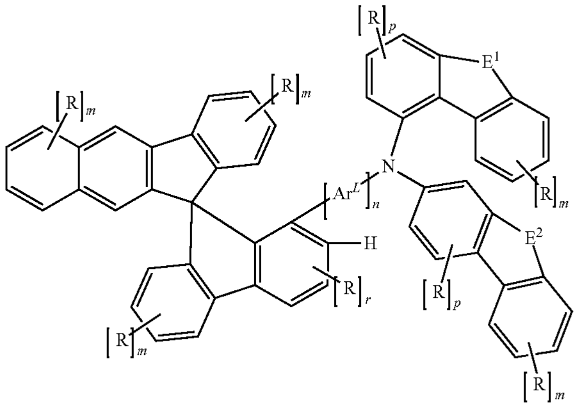
formula (1B-2-5)
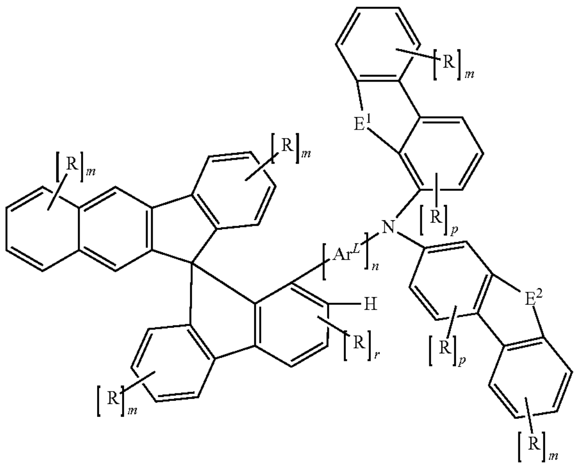
formula (1C-2-2)
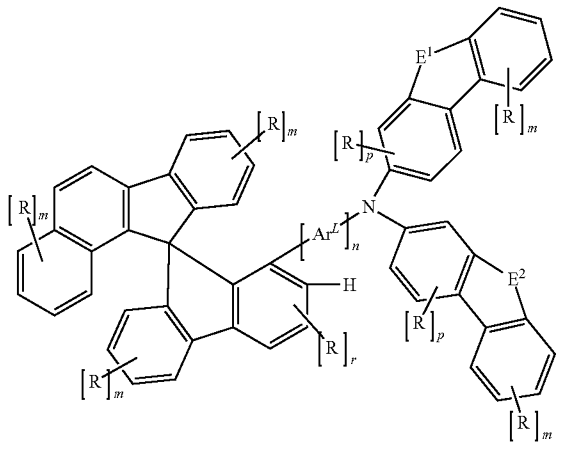

-continued
formula (1C-2-3)
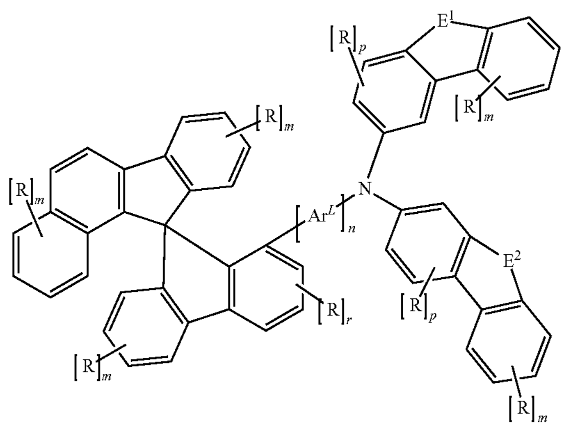
formula (1C-2-4)
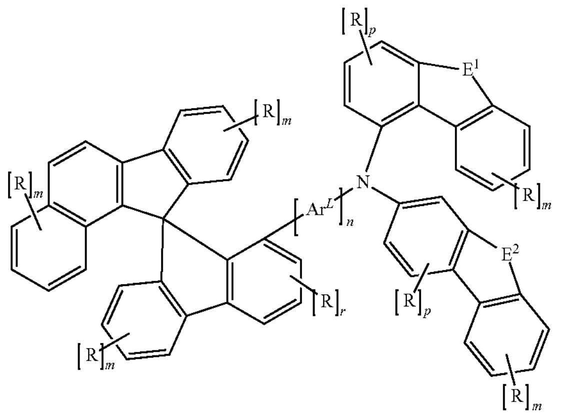
formula (1C-2-5)
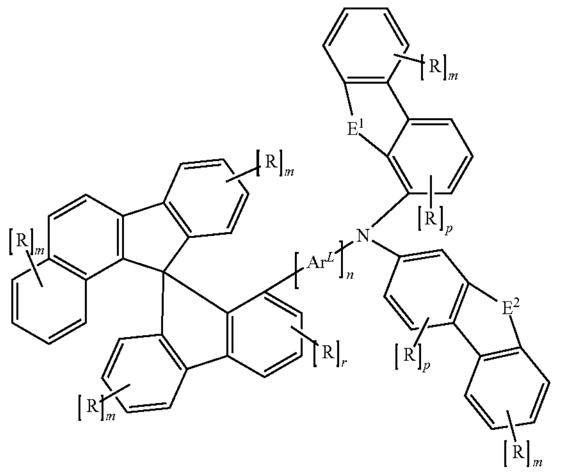
It is very particularly preferred that the compounds of formula (1) and of the preferred formulae of formula (1) are selected from the compounds of the following formulae (1A-1-6) to (1A-1-9), (1B-1-6) to (1B-1-9), (1C-1-6) to (1C-1-9), (1A-2-6) to (1A-2-9), (1B-2-6) to (1B-2-9) and (1C-2-6) to (1C-2-9),
formula (1A-1-6)
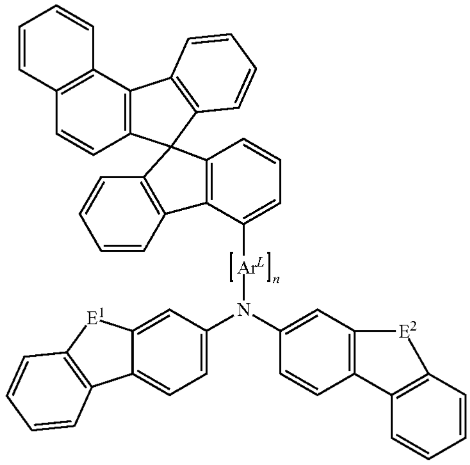
formula (1A-1-7)
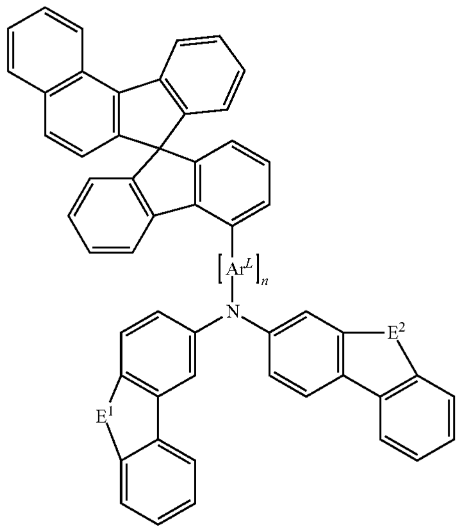
formula (1A-1-8)
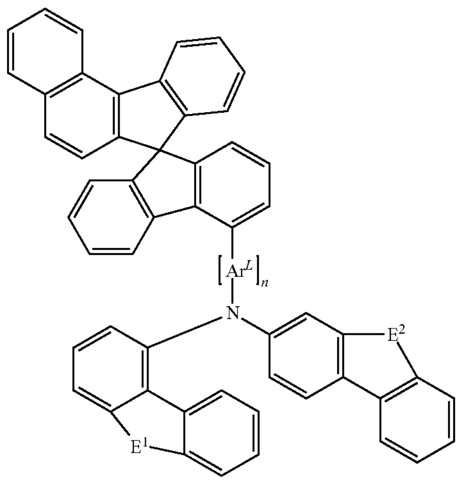

-continued
formula (1A-1-9)
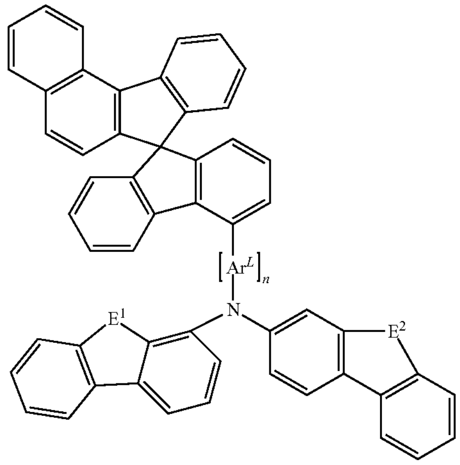
formula (1B-1-6)
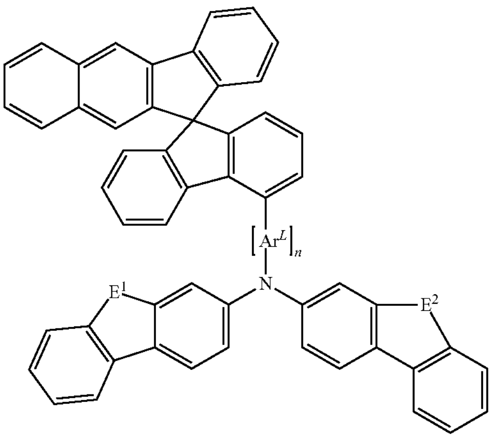
formula (1B-1-7)
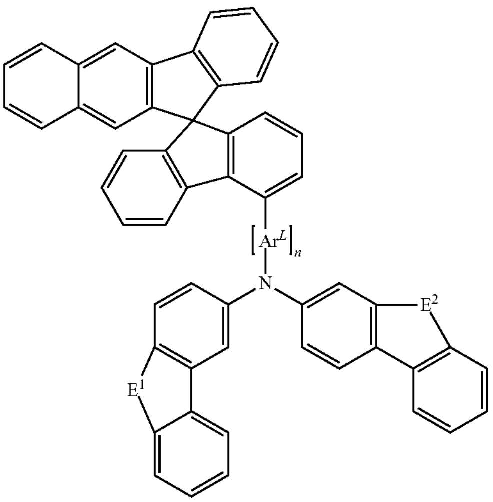
-continued
formula (1B-1-8)
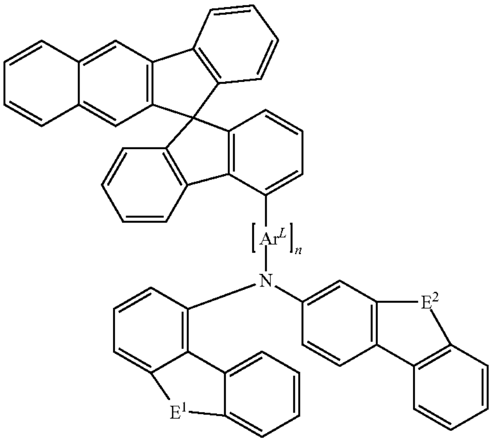
formula (1B-1-9)
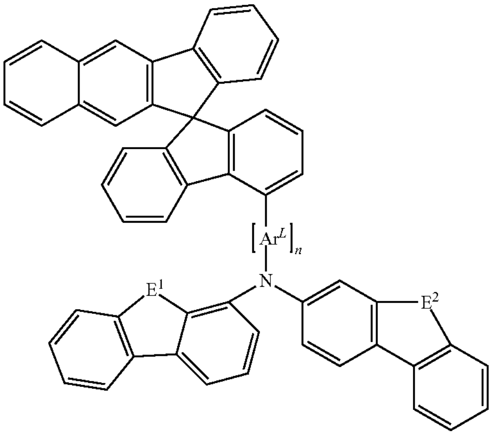
formula (1C-1-6)
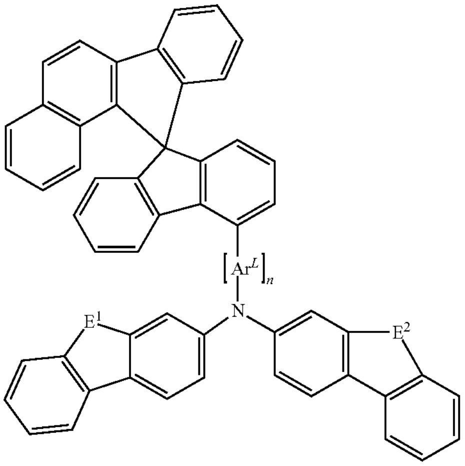

-continued
formula (1C-1-7)
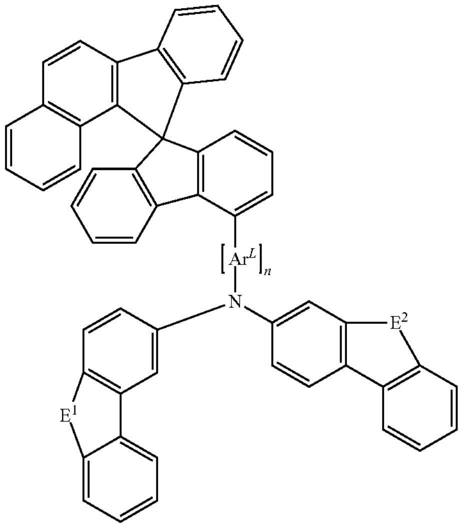
formula (1C-1-8)
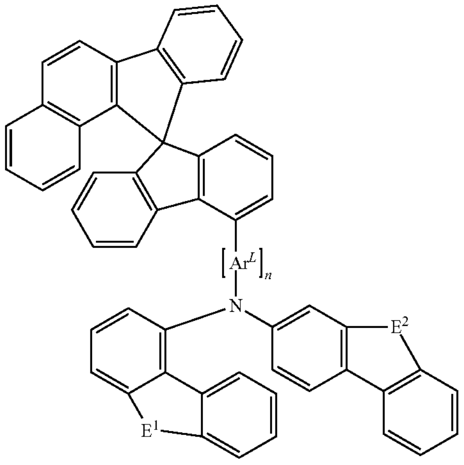
formula (1C-1-9)
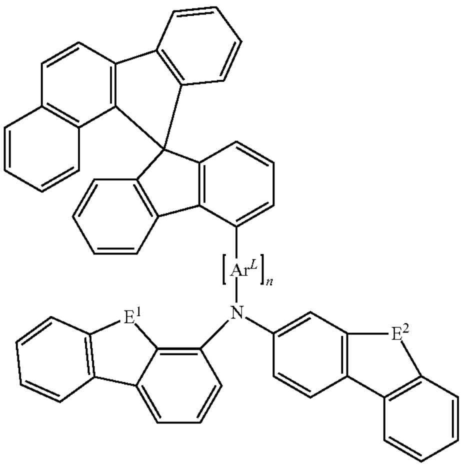
-continued
formula (1A-2-6)
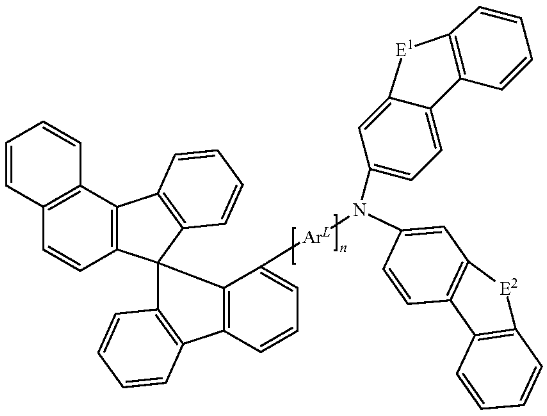
formula (1A-2-7)
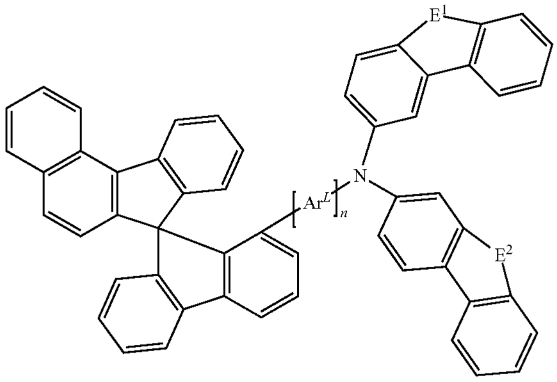
formula (1A-2-8)
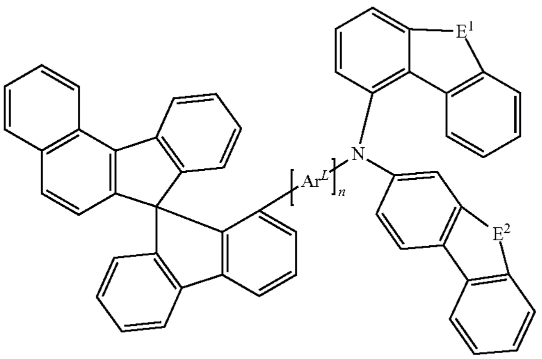

-continued
formula (1A-2-9)
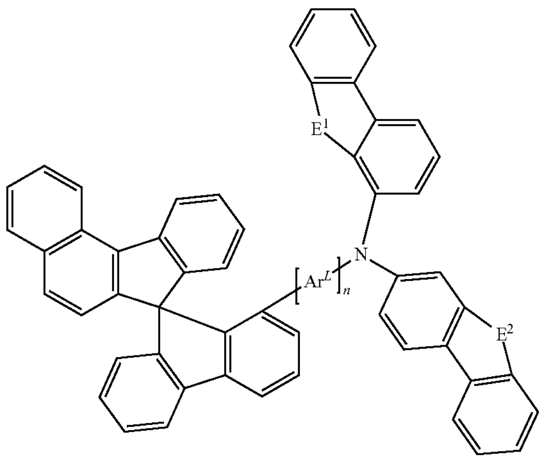
formula (1B-2-6)
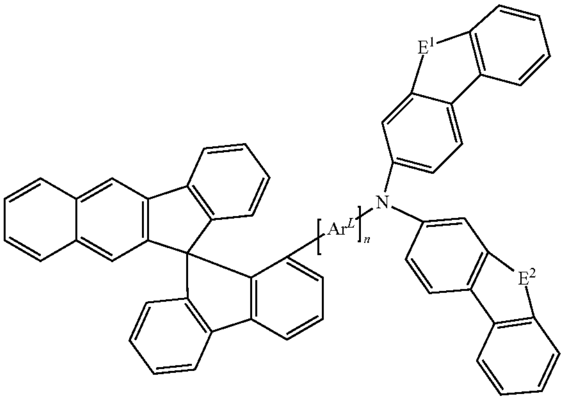
formula (1B-2-7)
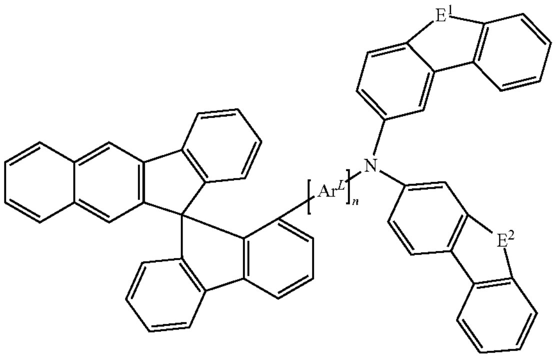
formula (1B-2-8)
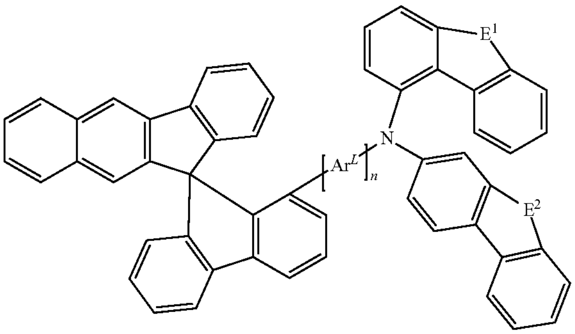
-continued
formula (1B-2-9)
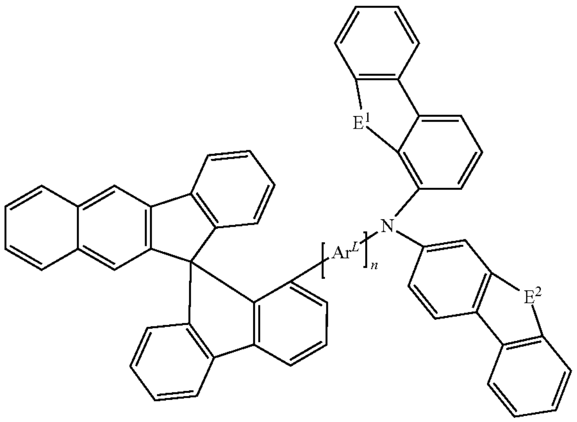
formula (1C-2-6)
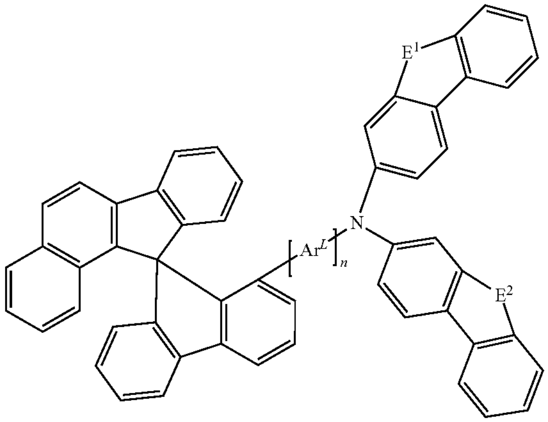
formula (1C-2-7)
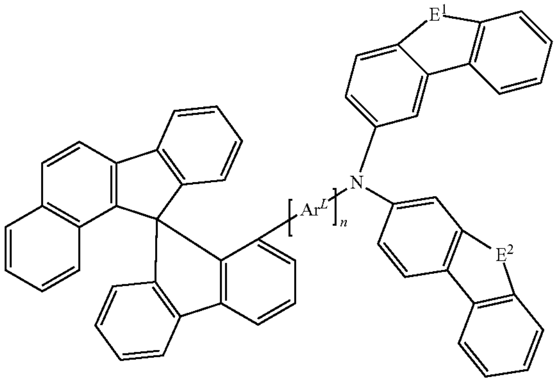
formula (1C-2-8)
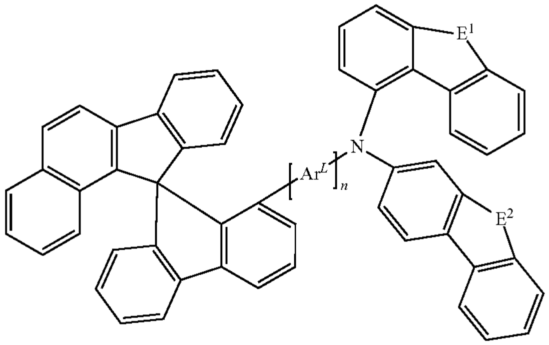

-continued formula (1C-2-9)

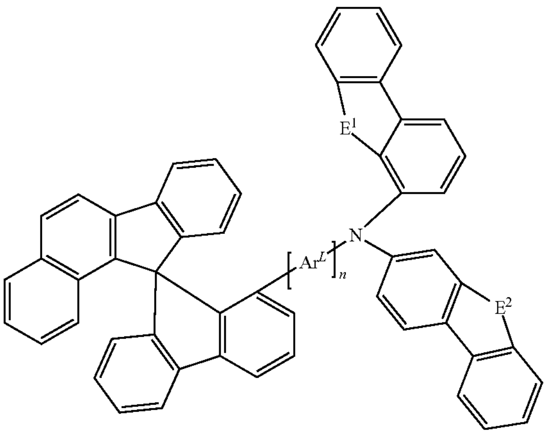

where the symbols and indices have the same meaning as above.

The group $Ar^L$ is, identically or differently on each occurrence, selected from aromatic or heteroaromatic ring systems having 5 to 40, preferably 5 to 30, more preferably 5 to 14 aromatic ring atoms, which may in each case also be substituted by one or more radicals R.

More preferably, $Ar^L$ is selected from benzene, biphenyl, fluorene, dibenzofurane, dibenzothiophene, carbazole, which may in each case be substituted by one or more radicals R. Very more preferably, $Ar^L$ is selected from benzene, which may be substituted by one or more radicals R but is preferably not substituted.

Suitable groups $Ar^L$ are for example the groups of formulae ($Ar^L$-1) to ($Ar^L$-37) below:

($Ar^L$-1)

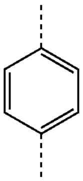

($Ar^L$-2)

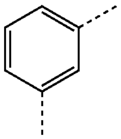

($Ar^L$-3)

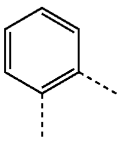

-continued ($Ar^L$-4)

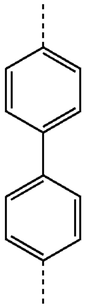

($Ar^L$-5)

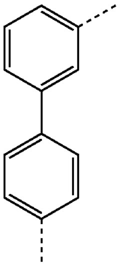

($Ar^L$-6)

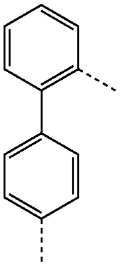

($Ar^L$-7)

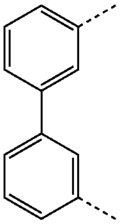

($Ar^L$-8)

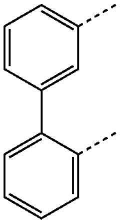

($Ar^L$-9)

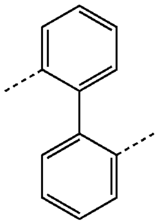

-continued
(Ar$^L$-10)
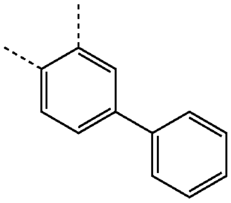
(Ar$^L$-11)
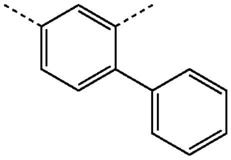
(Ar$^L$-12)
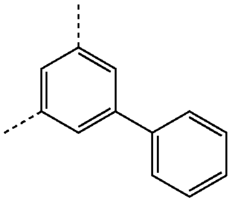
(Ar$^L$-13)
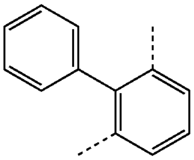
(Ar$^L$-14)
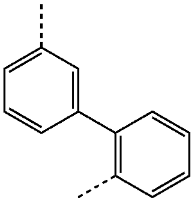
(Ar$^L$-15)
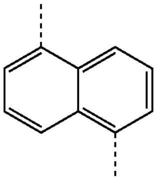
(Ar$^L$-16)
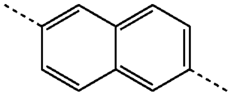
(Ar$^L$-17)
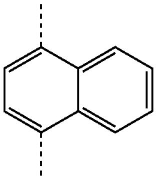
-continued
(Ar$^L$-18)
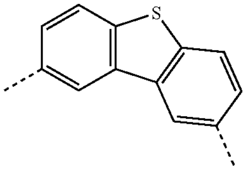
(Ar$^L$-19)
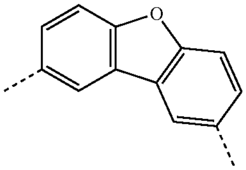
(Ar$^L$-20)
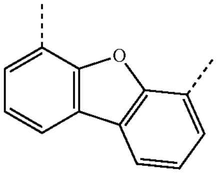
(Ar$^L$-21)
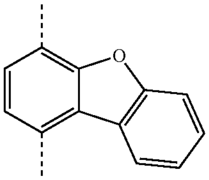
(Ar$^L$-22)
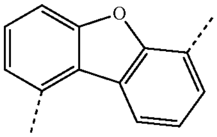
(Ar$^L$-23)
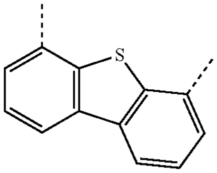
(Ar$^L$-24)
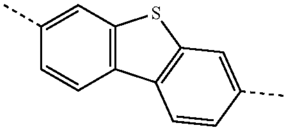
(Ar$^L$-25)
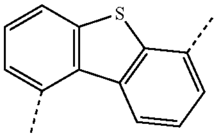
(Ar$^L$-26)
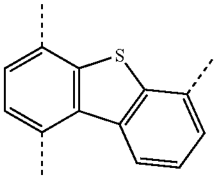

-continued ($Ar^L$-27)

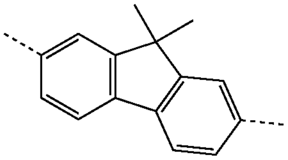

($Ar^L$-28)

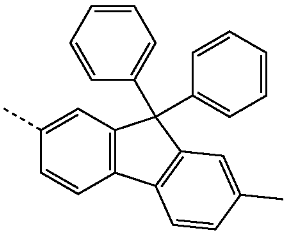

($Ar^L$-29)

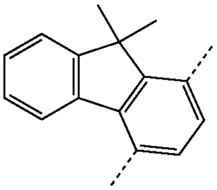

($Ar^L$-30)

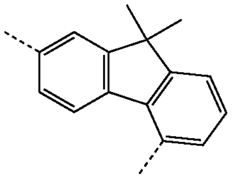

($Ar^L$-31)

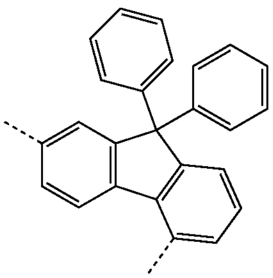

($Ar^L$-32)

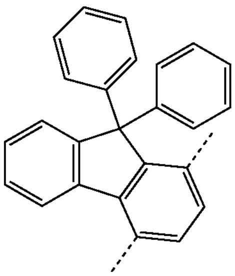

-continued ($Ar^L$-33)

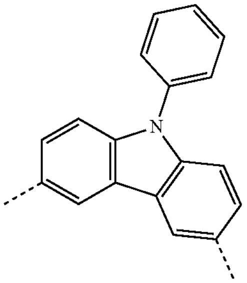

($Ar^L$-34)

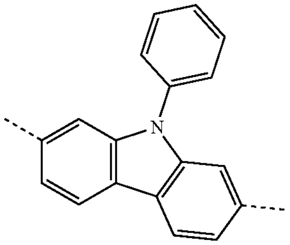

($Ar^L$-35)

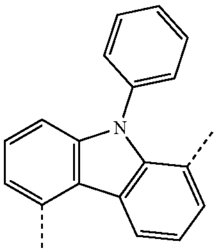

($Ar^L$-36)

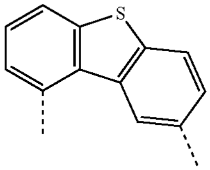

($Ar^L$-37)

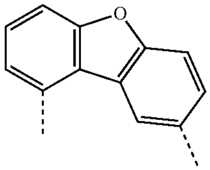

where the dashed bonds indicate the bonds to the spirobifluorene and to the amine, and where the groups ($Ar^L$-1) to ($Ar^L$-37) may be substituted at each free position by a group R but are preferably unsubstituted.

Among the groups of formulae (ArL-1) to (ArL-37), the groups ($Ar^L$-1) ($Ar^L$-2) and ($Ar^L$-3) are preferred.

In accordance with a preferred embodiment, $E^1$ and $E^2$ are, identically or differently, on each occurrence, selected from $C(R^0)_2$, O, S and $N(R^0)$. It is more preferred that at least one of the group $E^1$ and $E^2$ is selected from $C(R^0)_2$.

It is preferred that $R^0$ stands on each occurrence, identically or differently, for H, D, F, CN, $Si(R^1)_3$, a straight-chain alkyl groups having 1 to 10 C atoms or a branched or cyclic alkyl groups having 3 to 10 C atoms, each of which may be substituted by one or more radicals $R^1$, where in each case one or more H atoms may be replaced by F, or an aryl or heteroaryl groups having 5 to 40 aromatic ring atoms, which may in each case be substituted by one or more radicals $R^1$, where two adjacent substituents $R^0$ may form a mono- or polycyclic, aliphatic ring system or aromatic ring system, which may be substituted by one or more radicals $R^1$.

It is very preferred that $R^0$ stands on each occurrence, identically or differently, for H, D, F, CN, a straight-chain alkyl groups having 1 to 6 C atoms or a branched or cyclic alkyl groups having 3 to 6 C atoms, each of which may be substituted by one or more radicals R, where in each case one or more H atoms may be replaced by F, or an aryl or heteroaryl groups having 5 to 18 aromatic ring atoms, which may in each case be substituted by one or more radicals R, where two adjacent substituents $R^0$ may form a mono- or polycyclic, aliphatic ring system or aromatic ring system, which may be substituted by one or more radicals R.

In accordance with a preferred embodiment, R stands on each occurrence, identically or differently, for H, D, F, CN, a straight-chain alkyl or alkoxy group having 1 to 10 C atoms or a branched or cyclic alkyl or alkoxy group having 3 to 10 C atoms, each of which may be substituted by one or more radicals $R^1$, where one or more non-adjacent $CH_2$ groups may be replaced by O and where one or more H atoms may be replaced by F, or an aromatic or heteroaromatic ring systems having 5 to 24 aromatic ring atoms, which may in each case be substituted by one or more radicals $R^1$.

It is very preferred that R stands on each occurrence, identically or differently, for H, D, F, CN, a straight-chain alkyl having 1 to 8 C atoms or a branched or cyclic alkyl group having 3 to 8 C atoms, each of which may be substituted by one or more radicals $R^1$, or an aromatic or heteroaromatic ring systems having 5 to 12 aromatic ring atoms, which may in each case be substituted by one or more radicals $R^1$.

In accordance with a preferred embodiment, $R^1$ stands on each occurrence, identically or differently, for H, D, F, CN, a straight-chain alkyl or alkoxy group having 1 to 10 C atoms or a branched or cyclic alkyl or alkoxy group having 3 to 10 C atoms, each of which may be substituted by one or more radicals $R^2$, where one or more non-adjacent $CH_2$ groups may be replaced by O and where one or more H atoms may be replaced by F, or an aromatic or heteroaromatic ring systems having 5 to 24 aromatic ring atoms, which may in each case be substituted by one or more radicals $R^2$.

It is very preferred that $R^1$ stands on each occurrence, identically or differently, for H, D, F, CN, a straight-chain alkyl having 1 to 8 C atoms or a branched or cyclic alkyl group having 3 to 8 C atoms, each of which may be substituted by one or more radicals $R^2$, or an aromatic or heteroaromatic ring systems having 5 to 12 aromatic ring atoms, which may in each case be substituted by one or more radicals $R^2$.

For compounds which are processed by vacuum evaporation, the alkyl groups preferably have not more than four C atoms, particularly preferably not more than 1 C atom. For compounds which are processed from solution, suitable compounds are also those which are substituted by linear, branched or cyclic alkyl groups having up to 10 C atoms or which are substituted by oligoarylene groups, for example ortho-, meta-, para- or branched terphenyl or quaterphenyl groups.

Examples of suitable structures for compounds according to formula (1) are compounds of formulae (1A-1-6), (1A-1-7), (1A-1-8), (1A-1-9), (1B-1-6), (1B-1-7), (1B-1-8), (1B-1-9), (1C-1-6), (1C-1-7), (1C-1-8), (1C-1-9), (1A-2-6), (1A-2-7), (1A-2-8), (1A-2-9), (1B-2-6), (1B-2-7), (1B-2-8), (1B-2-9), (1C-2-6), (1C-2-7), (1C-2-8) and (1C-2-9), where:

$Ar^L$ is either absent or selected from the groups ($Ar^L$-1), ($Ar^L$-2) and ($Ar^L$-3);

$E^1$ is a group —$C(R^0)_2$—, selected from —$C(CH_3)_2$— or —$C(Ph)_2$-;

$E^2$ is —O—, —S—, —NPh-, —$C(CH_3)_2$— or —$C(Ph)_2$-;

with Ph=phenyl.

Examples of the preferred compounds are given in the table below:

| formula | $Ar^L$ | $E^1$ | $E^2$ | formula | $Ar^L$ | $E^1$ | $E^2$ |
|---|---|---|---|---|---|---|---|
| 1A-1-6 | absent | —$C(CH_3)_2$— | —O— | 1A-2-6 | absent | —$C(CH_3)_2$— | —O— |
| 1A-1-7 | absent | —$C(CH_3)_2$— | —O— | 1A-2-7 | absent | —$C(CH_3)_2$— | —O— |
| 1A-1-8 | absent | —$C(CH_3)_2$— | —O— | 1A-2-8 | absent | —$C(CH_3)_2$— | —O— |
| 1A-1-9 | absent | —$C(CH_3)_2$— | —O— | 1A-2-9 | absent | —$C(CH_3)_2$— | —O— |
| 1B-1-6 | absent | —$C(CH_3)_2$— | —O— | 1B-2-6 | absent | —$C(CH_3)_2$— | —O— |
| 1B-1-7 | absent | —$C(CH_3)_2$— | —O— | 1B-2-7 | absent | —$C(CH_3)_2$— | —O— |
| 1B-1-8 | absent | —$C(CH_3)_2$— | —O— | 1B-2-8 | absent | —$C(CH_3)_2$— | —O— |
| 1B-1-9 | absent | —$C(CH_3)_2$— | —O— | 1B-2-9 | absent | —$C(CH_3)_2$— | —O— |
| 1C-1-6 | absent | —$C(CH_3)_2$— | —O— | 1C-2-6 | absent | —$C(CH_3)_2$— | —O— |
| 1C-1-7 | absent | —$C(CH_3)_2$— | —O— | 1C-2-7 | absent | —$C(CH_3)_2$— | —O— |
| 1C-1-8 | absent | —$C(CH_3)_2$— | —O— | 1C-2-8 | absent | —$C(CH_3)_2$— | —O— |
| 1C-1-9 | absent | —$C(CH_3)_2$— | —O— | 1C-2-9 | absent | —$C(CH_3)_2$— | —O— |
| 1A-1-6 | ($Ar^L$-1) | —$C(CH_3)_2$— | —O— | 1A-2-6 | ($Ar^L$-1) | —$C(CH_3)_2$— | —O— |
| 1A-1-7 | ($Ar^L$-1) | —$C(CH_3)_2$— | —O— | 1A-2-7 | ($Ar^L$-1) | —$C(CH_3)_2$— | —O— |
| 1A-1-8 | ($Ar^L$-1) | —$C(CH_3)_2$— | —O— | 1A-2-8 | ($Ar^L$-1) | —$C(CH_3)_2$— | —O— |
| 1A-1-9 | ($Ar^L$-1) | —$C(CH_3)_2$— | —O— | 1A-2-9 | ($Ar^L$-1) | —$C(CH_3)_2$— | —O— |
| 1B-1-6 | ($Ar^L$-1) | —$C(CH_3)_2$— | —O— | 1B-2-6 | ($Ar^L$-1) | —$C(CH_3)_2$— | —O— |
| 1B-1-7 | ($Ar^L$-1) | —$C(CH_3)_2$— | —O— | 1B-2-7 | ($Ar^L$-1) | —$C(CH_3)_2$— | —O— |
| 1B-1-8 | ($Ar^L$-1) | —$C(CH_3)_2$— | —O— | 1B-2-8 | ($Ar^L$-1) | —$C(CH_3)_2$— | —O— |
| 1B-1-9 | ($Ar^L$-1) | —$C(CH_3)_2$— | —O— | 1B-2-9 | ($Ar^L$-1) | —$C(CH_3)_2$— | —O— |
| 1C-1-6 | ($Ar^L$-1) | —$C(CH_3)_2$— | —O— | 1C-2-6 | ($Ar^L$-1) | —$C(CH_3)_2$— | —O— |
| 1C-1-7 | ($Ar^L$-1) | —$C(CH_3)_2$— | —O— | 1C-2-7 | ($Ar^L$-1) | —$C(CH_3)_2$— | —O— |
| 1C-1-8 | ($Ar^L$-1) | —$C(CH_3)_2$— | —O— | 1C-2-8 | ($Ar^L$-1) | —$C(CH_3)_2$— | —O— |
| 1C-1-9 | ($Ar^L$-1) | —$C(CH_3)_2$— | —O— | 1C-2-9 | ($Ar^L$-1) | —$C(CH_3)_2$— | —O— |
| 1A-1-6 | ($Ar^L$-2) | —$C(CH_3)_2$— | —O— | 1A-2-6 | ($Ar^L$-2) | —$C(CH_3)_2$— | —O— |
| 1A-1-7 | ($Ar^L$-2) | —$C(CH_3)_2$— | —O— | 1A-2-7 | ($Ar^L$-2) | —$C(CH_3)_2$— | —O— |
| 1A-1-8 | ($Ar^L$-2) | —$C(CH_3)_2$— | —O— | 1A-2-8 | ($Ar^L$-2) | —$C(CH_3)_2$— | —O— |
| 1A-1-9 | ($Ar^L$-2) | —$C(CH_3)_2$— | —O— | 1A-2-9 | ($Ar^L$-2) | —$C(CH_3)_2$— | —O— |
| 1B-1-6 | ($Ar^L$-2) | —$C(CH_3)_2$— | —O— | 1B-2-6 | ($Ar^L$-2) | —$C(CH_3)_2$— | —O— |

-continued

| formula | $Ar^L$ | $E^1$ | $E^2$ | formula | $Ar^L$ | $E^1$ | $E^2$ |
|---|---|---|---|---|---|---|---|
| 1B-1-7 | ($Ar^L$-2) | $—C(CH_3)_2—$ | —O— | 1B-2-7 | ($Ar^L$-2) | $—C(CH_3)_2—$ | —O— |
| 1B-1-8 | ($Ar^L$-2) | $—C(CH_3)_2—$ | —O— | 1B-2-8 | ($Ar^L$-2) | $—C(CH_3)_2—$ | —O— |
| 1B-1-9 | ($Ar^L$-2) | $—C(CH_3)_2—$ | —O— | 1B-2-9 | ($Ar^L$-2) | $—C(CH_3)_2—$ | —O— |
| 1C-1-6 | ($Ar^L$-2) | $—C(CH_3)_2—$ | —O— | 1C-2-6 | ($Ar^L$-2) | $—C(CH_3)_2—$ | —O— |
| 1C-1-7 | ($Ar^L$-2) | $—C(CH_3)_2—$ | —O— | 1C-2-7 | ($Ar^L$-2) | $—C(CH_3)_2—$ | —O— |
| 1C-1-8 | ($Ar^L$-2) | $—C(CH_3)_2—$ | —O— | 1C-2-8 | ($Ar^L$-2) | $—C(CH_3)_2—$ | —O— |
| 1C-1-9 | ($Ar^L$-2) | $—C(CH_3)_2—$ | —O— | 1C-2-9 | ($Ar^L$-2) | $—C(CH_3)_2—$ | —O— |
| 1A-1-6 | ($Ar^L$-3) | $—C(CH_3)_2—$ | —O— | 1A-2-6 | ($Ar^L$-3) | $—C(CH_3)_2—$ | —O— |
| 1A-1-7 | ($Ar^L$-3) | $—C(CH_3)_2—$ | —O— | 1A-2-7 | ($Ar^L$-3) | $—C(CH_3)_2—$ | —O— |
| 1A-1-8 | ($Ar^L$-3) | $—C(CH_3)_2—$ | —O— | 1A-2-8 | ($Ar^L$-3) | $—C(CH_3)_2—$ | —O— |
| 1A-1-9 | ($Ar^L$-3) | $—C(CH_3)_2—$ | —O— | 1A-2-9 | ($Ar^L$-3) | $—C(CH_3)_2—$ | —O— |
| 1B-1-6 | ($Ar^L$-3) | $—C(CH_3)_2—$ | —O— | 1B-2-6 | ($Ar^L$-3) | $—C(CH_3)_2—$ | —O— |
| 1B-1-7 | ($Ar^L$-3) | $—C(CH_3)_2—$ | —O— | 1B-2-7 | ($Ar^L$-3) | $—C(CH_3)_2—$ | —O— |
| 1B-1-8 | ($Ar^L$-3) | $—C(CH_3)_2—$ | —O— | 1B-2-8 | ($Ar^L$-3) | $—C(CH_3)_2—$ | —O— |
| 1B-1-9 | ($Ar^L$-3) | $—C(CH_3)_2—$ | —O— | 1B-2-9 | ($Ar^L$-3) | $—C(CH_3)_2—$ | —O— |
| 1C-1-6 | ($Ar^L$-3) | $—C(CH_3)_2—$ | —O— | 1C-2-6 | ($Ar^L$-3) | $—C(CH_3)_2—$ | —O— |
| 1C-1-7 | ($Ar^L$-3) | $—C(CH_3)_2—$ | —O— | 1C-2-7 | ($Ar^L$-3) | $—C(CH_3)_2—$ | —O— |
| 1C-1-8 | ($Ar^L$-3) | $—C(CH_3)_2—$ | —O— | 1C-2-8 | ($Ar^L$-3) | $—C(CH_3)_2—$ | —O— |
| 1C-1-9 | ($Ar^L$-3) | $—C(CH_3)_2—$ | —O— | 1C-2-9 | ($Ar^L$-3) | $—C(CH_3)_2—$ | —O— |
| 1A-1-6 | absent | $—C(Ph)_2—$ | —O— | 1A-2-6 | absent | $—C(Ph)_2—$ | —O— |
| 1A-1-7 | absent | $—C(Ph)_2—$ | —O— | 1A-2-7 | absent | $—C(Ph)_2—$ | —O— |
| 1A-1-8 | absent | $—C(Ph)_2—$ | —O— | 1A-2-8 | absent | $—C(Ph)_2—$ | —O— |
| 1A-1-9 | absent | $—C(Ph)_2—$ | —O— | 1A-2-9 | absent | $—C(Ph)_2—$ | —O— |
| 1B-1-6 | absent | $—C(Ph)_2—$ | —O— | 1B-2-6 | absent | $—C(Ph)_2—$ | —O— |
| 1B-1-7 | absent | $—C(Ph)_2—$ | —O— | 1B-2-7 | absent | $—C(Ph)_2—$ | —O— |
| 1B-1-8 | absent | $—C(Ph)_2—$ | —O— | 1B-2-8 | absent | $—C(Ph)_2—$ | —O— |
| 1B-1-9 | absent | $—C(Ph)_2—$ | —O— | 1B-2-9 | absent | $—C(Ph)_2—$ | —O— |
| 1C-1-6 | absent | $—C(Ph)_2—$ | —O— | 1C-2-6 | absent | $—C(Ph)_2—$ | —O— |
| 1C-1-7 | absent | $—C(Ph)_2—$ | —O— | 1C-2-7 | absent | $—C(Ph)_2—$ | —O— |
| 1C-1-8 | absent | $—C(Ph)_2—$ | —O— | 1C-2-8 | absent | $—C(Ph)_2—$ | —O— |
| 1C-1-9 | absent | $—C(Ph)_2—$ | —O— | 1C-2-9 | absent | $—C(Ph)_2—$ | —O— |
| 1A-1-6 | ($Ar^L$-1) | $—C(Ph)_2—$ | —O— | 1A-2-6 | ($Ar^L$-1) | $—C(Ph)_2—$ | —O— |
| 1A-1-7 | ($Ar^L$-1) | $—C(Ph)_2—$ | —O— | 1A-2-7 | ($Ar^L$-1) | $—C(Ph)_2—$ | —O— |
| 1A-1-8 | ($Ar^L$-1) | $—C(Ph)_2—$ | —O— | 1A-2-8 | ($Ar^L$-1) | $—C(Ph)_2—$ | —O— |
| 1A-1-9 | ($Ar^L$-1) | $—C(Ph)_2—$ | —O— | 1A-2-9 | ($Ar^L$-1) | $—C(Ph)_2—$ | —O— |
| 1B-1-6 | ($Ar^L$-1) | $—C(Ph)_2—$ | —O— | 1B-2-6 | ($Ar^L$-1) | $—C(Ph)_2—$ | —O— |
| 1B-1-7 | ($Ar^L$-1) | $—C(Ph)_2—$ | —O— | 1B-2-7 | ($Ar^L$-1) | $—C(Ph)_2—$ | —O— |
| 1B-1-8 | ($Ar^L$-1) | $—C(Ph)_2—$ | —O— | 1B-2-8 | ($Ar^L$-1) | $—C(Ph)_2—$ | —O— |
| 1B-1-9 | ($Ar^L$-1) | $—C(Ph)_2—$ | —O— | 1B-2-9 | ($Ar^L$-1) | $—C(Ph)_2—$ | —O— |
| 1C-1-6 | ($Ar^L$-1) | $—C(Ph)_2—$ | —O— | 1C-2-6 | ($Ar^L$-1) | $—C(Ph)_2—$ | —O— |
| 1C-1-7 | ($Ar^L$-1) | $—C(Ph)_2—$ | —O— | 1C-2-7 | ($Ar^L$-1) | $—C(Ph)_2—$ | —O— |
| 1C-1-8 | ($Ar^L$-1) | $—C(Ph)_2—$ | —O— | 1C-2-8 | ($Ar^L$-1) | $—C(Ph)_2—$ | —O— |
| 1C-1-9 | ($Ar^L$-1) | $—C(Ph)_2—$ | —O— | 1C-2-9 | ($Ar^L$-1) | $—C(Ph)_2—$ | —O— |
| 1A-1-6 | ($Ar^L$-2) | $—C(Ph)_2—$ | —O— | 1A-2-6 | ($Ar^L$-2) | $—C(Ph)_2—$ | —O— |
| 1A-1-7 | ($Ar^L$-2) | $—C(Ph)_2—$ | —O— | 1A-2-7 | ($Ar^L$-2) | $—C(Ph)_2—$ | —O— |
| 1A-1-8 | ($Ar^L$-2) | $—C(Ph)_2—$ | —O— | 1A-2-8 | ($Ar^L$-2) | $—C(Ph)_2—$ | —O— |
| 1A-1-9 | ($Ar^L$-2) | $—C(Ph)_2—$ | —O— | 1A-2-9 | ($Ar^L$-2) | $—C(Ph)_2—$ | —O— |
| 1B-1-6 | ($Ar^L$-2) | $—C(Ph)_2—$ | —O— | 1B-2-6 | ($Ar^L$-2) | $—C(Ph)_2—$ | —O— |
| 1B-1-7 | ($Ar^L$-2) | $—C(Ph)_2—$ | —O— | 1B-2-7 | ($Ar^L$-2) | $—C(Ph)_2—$ | —O— |
| 1B-1-8 | ($Ar^L$-2) | $—C(Ph)_2—$ | —O— | 1B-2-8 | ($Ar^L$-2) | $—C(Ph)_2—$ | —O— |
| 1B-1-9 | ($Ar^L$-2) | $—C(Ph)_2—$ | —O— | 1B-2-9 | ($Ar^L$-2) | $—C(Ph)_2—$ | —O— |
| 1C-1-6 | ($Ar^L$-2) | $—C(Ph)_2—$ | —O— | 1C-2-6 | ($Ar^L$-2) | $—C(Ph)_2—$ | —O— |
| 1C-1-7 | ($Ar^L$-2) | $—C(Ph)_2—$ | —O— | 1C-2-7 | ($Ar^L$-2) | $—C(Ph)_2—$ | —O— |
| 1C-1-8 | ($Ar^L$-2) | $—C(Ph)_2—$ | —O— | 1C-2-8 | ($Ar^L$-2) | $—C(Ph)_2—$ | —O— |
| 1C-1-9 | ($Ar^L$-2) | $—C(Ph)_2—$ | —O— | 1C-2-9 | ($Ar^L$-2) | $—C(Ph)_2—$ | —O— |
| 1A-1-6 | ($Ar^L$-3) | $—C(Ph)_2—$ | —O— | 1A-2-6 | ($Ar^L$-3) | $—C(Ph)_2—$ | —O— |
| 1A-1-7 | ($Ar^L$-3) | $—C(Ph)_2—$ | —O— | 1A-2-7 | ($Ar^L$-3) | $—C(Ph)_2—$ | —O— |
| 1A-1-8 | ($Ar^L$-3) | $—C(Ph)_2—$ | —O— | 1A-2-8 | ($Ar^L$-3) | $—C(Ph)_2—$ | —O— |
| 1A-1-9 | ($Ar^L$-3) | $—C(Ph)_2—$ | —O— | 1A-2-9 | ($Ar^L$-3) | $—C(Ph)_2—$ | —O— |
| 1B-1-6 | ($Ar^L$-3) | $—C(Ph)_2—$ | —O— | 1B-2-6 | ($Ar^L$-3) | $—C(Ph)_2—$ | —O— |
| 1B-1-7 | ($Ar^L$-3) | $—C(Ph)_2—$ | —O— | 1B-2-7 | ($Ar^L$-3) | $—C(Ph)_2—$ | —O— |
| 1B-1-8 | ($Ar^L$-3) | $—C(Ph)_2—$ | —O— | 1B-2-8 | ($Ar^L$-3) | $—C(Ph)_2—$ | —O— |
| 1B-1-9 | ($Ar^L$-3) | $—C(Ph)_2—$ | —O— | 1B-2-9 | ($Ar^L$-3) | $—C(Ph)_2—$ | —O— |
| 1C-1-6 | ($Ar^L$-3) | $—C(Ph)_2—$ | —O— | 1C-2-6 | ($Ar^L$-3) | $—C(Ph)_2—$ | —O— |
| 1C-1-7 | ($Ar^L$-3) | $—C(Ph)_2—$ | —O— | 1C-2-7 | ($Ar^L$-3) | $—C(Ph)_2—$ | —O— |
| 1C-1-8 | ($Ar^L$-3) | $—C(Ph)_2—$ | —O— | 1C-2-8 | ($Ar^L$-3) | $—C(Ph)_2—$ | —O— |
| 1C-1-9 | ($Ar^L$-3) | $—C(Ph)_2—$ | —O— | 1C-2-9 | ($Ar^L$-3) | $—C(Ph)_2—$ | —O— |
| 1A-1-6 | absent | $—C(CH_3)_2—$ | —S— | 1A-2-6 | absent | $—C(CH_3)_2—$ | —S— |
| 1A-1-7 | absent | $—C(CH_3)_2—$ | —S— | 1A-2-7 | absent | $—C(CH_3)_2—$ | —S— |
| 1A-1-8 | absent | $—C(CH_3)_2—$ | —S— | 1A-2-8 | absent | $—C(CH_3)_2—$ | —S— |
| 1A-1-9 | absent | $—C(CH_3)_2—$ | —S— | 1A-2-9 | absent | $—C(CH_3)_2—$ | —S— |
| 1B-1-6 | absent | $—C(CH_3)_2—$ | —S— | 1B-2-6 | absent | $—C(CH_3)_2—$ | —S— |
| 1B-1-7 | absent | $—C(CH_3)_2—$ | —S— | 1B-2-7 | absent | $—C(CH_3)_2—$ | —S— |
| 1B-1-8 | absent | $—C(CH_3)_2—$ | —S— | 1B-2-8 | absent | $—C(CH_3)_2—$ | —S— |
| 1B-1-9 | absent | $—C(CH_3)_2—$ | —S— | 1B-2-9 | absent | $—C(CH_3)_2—$ | —S— |
| 1C-1-6 | absent | $—C(CH_3)_2—$ | —S— | 1C-2-6 | absent | $—C(CH_3)_2—$ | —S— |
| 1C-1-7 | absent | $—C(CH_3)_2—$ | —S— | 1C-2-7 | absent | $—C(CH_3)_2—$ | —S— |

-continued

| formula | $Ar^L$ | $E^1$ | $E^2$ | formula | $Ar^L$ | $E^1$ | $E^2$ |
|---|---|---|---|---|---|---|---|
| 1C-1-8 | absent | $—C(CH_3)_2—$ | —S— | 1C-2-8 | absent | $—C(CH_3)_2—$ | —S— |
| 1C-1-9 | absent | $—C(CH_3)_2—$ | —S— | 1C-2-9 | absent | $—C(CH_3)_2—$ | —S— |
| 1A-1-6 | ($Ar^L$-1) | $—C(CH_3)_2—$ | —S— | 1A-2-6 | ($Ar^L$-1) | $—C(CH_3)_2—$ | —S— |
| 1A-1-7 | ($Ar^L$-1) | $—C(CH_3)_2—$ | —S— | 1A-2-7 | ($Ar^L$-1) | $—C(CH_3)_2—$ | —S— |
| 1A-1-8 | ($Ar^L$-1) | $—C(CH_3)_2—$ | —S— | 1A-2-8 | ($Ar^L$-1) | $—C(CH_3)_2—$ | —S— |
| 1A-1-9 | ($Ar^L$-1) | $—C(CH_3)_2—$ | —S— | 1A-2-9 | ($Ar^L$-1) | $—C(CH_3)_2—$ | —S— |
| 1B-1-6 | ($Ar^L$-1) | $—C(CH_3)_2—$ | —S— | 1B-2-6 | ($Ar^L$-1) | $—C(CH_3)_2—$ | —S— |
| 1B-1-7 | ($Ar^L$-1) | $—C(CH_3)_2—$ | —S— | 1B-2-7 | ($Ar^L$-1) | $—C(CH_3)_2—$ | —S— |
| 1B-1-8 | ($Ar^L$-1) | $—C(CH_3)_2—$ | —S— | 1B-2-8 | ($Ar^L$-1) | $—C(CH_3)_2—$ | —S— |
| 1B-1-9 | ($Ar^L$-1) | $—C(CH_3)_2—$ | —S— | 1B-2-9 | ($Ar^L$-1) | $—C(CH_3)_2—$ | —S— |
| 1C-1-6 | ($Ar^L$-1) | $—C(CH_3)_2—$ | —S— | 1C-2-6 | ($Ar^L$-1) | $—C(CH_3)_2—$ | —S— |
| 1C-1-7 | ($Ar^L$-1) | $—C(CH_3)_2—$ | —S— | 1C-2-7 | ($Ar^L$-1) | $—C(CH_3)_2—$ | —S— |
| 1C-1-8 | ($Ar^L$-1) | $—C(CH_3)_2—$ | —S— | 1C-2-8 | ($Ar^L$-1) | $—C(CH_3)_2—$ | —S— |
| 1C-1-9 | ($Ar^L$-1) | $—C(CH_3)_2—$ | —S— | 1C-2-9 | ($Ar^L$-1) | $—C(CH_3)_2—$ | —S— |
| 1A-1-6 | ($Ar^L$-2) | $—C(CH_3)_2—$ | —S— | 1A-2-6 | ($Ar^L$-2) | $—C(CH_3)_2—$ | —S— |
| 1A-1-7 | ($Ar^L$-2) | $—C(CH_3)_2—$ | —S— | 1A-2-7 | ($Ar^L$-2) | $—C(CH_3)_2—$ | —S— |
| 1A-1-8 | ($Ar^L$-2) | $—C(CH_3)_2—$ | —S— | 1A-2-8 | ($Ar^L$-2) | $—C(CH_3)_2—$ | —S— |
| 1A-1-9 | ($Ar^L$-2) | $—C(CH_3)_2—$ | —S— | 1A-2-9 | ($Ar^L$-2) | $—C(CH_3)_2—$ | —S— |
| 1B-1-6 | ($Ar^L$-2) | $—C(CH_3)_2—$ | —S— | 1B-2-6 | ($Ar^L$-2) | $—C(CH_3)_2—$ | —S— |
| 1B-1-7 | ($Ar^L$-2) | $—C(CH_3)_2—$ | —S— | 1B-2-7 | ($Ar^L$-2) | $—C(CH_3)_2—$ | —S— |
| 1B-1-8 | ($Ar^L$-2) | $—C(CH_3)_2—$ | —S— | 1B-2-8 | ($Ar^L$-2) | $—C(CH_3)_2—$ | —S— |
| 1B-1-9 | ($Ar^L$-2) | $—C(CH_3)_2—$ | —S— | 1B-2-9 | ($Ar^L$-2) | $—C(CH_3)_2—$ | —S— |
| 1C-1-6 | ($Ar^L$-2) | $—C(CH_3)_2—$ | —S— | 1C-2-6 | ($Ar^L$-2) | $—C(CH_3)_2—$ | —S— |
| 1C-1-7 | ($Ar^L$-2) | $—C(CH_3)_2—$ | —S— | 1C-2-7 | ($Ar^L$-2) | $—C(CH_3)_2—$ | —S— |
| 1C-1-8 | ($Ar^L$-2) | $—C(CH_3)_2—$ | —S— | 1C-2-8 | ($Ar^L$-2) | $—C(CH_3)_2—$ | —S— |
| 1C-1-9 | ($Ar^L$-2) | $—C(CH_3)_2—$ | —S— | 1C-2-9 | ($Ar^L$-2) | $—C(CH_3)_2—$ | —S— |
| 1A-1-6 | ($Ar^L$-3) | $—C(CH_3)_2—$ | —S— | 1A-2-6 | ($Ar^L$-3) | $—C(CH_3)_2—$ | —S— |
| 1A-1-7 | ($Ar^L$-3) | $—C(CH_3)_2—$ | —S— | 1A-2-7 | ($Ar^L$-3) | $—C(CH_3)_2—$ | —S— |
| 1A-1-8 | ($Ar^L$-3) | $—C(CH_3)_2—$ | —S— | 1A-2-8 | ($Ar^L$-3) | $—C(CH_3)_2—$ | —S— |
| 1A-1-9 | ($Ar^L$-3) | $—C(CH_3)_2—$ | —S— | 1A-2-9 | ($Ar^L$-3) | $—C(CH_3)_2—$ | —S— |
| 1B-1-6 | ($Ar^L$-3) | $—C(CH_3)_2—$ | —S— | 1B-2-6 | ($Ar^L$-3) | $—C(CH_3)_2—$ | —S— |
| 1B-1-7 | ($Ar^L$-3) | $—C(CH_3)_2—$ | —S— | 1B-2-7 | ($Ar^L$-3) | $—C(CH_3)_2—$ | —S— |
| 1B-1-8 | ($Ar^L$-3) | $—C(CH_3)_2—$ | —S— | 1B-2-8 | ($Ar^L$-3) | $—C(CH_3)_2—$ | —S— |
| 1B-1-9 | ($Ar^L$-3) | $—C(CH_3)_2—$ | —S— | 1B-2-9 | ($Ar^L$-3) | $—C(CH_3)_2—$ | —S— |
| 1C-1-6 | ($Ar^L$-3) | $—C(CH_3)_2—$ | —S— | 1C-2-6 | ($Ar^L$-3) | $—C(CH_3)_2—$ | —S— |
| 1C-1-7 | ($Ar^L$-3) | $—C(CH_3)_2—$ | —S— | 1C-2-7 | ($Ar^L$-3) | $—C(CH_3)_2—$ | —S— |
| 1C-1-8 | ($Ar^L$-3) | $—C(CH_3)_2—$ | —S— | 1C-2-8 | ($Ar^L$-3) | $—C(CH_3)_2—$ | —S— |
| 1C-1-9 | ($Ar^L$-3) | $—C(CH_3)_2—$ | —S— | 1C-2-9 | ($Ar^L$-3) | $—C(CH_3)_2—$ | —S— |
| 1A-1-6 | absent | $—C(Ph)_2—$ | —S— | 1A-2-6 | absent | $—C(Ph)_2—$ | —S— |
| 1A-1-7 | absent | $—C(Ph)_2—$ | —S— | 1A-2-7 | absent | $—C(Ph)_2—$ | —S— |
| 1A-1-8 | absent | $—C(Ph)_2—$ | —S— | 1A-2-8 | absent | $—C(Ph)_2—$ | —S— |
| 1A-1-9 | absent | $—C(Ph)_2—$ | —S— | 1A-2-9 | absent | $—C(Ph)_2—$ | —S— |
| 1B-1-6 | absent | $—C(Ph)_2—$ | —S— | 1B-2-6 | absent | $—C(Ph)_2—$ | —S— |
| 1B-1-7 | absent | $—C(Ph)_2—$ | —S— | 1B-2-7 | absent | $—C(Ph)_2—$ | —S— |
| 1B-1-8 | absent | $—C(Ph)_2—$ | —S— | 1B-2-8 | absent | $—C(Ph)_2—$ | —S— |
| 1B-1-9 | absent | $—C(Ph)_2—$ | —S— | 1B-2-9 | absent | $—C(Ph)_2—$ | —S— |
| 1C-1-6 | absent | $—C(Ph)_2—$ | —S— | 1C-2-6 | absent | $—C(Ph)_2—$ | —S— |
| 1C-1-7 | absent | $—C(Ph)_2—$ | —S— | 1C-2-7 | absent | $—C(Ph)_2—$ | —S— |
| 1C-1-8 | absent | $—C(Ph)_2—$ | —S— | 1C-2-8 | absent | $—C(Ph)_2—$ | —S— |
| 1C-1-9 | absent | $—C(Ph)_2—$ | —S— | 1C-2-9 | absent | $—C(Ph)_2—$ | —S— |
| 1A-1-6 | ($Ar^L$-1) | $—C(Ph)_2—$ | —S— | 1A-2-6 | ($Ar^L$-1) | $—C(Ph)_2—$ | —S— |
| 1A-1-7 | ($Ar^L$-1) | $—C(Ph)_2—$ | —S— | 1A-2-7 | ($Ar^L$-1) | $—C(Ph)_2—$ | —S— |
| 1A-1-8 | ($Ar^L$-1) | $—C(Ph)_2—$ | —S— | 1A-2-8 | ($Ar^L$-1) | $—C(Ph)_2—$ | —S— |
| 1A-1-9 | ($Ar^L$-1) | $—C(Ph)_2—$ | —S— | 1A-2-9 | ($Ar^L$-1) | $—C(Ph)_2—$ | —S— |
| 1B-1-6 | ($Ar^L$-1) | $—C(Ph)_2—$ | —S— | 1B-2-6 | ($Ar^L$-1) | $—C(Ph)_2—$ | —S— |
| 1B-1-7 | ($Ar^L$-1) | $—C(Ph)_2—$ | —S— | 1B-2-7 | ($Ar^L$-1) | $—C(Ph)_2—$ | —S— |
| 1B-1-8 | ($Ar^L$-1) | $—C(Ph)_2—$ | —S— | 1B-2-8 | ($Ar^L$-1) | $—C(Ph)_2—$ | —S— |
| 1B-1-9 | ($Ar^L$-1) | $—C(Ph)_2—$ | —S— | 1B-2-9 | ($Ar^L$-1) | $—C(Ph)_2—$ | —S— |
| 1C-1-6 | ($Ar^L$-1) | $—C(Ph)_2—$ | —S— | 1C-2-6 | ($Ar^L$-1) | $—C(Ph)_2—$ | —S— |
| 1C-1-7 | ($Ar^L$-1) | $—C(Ph)_2—$ | —S— | 1C-2-7 | ($Ar^L$-1) | $—C(Ph)_2—$ | —S— |
| 1C-1-8 | ($Ar^L$-1) | $—C(Ph)_2—$ | —S— | 1C-2-8 | ($Ar^L$-1) | $—C(Ph)_2—$ | —S— |
| 1C-1-9 | ($Ar^L$-1) | $—C(Ph)_2—$ | —S— | 1C-2-9 | ($Ar^L$-1) | $—C(Ph)_2—$ | —S— |
| 1A-1-6 | ($Ar^L$-2) | $—C(Ph)_2—$ | —S— | 1A-2-6 | ($Ar^L$-2) | $—C(Ph)_2—$ | —S— |
| 1A-1-7 | ($Ar^L$-2) | $—C(Ph)_2—$ | —S— | 1A-2-7 | ($Ar^L$-2) | $—C(Ph)_2—$ | —S— |
| 1A-1-8 | ($Ar^L$-2) | $—C(Ph)_2—$ | —S— | 1A-2-8 | ($Ar^L$-2) | $—C(Ph)_2—$ | —S— |
| 1A-1-9 | ($Ar^L$-2) | $—C(Ph)_2—$ | —S— | 1A-2-9 | ($Ar^L$-2) | $—C(Ph)_2—$ | —S— |
| 1B-1-6 | ($Ar^L$-2) | $—C(Ph)_2—$ | —S— | 1B-2-6 | ($Ar^L$-2) | $—C(Ph)_2—$ | —S— |
| 1B-1-7 | ($Ar^L$-2) | $—C(Ph)_2—$ | —S— | 1B-2-7 | ($Ar^L$-2) | $—C(Ph)_2—$ | —S— |
| 1B-1-8 | ($Ar^L$-2) | $—C(Ph)_2—$ | —S— | 1B-2-8 | ($Ar^L$-2) | $—C(Ph)_2—$ | —S— |
| 1B-1-9 | ($Ar^L$-2) | $—C(Ph)_2—$ | —S— | 1B-2-9 | ($Ar^L$-2) | $—C(Ph)_2—$ | —S— |
| 1C-1-6 | ($Ar^L$-2) | $—C(Ph)_2—$ | —S— | 1C-2-6 | ($Ar^L$-2) | $—C(Ph)_2—$ | —S— |
| 1C-1-7 | ($Ar^L$-2) | $—C(Ph)_2—$ | —S— | 1C-2-7 | ($Ar^L$-2) | $—C(Ph)_2—$ | —S— |
| 1C-1-8 | ($Ar^L$-2) | $—C(Ph)_2—$ | —S— | 1C-2-8 | ($Ar^L$-2) | $—C(Ph)_2—$ | —S— |
| 1C-1-9 | ($Ar^L$-2) | $—C(Ph)_2—$ | —S— | 1C-2-9 | ($Ar^L$-2) | $—C(Ph)_2—$ | —S— |
| 1A-1-6 | ($Ar^L$-3) | $—C(Ph)_2—$ | —S— | 1A-2-6 | ($Ar^L$-3) | $—C(Ph)_2—$ | —S— |
| 1A-1-7 | ($Ar^L$-3) | $—C(Ph)_2—$ | —S— | 1A-2-7 | ($Ar^L$-3) | $—C(Ph)_2—$ | —S— |
| 1A-1-8 | ($Ar^L$-3) | $—C(Ph)_2—$ | —S— | 1A-2-8 | ($Ar^L$-3) | $—C(Ph)_2—$ | —S— |

-continued

| formula | Ar$^L$ | E$^1$ | E$^2$ | formula | Ar$^L$ | E$^1$ | E$^2$ |
|---|---|---|---|---|---|---|---|
| 1A-1-9 | (Ar$^L$-3) | —C(Ph)$_2$— | —S— | 1A-2-9 | (Ar$^L$-3) | —C(Ph)$_2$— | —S— |
| 1B-1-6 | (Ar$^L$-3) | —C(Ph)$_2$— | —S— | 1B-2-6 | (Ar$^L$-3) | —C(Ph)$_2$— | —S— |
| 1B-1-7 | (Ar$^L$-3) | —C(Ph)$_2$— | —S— | 1B-2-7 | (Ar$^L$-3) | —C(Ph)$_2$— | —S— |
| 1B-1-8 | (Ar$^L$-3) | —C(Ph)$_2$— | —S— | 1B-2-8 | (Ar$^L$-3) | —C(Ph)$_2$— | —S— |
| 1B-1-9 | (Ar$^L$-3) | —C(Ph)$_2$— | —S— | 1B-2-9 | (Ar$^L$-3) | —C(Ph)$_2$— | —S— |
| 1C-1-6 | (Ar$^L$-3) | —C(Ph)$_2$— | —S— | 1C-2-6 | (Ar$^L$-3) | —C(Ph)$_2$— | —S— |
| 1C-1-7 | (Ar$^L$-3) | —C(Ph)$_2$— | —S— | 1C-2-7 | (Ar$^L$-3) | —C(Ph)$_2$— | —S— |
| 1C-1-8 | (Ar$^L$-3) | —C(Ph)$_2$— | —S— | 1C-2-8 | (Ar$^L$-3) | —C(Ph)$_2$— | —S— |
| 1C-1-9 | (Ar$^L$-3) | —C(Ph)$_2$— | —S— | 1C-2-9 | (Ar$^L$-3) | —C(Ph)$_2$— | —S— |
| 1A-1-6 | absent | —C(CH$_3$)$_2$— | —NPh— | 1A-2-6 | absent | —C(CH$_3$)$_2$— | —NPh— |
| 1A-1-7 | absent | —C(CH$_3$)$_2$— | —NPh— | 1A-2-7 | absent | —C(CH$_3$)$_2$— | —NPh— |
| 1A-1-8 | absent | —C(CH$_3$)$_2$— | —NPh— | 1A-2-8 | absent | —C(CH$_3$)$_2$— | —NPh— |
| 1A-1-9 | absent | —C(CH$_3$)$_2$— | —NPh— | 1A-2-9 | absent | —C(CH$_3$)$_2$— | —NPh— |
| 1B-1-6 | absent | —C(CH$_3$)$_2$— | —NPh— | 1B-2-6 | absent | —C(CH$_3$)$_2$— | —NPh— |
| 1B-1-7 | absent | —C(CH$_3$)$_2$— | —NPh— | 1B-2-7 | absent | —C(CH$_3$)$_2$— | —NPh— |
| 1B-1-8 | absent | —C(CH$_3$)$_2$— | —NPh— | 1B-2-8 | absent | —C(CH$_3$)$_2$— | —NPh— |
| 1B-1-9 | absent | —C(CH$_3$)$_2$— | —NPh— | 1B-2-9 | absent | —C(CH$_3$)$_2$— | —NPh— |
| 1C-1-6 | absent | —C(CH$_3$)$_2$— | —NPh— | 1C-2-6 | absent | —C(CH$_3$)$_2$— | —NPh— |
| 1C-1-7 | absent | —C(CH$_3$)$_2$— | —NPh— | 1C-2-7 | absent | —C(CH$_3$)$_2$— | —NPh— |
| 1C-1-8 | absent | —C(CH$_3$)$_2$— | —NPh— | 1C-2-8 | absent | —C(CH$_3$)$_2$— | —NPh— |
| 1C-1-9 | absent | —C(CH$_3$)$_2$— | —NPh— | 1C-2-9 | absent | —C(CH$_3$)$_2$— | —NPh— |
| 1A-1-6 | (Ar$^L$-1) | —C(CH$_3$)$_2$— | —NPh— | 1A-2-6 | (Ar$^L$-1) | —C(CH$_3$)$_2$— | —NPh— |
| 1A-1-7 | (Ar$^L$-1) | —C(CH$_3$)$_2$— | —NPh— | 1A-2-7 | (Ar$^L$-1) | —C(CH$_3$)$_2$— | —NPh— |
| 1A-1-8 | (Ar$^L$-1) | —C(CH$_3$)$_2$— | —NPh— | 1A-2-8 | (Ar$^L$-1) | —C(CH$_3$)$_2$— | —NPh— |
| 1A-1-9 | (Ar$^L$-1) | —C(CH$_3$)$_2$— | —NPh— | 1A-2-9 | (Ar$^L$-1) | —C(CH$_3$)$_2$— | —NPh— |
| 1B-1-6 | (Ar$^L$-1) | —C(CH$_3$)$_2$— | —NPh— | 1B-2-6 | (Ar$^L$-1) | —C(CH$_3$)$_2$— | —NPh— |
| 1B-1-7 | (Ar$^L$-1) | —C(CH$_3$)$_2$— | —NPh— | 1B-2-7 | (Ar$^L$-1) | —C(CH$_3$)$_2$— | —NPh— |
| 1B-1-8 | (Ar$^L$-1) | —C(CH$_3$)$_2$— | —NPh— | 1B-2-8 | (Ar$^L$-1) | —C(CH$_3$)$_2$— | —NPh— |
| 1B-1-9 | (Ar$^L$-1) | —C(CH$_3$)$_2$— | —NPh— | 1B-2-9 | (Ar$^L$-1) | —C(CH$_3$)$_2$— | —NPh— |
| 1C-1-6 | (Ar$^L$-1) | —C(CH$_3$)$_2$— | —NPh— | 1C-2-6 | (Ar$^L$-1) | —C(CH$_3$)$_2$— | —NPh— |
| 1C-1-7 | (Ar$^L$-1) | —C(CH$_3$)$_2$— | —NPh— | 1C-2-7 | (Ar$^L$-1) | —C(CH$_3$)$_2$— | —NPh— |
| 1C-1-8 | (Ar$^L$-1) | —C(CH$_3$)$_2$— | —NPh— | 1C-2-8 | (Ar$^L$-1) | —C(CH$_3$)$_2$— | —NPh— |
| 1C-1-9 | (Ar$^L$-1) | —C(CH$_3$)$_2$— | —NPh— | 1C-2-9 | (Ar$^L$-1) | —C(CH$_3$)$_2$— | —NPh— |
| 1A-1-6 | (Ar$^L$-2) | —C(CH$_3$)$_2$— | —NPh— | 1A-2-6 | (Ar$^L$-2) | —C(CH$_3$)$_2$— | —NPh— |
| 1A-1-7 | (Ar$^L$-2) | —C(CH$_3$)$_2$— | —NPh— | 1A-2-7 | (Ar$^L$-2) | —C(CH$_3$)$_2$— | —NPh— |
| 1A-1-8 | (Ar$^L$-2) | —C(CH$_3$)$_2$— | —NPh— | 1A-2-8 | (Ar$^L$-2) | —C(CH$_3$)$_2$— | —NPh— |
| 1A-1-9 | (Ar$^L$-2) | —C(CH$_3$)$_2$— | —NPh— | 1A-2-9 | (Ar$^L$-2) | —C(CH$_3$)$_2$— | —NPh— |
| 1B-1-6 | (Ar$^L$-2) | —C(CH$_3$)$_2$— | —NPh— | 1B-2-6 | (Ar$^L$-2) | —C(CH$_3$)$_2$— | —NPh— |
| 1B-1-7 | (Ar$^L$-2) | —C(CH$_3$)$_2$— | —NPh— | 1B-2-7 | (Ar$^L$-2) | —C(CH$_3$)$_2$— | —NPh— |
| 1B-1-8 | (Ar$^L$-2) | —C(CH$_3$)$_2$— | —NPh— | 1B-2-8 | (Ar$^L$-2) | —C(CH$_3$)$_2$— | —NPh— |
| 1B-1-9 | (Ar$^L$-2) | —C(CH$_3$)$_2$— | —NPh— | 1B-2-9 | (Ar$^L$-2) | —C(CH$_3$)$_2$— | —NPh— |
| 1C-1-6 | (Ar$^L$-2) | —C(CH$_3$)$_2$— | —NPh— | 1C-2-6 | (Ar$^L$-2) | —C(CH$_3$)$_2$— | —NPh— |
| 1C-1-7 | (Ar$^L$-2) | —C(CH$_3$)$_2$— | —NPh— | 1C-2-7 | (Ar$^L$-2) | —C(CH$_3$)$_2$— | —NPh— |
| 1C-1-8 | (Ar$^L$-2) | —C(CH$_3$)$_2$— | —NPh— | 1C-2-8 | (Ar$^L$-2) | —C(CH$_3$)$_2$— | —NPh— |
| 1C-1-9 | (Ar$^L$-2) | —C(CH$_3$)$_2$— | —NPh— | 1C-2-9 | (Ar$^L$-2) | —C(CH$_3$)$_2$— | —NPh— |
| 1A-1-6 | (Ar$^L$-3) | —C(CH$_3$)$_2$— | —NPh— | 1A-2-6 | (Ar$^L$-3) | —C(CH$_3$)$_2$— | —NPh— |
| 1A-1-7 | (Ar$^L$-3) | —C(CH$_3$)$_2$— | —NPh— | 1A-2-7 | (Ar$^L$-3) | —C(CH$_3$)$_2$— | —NPh— |
| 1A-1-8 | (Ar$^L$-3) | —C(CH$_3$)$_2$— | —NPh— | 1A-2-8 | (Ar$^L$-3) | —C(CH$_3$)$_2$— | —NPh— |
| 1A-1-9 | (Ar$^L$-3) | —C(CH$_3$)$_2$— | —NPh— | 1A-2-9 | (Ar$^L$-3) | —C(CH$_3$)$_2$— | —NPh— |
| 1B-1-6 | (Ar$^L$-3) | —C(CH$_3$)$_2$— | —NPh— | 1B-2-6 | (Ar$^L$-3) | —C(CH$_3$)$_2$— | —NPh— |
| 1B-1-7 | (Ar$^L$-3) | —C(CH$_3$)$_2$— | —NPh— | 1B-2-7 | (Ar$^L$-3) | —C(CH$_3$)$_2$— | —NPh— |
| 1B-1-8 | (Ar$^L$-3) | —C(CH$_3$)$_2$— | —NPh— | 1B-2-8 | (Ar$^L$-3) | —C(CH$_3$)$_2$— | —NPh— |
| 1B-1-9 | (Ar$^L$-3) | —C(CH$_3$)$_2$— | —NPh— | 1B-2-9 | (Ar$^L$-3) | —C(CH$_3$)$_2$— | —NPh— |
| 1C-1-6 | (Ar$^L$-3) | —C(CH$_3$)$_2$— | —NPh— | 1C-2-6 | (Ar$^L$-3) | —C(CH$_3$)$_2$— | —NPh— |
| 1C-1-7 | (Ar$^L$-3) | —C(CH$_3$)$_2$— | —NPh— | 1C-2-7 | (Ar$^L$-3) | —C(CH$_3$)$_2$— | —NPh— |
| 1C-1-8 | (Ar$^L$-3) | —C(CH$_3$)$_2$— | —NPh— | 1C-2-8 | (Ar$^L$-3) | —C(CH$_3$)$_2$— | —NPh— |
| 1C-1-9 | (Ar$^L$-3) | —C(CH$_3$)$_2$— | —NPh— | 1C-2-9 | (Ar$^L$-3) | —C(CH$_3$)$_2$— | —NPh— |
| 1A-1-6 | absent | —C(Ph)$_2$— | —NPh— | 1A-2-6 | absent | —C(Ph)$_2$— | —NPh— |
| 1A-1-7 | absent | —C(Ph)$_2$— | —NPh— | 1A-2-7 | absent | —C(Ph)$_2$— | —NPh— |
| 1A-1-8 | absent | —C(Ph)$_2$— | —NPh— | 1A-2-8 | absent | —C(Ph)$_2$— | —NPh— |
| 1A-1-9 | absent | —C(Ph)$_2$— | —NPh— | 1A-2-9 | absent | —C(Ph)$_2$— | —NPh— |
| 1B-1-6 | absent | —C(Ph)$_2$— | —NPh— | 1B-2-6 | absent | —C(Ph)$_2$— | —NPh— |
| 1B-1-7 | absent | —C(Ph)$_2$— | —NPh— | 1B-2-7 | absent | —C(Ph)$_2$— | —NPh— |
| 1B-1-8 | absent | —C(Ph)$_2$— | —NPh— | 1B-2-8 | absent | —C(Ph)$_2$— | —NPh— |
| 1B-1-9 | absent | —C(Ph)$_2$— | —NPh— | 1B-2-9 | absent | —C(Ph)$_2$— | —NPh— |
| 1C-1-6 | absent | —C(Ph)$_2$— | —NPh— | 1C-2-6 | absent | —C(Ph)$_2$— | —NPh— |
| 1C-1-7 | absent | —C(Ph)$_2$— | —NPh— | 1C-2-7 | absent | —C(Ph)$_2$— | —NPh— |
| 1C-1-8 | absent | —C(Ph)$_2$— | —NPh— | 1C-2-8 | absent | —C(Ph)$_2$— | —NPh— |
| 1C-1-9 | absent | —C(Ph)$_2$— | —NPh— | 1C-2-9 | absent | —C(Ph)$_2$— | —NPh— |
| 1A-1-6 | (Ar$^L$-1) | —C(Ph)$_2$— | —NPh— | 1A-2-6 | (Ar$^L$-1) | —C(Ph)$_2$— | —NPh— |
| 1A-1-7 | (Ar$^L$-1) | —C(Ph)$_2$— | —NPh— | 1A-2-7 | (Ar$^L$-1) | —C(Ph)$_2$— | —NPh— |
| 1A-1-8 | (Ar$^L$-1) | —C(Ph)$_2$— | —NPh— | 1A-2-8 | (Ar$^L$-1) | —C(Ph)$_2$— | —NPh— |
| 1A-1-9 | (Ar$^L$-1) | —C(Ph)$_2$— | —NPh— | 1A-2-9 | (Ar$^L$-1) | —C(Ph)$_2$— | —NPh— |
| 1B-1-6 | (Ar$^L$-1) | —C(Ph)$_2$— | —NPh— | 1B-2-6 | (Ar$^L$-1) | —C(Ph)$_2$— | —NPh— |
| 1B-1-7 | (Ar$^L$-1) | —C(Ph)$_2$— | —NPh— | 1B-2-7 | (Ar$^L$-1) | —C(Ph)$_2$— | —NPh— |
| 1B-1-8 | (Ar$^L$-1) | —C(Ph)$_2$— | —NPh— | 1B-2-8 | (Ar$^L$-1) | —C(Ph)$_2$— | —NPh— |
| 1B-1-9 | (Ar$^L$-1) | —C(Ph)$_2$— | —NPh— | 1B-2-9 | (Ar$^L$-1) | —C(Ph)$_2$— | —NPh— |

-continued

| formula | $Ar^L$ | $E^1$ | $E^2$ | formula | $Ar^L$ | $E^1$ | $E^2$ |
|---|---|---|---|---|---|---|---|
| 1C-1-6 | ($Ar^L$-1) | —C(Ph)$_2$— | —NPh— | 1C-2-6 | ($Ar^L$-1) | —C(Ph)$_2$— | —NPh— |
| 1C-1-7 | ($Ar^L$-1) | —C(Ph)$_2$— | —NPh— | 1C-2-7 | ($Ar^L$-1) | —C(Ph)$_2$— | —NPh— |
| 1C-1-8 | ($Ar^L$-1) | —C(Ph)$_2$— | —NPh— | 1C-2-8 | ($Ar^L$-1) | —C(Ph)$_2$— | —NPh— |
| 1C-1-9 | ($Ar^L$-1) | —C(Ph)$_2$— | —NPh— | 1C-2-9 | ($Ar^L$-1) | —C(Ph)$_2$— | —NPh— |
| 1A-1-6 | ($Ar^L$-2) | —C(Ph)$_2$— | —NPh— | 1A-2-6 | ($Ar^L$-2) | —C(Ph)$_2$— | —NPh— |
| 1A-1-7 | ($Ar^L$-2) | —C(Ph)$_2$— | —NPh— | 1A-2-7 | ($Ar^L$-2) | —C(Ph)$_2$— | —NPh— |
| 1A-1-8 | ($Ar^L$-2) | —C(Ph)$_2$— | —NPh— | 1A-2-8 | ($Ar^L$-2) | —C(Ph)$_2$— | —NPh— |
| 1A-1-9 | ($Ar^L$-2) | —C(Ph)$_2$— | —NPh— | 1A-2-9 | ($Ar^L$-2) | —C(Ph)$_2$— | —NPh— |
| 1B-1-6 | ($Ar^L$-2) | —C(Ph)$_2$— | —NPh— | 1B-2-6 | ($Ar^L$-2) | —C(Ph)$_2$— | —NPh— |
| 1B-1-7 | ($Ar^L$-2) | —C(Ph)$_2$— | —NPh— | 1B-2-7 | ($Ar^L$-2) | —C(Ph)$_2$— | —NPh— |
| 1B-1-8 | ($Ar^L$-2) | —C(Ph)$_2$— | —NPh— | 1B-2-8 | ($Ar^L$-2) | —C(Ph)$_2$— | —NPh— |
| 1B-1-9 | ($Ar^L$-2) | —C(Ph)$_2$— | —NPh— | 1B-2-9 | ($Ar^L$-2) | —C(Ph)$_2$— | —NPh— |
| 1C-1-6 | ($Ar^L$-2) | —C(Ph)$_2$— | —NPh— | 1C-2-6 | ($Ar^L$-2) | —C(Ph)$_2$— | —NPh— |
| 1C-1-7 | ($Ar^L$-2) | —C(Ph)$_2$— | —NPh— | 1C-2-7 | ($Ar^L$-2) | —C(Ph)$_2$— | —NPh— |
| 1C-1-8 | ($Ar^L$-2) | —C(Ph)$_2$— | —NPh— | 1C-2-8 | ($Ar^L$-2) | —C(Ph)$_2$— | —NPh— |
| 1C-1-9 | ($Ar^L$-2) | —C(Ph)$_2$— | —NPh— | 1C-2-9 | ($Ar^L$-2) | —C(Ph)$_2$— | —NPh— |
| 1A-1-6 | ($Ar^L$-3) | —C(Ph)$_2$— | —NPh— | 1A-2-6 | ($Ar^L$-3) | —C(Ph)$_2$— | —NPh— |
| 1A-1-7 | ($Ar^L$-3) | —C(Ph)$_2$— | —NPh— | 1A-2-7 | ($Ar^L$-3) | —C(Ph)$_2$— | —NPh— |
| 1A-1-8 | ($Ar^L$-3) | —C(Ph)$_2$— | —NPh— | 1A-2-8 | ($Ar^L$-3) | —C(Ph)$_2$— | —NPh— |
| 1A-1-9 | ($Ar^L$-3) | —C(Ph)$_2$— | —NPh— | 1A-2-9 | ($Ar^L$-3) | —C(Ph)$_2$— | —NPh— |
| 1B-1-6 | ($Ar^L$-3) | —C(Ph)$_2$— | —NPh— | 1B-2-6 | ($Ar^L$-3) | —C(Ph)$_2$— | —NPh— |
| 1B-1-7 | ($Ar^L$-3) | —C(Ph)$_2$— | —NPh— | 1B-2-7 | ($Ar^L$-3) | —C(Ph)$_2$— | —NPh— |
| 1B-1-8 | ($Ar^L$-3) | —C(Ph)$_2$— | —NPh— | 1B-2-8 | ($Ar^L$-3) | —C(Ph)$_2$— | —NPh— |
| 1B-1-9 | ($Ar^L$-3) | —C(Ph)$_2$— | —NPh— | 1B-2-9 | ($Ar^L$-3) | —C(Ph)$_2$— | —NPh— |
| 1C-1-6 | ($Ar^L$-3) | —C(Ph)$_2$— | —NPh— | 1C-2-6 | ($Ar^L$-3) | —C(Ph)$_2$— | —NPh— |
| 1C-1-7 | ($Ar^L$-3) | —C(Ph)$_2$— | —NPh— | 1C-2-7 | ($Ar^L$-3) | —C(Ph)$_2$— | —NPh— |
| 1C-1-8 | ($Ar^L$-3) | —C(Ph)$_2$— | —NPh— | 1C-2-8 | ($Ar^L$-3) | —C(Ph)$_2$— | —NPh— |
| 1C-1-9 | ($Ar^L$-3) | —C(Ph)$_2$— | —NPh— | 1C-2-9 | ($Ar^L$-3) | —C(Ph)$_2$— | —NPh— |
| 1A-1-6 | absent | —C(CH$_3$)$_2$— | —C(CH$_3$)$_2$— | 1A-2-6 | absent | —C(CH$_3$)$_2$— | —C(CH$_3$)$_2$— |
| 1A-1-7 | absent | —C(CH$_3$)$_2$— | —C(CH$_3$)$_2$— | 1A-2-7 | absent | —C(CH$_3$)$_2$— | —C(CH$_3$)$_2$— |
| 1A-1-8 | absent | —C(CH$_3$)$_2$— | —C(CH$_3$)$_2$— | 1A-2-8 | absent | —C(CH$_3$)$_2$— | —C(CH$_3$)$_2$— |
| 1A-1-9 | absent | —C(CH$_3$)$_2$— | —C(CH$_3$)$_2$— | 1A-2-9 | absent | —C(CH$_3$)$_2$— | —C(CH$_3$)$_2$— |
| 1B-1-6 | absent | —C(CH$_3$)$_2$— | —C(CH$_3$)$_2$— | 1B-2-6 | absent | —C(CH$_3$)$_2$— | —C(CH$_3$)$_2$— |
| 1B-1-7 | absent | —C(CH$_3$)$_2$— | —C(CH$_3$)$_2$— | 1B-2-7 | absent | —C(CH$_3$)$_2$— | —C(CH$_3$)$_2$— |
| 1B-1-8 | absent | —C(CH$_3$)$_2$— | —C(CH$_3$)$_2$— | 1B-2-8 | absent | —C(CH$_3$)$_2$— | —C(CH$_3$)$_2$— |
| 1B-1-9 | absent | —C(CH$_3$)$_2$— | —C(CH$_3$)$_2$— | 1B-2-9 | absent | —C(CH$_3$)$_2$— | —C(CH$_3$)$_2$— |
| 1C-1-6 | absent | —C(CH$_3$)$_2$— | —C(CH$_3$)$_2$— | 1C-2-6 | absent | —C(CH$_3$)$_2$— | —C(CH$_3$)$_2$— |
| 1C-1-7 | absent | —C(CH$_3$)$_2$— | —C(CH$_3$)$_2$— | 1C-2-7 | absent | —C(CH$_3$)$_2$— | —C(CH$_3$)$_2$— |
| 1C-1-8 | absent | —C(CH$_3$)$_2$— | —C(CH$_3$)$_2$— | 1C-2-8 | absent | —C(CH$_3$)$_2$— | —C(CH$_3$)$_2$— |
| 1C-1-9 | absent | —C(CH$_3$)$_2$— | —C(CH$_3$)$_2$— | 1C-2-9 | absent | —C(CH$_3$)$_2$— | —C(CH$_3$)$_2$— |
| 1A-1-6 | ($Ar^L$-1) | —C(CH$_3$)$_2$— | —C(CH$_3$)$_2$— | 1A-2-6 | ($Ar^L$-1) | —C(CH$_3$)$_2$— | —C(CH$_3$)$_2$— |
| 1A-1-7 | ($Ar^L$-1) | —C(CH$_3$)$_2$— | —C(CH$_3$)$_2$— | 1A-2-7 | ($Ar^L$-1) | —C(CH$_3$)$_2$— | —C(CH$_3$)$_2$— |
| 1A-1-8 | ($Ar^L$-1) | —C(CH$_3$)$_2$— | —C(CH$_3$)$_2$— | 1A-2-8 | ($Ar^L$-1) | —C(CH$_3$)$_2$— | —C(CH$_3$)$_2$— |
| 1A-1-9 | ($Ar^L$-1) | —C(CH$_3$)$_2$— | —C(CH$_3$)$_2$— | 1A-2-9 | ($Ar^L$-1) | —C(CH$_3$)$_2$— | —C(CH$_3$)$_2$— |
| 1B-1-6 | ($Ar^L$-1) | —C(CH$_3$)$_2$— | —C(CH$_3$)$_2$— | 1B-2-6 | ($Ar^L$-1) | —C(CH$_3$)$_2$— | —C(CH$_3$)$_2$— |
| 1B-1-7 | ($Ar^L$-1) | —C(CH$_3$)$_2$— | —C(CH$_3$)$_2$— | 1B-2-7 | ($Ar^L$-1) | —C(CH$_3$)$_2$— | —C(CH$_3$)$_2$— |
| 1B-1-8 | ($Ar^L$-1) | —C(CH$_3$)$_2$— | —C(CH$_3$)$_2$— | 1B-2-8 | ($Ar^L$-1) | —C(CH$_3$)$_2$— | —C(CH$_3$)$_2$— |
| 1B-1-9 | ($Ar^L$-1) | —C(CH$_3$)$_2$— | —C(CH$_3$)$_2$— | 1B-2-9 | ($Ar^L$-1) | —C(CH$_3$)$_2$— | —C(CH$_3$)$_2$— |
| 1C-1-6 | ($Ar^L$-1) | —C(CH$_3$)$_2$— | —C(CH$_3$)$_2$— | 1C-2-6 | ($Ar^L$-1) | —C(CH$_3$)$_2$— | —C(CH$_3$)$_2$— |
| 1C-1-7 | ($Ar^L$-1) | —C(CH$_3$)$_2$— | —C(CH$_3$)$_2$— | 1C-2-7 | ($Ar^L$-1) | —C(CH$_3$)$_2$— | —C(CH$_3$)$_2$— |
| 1C-1-8 | ($Ar^L$-1) | —C(CH$_3$)$_2$— | —C(CH$_3$)$_2$— | 1C-2-8 | ($Ar^L$-1) | —C(CH$_3$)$_2$— | —C(CH$_3$)$_2$— |
| 1C-1-9 | ($Ar^L$-1) | —C(CH$_3$)$_2$— | —C(CH$_3$)$_2$— | 1C-2-9 | ($Ar^L$-1) | —C(CH$_3$)$_2$— | —C(CH$_3$)$_2$— |
| 1A-1-6 | ($Ar^L$-2) | —C(CH$_3$)$_2$— | —C(CH$_3$)$_2$— | 1A-2-6 | ($Ar^L$-2) | —C(CH$_3$)$_2$— | —C(CH$_3$)$_2$— |
| 1A-1-7 | ($Ar^L$-2) | —C(CH$_3$)$_2$— | —C(CH$_3$)$_2$— | 1A-2-7 | ($Ar^L$-2) | —C(CH$_3$)$_2$— | —C(CH$_3$)$_2$— |
| 1A-1-8 | ($Ar^L$-2) | —C(CH$_3$)$_2$— | —C(CH$_3$)$_2$— | 1A-2-8 | ($Ar^L$-2) | —C(CH$_3$)$_2$— | —C(CH$_3$)$_2$— |
| 1A-1-9 | ($Ar^L$-2) | —C(CH$_3$)$_2$— | —C(CH$_3$)$_2$— | 1A-2-9 | ($Ar^L$-2) | —C(CH$_3$)$_2$— | —C(CH$_3$)$_2$— |
| 1B-1-6 | ($Ar^L$-2) | —C(CH$_3$)$_2$— | —C(CH$_3$)$_2$— | 1B-2-6 | ($Ar^L$-2) | —C(CH$_3$)$_2$— | —C(CH$_3$)$_2$— |
| 1B-1-7 | ($Ar^L$-2) | —C(CH$_3$)$_2$— | —C(CH$_3$)$_2$— | 1B-2-7 | ($Ar^L$-2) | —C(CH$_3$)$_2$— | —C(CH$_3$)$_2$— |
| 1B-1-8 | ($Ar^L$-2) | —C(CH$_3$)$_2$— | —C(CH$_3$)$_2$— | 1B-2-8 | ($Ar^L$-2) | —C(CH$_3$)$_2$— | —C(CH$_3$)$_2$— |
| 1B-1-9 | ($Ar^L$-2) | —C(CH$_3$)$_2$— | —C(CH$_3$)$_2$— | 1B-2-9 | ($Ar^L$-2) | —C(CH$_3$)$_2$— | —C(CH$_3$)$_2$— |
| 1C-1-6 | ($Ar^L$-2) | —C(CH$_3$)$_2$— | —C(CH$_3$)$_2$— | 1C-2-6 | ($Ar^L$-2) | —C(CH$_3$)$_2$— | —C(CH$_3$)$_2$— |
| 1C-1-7 | ($Ar^L$-2) | —C(CH$_3$)$_2$— | —C(CH$_3$)$_2$— | 1C-2-7 | ($Ar^L$-2) | —C(CH$_3$)$_2$— | —C(CH$_3$)$_2$— |
| 1C-1-8 | ($Ar^L$-2) | —C(CH$_3$)$_2$— | —C(CH$_3$)$_2$— | 1C-2-8 | ($Ar^L$-2) | —C(CH$_3$)$_2$— | —C(CH$_3$)$_2$— |
| 1C-1-9 | ($Ar^L$-2) | —C(CH$_3$)$_2$— | —C(CH$_3$)$_2$— | 1C-2-9 | ($Ar^L$-2) | —C(CH$_3$)$_2$— | —C(CH$_3$)$_2$— |
| 1A-1-6 | ($Ar^L$-3) | —C(CH$_3$)$_2$— | —C(CH$_3$)$_2$— | 1A-2-6 | ($Ar^L$-3) | —C(CH$_3$)$_2$— | —C(CH$_3$)$_2$— |
| 1A-1-7 | ($Ar^L$-3) | —C(CH$_3$)$_2$— | —C(CH$_3$)$_2$— | 1A-2-7 | ($Ar^L$-3) | —C(CH$_3$)$_2$— | —C(CH$_3$)$_2$— |
| 1A-1-8 | ($Ar^L$-3) | —C(CH$_3$)$_2$— | —C(CH$_3$)$_2$— | 1A-2-8 | ($Ar^L$-3) | —C(CH$_3$)$_2$— | —C(CH$_3$)$_2$— |
| 1A-1-9 | ($Ar^L$-3) | —C(CH$_3$)$_2$— | —C(CH$_3$)$_2$— | 1A-2-9 | ($Ar^L$-3) | —C(CH$_3$)$_2$— | —C(CH$_3$)$_2$— |
| 1B-1-6 | ($Ar^L$-3) | —C(CH$_3$)$_2$— | —C(CH$_3$)$_2$— | 1B-2-6 | ($Ar^L$-3) | —C(CH$_3$)$_2$— | —C(CH$_3$)$_2$— |
| 1B-1-7 | ($Ar^L$-3) | —C(CH$_3$)$_2$— | —C(CH$_3$)$_2$— | 1B-2-7 | ($Ar^L$-3) | —C(CH$_3$)$_2$— | —C(CH$_3$)$_2$— |
| 1B-1-8 | ($Ar^L$-3) | —C(CH$_3$)$_2$— | —C(CH$_3$)$_2$— | 1B-2-8 | ($Ar^L$-3) | —C(CH$_3$)$_2$— | —C(CH$_3$)$_2$— |
| 1B-1-9 | ($Ar^L$-3) | —C(CH$_3$)$_2$— | —C(CH$_3$)$_2$— | 1B-2-9 | ($Ar^L$-3) | —C(CH$_3$)$_2$— | —C(CH$_3$)$_2$— |
| 1C-1-6 | ($Ar^L$-3) | —C(CH$_3$)$_2$— | —C(CH$_3$)$_2$— | 1C-2-6 | ($Ar^L$-3) | —C(CH$_3$)$_2$— | —C(CH$_3$)$_2$— |
| 1C-1-7 | ($Ar^L$-3) | —C(CH$_3$)$_2$— | —C(CH$_3$)$_2$— | 1C-2-7 | ($Ar^L$-3) | —C(CH$_3$)$_2$— | —C(CH$_3$)$_2$— |
| 1C-1-8 | ($Ar^L$-3) | —C(CH$_3$)$_2$— | —C(CH$_3$)$_2$— | 1C-2-8 | ($Ar^L$-3) | —C(CH$_3$)$_2$— | —C(CH$_3$)$_2$— |
| 1C-1-9 | ($Ar^L$-3) | —C(CH$_3$)$_2$— | —C(CH$_3$)$_2$— | 1C-2-9 | ($Ar^L$-3) | —C(CH$_3$)$_2$— | —C(CH$_3$)$_2$— |
| 1A-1-6 | absent | —C(Ph)$_2$— | —C(CH$_3$)$_2$— | 1A-2-6 | absent | —C(Ph)$_2$— | —C(CH$_3$)$_2$— |

-continued

| formula | $Ar^L$ | $E^1$ | $E^2$ | formula | $Ar^L$ | $E^1$ | $E^2$ |
|---|---|---|---|---|---|---|---|
| 1A-1-7 | absent | —C(Ph)$_2$— | —C(CH$_3$)$_2$— | 1A-2-7 | absent | —C(Ph)$_2$— | —C(CH$_3$)$_2$— |
| 1A-1-8 | absent | —C(Ph)$_2$— | —C(CH$_3$)$_2$— | 1A-2-8 | absent | —C(Ph)$_2$— | —C(CH$_3$)$_2$— |
| 1A-1-9 | absent | —C(Ph)$_2$— | —C(CH$_3$)$_2$— | 1A-2-9 | absent | —C(Ph)$_2$— | —C(CH$_3$)$_2$— |
| 1B-1-6 | absent | —C(Ph)$_2$— | —C(CH$_3$)$_2$— | 1B-2-6 | absent | —C(Ph)$_2$— | —C(CH$_3$)$_2$— |
| 1B-1-7 | absent | —C(Ph)$_2$— | —C(CH$_3$)$_2$— | 1B-2-7 | absent | —C(Ph)$_2$— | —C(CH$_3$)$_2$— |
| 1B-1-8 | absent | —C(Ph)$_2$— | —C(CH$_3$)$_2$— | 1B-2-8 | absent | —C(Ph)$_2$— | —C(CH$_3$)$_2$— |
| 1B-1-9 | absent | —C(Ph)$_2$— | —C(CH$_3$)$_2$— | 1B-2-9 | absent | —C(Ph)$_2$— | —C(CH$_3$)$_2$— |
| 1C-1-6 | absent | —C(Ph)$_2$— | —C(CH$_3$)$_2$— | 1C-2-6 | absent | —C(Ph)$_2$— | —C(CH$_3$)$_2$— |
| 1C-1-7 | absent | —C(Ph)$_2$— | —C(CH$_3$)$_2$— | 1C-2-7 | absent | —C(Ph)$_2$— | —C(CH$_3$)$_2$— |
| 1C-1-8 | absent | —C(Ph)$_2$— | —C(CH$_3$)$_2$— | 1C-2-8 | absent | —C(Ph)$_2$— | —C(CH$_3$)$_2$— |
| 1C-1-9 | absent | —C(Ph)$_2$— | —C(CH$_3$)$_2$— | 1C-2-9 | absent | —C(Ph)$_2$— | —C(CH$_3$)$_2$— |
| 1A-1-6 | ($Ar^L$-1) | —C(Ph)$_2$— | —C(CH$_3$)$_2$— | 1A-2-6 | ($Ar^L$-1) | —C(Ph)$_2$— | —C(CH$_3$)$_2$— |
| 1A-1-7 | ($Ar^L$-1) | —C(Ph)$_2$— | —C(CH$_3$)$_2$— | 1A-2-7 | ($Ar^L$-1) | —C(Ph)$_2$— | —C(CH$_3$)$_2$— |
| 1A-1-8 | ($Ar^L$-1) | —C(Ph)$_2$— | —C(CH$_3$)$_2$— | 1A-2-8 | ($Ar^L$-1) | —C(Ph)$_2$— | —C(CH$_3$)$_2$— |
| 1A-1-9 | ($Ar^L$-1) | —C(Ph)$_2$— | —C(CH$_3$)$_2$— | 1A-2-9 | ($Ar^L$-1) | —C(Ph)$_2$— | —C(CH$_3$)$_2$— |
| 1B-1-6 | ($Ar^L$-1) | —C(Ph)$_2$— | —C(CH$_3$)$_2$— | 1B-2-6 | ($Ar^L$-1) | —C(Ph)$_2$— | —C(CH$_3$)$_2$— |
| 1B-1-7 | ($Ar^L$-1) | —C(Ph)$_2$— | —C(CH$_3$)$_2$— | 1B-2-7 | ($Ar^L$-1) | —C(Ph)$_2$— | —C(CH$_3$)$_2$— |
| 1B-1-8 | ($Ar^L$-1) | —C(Ph)$_2$— | —C(CH$_3$)$_2$— | 1B-2-8 | ($Ar^L$-1) | —C(Ph)$_2$— | —C(CH$_3$)$_2$— |
| 1B-1-9 | ($Ar^L$-1) | —C(Ph)$_2$— | —C(CH$_3$)$_2$— | 1B-2-9 | ($Ar^L$-1) | —C(Ph)$_2$— | —C(CH$_3$)$_2$— |
| 1C-1-6 | ($Ar^L$-1) | —C(Ph)$_2$— | —C(CH$_3$)$_2$— | 1C-2-6 | ($Ar^L$-1) | —C(Ph)$_2$— | —C(CH$_3$)$_2$— |
| 1C-1-7 | ($Ar^L$-1) | —C(Ph)$_2$— | —C(CH$_3$)$_2$— | 1C-2-7 | ($Ar^L$-1) | —C(Ph)$_2$— | —C(CH$_3$)$_2$— |
| 1C-1-8 | ($Ar^L$-1) | —C(Ph)$_2$— | —C(CH$_3$)$_2$— | 1C-2-8 | ($Ar^L$-1) | —C(Ph)$_2$— | —C(CH$_3$)$_2$— |
| 1C-1-9 | ($Ar^L$-1) | —C(Ph)$_2$— | —C(CH$_3$)$_2$— | 1C-2-9 | ($Ar^L$-1) | —C(Ph)$_2$— | —C(CH$_3$)$_2$— |
| 1A-1-6 | ($Ar^L$-2) | —C(Ph)$_2$— | —C(CH$_3$)$_2$— | 1A-2-6 | ($Ar^L$-2) | —C(Ph)$_2$— | —C(CH$_3$)$_2$— |
| 1A-1-7 | ($Ar^L$-2) | —C(Ph)$_2$— | —C(CH$_3$)$_2$— | 1A-2-7 | ($Ar^L$-2) | —C(Ph)$_2$— | —C(CH$_3$)$_2$— |
| 1A-1-8 | ($Ar^L$-2) | —C(Ph)$_2$— | —C(CH$_3$)$_2$— | 1A-2-8 | ($Ar^L$-2) | —C(Ph)$_2$— | —C(CH$_3$)$_2$— |
| 1A-1-9 | ($Ar^L$-2) | —C(Ph)$_2$— | —C(CH$_3$)$_2$— | 1A-2-9 | ($Ar^L$-2) | —C(Ph)$_2$— | —C(CH$_3$)$_2$— |
| 1B-1-6 | ($Ar^L$-2) | —C(Ph)$_2$— | —C(CH$_3$)$_2$— | 1B-2-6 | ($Ar^L$-2) | —C(Ph)$_2$— | —C(CH$_3$)$_2$— |
| 1B-1-7 | ($Ar^L$-2) | —C(Ph)$_2$— | —C(CH$_3$)$_2$— | 1B-2-7 | ($Ar^L$-2) | —C(Ph)$_2$— | —C(CH$_3$)$_2$— |
| 1B-1-8 | ($Ar^L$-2) | —C(Ph)$_2$— | —C(CH$_3$)$_2$— | 1B-2-8 | ($Ar^L$-2) | —C(Ph)$_2$— | —C(CH$_3$)$_2$— |
| 1B-1-9 | ($Ar^L$-2) | —C(Ph)$_2$— | —C(CH$_3$)$_2$— | 1B-2-9 | ($Ar^L$-2) | —C(Ph)$_2$— | —C(CH$_3$)$_2$— |
| 1C-1-6 | ($Ar^L$-2) | —C(Ph)$_2$— | —C(CH$_3$)$_2$— | 1C-2-6 | ($Ar^L$-2) | —C(Ph)$_2$— | —C(CH$_3$)$_2$— |
| 1C-1-7 | ($Ar^L$-2) | —C(Ph)$_2$— | —C(CH$_3$)$_2$— | 1C-2-7 | ($Ar^L$-2) | —C(Ph)$_2$— | —C(CH$_3$)$_2$— |
| 1C-1-8 | ($Ar^L$-2) | —C(Ph)$_2$— | —C(CH$_3$)$_2$— | 1C-2-8 | ($Ar^L$-2) | —C(Ph)$_2$— | —C(CH$_3$)$_2$— |
| 1C-1-9 | ($Ar^L$-2) | —C(Ph)$_2$— | —C(CH$_3$)$_2$— | 1C-2-9 | ($Ar^L$-2) | —C(Ph)$_2$— | —C(CH$_3$)$_2$— |
| 1A-1-6 | ($Ar^L$-3) | —C(Ph)$_2$— | —C(CH$_3$)$_2$— | 1A-2-6 | ($Ar^L$-3) | —C(Ph)$_2$— | —C(CH$_3$)$_2$— |
| 1A-1-7 | ($Ar^L$-3) | —C(Ph)$_2$— | —C(CH$_3$)$_2$— | 1A-2-7 | ($Ar^L$-3) | —C(Ph)$_2$— | —C(CH$_3$)$_2$— |
| 1A-1-8 | ($Ar^L$-3) | —C(Ph)$_2$— | —C(CH$_3$)$_2$— | 1A-2-8 | ($Ar^L$-3) | —C(Ph)$_2$— | —C(CH$_3$)$_2$— |
| 1A-1-9 | ($Ar^L$-3) | —C(Ph)$_2$— | —C(CH$_3$)$_2$— | 1A-2-9 | ($Ar^L$-3) | —C(Ph)$_2$— | —C(CH$_3$)$_2$— |
| 1B-1-6 | ($Ar^L$-3) | —C(Ph)$_2$— | —C(CH$_3$)$_2$— | 1B-2-6 | ($Ar^L$-3) | —C(Ph)$_2$— | —C(CH$_3$)$_2$— |
| 1B-1-7 | ($Ar^L$-3) | —C(Ph)$_2$— | —C(CH$_3$)$_2$— | 1B-2-7 | ($Ar^L$-3) | —C(Ph)$_2$— | —C(CH$_3$)$_2$— |
| 1B-1-8 | ($Ar^L$-3) | —C(Ph)$_2$— | —C(CH$_3$)$_2$— | 1B-2-8 | ($Ar^L$-3) | —C(Ph)$_2$— | —C(CH$_3$)$_2$— |
| 1B-1-9 | ($Ar^L$-3) | —C(Ph)$_2$— | —C(CH$_3$)$_2$— | 1B-2-9 | ($Ar^L$-3) | —C(Ph)$_2$— | —C(CH$_3$)$_2$— |
| 1C-1-6 | ($Ar^L$-3) | —C(Ph)$_2$— | —C(CH$_3$)$_2$— | 1C-2-6 | ($Ar^L$-3) | —C(Ph)$_2$— | —C(CH$_3$)$_2$— |
| 1C-1-7 | ($Ar^L$-3) | —C(Ph)$_2$— | —C(CH$_3$)$_2$— | 1C-2-7 | ($Ar^L$-3) | —C(Ph)$_2$— | —C(CH$_3$)$_2$— |
| 1C-1-8 | ($Ar^L$-3) | —C(Ph)$_2$— | —C(CH$_3$)$_2$— | 1C-2-8 | ($Ar^L$-3) | —C(Ph)$_2$— | —C(CH$_3$)$_2$— |
| 1C-1-9 | ($Ar^L$-3) | —C(Ph)$_2$— | —C(CH$_3$)$_2$— | 1C-2-9 | ($Ar^L$-3) | —C(Ph)$_2$— | —C(CH$_3$)$_2$— |
| 1A-1-6 | absent | —C(CH$_3$)$_2$— | —C(Ph)$_2$— | 1A-2-6 | absent | —C(CH$_3$)$_2$— | —C(Ph)$_2$— |
| 1A-1-7 | absent | —C(CH$_3$)$_2$— | —C(Ph)$_2$— | 1A-2-7 | absent | —C(CH$_3$)$_2$— | —C(Ph)$_2$— |
| 1A-1-8 | absent | —C(CH$_3$)$_2$— | —C(Ph)$_2$— | 1A-2-8 | absent | —C(CH$_3$)$_2$— | —C(Ph)$_2$— |
| 1A-1-9 | absent | —C(CH$_3$)$_2$— | —C(Ph)$_2$— | 1A-2-9 | absent | —C(CH$_3$)$_2$— | —C(Ph)$_2$— |
| 1B-1-6 | absent | —C(CH$_3$)$_2$— | —C(Ph)$_2$— | 1B-2-6 | absent | —C(CH$_3$)$_2$— | —C(Ph)$_2$— |
| 1B-1-7 | absent | —C(CH$_3$)$_2$— | —C(Ph)$_2$— | 1B-2-7 | absent | —C(CH$_3$)$_2$— | —C(Ph)$_2$— |
| 1B-1-8 | absent | —C(CH$_3$)$_2$— | —C(Ph)$_2$— | 1B-2-8 | absent | —C(CH$_3$)$_2$— | —C(Ph)$_2$— |
| 1B-1-9 | absent | —C(CH$_3$)$_2$— | —C(Ph)$_2$— | 1B-2-9 | absent | —C(CH$_3$)$_2$— | —C(Ph)$_2$— |
| 1C-1-6 | absent | —C(CH$_3$)$_2$— | —C(Ph)$_2$— | 1C-2-6 | absent | —C(CH$_3$)$_2$— | —C(Ph)$_2$— |
| 1C-1-7 | absent | —C(CH$_3$)$_2$— | —C(Ph)$_2$— | 1C-2-7 | absent | —C(CH$_3$)$_2$— | —C(Ph)$_2$— |
| 1C-1-8 | absent | —C(CH$_3$)$_2$— | —C(Ph)$_2$— | 1C-2-8 | absent | —C(CH$_3$)$_2$— | —C(Ph)$_2$— |
| 1C-1-9 | absent | —C(CH$_3$)$_2$— | —C(Ph)$_2$— | 1C-2-9 | absent | —C(CH$_3$)$_2$— | —C(Ph)$_2$— |
| 1A-1-6 | ($Ar^L$-1) | —C(CH$_3$)$_2$— | —C(Ph)$_2$— | 1A-2-6 | ($Ar^L$-1) | —C(CH$_3$)$_2$— | —C(Ph)$_2$— |
| 1A-1-7 | ($Ar^L$-1) | —C(CH$_3$)$_2$— | —C(Ph)$_2$— | 1A-2-7 | ($Ar^L$-1) | —C(CH$_3$)$_2$— | —C(Ph)$_2$— |
| 1A-1-8 | ($Ar^L$-1) | —C(CH$_3$)$_2$— | —C(Ph)$_2$— | 1A-2-8 | ($Ar^L$-1) | —C(CH$_3$)$_2$— | —C(Ph)$_2$— |
| 1A-1-9 | ($Ar^L$-1) | —C(CH$_3$)$_2$— | —C(Ph)$_2$— | 1A-2-9 | ($Ar^L$-1) | —C(CH$_3$)$_2$— | —C(Ph)$_2$— |
| 1B-1-6 | ($Ar^L$-1) | —C(CH$_3$)$_2$— | —C(Ph)$_2$— | 1B-2-6 | ($Ar^L$-1) | —C(CH$_3$)$_2$— | —C(Ph)$_2$— |
| 1B-1-7 | ($Ar^L$-1) | —C(CH$_3$)$_2$— | —C(Ph)$_2$— | 1B-2-7 | ($Ar^L$-1) | —C(CH$_3$)$_2$— | —C(Ph)$_2$— |
| 1B-1-8 | ($Ar^L$-1) | —C(CH$_3$)$_2$— | —C(Ph)$_2$— | 1B-2-8 | ($Ar^L$-1) | —C(CH$_3$)$_2$— | —C(Ph)$_2$— |
| 1B-1-9 | ($Ar^L$-1) | —C(CH$_3$)$_2$— | —C(Ph)$_2$— | 1B-2-9 | ($Ar^L$-1) | —C(CH$_3$)$_2$— | —C(Ph)$_2$— |
| 1C-1-6 | ($Ar^L$-1) | —C(CH$_3$)$_2$— | —C(Ph)$_2$— | 1C-2-6 | ($Ar^L$-1) | —C(CH$_3$)$_2$— | —C(Ph)$_2$— |
| 1C-1-7 | ($Ar^L$-1) | —C(CH$_3$)$_2$— | —C(Ph)$_2$— | 1C-2-7 | ($Ar^L$-1) | —C(CH$_3$)$_2$— | —C(Ph)$_2$— |
| 1C-1-8 | ($Ar^L$-1) | —C(CH$_3$)$_2$— | —C(Ph)$_2$— | 1C-2-8 | ($Ar^L$-1) | —C(CH$_3$)$_2$— | —C(Ph)$_2$— |
| 1C-1-9 | ($Ar^L$-1) | —C(CH$_3$)$_2$— | —C(Ph)$_2$— | 1C-2-9 | ($Ar^L$-1) | —C(CH$_3$)$_2$— | —C(Ph)$_2$— |
| 1A-1-6 | ($Ar^L$-2) | —C(CH$_3$)$_2$— | —C(Ph)$_2$— | 1A-2-6 | ($Ar^L$-2) | —C(CH$_3$)$_2$— | —C(Ph)$_2$— |
| 1A-1-7 | ($Ar^L$-2) | —C(CH$_3$)$_2$— | —C(Ph)$_2$— | 1A-2-7 | ($Ar^L$-2) | —C(CH$_3$)$_2$— | —C(Ph)$_2$— |
| 1A-1-8 | ($Ar^L$-2) | —C(CH$_3$)$_2$— | —C(Ph)$_2$— | 1A-2-8 | ($Ar^L$-2) | —C(CH$_3$)$_2$— | —C(Ph)$_2$— |
| 1A-1-9 | ($Ar^L$-2) | —C(CH$_3$)$_2$— | —C(Ph)$_2$— | 1A-2-9 | ($Ar^L$-2) | —C(CH$_3$)$_2$— | —C(Ph)$_2$— |
| 1B-1-6 | ($Ar^L$-2) | —C(CH$_3$)$_2$— | —C(Ph)$_2$— | 1B-2-6 | ($Ar^L$-2) | —C(CH$_3$)$_2$— | —C(Ph)$_2$— |
| 1B-1-7 | ($Ar^L$-2) | —C(CH$_3$)$_2$— | —C(Ph)$_2$— | 1B-2-7 | ($Ar^L$-2) | —C(CH$_3$)$_2$— | —C(Ph)$_2$— |

-continued

| formula | $Ar^L$ | $E^1$ | $E^2$ | formula | $Ar^L$ | $E^1$ | $E^2$ |
|---|---|---|---|---|---|---|---|
| 1B-1-8 | ($Ar^L$-2) | —$C(CH_3)_2$— | —$C(Ph)_2$— | 1B-2-8 | ($Ar^L$-2) | —$C(CH_3)_2$— | —$C(Ph)_2$— |
| 1B-1-9 | ($Ar^L$-2) | —$C(CH_3)_2$— | —$C(Ph)_2$— | 1B-2-9 | ($Ar^L$-2) | —$C(CH_3)_2$— | —$C(Ph)_2$— |
| 1C-1-6 | ($Ar^L$-2) | —$C(CH_3)_2$— | —$C(Ph)_2$— | 1C-2-6 | ($Ar^L$-2) | —$C(CH_3)_2$— | —$C(Ph)_2$— |
| 1C-1-7 | ($Ar^L$-2) | —$C(CH_3)_2$— | —$C(Ph)_2$— | 1C-2-7 | ($Ar^L$-2) | —$C(CH_3)_2$— | —$C(Ph)_2$— |
| 1C-1-8 | ($Ar^L$-2) | —$C(CH_3)_2$— | —$C(Ph)_2$— | 1C-2-8 | ($Ar^L$-2) | —$C(CH_3)_2$— | —$C(Ph)_2$— |
| 1C-1-9 | ($Ar^L$-2) | —$C(CH_3)_2$— | —$C(Ph)_2$— | 1C-2-9 | ($Ar^L$-2) | —$C(CH_3)_2$— | —$C(Ph)_2$— |
| 1A-1-6 | ($Ar^L$-3) | —$C(CH_3)_2$— | —$C(Ph)_2$— | 1A-2-6 | ($Ar^L$-3) | —$C(CH_3)_2$— | —$C(Ph)_2$— |
| 1A-1-7 | ($Ar^L$-3) | —$C(CH_3)_2$— | —$C(Ph)_2$— | 1A-2-7 | ($Ar^L$-3) | —$C(CH_3)_2$— | —$C(Ph)_2$— |
| 1A-1-8 | ($Ar^L$-3) | —$C(CH_3)_2$— | —$C(Ph)_2$— | 1A-2-8 | ($Ar^L$-3) | —$C(CH_3)_2$— | —$C(Ph)_2$— |
| 1A-1-9 | ($Ar^L$-3) | —$C(CH_3)_2$— | —$C(Ph)_2$— | 1A-2-9 | ($Ar^L$-3) | —$C(CH_3)_2$— | —$C(Ph)_2$— |
| 1B-1-6 | ($Ar^L$-3) | —$C(CH_3)_2$— | —$C(Ph)_2$— | 1B-2-6 | ($Ar^L$-3) | —$C(CH_3)_2$— | —$C(Ph)_2$— |
| 1B-1-7 | ($Ar^L$-3) | —$C(CH_3)_2$— | —$C(Ph)_2$— | 1B-2-7 | ($Ar^L$-3) | —$C(CH_3)_2$— | —$C(Ph)_2$— |
| 1B-1-8 | ($Ar^L$-3) | —$C(CH_3)_2$— | —$C(Ph)_2$— | 1B-2-8 | ($Ar^L$-3) | —$C(CH_3)_2$— | —$C(Ph)_2$— |
| 1B-1-9 | ($Ar^L$-3) | —$C(CH_3)_2$— | —$C(Ph)_2$— | 1B-2-9 | ($Ar^L$-3) | —$C(CH_3)_2$— | —$C(Ph)_2$— |
| 1C-1-6 | ($Ar^L$-3) | —$C(CH_3)_2$— | —$C(Ph)_2$— | 1C-2-6 | ($Ar^L$-3) | —$C(CH_3)_2$— | —$C(Ph)_2$— |
| 1C-1-7 | ($Ar^L$-3) | —$C(CH_3)_2$— | —$C(Ph)_2$— | 1C-2-7 | ($Ar^L$-3) | —$C(CH_3)_2$— | —$C(Ph)_2$— |
| 1C-1-8 | ($Ar^L$-3) | —$C(CH_3)_2$— | —$C(Ph)_2$— | 1C-2-8 | ($Ar^L$-3) | —$C(CH_3)_2$— | —$C(Ph)_2$— |
| 1C-1-9 | ($Ar^L$-3) | —$C(CH_3)_2$— | —$C(Ph)_2$— | 1C-2-9 | ($Ar^L$-3) | —$C(CH_3)_2$— | —$C(Ph)_2$— |
| 1A-1-6 | absent | —$C(Ph)_2$— | —$C(Ph)_2$— | 1A-2-6 | absent | —$C(Ph)_2$— | —$C(Ph)_2$— |
| 1A-1-7 | absent | —$C(Ph)_2$— | —$C(Ph)_2$— | 1A-2-7 | absent | —$C(Ph)_2$— | —$C(Ph)_2$— |
| 1A-1-8 | absent | —$C(Ph)_2$— | —$C(Ph)_2$— | 1A-2-8 | absent | —$C(Ph)_2$— | —$C(Ph)_2$— |
| 1A-1-9 | absent | —$C(Ph)_2$— | —$C(Ph)_2$— | 1A-2-9 | absent | —$C(Ph)_2$— | —$C(Ph)_2$— |
| 1B-1-6 | absent | —$C(Ph)_2$— | —$C(Ph)_2$— | 1B-2-6 | absent | —$C(Ph)_2$— | —$C(Ph)_2$— |
| 1B-1-7 | absent | —$C(Ph)_2$— | —$C(Ph)_2$— | 1B-2-7 | absent | —$C(Ph)_2$— | —$C(Ph)_2$— |
| 1B-1-8 | absent | —$C(Ph)_2$— | —$C(Ph)_2$— | 1B-2-8 | absent | —$C(Ph)_2$— | —$C(Ph)_2$— |
| 1B-1-9 | absent | —$C(Ph)_2$— | —$C(Ph)_2$— | 1B-2-9 | absent | —$C(Ph)_2$— | —$C(Ph)_2$— |
| 1C-1-6 | absent | —$C(Ph)_2$— | —$C(Ph)_2$— | 1C-2-6 | absent | —$C(Ph)_2$— | —$C(Ph)_2$— |
| 1C-1-7 | absent | —$C(Ph)_2$— | —$C(Ph)_2$— | 1C-2-7 | absent | —$C(Ph)_2$— | —$C(Ph)_2$— |
| 1C-1-8 | absent | —$C(Ph)_2$— | —$C(Ph)_2$— | 1C-2-8 | absent | —$C(Ph)_2$— | —$C(Ph)_2$— |
| 1C-1-9 | absent | —$C(Ph)_2$— | —$C(Ph)_2$— | 1C-2-9 | absent | —$C(Ph)_2$— | —$C(Ph)_2$— |
| 1A-1-6 | ($Ar^L$-1) | —$C(Ph)_2$— | —$C(Ph)_2$— | 1A-2-6 | ($Ar^L$-1) | —$C(Ph)_2$— | —$C(Ph)_2$— |
| 1A-1-7 | ($Ar^L$-1) | —$C(Ph)_2$— | —$C(Ph)_2$— | 1A-2-7 | ($Ar^L$-1) | —$C(Ph)_2$— | —$C(Ph)_2$— |
| 1A-1-8 | ($Ar^L$-1) | —$C(Ph)_2$— | —$C(Ph)_2$— | 1A-2-8 | ($Ar^L$-1) | —$C(Ph)_2$— | —$C(Ph)_2$— |
| 1A-1-9 | ($Ar^L$-1) | —$C(Ph)_2$— | —$C(Ph)_2$— | 1A-2-9 | ($Ar^L$-1) | —$C(Ph)_2$— | —$C(Ph)_2$— |
| 1B-1-6 | ($Ar^L$-1) | —$C(Ph)_2$— | —$C(Ph)_2$— | 1B-2-6 | ($Ar^L$-1) | —$C(Ph)_2$— | —$C(Ph)_2$— |
| 1B-1-7 | ($Ar^L$-1) | —$C(Ph)_2$— | —$C(Ph)_2$— | 1B-2-7 | ($Ar^L$-1) | —$C(Ph)_2$— | —$C(Ph)_2$— |
| 1B-1-8 | ($Ar^L$-1) | —$C(Ph)_2$— | —$C(Ph)_2$— | 1B-2-8 | ($Ar^L$-1) | —$C(Ph)_2$— | —$C(Ph)_2$— |
| 1B-1-9 | ($Ar^L$-1) | —$C(Ph)_2$— | —$C(Ph)_2$— | 1B-2-9 | ($Ar^L$-1) | —$C(Ph)_2$— | —$C(Ph)_2$— |
| 1C-1-6 | ($Ar^L$-1) | —$C(Ph)_2$— | —$C(Ph)_2$— | 1C-2-6 | ($Ar^L$-1) | —$C(Ph)_2$— | —$C(Ph)_2$— |
| 1C-1-7 | ($Ar^L$-1) | —$C(Ph)_2$— | —$C(Ph)_2$— | 1C-2-7 | ($Ar^L$-1) | —$C(Ph)_2$— | —$C(Ph)_2$— |
| 1C-1-8 | ($Ar^L$-1) | —$C(Ph)_2$— | —$C(Ph)_2$— | 1C-2-8 | ($Ar^L$-1) | —$C(Ph)_2$— | —$C(Ph)_2$— |
| 1C-1-9 | ($Ar^L$-1) | —$C(Ph)_2$— | —$C(Ph)_2$— | 1C-2-9 | ($Ar^L$-1) | —$C(Ph)_2$— | —$C(Ph)_2$— |
| 1A-1-6 | ($Ar^L$-2) | —$C(Ph)_2$— | —$C(Ph)_2$— | 1A-2-6 | ($Ar^L$-2) | —$C(Ph)_2$— | —$C(Ph)_2$— |
| 1A-1-7 | ($Ar^L$-2) | —$C(Ph)_2$— | —$C(Ph)_2$— | 1A-2-7 | ($Ar^L$-2) | —$C(Ph)_2$— | —$C(Ph)_2$— |
| 1A-1-8 | ($Ar^L$-2) | —$C(Ph)_2$— | —$C(Ph)_2$— | 1A-2-8 | ($Ar^L$-2) | —$C(Ph)_2$— | —$C(Ph)_2$— |
| 1A-1-9 | ($Ar^L$-2) | —$C(Ph)_2$— | —$C(Ph)_2$— | 1A-2-9 | ($Ar^L$-2) | —$C(Ph)_2$— | —$C(Ph)_2$— |
| 1B-1-6 | ($Ar^L$-2) | —$C(Ph)_2$— | —$C(Ph)_2$— | 1B-2-6 | ($Ar^L$-2) | —$C(Ph)_2$— | —$C(Ph)_2$— |
| 1B-1-7 | ($Ar^L$-2) | —$C(Ph)_2$— | —$C(Ph)_2$— | 1B-2-7 | ($Ar^L$-2) | —$C(Ph)_2$— | —$C(Ph)_2$— |
| 1B-1-8 | ($Ar^L$-2) | —$C(Ph)_2$— | —$C(Ph)_2$— | 1B-2-8 | ($Ar^L$-2) | —$C(Ph)_2$— | —$C(Ph)_2$— |
| 1B-1-9 | ($Ar^L$-2) | —$C(Ph)_2$— | —$C(Ph)_2$— | 1B-2-9 | ($Ar^L$-2) | —$C(Ph)_2$— | —$C(Ph)_2$— |
| 1C-1-6 | ($Ar^L$-2) | —$C(Ph)_2$— | —$C(Ph)_2$— | 1C-2-6 | ($Ar^L$-2) | —$C(Ph)_2$— | —$C(Ph)_2$— |
| 1C-1-7 | ($Ar^L$-2) | —$C(Ph)_2$— | —$C(Ph)_2$— | 1C-2-7 | ($Ar^L$-2) | —$C(Ph)_2$— | —$C(Ph)_2$— |
| 1C-1-8 | ($Ar^L$-2) | —$C(Ph)_2$— | —$C(Ph)_2$— | 1C-2-8 | ($Ar^L$-2) | —$C(Ph)_2$— | —$C(Ph)_2$— |
| 1C-1-9 | ($Ar^L$-2) | —$C(Ph)_2$— | —$C(Ph)_2$— | 1C-2-9 | ($Ar^L$-2) | —$C(Ph)_2$— | —$C(Ph)_2$— |
| 1A-1-6 | ($Ar^L$-3) | —$C(Ph)_2$— | —$C(Ph)_2$— | 1A-2-6 | ($Ar^L$-3) | —$C(Ph)_2$— | —$C(Ph)_2$— |
| 1A-1-7 | ($Ar^L$-3) | —$C(Ph)_2$— | —$C(Ph)_2$— | 1A-2-7 | ($Ar^L$-3) | —$C(Ph)_2$— | —$C(Ph)_2$— |
| 1A-1-8 | ($Ar^L$-3) | —$C(Ph)_2$— | —$C(Ph)_2$— | 1A-2-8 | ($Ar^L$-3) | —$C(Ph)_2$— | —$C(Ph)_2$— |
| 1A-1-9 | ($Ar^L$-3) | —$C(Ph)_2$— | —$C(Ph)_2$— | 1A-2-9 | ($Ar^L$-3) | —$C(Ph)_2$— | —$C(Ph)_2$— |
| 1B-1-6 | ($Ar^L$-3) | —$C(Ph)_2$— | —$C(Ph)_2$— | 1B-2-6 | ($Ar^L$-3) | —$C(Ph)_2$— | —$C(Ph)_2$— |
| 1B-1-7 | ($Ar^L$-3) | —$C(Ph)_2$— | —$C(Ph)_2$— | 1B-2-7 | ($Ar^L$-3) | —$C(Ph)_2$— | —$C(Ph)_2$— |
| 1B-1-8 | ($Ar^L$-3) | —$C(Ph)_2$— | —$C(Ph)_2$— | 1B-2-8 | ($Ar^L$-3) | —$C(Ph)_2$— | —$C(Ph)_2$— |
| 1B-1-9 | ($Ar^L$-3) | —$C(Ph)_2$— | —$C(Ph)_2$— | 1B-2-9 | ($Ar^L$-3) | —$C(Ph)_2$— | —$C(Ph)_2$— |
| 1C-1-6 | ($Ar^L$-3) | —$C(Ph)_2$— | —$C(Ph)_2$— | 1C-2-6 | ($Ar^L$-3) | —$C(Ph)_2$— | —$C(Ph)_2$— |
| 1C-1-7 | ($Ar^L$-3) | —$C(Ph)_2$— | —$C(Ph)_2$— | 1C-2-7 | ($Ar^L$-3) | —$C(Ph)_2$— | —$C(Ph)_2$— |
| 1C-1-8 | ($Ar^L$-3) | —$C(Ph)_2$— | —$C(Ph)_2$— | 1C-2-8 | ($Ar^L$-3) | —$C(Ph)_2$— | —$C(Ph)_2$— |
| 1C-1-9 | ($Ar^L$-3) | —$C(Ph)_2$— | —$C(Ph)_2$— | 1C-2-9 | ($Ar^L$-3) | —$C(Ph)_2$— | —$C(Ph)_2$— |

Other examples of suitable compounds according to the invention are the compounds shown in the following table:
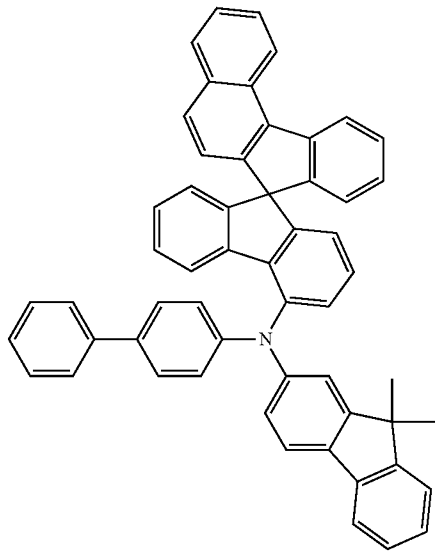 [SMILES: CC1(C)c2ccccc2-c2ccc(N(c3ccc(-c4ccccc4)cc3)c3cccc4c3-c3ccccc3C43c4ccccc4-c4c3ccc3ccccc43)cc21]
1
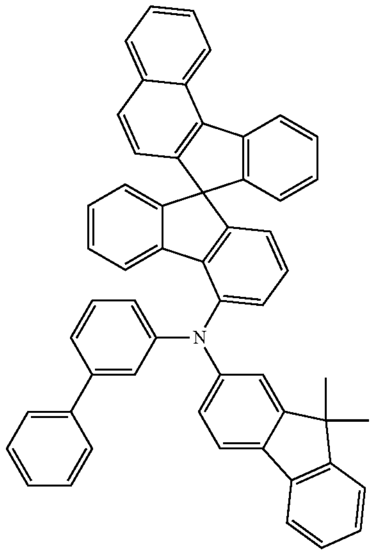 [SMILES: CC1(C)c2ccccc2-c2ccc(N(c3cccc(-c4ccccc4)c3)c3cccc4c3-c3ccccc3C43c4ccccc4-c4c3ccc3ccccc43)cc21]
2

-continued
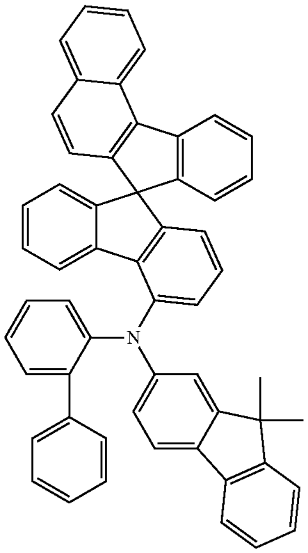 [SMILES: CC1(C)c2ccccc2-c2ccc(N(c3ccccc3-c3ccccc3)c3cccc4c3-c3ccccc3C43c4ccccc4-c4c3ccc3ccccc43)cc21]
3
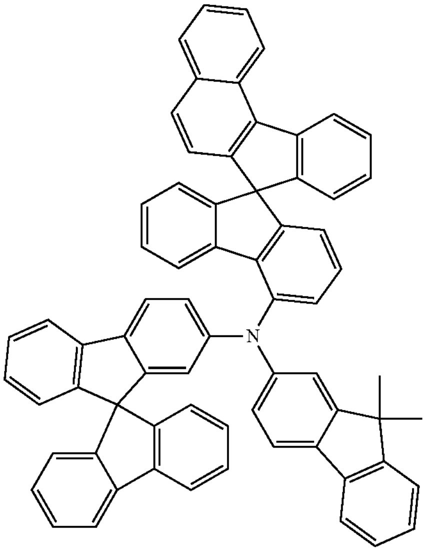 [SMILES: CC1(C)c2ccccc2-c2ccc(N(c3ccc4c(c3)C3(c5ccccc5-c5ccccc53)c3ccccc3-4)c3cccc4c3-c3ccccc3C43c4ccccc4-c4c3ccc3ccccc43)cc21]
4

-continued
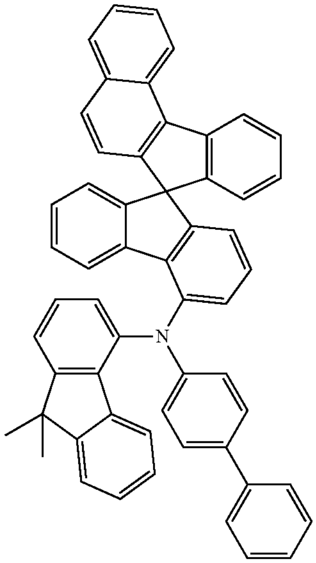 [SMILES: CC1(C)c2ccccc2-c2c(N(c3ccc(-c4ccccc4)cc3)c3cccc4c3-c3ccccc3C43c4ccccc4-c4c3ccc3ccccc43)cccc21]
5
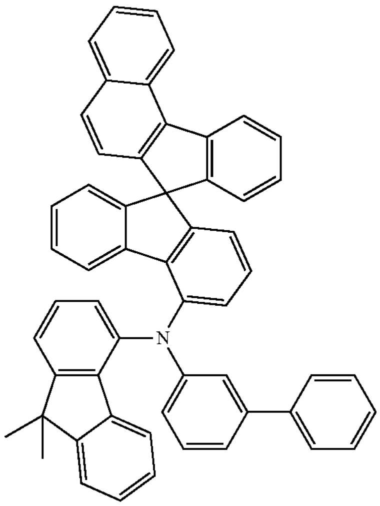 [SMILES: CC1(C)c2ccccc2-c2c(N(c3cccc(-c4ccccc4)c3)c3cccc4c3-c3ccccc3C43c4ccccc4-c4c3ccc3ccccc43)cccc21]
6
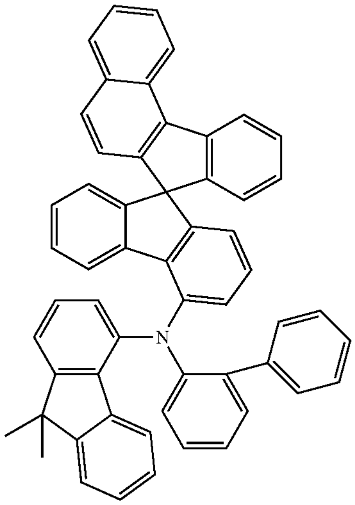 [SMILES: CC1(C)c2ccccc2-c2c(N(c3ccccc3-c3ccccc3)c3cccc4c3-c3ccccc3C43c4ccccc4-c4c3ccc3ccccc43)cccc21]
7

-continued
8
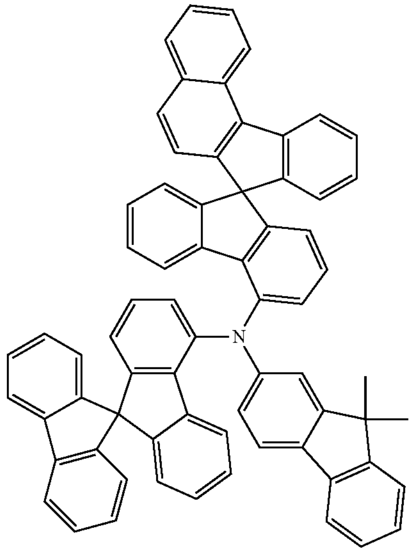 [SMILES: CC1(C)c2ccccc2-c2ccc(N(c3cccc4c3-c3ccccc3C43c4ccccc4-c4ccccc43)c3cccc4c3-c3ccccc3C43c4ccccc4-c4c3ccc3ccccc43)cc21]
9
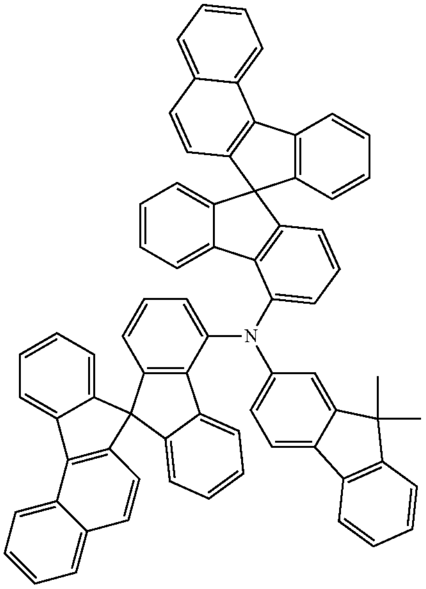 [SMILES: CC1(C)c2ccccc2-c2ccc(N(c3cccc4c3-c3ccccc3C43c4ccccc4-c4c3ccc3ccccc43)c3cccc4c3-c3ccccc3C43c4ccccc4-c4c3ccc3ccccc43)cc21]

-continued
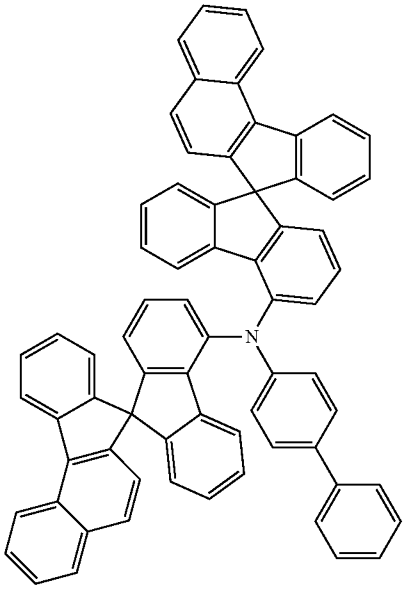 [SMILES: c1ccc(-c2ccc(N(c3cccc4c3-c3ccccc3C43c4ccccc4-c4c3ccc3ccccc43)c3cccc4c3-c3ccccc3C43c4ccccc4-c4c3ccc3ccccc43)cc2)cc1]
10
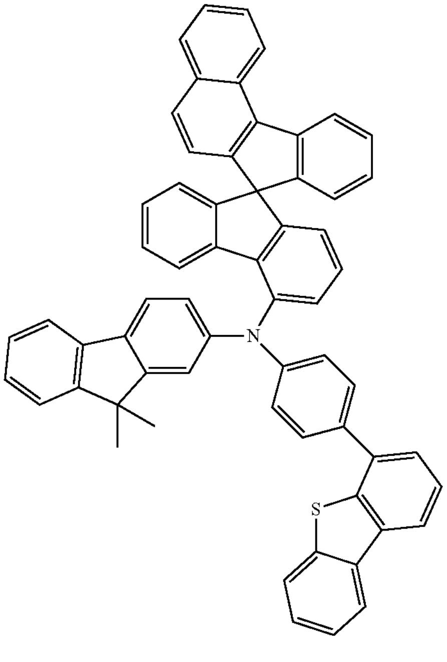
11

-continued
12
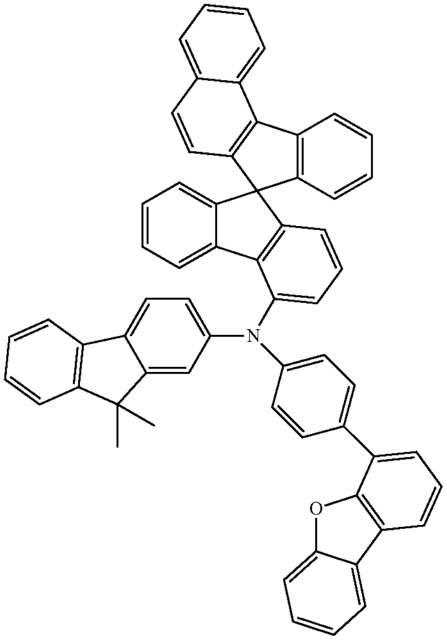 [SMILES: CC1(C)c2ccccc2-c2ccc(N(c3ccc(-c4cccc5c4oc4ccccc45)cc3)c3cccc4c3-c3ccccc3C43c4ccccc4-c4c3ccc3ccccc43)cc21]
13
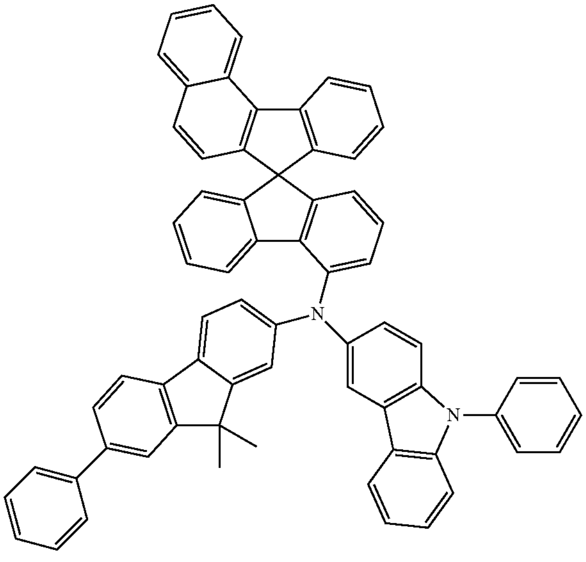 [SMILES: CC1(C)c2cc(-c3ccccc3)ccc2-c2ccc(N(c3ccc4c(c3)c3ccccc3n4-c3ccccc3)c3cccc4c3-c3ccccc3C43c4ccccc4-c4c3ccc3ccccc43)cc21]

-continued
14
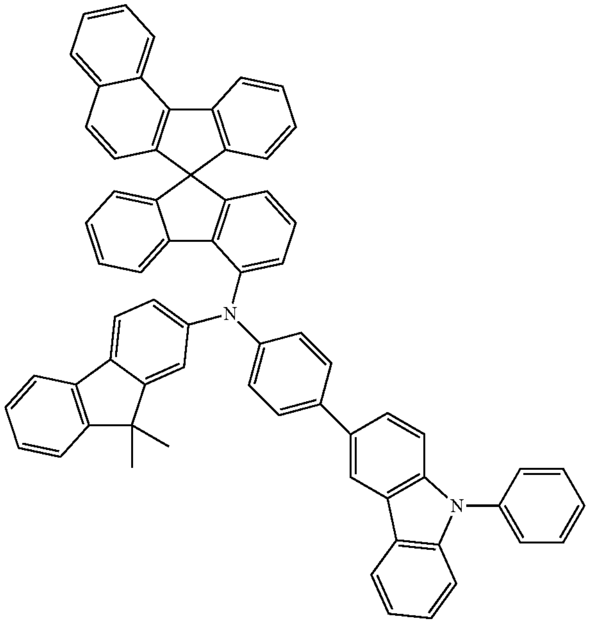 [SMILES: CC1(C)c2ccccc2-c2ccc(N(c3ccc(-c4ccc5c(c4)c4ccccc4n5-c4ccccc4)cc3)c3cccc4c3-c3ccccc3C43c4ccccc4-c4c3ccc3ccccc43)cc21]
15
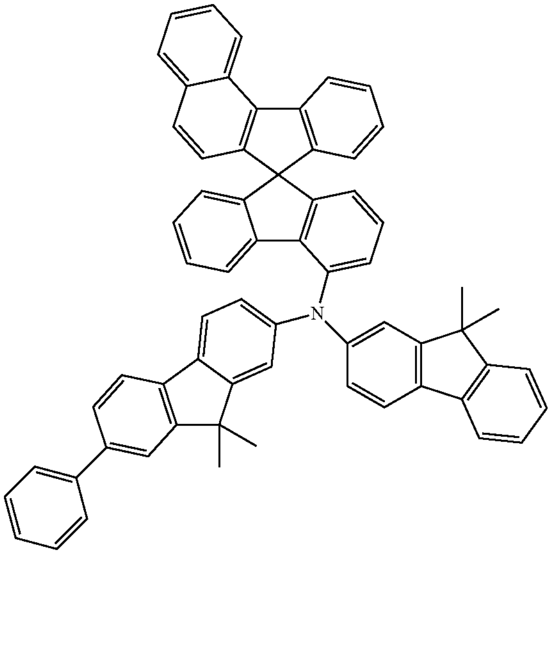 [SMILES: CC1(C)c2ccccc2-c2ccc(N(c3ccc4c(c3)C(C)(C)c3cc(-c5ccccc5)ccc3-4)c3cccc4c3-c3ccccc3C43c4ccccc4-c4c3ccc3ccccc43)cc21]

-continued
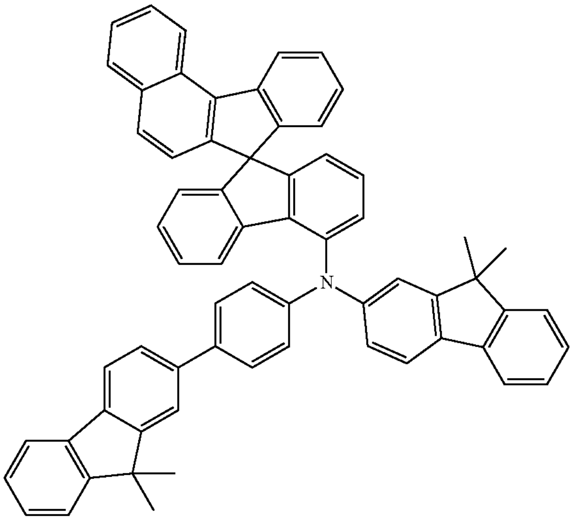 [SMILES: CC1(C)c2ccccc2-c2ccc(-c3ccc(N(c4ccc5c(c4)C(C)(C)c4ccccc4-5)c4cccc5c4-c4ccccc4C54c5ccccc5-c5c4ccc4ccccc54)cc3)cc21]
16
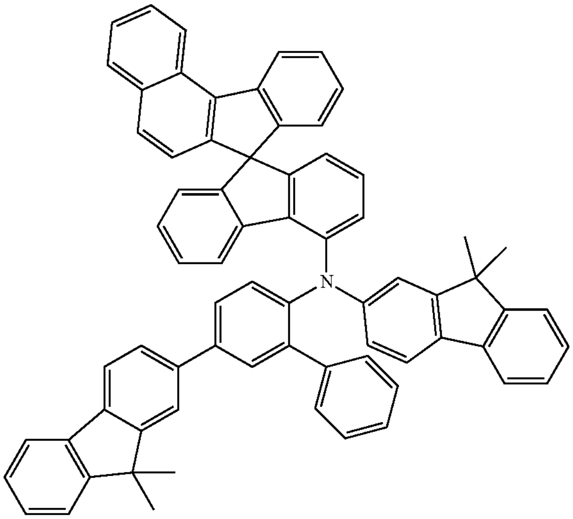 [SMILES: CC1(C)c2ccccc2-c2ccc(-c3ccc(N(c4ccc5c(c4)C(C)(C)c4ccccc4-5)c4cccc5c4-c4ccccc4C54c5ccccc5-c5c4ccc4ccccc54)c(-c4ccccc4)c3)cc21]
17
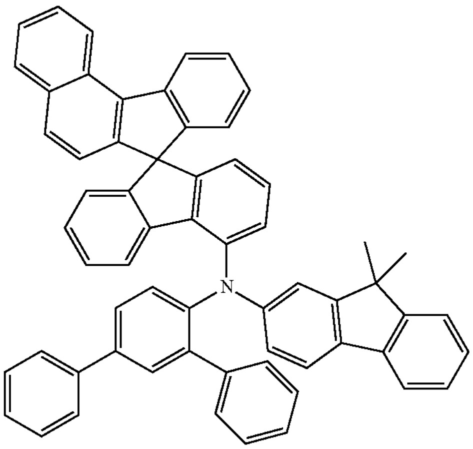 [SMILES: CC1(C)c2ccccc2-c2ccc(N(c3ccc(-c4ccccc4)cc3-c3ccccc3)c3cccc4c3-c3ccccc3C43c4ccccc4-c4c3ccc3ccccc43)cc21]
18

-continued
19
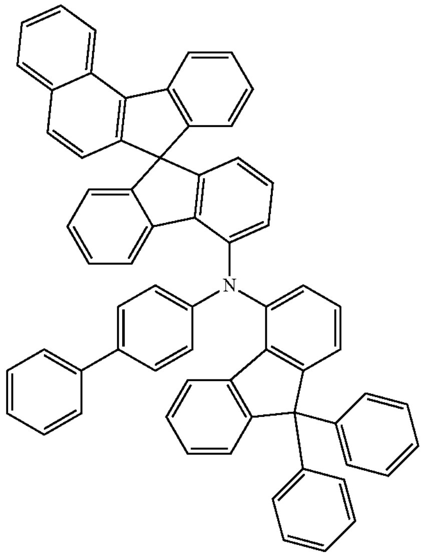 [SMILES: c1ccc(-c2ccc(N(c3cccc4c3-c3ccccc3C4(c3ccccc3)c3ccccc3)c3cccc4c3-c3ccccc3C43c4ccccc4-c4c3ccc3ccccc43)cc2)cc1]
20
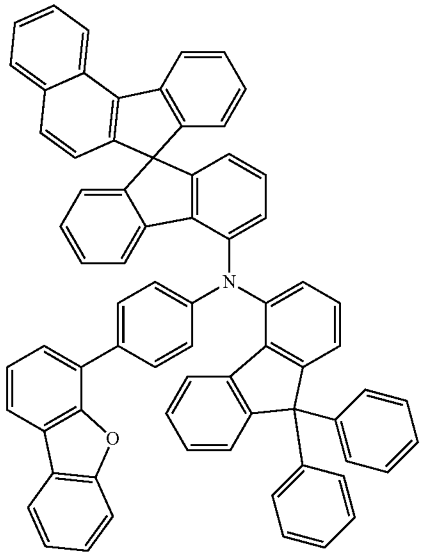 [SMILES: c1ccc(C2(c3ccccc3)c3ccccc3-c3c(N(c4ccc(-c5cccc6c5oc5ccccc56)cc4)c4cccc5c4-c4ccccc4C54c5ccccc5-c5c4ccc4ccccc54)cccc32)cc1]

-continued
21
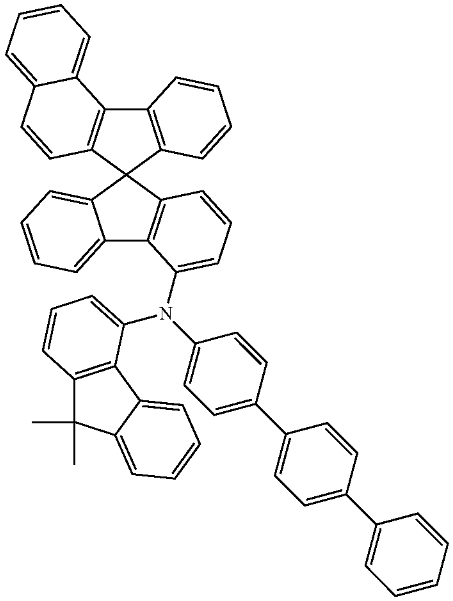 [SMILES: CC1(C)c2ccccc2-c2c(N(c3ccc(-c4ccc(-c5ccccc5)cc4)cc3)c3cccc4c3-c3ccccc3C43c4ccccc4-c4c3ccc3ccccc43)cccc21]
22
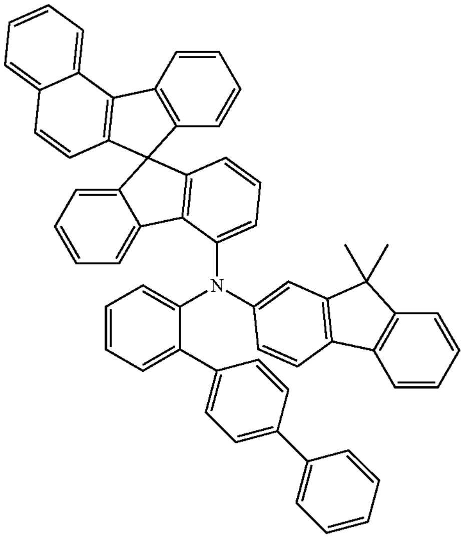 [SMILES: CC1(C)c2ccccc2-c2ccc(N(c3ccccc3-c3ccc(-c4ccccc4)cc3)c3cccc4c3-c3ccccc3C43c4ccccc4-c4c3ccc3ccccc43)cc21]

-continued
23
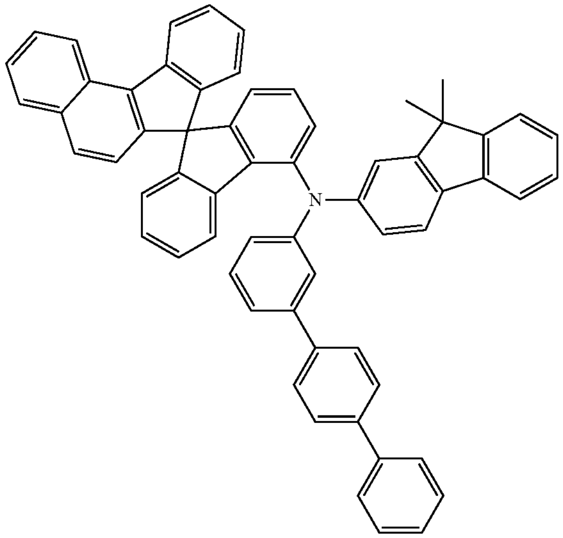 [SMILES: CC1(C)c2ccccc2-c2ccc(N(c3cccc(-c4ccc(-c5ccccc5)cc4)c3)c3cccc4c3-c3ccccc3C43c4ccccc4-c4c3ccc3ccccc43)cc21]
24
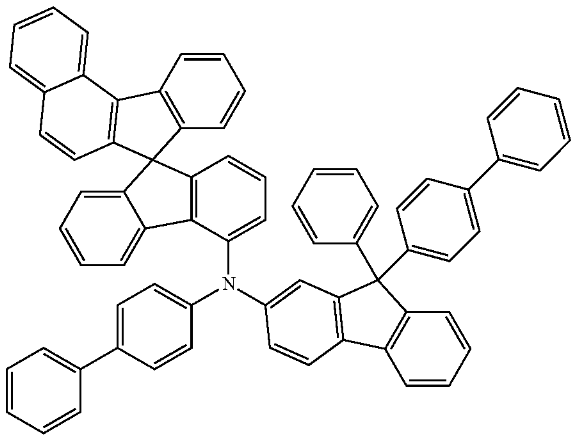 [SMILES: c1ccc(-c2ccc(N(c3ccc4c(c3)C(c3ccccc3)(c3ccc(-c5ccccc5)cc3)c3ccccc3-4)c3cccc4c3-c3ccccc3C43c4ccccc4-c4c3ccc3ccccc43)cc2)cc1]
25
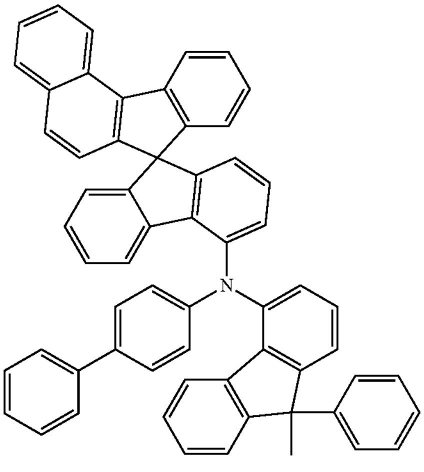 [SMILES: CC1(c2ccccc2)c2ccccc2-c2c(N(c3ccc(-c4ccccc4)cc3)c3cccc4c3-c3ccccc3C43c4ccccc4-c4c3ccc3ccccc43)cccc21]

-continued
26
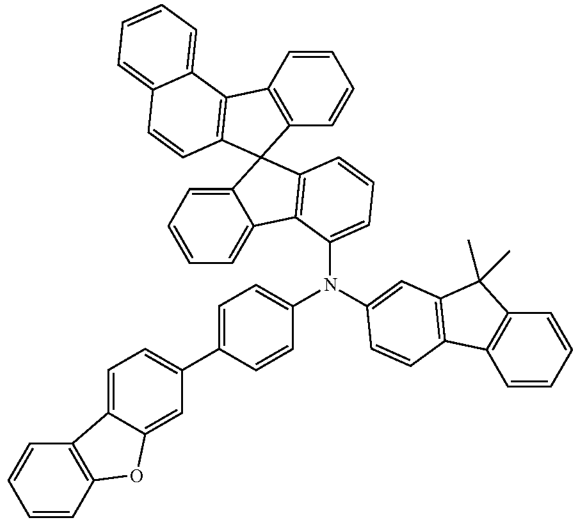 [SMILES: CC1(C)c2ccccc2-c2ccc(N(c3ccc(-c4ccc5c(c4)oc4ccccc45)cc3)c3cccc4c3-c3ccccc3C43c4ccccc4-c4c3ccc3ccccc43)cc21]
27
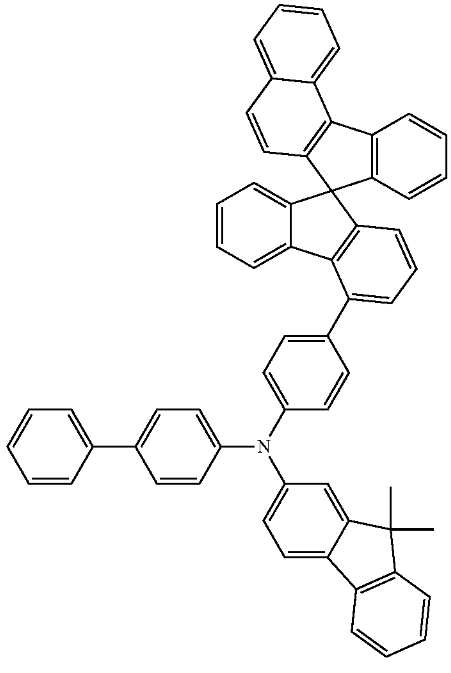 [SMILES: CC1(C)c2ccccc2-c2ccc(N(c3ccc(-c4ccccc4)cc3)c3ccc(-c4cccc5c4-c4ccccc4C54c5ccccc5-c5c4ccc4ccccc54)cc3)cc21]

-continued
28
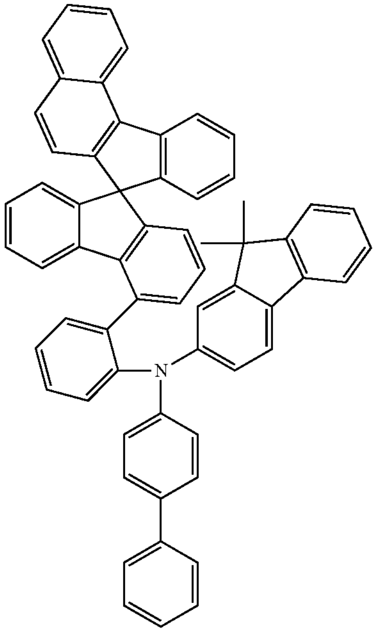 [SMILES: CC1(C)c2ccccc2-c2ccc(N(c3ccc(-c4ccccc4)cc3)c3ccccc3-c3cccc4c3-c3ccccc3C43c4ccccc4-c4c3ccc3ccccc43)cc21]
29
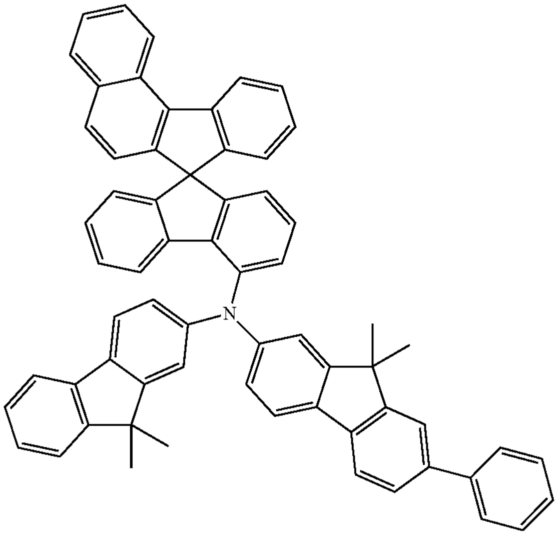 [SMILES: CC1(C)c2ccccc2-c2ccc(N(c3ccc4c(c3)C(C)(C)c3cc(-c5ccccc5)ccc3-4)c3cccc4c3-c3ccccc3C43c4ccccc4-c4c3ccc3ccccc43)cc21]

-continued
30
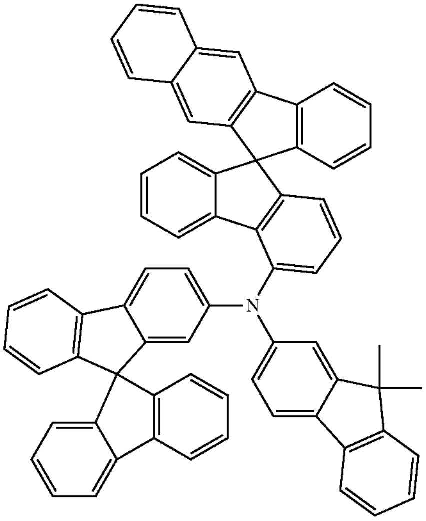 [SMILES: CC1(C)c2ccccc2-c2ccc(N(c3ccc4c(c3)C3(c5ccccc5-c5ccccc53)c3ccccc3-4)c3cccc4c3-c3ccccc3C43c4ccccc4-c4cc5ccccc5cc43)cc21]
31
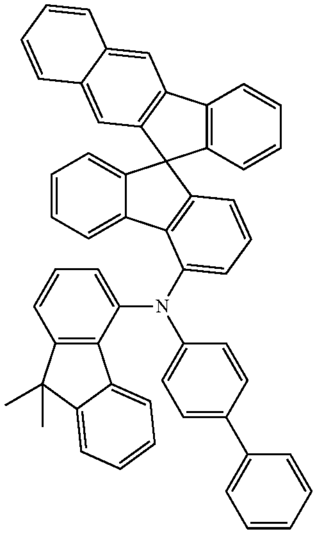 [SMILES: CC1(C)c2ccccc2-c2c(N(c3ccc(-c4ccccc4)cc3)c3cccc4c3-c3ccccc3C43c4ccccc4-c4cc5ccccc5cc43)cccc21]
32
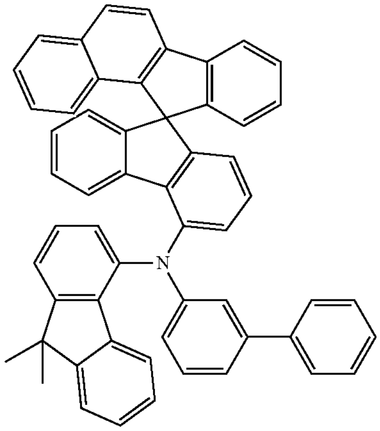 [SMILES: CC1(C)c2ccccc2-c2c(N(c3cccc(-c4ccccc4)c3)c3cccc4c3-c3ccccc3C43c4ccccc4-c4ccc5ccccc5c43)cccc21]

-continued
33
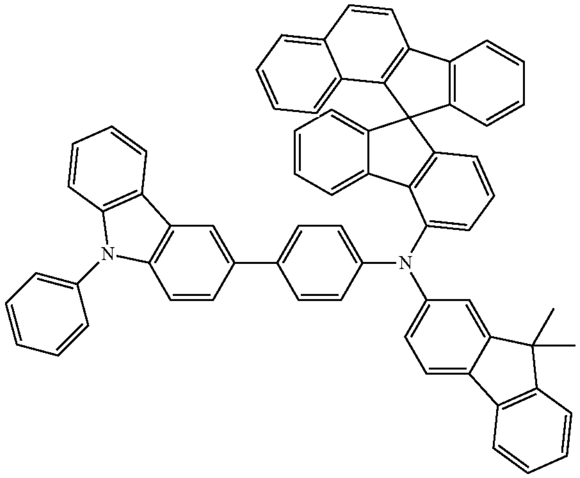 [SMILES: CC1(C)c2ccccc2-c2ccc(N(c3ccc(-c4ccc5c(c4)c4ccccc4n5-c4ccccc4)cc3)c3cccc4c3-c3ccccc3C43c4ccccc4-c4ccc5ccccc5c43)cc21]
34
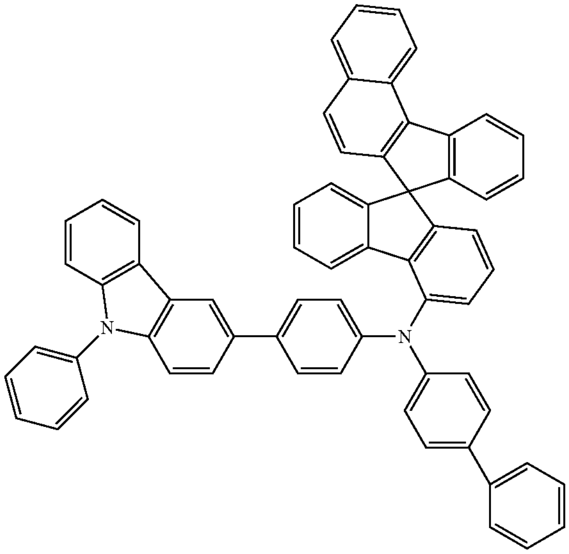 [SMILES: c1ccc(-c2ccc(N(c3ccc(-c4ccc5c(c4)c4ccccc4n5-c4ccccc4)cc3)c3cccc4c3-c3ccccc3C43c4ccccc4-c4c3ccc3ccccc43)cc2)cc1]
35
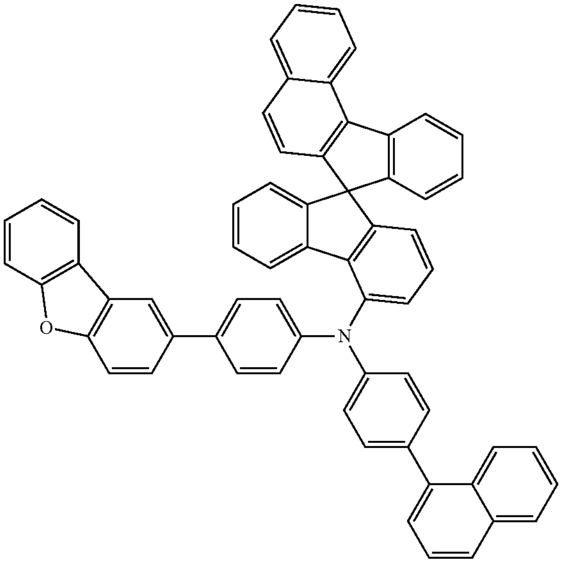 [SMILES: c1ccc2c(c1)-c1c(N(c3ccc(-c4ccc5oc6ccccc6c5c4)cc3)c3ccc(-c4cccc5ccccc45)cc3)cccc1C21c2ccccc2-c2c1ccc1ccccc21]

-continued
36
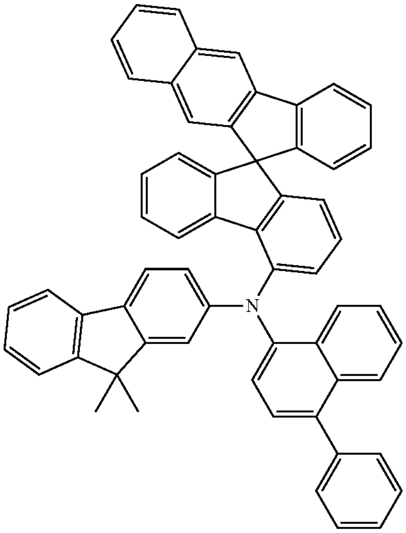 [SMILES: CC1(C)c2ccccc2-c2ccc(N(c3cccc4c3-c3ccccc3C43c4ccccc4-c4cc5ccccc5cc43)c3ccc(-c4ccccc4)c4ccccc34)cc21]
37
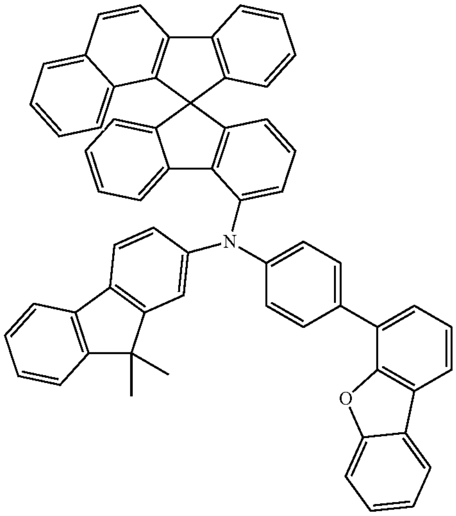 [SMILES: CC1(C)c2ccccc2-c2ccc(N(c3ccc(-c4cccc5c4oc4ccccc45)cc3)c3cccc4c3-c3ccccc3C43c4ccccc4-c4ccc5ccccc5c43)cc21]
38
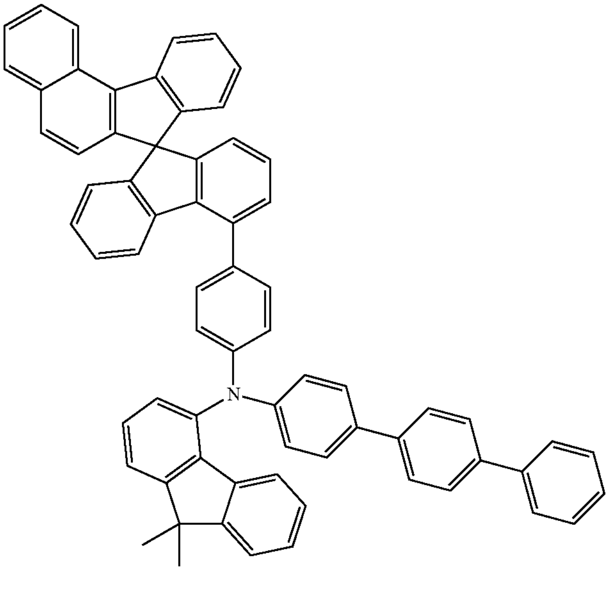 [SMILES: CC1(C)c2ccccc2-c2c(N(c3ccc(-c4ccc(-c5ccccc5)cc4)cc3)c3ccc(-c4cccc5c4-c4ccccc4C54c5ccccc5-c5c4ccc4ccccc54)cc3)cccc21]

-continued
39
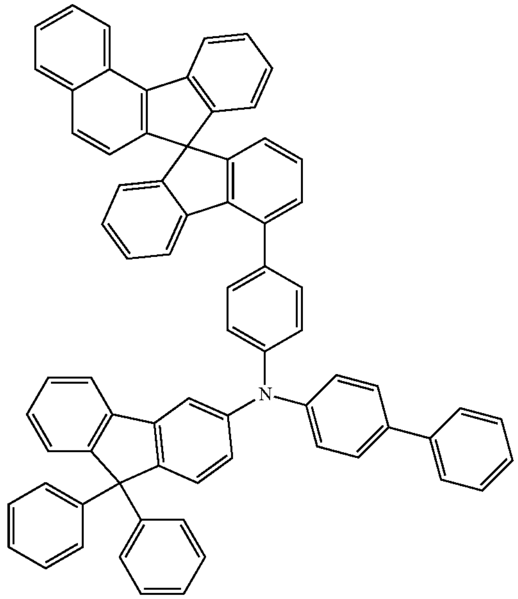 [SMILES: c1ccc(-c2ccc(N(c3ccc(-c4cccc5c4-c4ccccc4C54c5ccccc5-c5c4ccc4ccccc54)cc3)c3ccc4c(c3)-c3ccccc3C4(c3ccccc3)c3ccccc3)cc2)cc1]
40
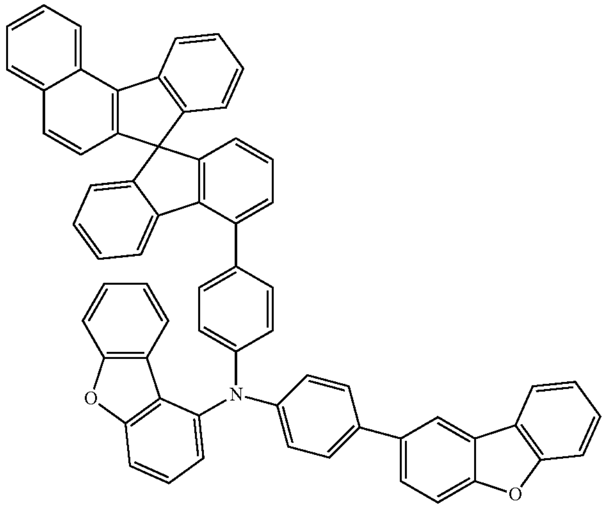 [SMILES: c1ccc2c(c1)-c1c(-c3ccc(N(c4ccc(-c5ccc6oc7ccccc7c6c5)cc4)c4cccc5oc6ccccc6c45)cc3)cccc1C21c2ccccc2-c2c1ccc1ccccc21]

-continued
41
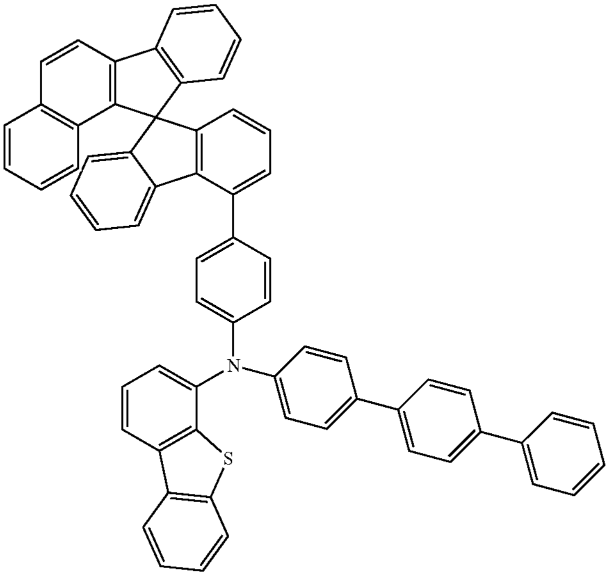 [SMILES: c1ccc(-c2ccc(-c3ccc(N(c4ccc(-c5cccc6c5-c5ccccc5C65c6ccccc6-c6ccc7ccccc7c65)cc4)c4cccc5c4sc4ccccc45)cc3)cc2)cc1]
42
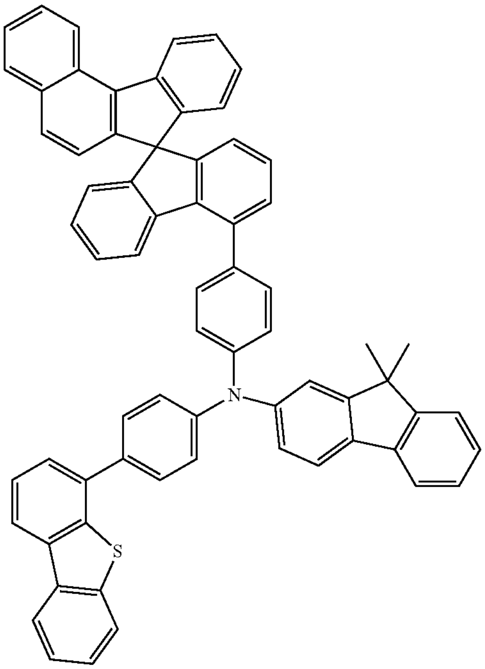 [SMILES: CC1(C)c2ccccc2-c2ccc(N(c3ccc(-c4cccc5c4-c4ccccc4C54c5ccccc5-c5c4ccc4ccccc54)cc3)c3ccc(-c4cccc5c4sc4ccccc45)cc3)cc21]

-continued
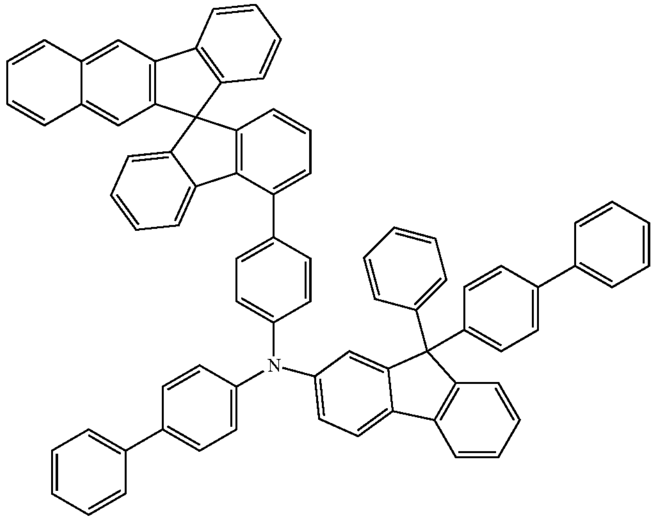 [SMILES: c1ccc(-c2ccc(N(c3ccc(-c4cccc5c4-c4ccccc4C54c5ccccc5-c5cc6ccccc6cc54)cc3)c3ccc4c(c3)C(c3ccccc3)(c3ccc(-c5ccccc5)cc3)c3ccccc3-4)cc2)cc1]
43
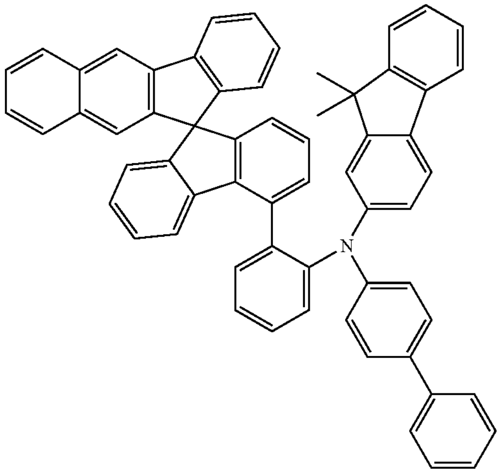 [SMILES: CC1(C)c2ccccc2-c2ccc(N(c3ccc(-c4ccccc4)cc3)c3ccccc3-c3cccc4c3-c3ccccc3C43c4ccccc4-c4cc5ccccc5cc43)cc21]
44
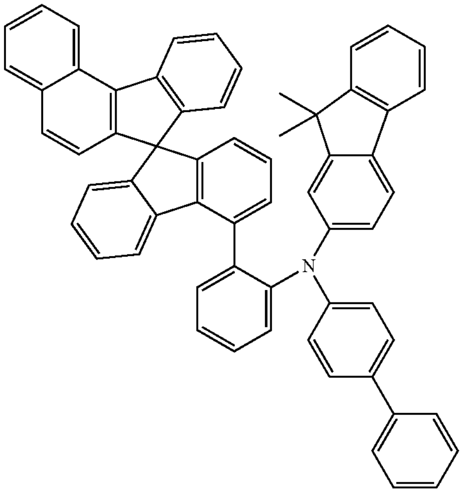 [SMILES: CC1(C)c2ccccc2-c2ccc(N(c3ccc(-c4ccccc4)cc3)c3ccccc3-c3cccc4c3-c3ccccc3C43c4ccccc4-c4c3ccc3ccccc43)cc21]
45

-continued
46
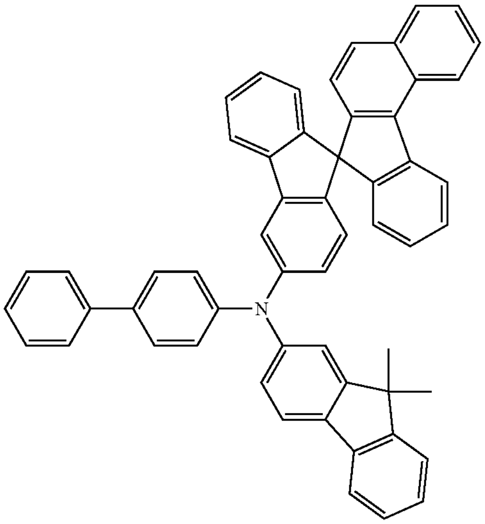 [SMILES: CC1(C)c2ccccc2-c2ccc(N(c3ccc(-c4ccccc4)cc3)c3ccc4c(c3)-c3ccccc3C43c4ccccc4-c4c3ccc3ccccc43)cc21]
47
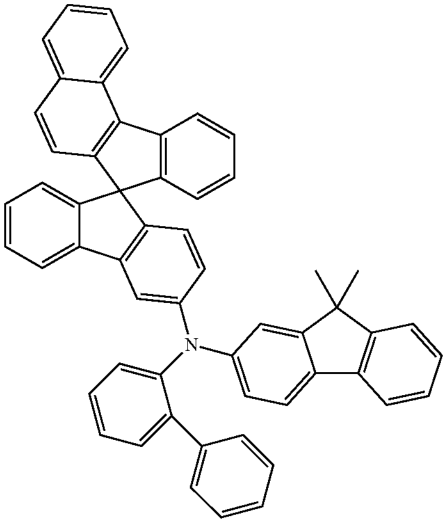 [SMILES: CC1(C)c2ccccc2-c2ccc(N(c3ccc4c(c3)-c3ccccc3C43c4ccccc4-c4c3ccc3ccccc43)c3ccccc3-c3ccccc3)cc21]
48
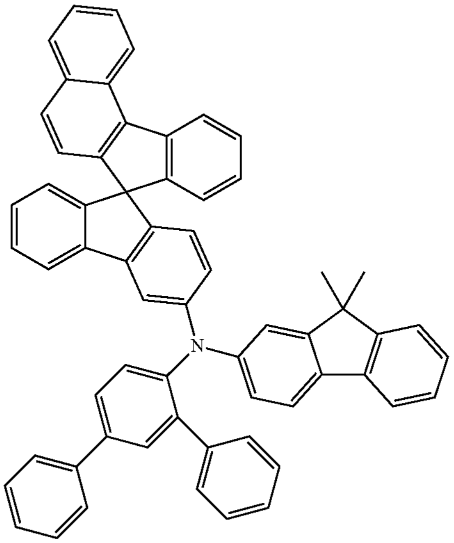 [SMILES: CC1(C)c2ccccc2-c2ccc(N(c3ccc4c(c3)-c3ccccc3C43c4ccccc4-c4c3ccc3ccccc43)c3ccc(-c4ccccc4)cc3-c3ccccc3)cc21]

-continued
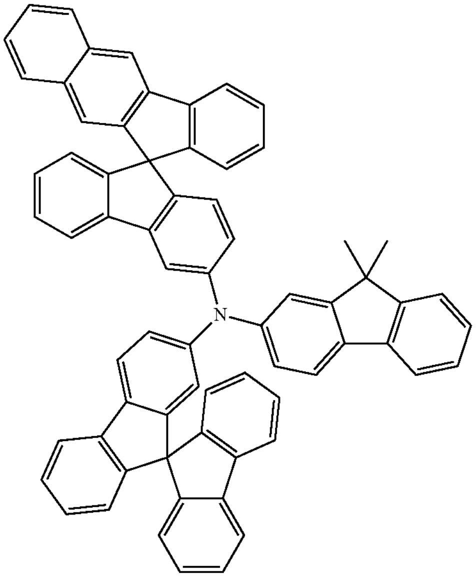 [SMILES: CC1(C)c2ccccc2-c2ccc(N(c3ccc4c(c3)-c3ccccc3C43c4ccccc4-c4cc5ccccc5cc43)c3ccc4c(c3)C3(c5ccccc5-c5ccccc53)c3ccccc3-4)cc21]
49
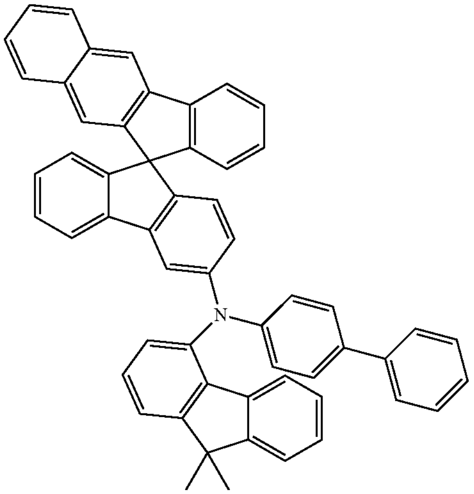 [SMILES: CC1(C)c2ccccc2-c2c(N(c3ccc(-c4ccccc4)cc3)c3ccc4c(c3)-c3ccccc3C43c4ccccc4-c4cc5ccccc5cc43)cccc21]
50

-continued
51
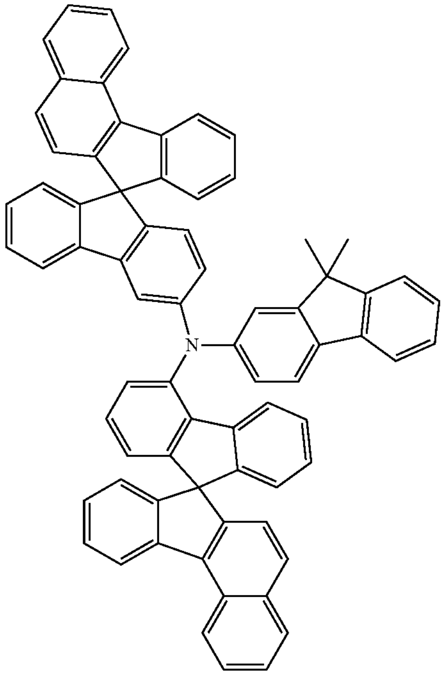 [SMILES: CC1(C)c2ccccc2-c2ccc(N(c3ccc4c(c3)-c3ccccc3C43c4ccccc4-c4c3ccc3ccccc43)c3cccc4c3-c3ccccc3C43c4ccccc4-c4c3ccc3ccccc43)cc21]
52
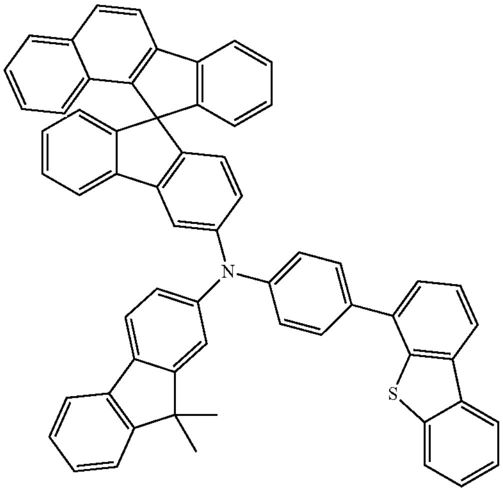 [SMILES: CC1(C)c2ccccc2-c2ccc(N(c3ccc(-c4cccc5c4sc4ccccc45)cc3)c3ccc4c(c3)-c3ccccc3C43c4ccccc4-c4ccc5ccccc5c43)cc21]

-continued
53
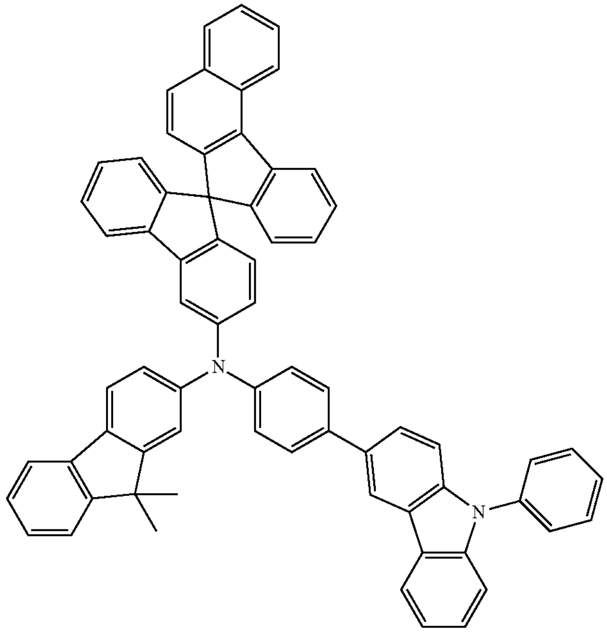 [SMILES: CC1(C)c2ccccc2-c2ccc(N(c3ccc(-c4ccc5c(c4)c4ccccc4n5-c4ccccc4)cc3)c3ccc4c(c3)-c3ccccc3C43c4ccccc4-c4c3ccc3ccccc43)cc21]
54
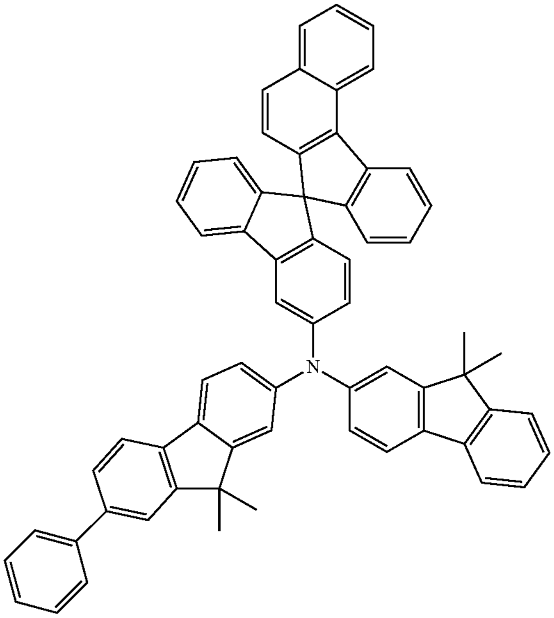 [SMILES: CC1(C)c2ccccc2-c2ccc(N(c3ccc4c(c3)-c3ccccc3C43c4ccccc4-c4c3ccc3ccccc43)c3ccc4c(c3)C(C)(C)c3cc(-c5ccccc5)ccc3-4)cc21]

-continued
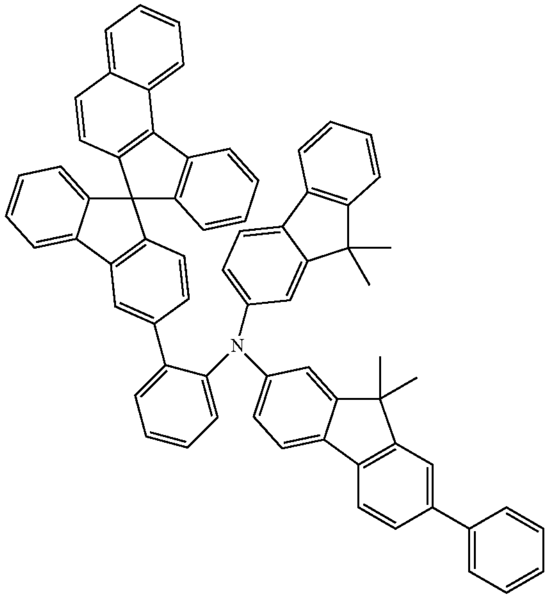 [SMILES: CC1(C)c2ccccc2-c2ccc(N(c3ccc4c(c3)C(C)(C)c3cc(-c5ccccc5)ccc3-4)c3ccccc3-c3ccc4c(c3)-c3ccccc3C43c4ccccc4-c4c3ccc3ccccc43)cc21]
55
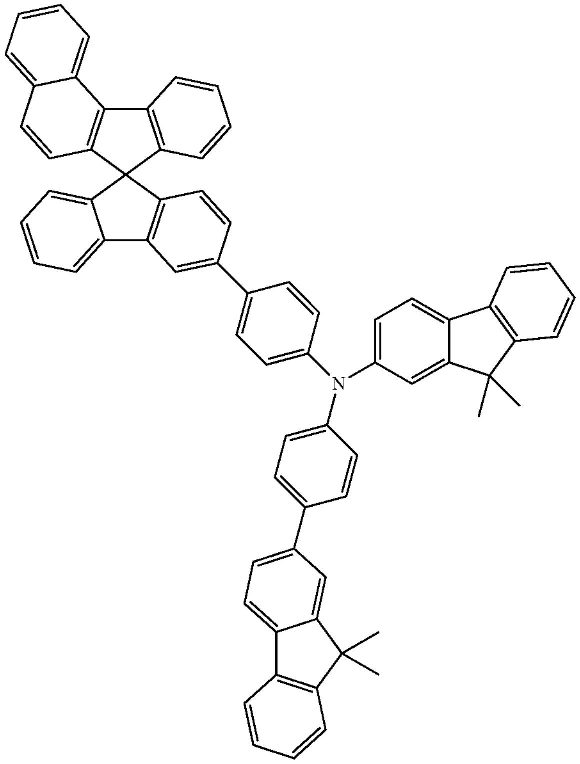 [SMILES: CC1(C)c2ccccc2-c2ccc(-c3ccc(N(c4ccc(-c5ccc6c(c5)-c5ccccc5C65c6ccccc6-c6c5ccc5ccccc65)cc4)c4ccc5c(c4)C(C)(C)c4ccccc4-5)cc3)cc21]
56

-continued
57
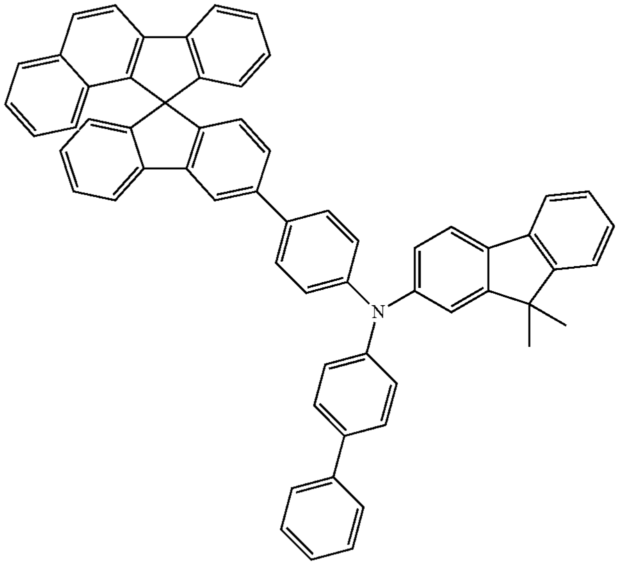 [SMILES: CC1(C)c2ccccc2-c2ccc(N(c3ccc(-c4ccccc4)cc3)c3ccc(-c4ccc5c(c4)-c4ccccc4C54c5ccccc5-c5ccc6ccccc6c54)cc3)cc21]
58
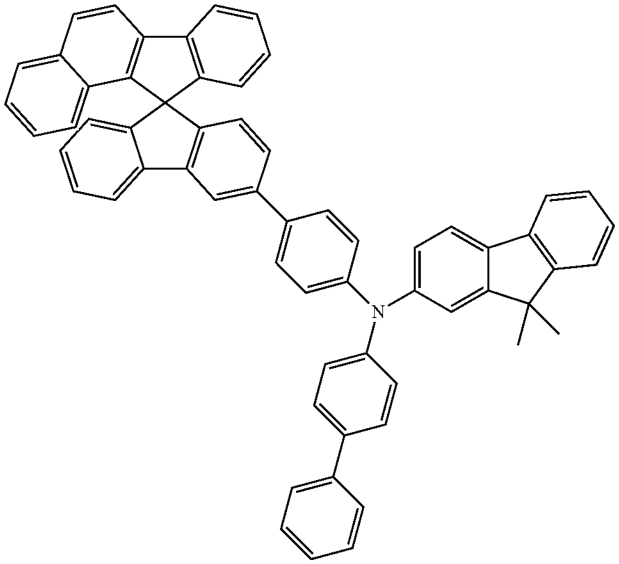 [SMILES: CC1(C)c2ccccc2-c2ccc(N(c3ccc(-c4ccccc4)cc3)c3ccc(-c4ccc5c(c4)-c4ccccc4C54c5ccccc5-c5ccc6ccccc6c54)cc3)cc21]

-continued
59
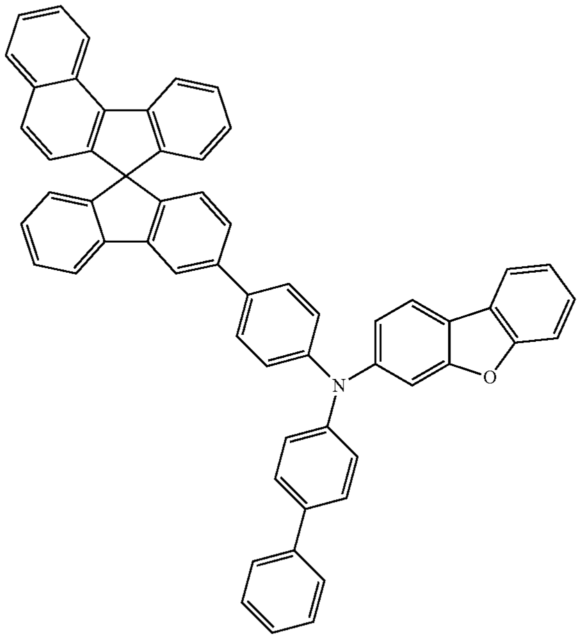 [SMILES: c1ccc(-c2ccc(N(c3ccc(-c4ccc5c(c4)-c4ccccc4C54c5ccccc5-c5c4ccc4ccccc54)cc3)c3ccc4c(c3)oc3ccccc34)cc2)cc1]
60
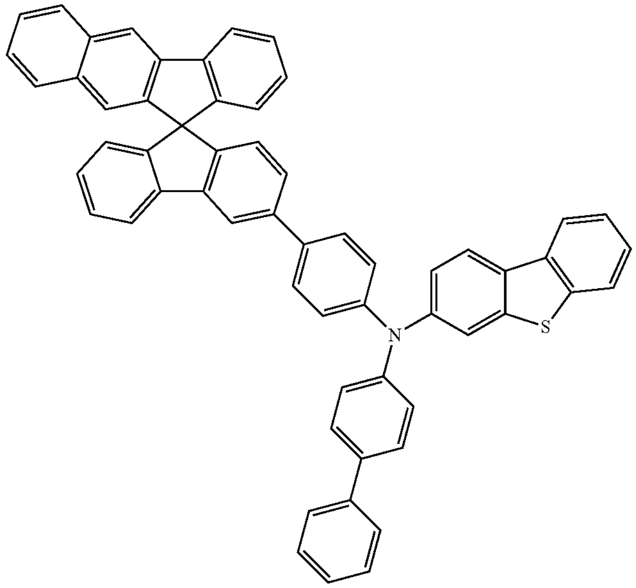 [SMILES: c1ccc(-c2ccc(N(c3ccc(-c4ccc5c(c4)-c4ccccc4C54c5ccccc5-c5cc6ccccc6cc54)cc3)c3ccc4c(c3)sc3ccccc34)cc2)cc1]

-continued
61
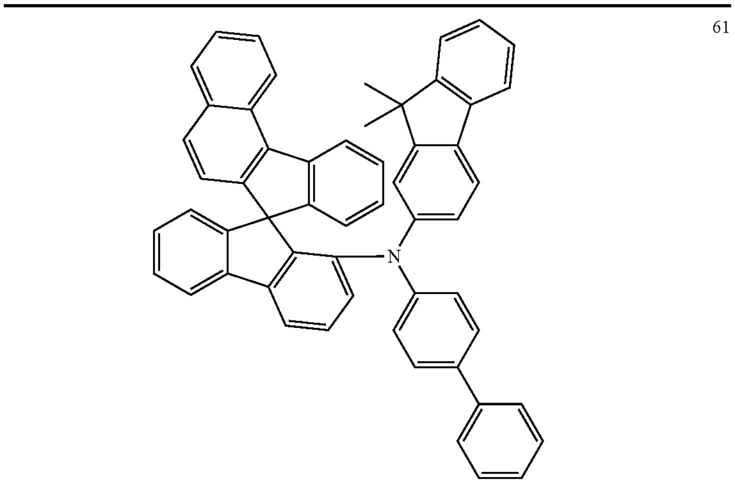
62
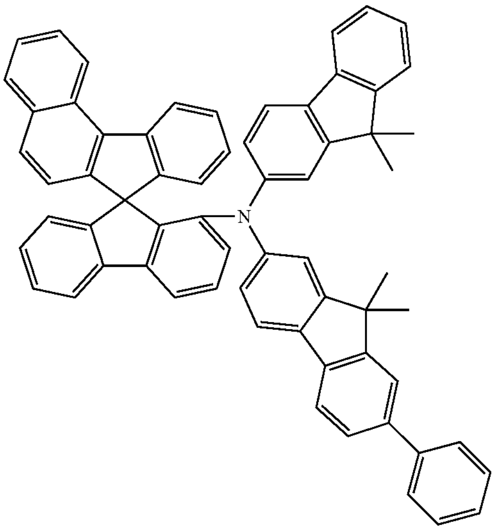 [SMILES: CC1(C)c2ccccc2-c2ccc(N(c3ccc4c(c3)C(C)(C)c3cc(-c5ccccc5)ccc3-4)c3cccc4c3C3(c5ccccc5-4)c4ccccc4-c4c3ccc3ccccc43)cc21]
63
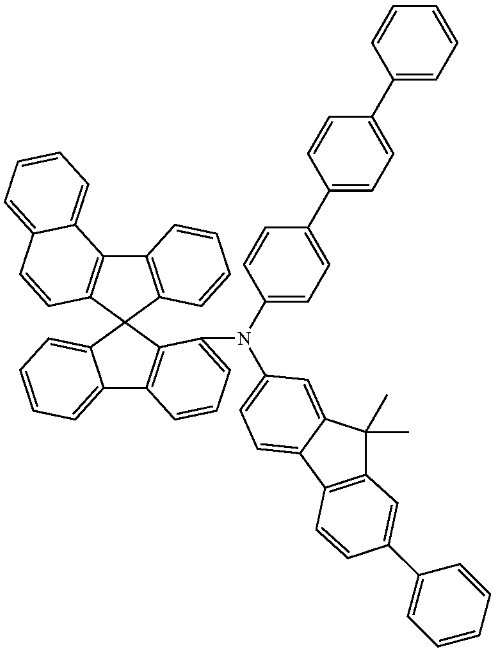 [SMILES: CC1(C)c2cc(-c3ccccc3)ccc2-c2ccc(N(c3ccc(-c4ccc(-c5ccccc5)cc4)cc3)c3cccc4c3C3(c5ccccc5-4)c4ccccc4-c4c3ccc3ccccc43)cc21]

-continued
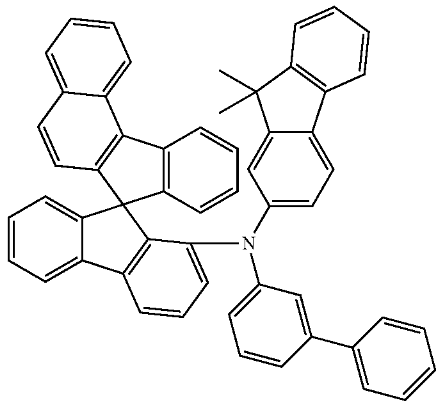 [SMILES: CC1(C)c2ccccc2-c2ccc(N(c3cccc(-c4ccccc4)c3)c3cccc4c3C3(c5ccccc5-4)c4ccccc4-c4c3ccc3ccccc43)cc21]
64
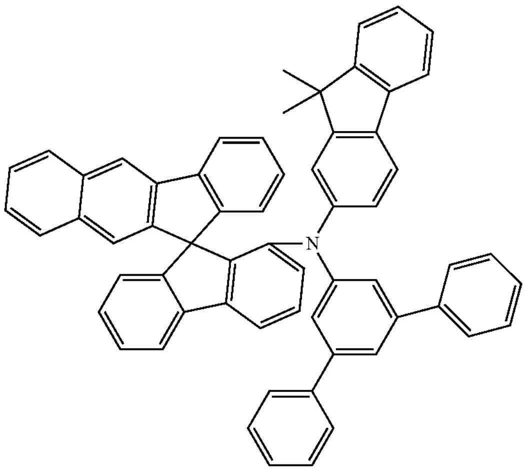 [SMILES: CC1(C)c2ccccc2-c2ccc(N(c3cc(-c4ccccc4)cc(-c4ccccc4)c3)c3cccc4c3C3(c5ccccc5-c5cc6ccccc6cc53)c3ccccc3-4)cc21]
65
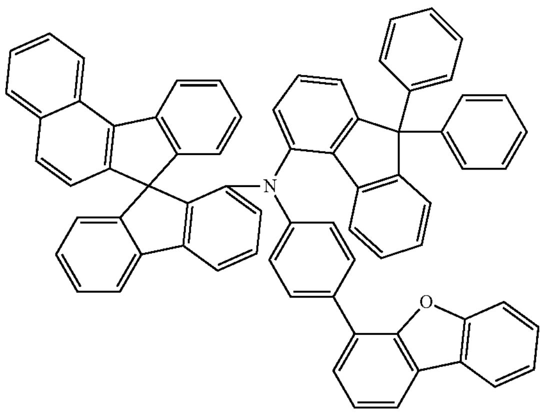 [SMILES: c1ccc(C2(c3ccccc3)c3ccccc3-c3c(N(c4ccc(-c5cccc6c5oc5ccccc56)cc4)c4cccc5c4C4(c6ccccc6-5)c5ccccc5-c5c4ccc4ccccc54)cccc32)cc1]
66

-continued
67
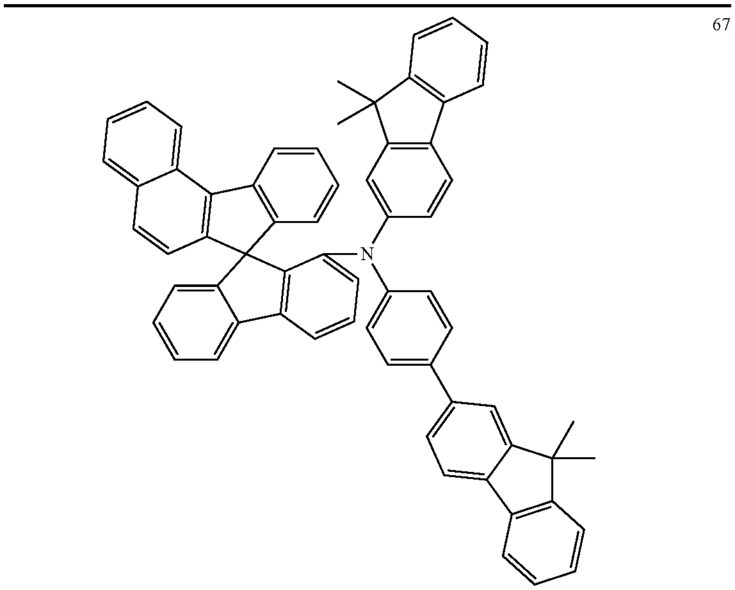
68
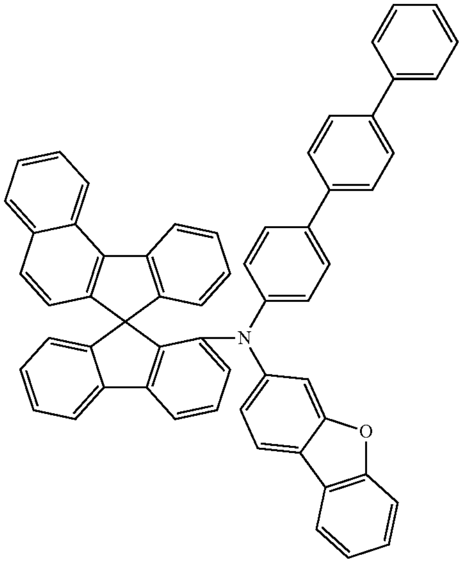 [SMILES: c1ccc(-c2ccc(-c3ccc(N(c4ccc5c(c4)oc4ccccc45)c4cccc5c4C4(c6ccccc6-5)c5ccccc5-c5c4ccc4ccccc54)cc3)cc2)cc1]
69
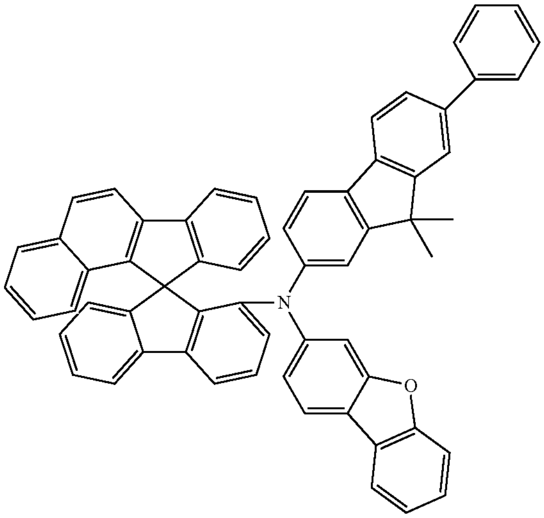 [SMILES: CC1(C)c2cc(-c3ccccc3)ccc2-c2ccc(N(c3ccc4c(c3)oc3ccccc34)c3cccc4c3C3(c5ccccc5-4)c4ccccc4-c4ccc5ccccc5c43)cc21]

-continued
70
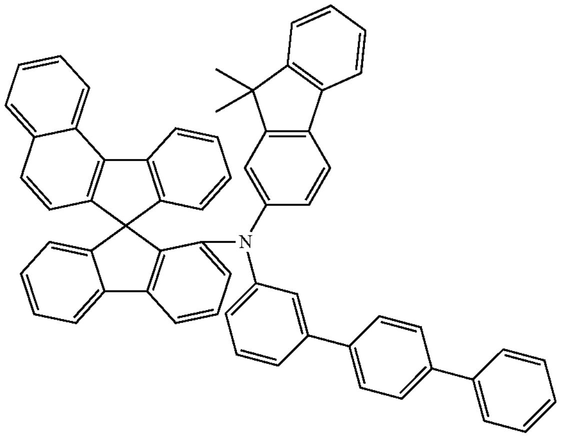 [SMILES: CC1(C)c2ccccc2-c2ccc(N(c3cccc(-c4ccc(-c5ccccc5)cc4)c3)c3cccc4c3C3(c5ccccc5-4)c4ccccc4-c4c3ccc3ccccc43)cc21]
71
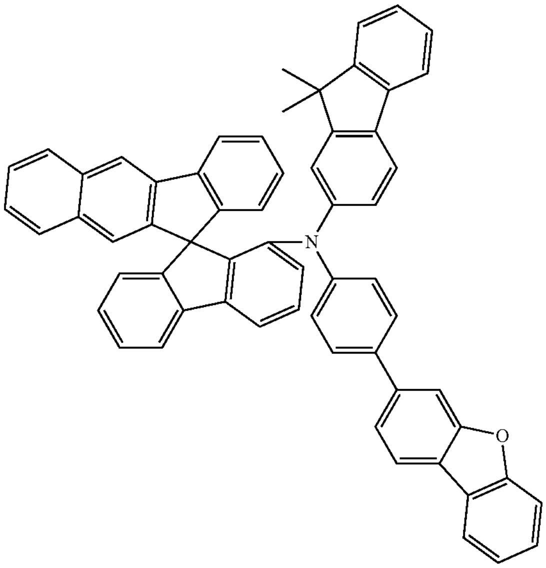 [SMILES: CC1(C)c2ccccc2-c2ccc(N(c3ccc(-c4ccc5c(c4)oc4ccccc45)cc3)c3cccc4c3C3(c5ccccc5-c5cc6ccccc6cc53)c3ccccc3-4)cc21]
72
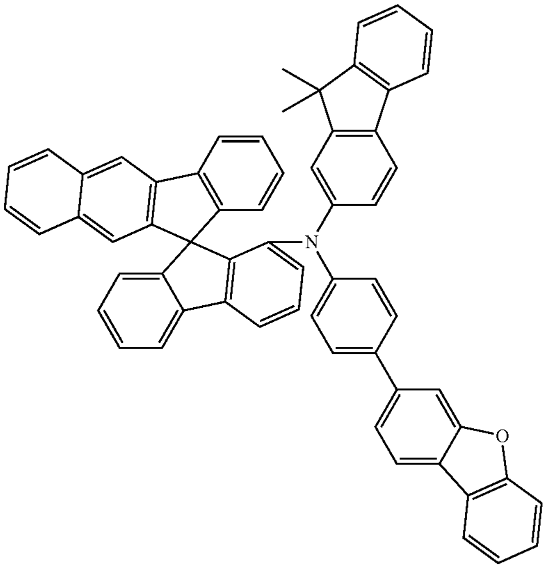 [SMILES: CC1(C)c2ccccc2-c2ccc(N(c3ccc(-c4ccc5c(c4)oc4ccccc45)cc3)c3cccc4c3C3(c5ccccc5-c5cc6ccccc6cc53)c3ccccc3-4)cc21]

-continued
73
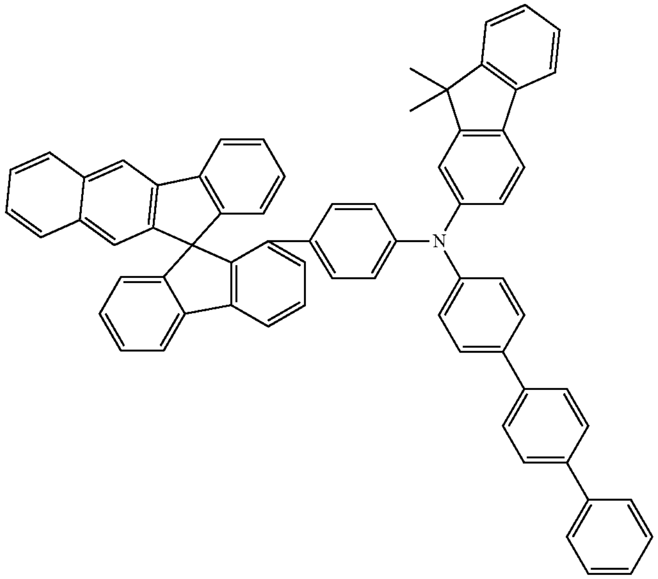 [SMILES: CC1(C)c2ccccc2-c2ccc(N(c3ccc(-c4ccc(-c5ccccc5)cc4)cc3)c3ccc(-c4cccc5c4C4(c6ccccc6-c6cc7ccccc7cc64)c4ccccc4-5)cc3)cc21]
74
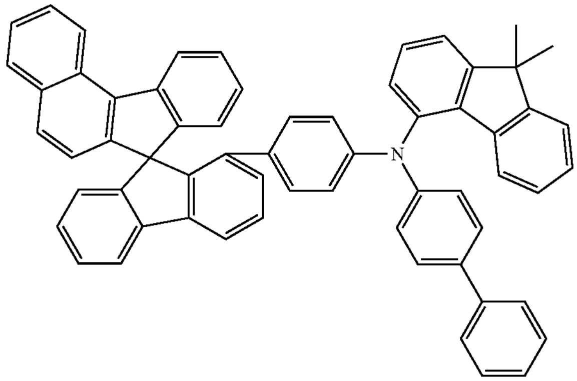 [SMILES: CC1(C)c2ccccc2-c2c(N(c3ccc(-c4ccccc4)cc3)c3ccc(-c4cccc5c4C4(c6ccccc6-5)c5ccccc5-c5c4ccc4ccccc54)cc3)cccc21]
75
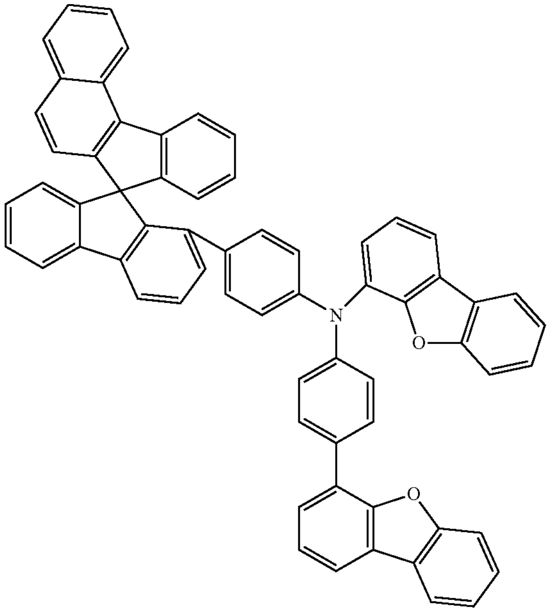 [SMILES: c1ccc2c(c1)-c1cccc(-c3ccc(N(c4ccc(-c5cccc6c5oc5ccccc56)cc4)c4cccc5c4oc4ccccc45)cc3)c1C21c2ccccc2-c2c1ccc1ccccc21]

-continued
76
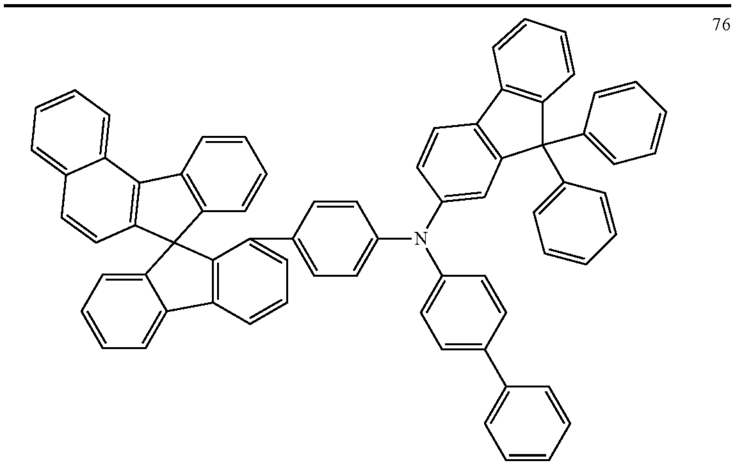
77
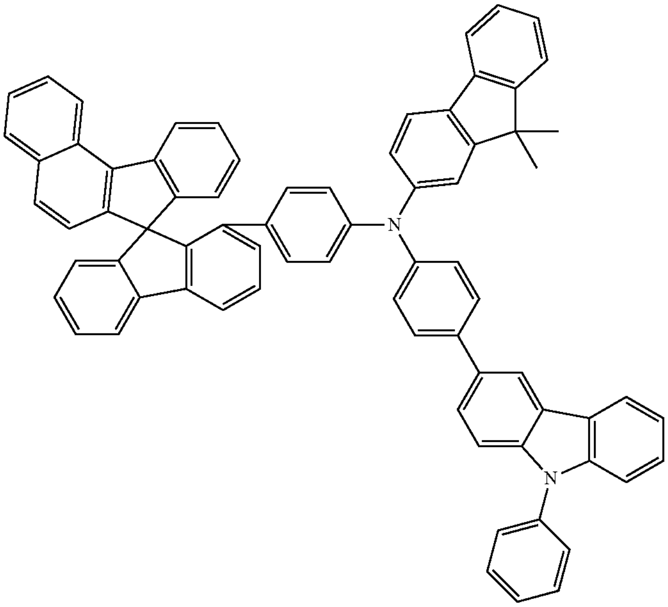 [SMILES: CC1(C)c2ccccc2-c2ccc(N(c3ccc(-c4ccc5c(c4)c4ccccc4n5-c4ccccc4)cc3)c3ccc(-c4cccc5c4C4(c6ccccc6-5)c5ccccc5-c5c4ccc4ccccc54)cc3)cc21]
78
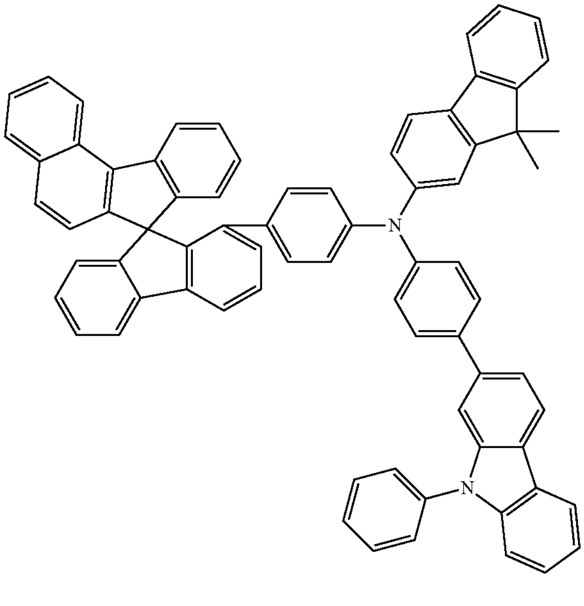 [SMILES: CC1(C)c2ccccc2-c2ccc(N(c3ccc(-c4ccc5c6ccccc6n(-c6ccccc6)c5c4)cc3)c3ccc(-c4cccc5c4C4(c6ccccc6-5)c5ccccc5-c5c4ccc4ccccc54)cc3)cc21]

-continued
79
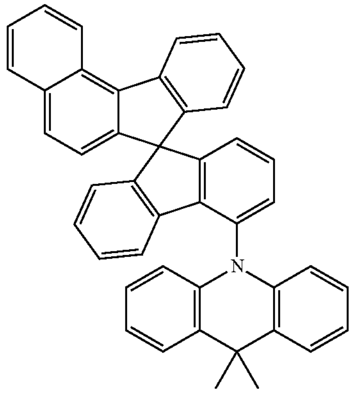 [SMILES: CC1(C)c2ccccc2N(c2cccc3c2-c2ccccc2C32c3ccccc3-c3c2ccc2ccccc32)c2ccccc21]
80
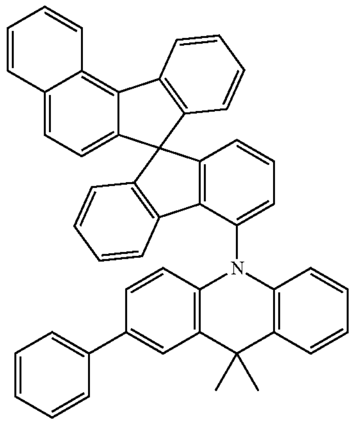 [SMILES: CC1(C)c2ccccc2N(c2cccc3c2-c2ccccc2C32c3ccccc3-c3c2ccc2ccccc32)c2ccc(-c3ccccc3)cc21]
81
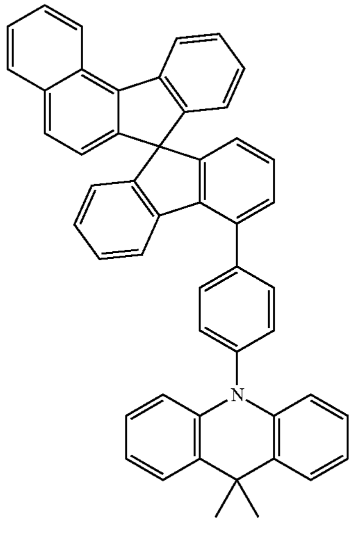 [SMILES: CC1(C)c2ccccc2N(c2ccc(-c3cccc4c3-c3ccccc3C43c4ccccc4-c4c3ccc3ccccc43)cc2)c2ccccc21]

-continued
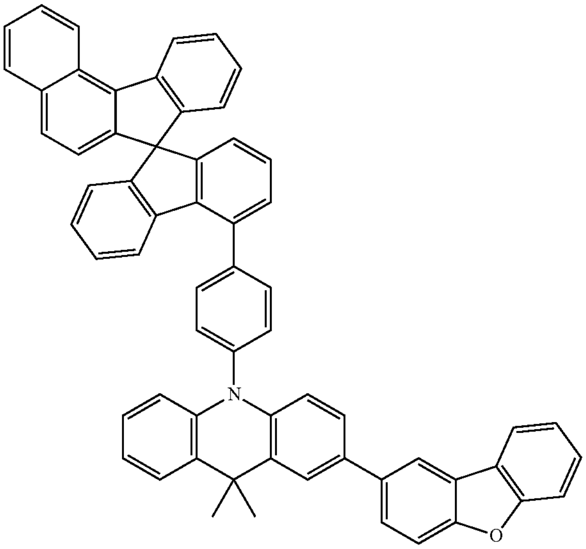 [SMILES: CC1(C)c2ccccc2N(c2ccc(-c3cccc4c3-c3ccccc3C43c4ccccc4-c4c3ccc3ccccc43)cc2)c2ccc(-c3ccc4oc5ccccc5c4c3)cc21]
82
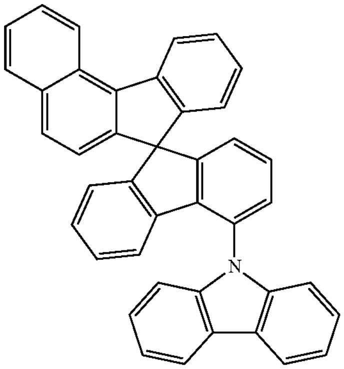 [SMILES: c1ccc2c(c1)-c1c(-n3c4ccccc4c4ccccc43)cccc1C21c2ccccc2-c2c1ccc1ccccc21]
83
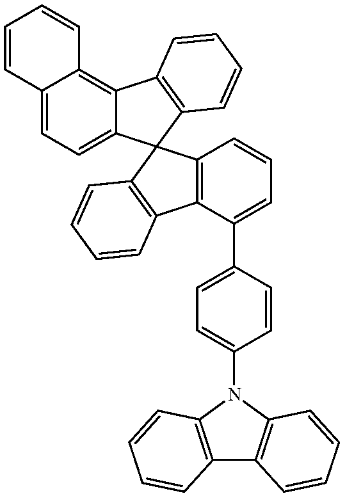 [SMILES: c1ccc2c(c1)-c1c(-c3ccc(-n4c5ccccc5c5ccccc54)cc3)cccc1C21c2ccccc2-c2c1ccc1ccccc21]
84

-continued
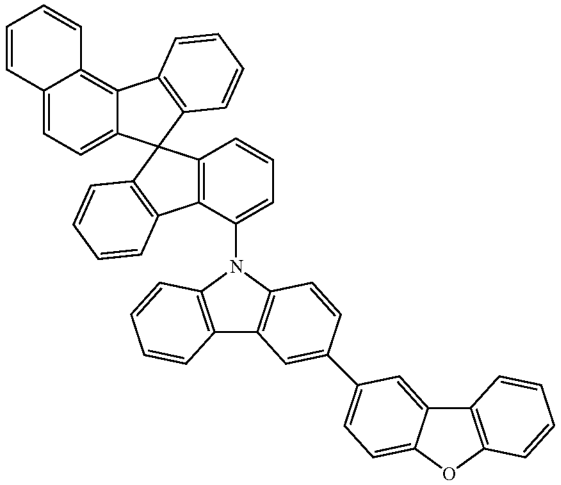 [SMILES: c1ccc2c(c1)-c1c(-n3c4ccccc4c4cc(-c5ccc6oc7ccccc7c6c5)ccc43)cccc1C21c2ccccc2-c2c1ccc1ccccc21]
85
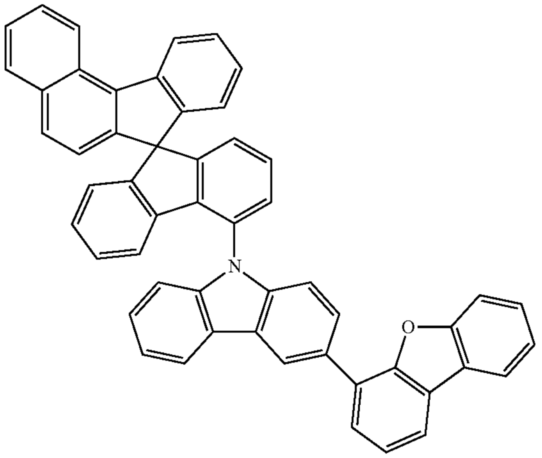
86
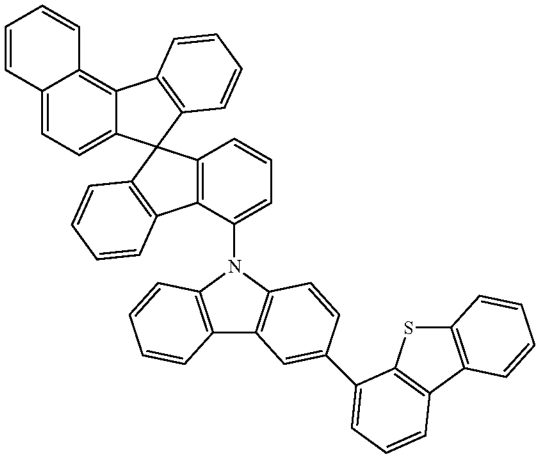 [SMILES: c1ccc2c(c1)-c1c(-n3c4ccccc4c4cc(-c5cccc6c5oc5ccccc56)ccc43)cccc1C21c2ccccc2-c2c1ccc1ccccc21]
87

-continued
88
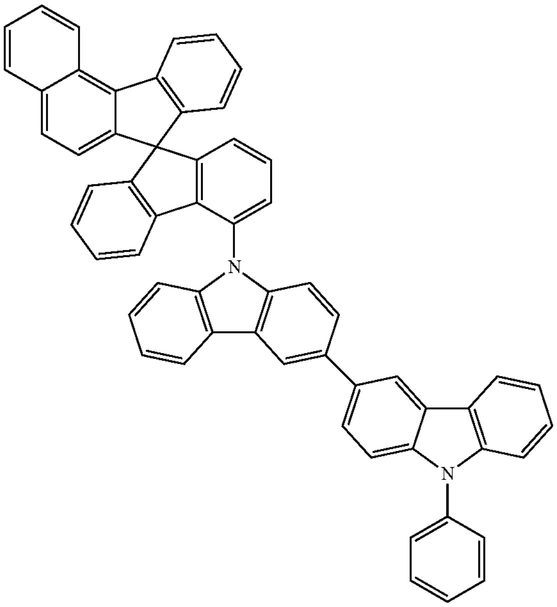 [SMILES: c1ccc(-n2c3ccccc3c3cc(-c4ccc5c(c4)c4ccccc4n5-c4cccc5c4-c4ccccc4C54c5ccccc5-c5c4ccc4ccccc54)ccc32)cc1]
89
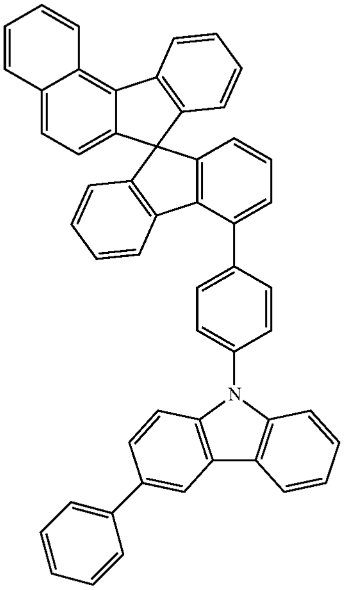 [SMILES: c1ccc(-c2ccc3c(c2)c2ccccc2n3-c2ccc(-c3cccc4c3-c3ccccc3C43c4ccccc4-c4c3ccc3ccccc43)cc2)cc1]

-continued
90
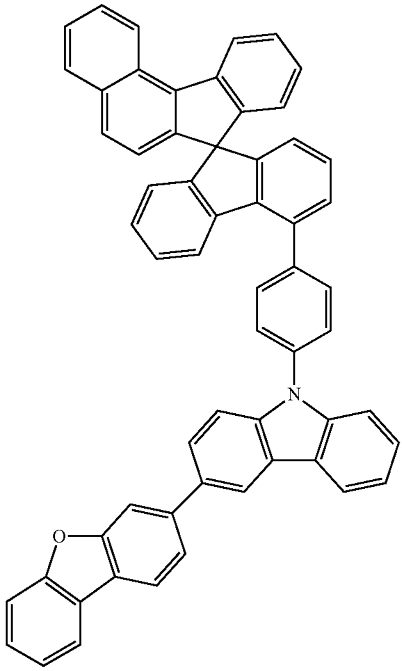 [SMILES: c1ccc2c(c1)-c1c(-c3ccc(-n4c5ccccc5c5cc(-c6ccc7c(c6)oc6ccccc67)ccc54)cc3)cccc1C21c2ccccc2-c2c1ccc1ccccc21]
91
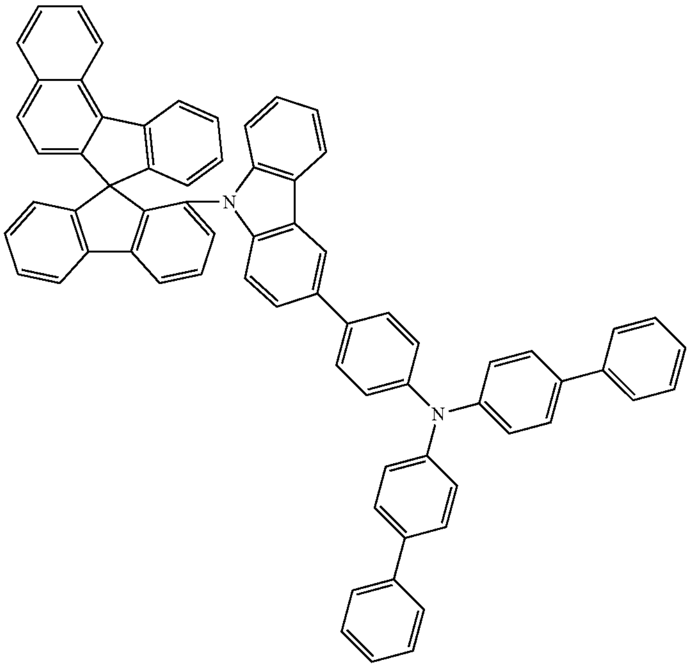 [SMILES: c1ccc(-c2ccc(N(c3ccc(-c4ccccc4)cc3)c3ccc(-c4ccc5c(c4)c4ccccc4n5-c4cccc5c4C4(c6ccccc6-5)c5ccccc5-c5c4ccc4ccccc54)cc3)cc2)cc1]

-continued
92
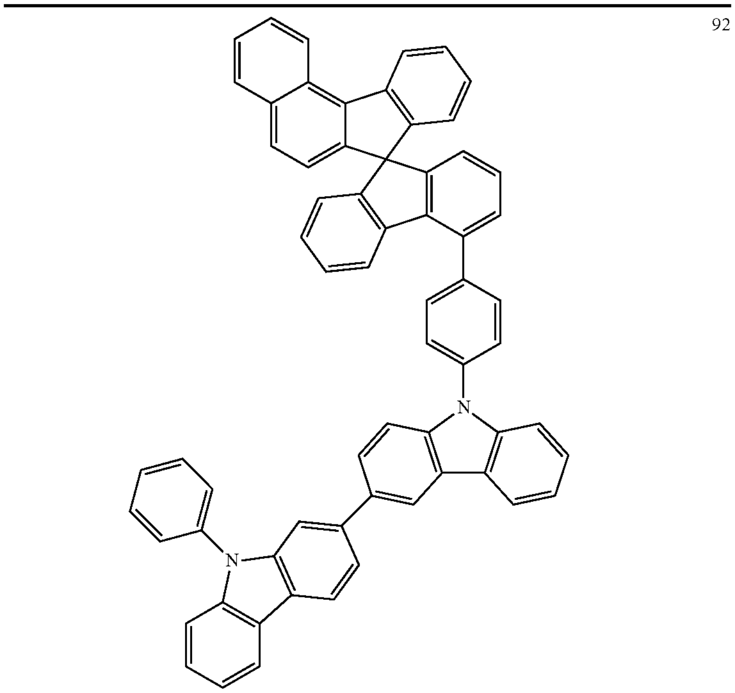
93
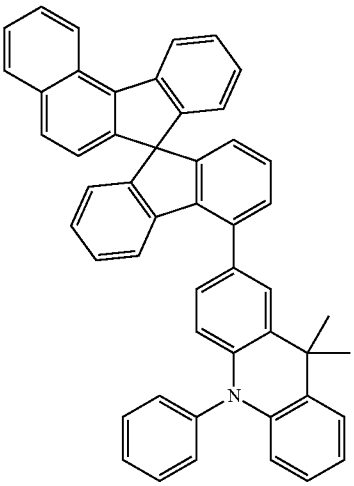 [SMILES: CC1(C)c2ccccc2N(c2ccccc2)c2ccc(-c3cccc4c3-c3ccccc3C43c4ccccc4-c4c3ccc3ccccc43)cc21]
94
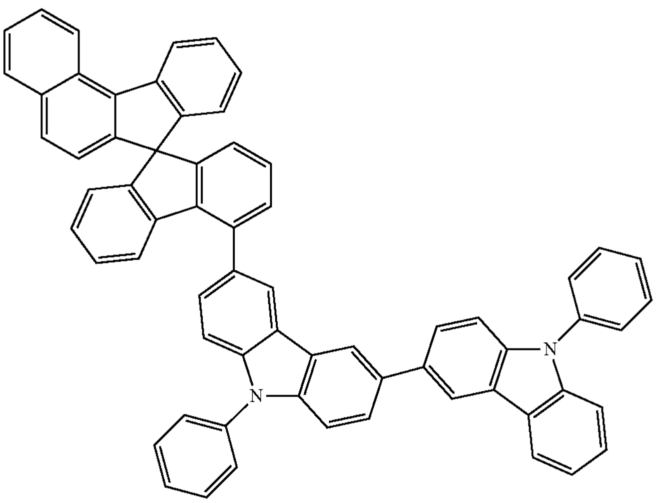 [SMILES: c1ccc(-n2c3ccccc3c3cc(-c4ccc5c(c4)c4cc(-c6cccc7c6-c6ccccc6C76c7ccccc7-c7c6ccc6ccccc76)ccc4n5-c4ccccc4)ccc32)cc1]

-continued
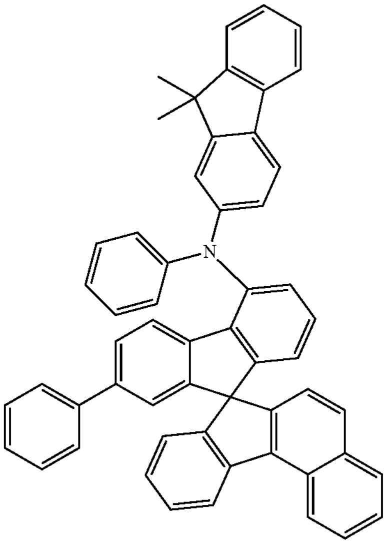 [SMILES: CC1(C)c2ccccc2-c2ccc(N(c3ccccc3)c3cccc4c3-c3ccc(-c5ccccc5)cc3C43c4ccccc4-c4c3ccc3ccccc43)cc21]
95
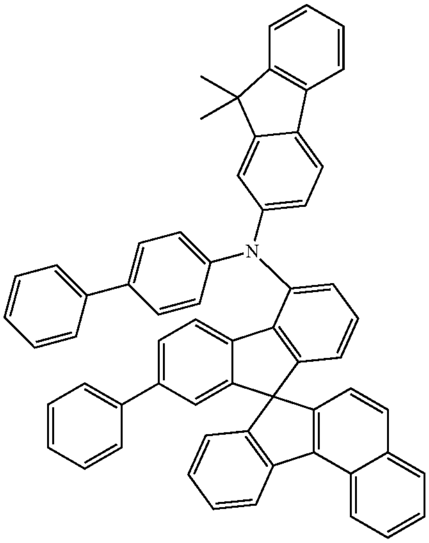 [SMILES: CC1(C)c2ccccc2-c2ccc(N(c3ccc(-c4ccccc4)cc3)c3cccc4c3-c3ccc(-c5ccccc5)cc3C43c4ccccc4-c4c3ccc3ccccc43)cc21]
96
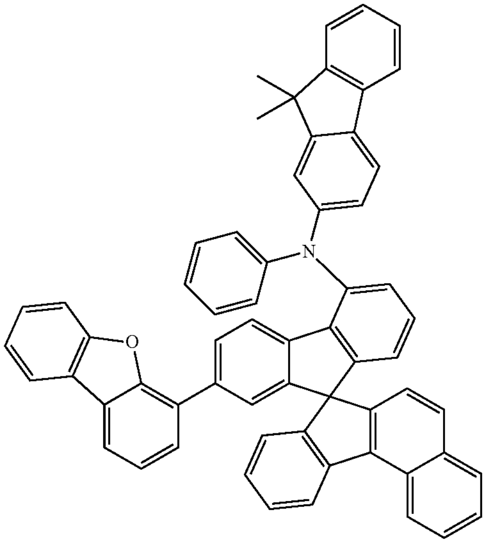 [SMILES: CC1(C)c2ccccc2-c2ccc(N(c3ccccc3)c3cccc4c3-c3ccc(-c5cccc6c5oc5ccccc56)cc3C43c4ccccc4-c4c3ccc3ccccc43)cc21]
97

-continued
98
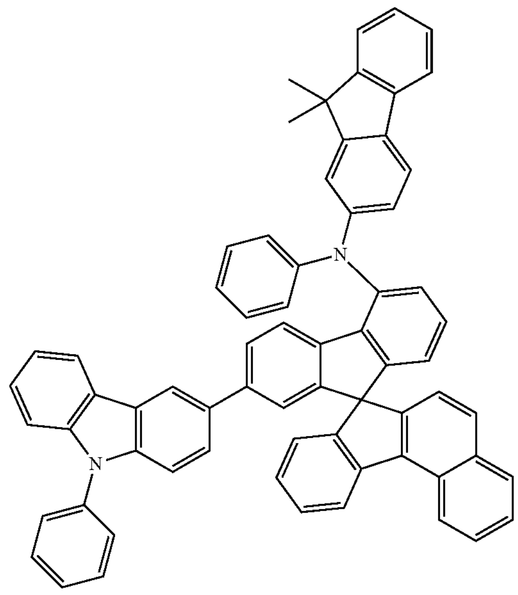 [SMILES: CC1(C)c2ccccc2-c2ccc(N(c3ccccc3)c3cccc4c3-c3ccc(-c5ccc6c(c5)c5ccccc5n6-c5ccccc5)cc3C43c4ccccc4-c4c3ccc3ccccc43)cc21]
99
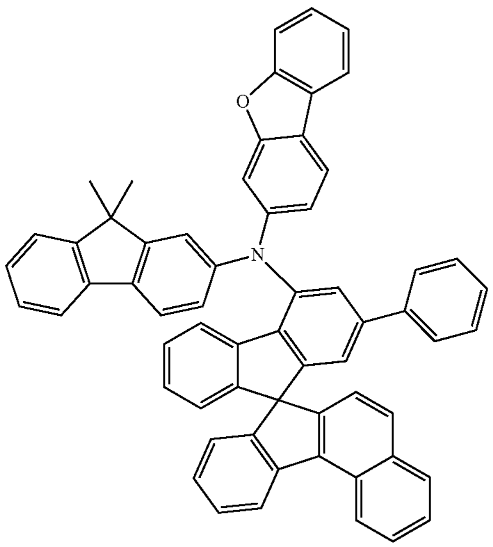 [SMILES: CC1(C)c2ccccc2-c2ccc(N(c3ccc4c(c3)oc3ccccc34)c3cc(-c4ccccc4)cc4c3-c3ccccc3C43c4ccccc4-c4c3ccc3ccccc43)cc21]

-continued
100
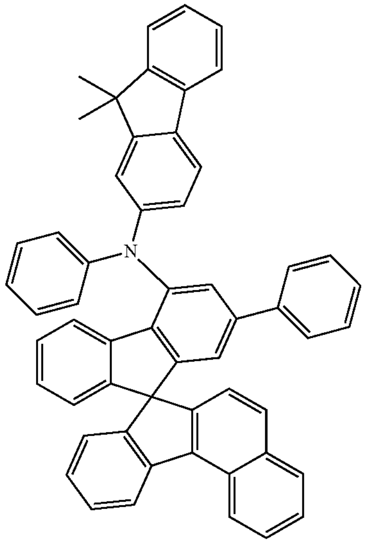 [SMILES: CC1(C)c2ccccc2-c2ccc(N(c3ccccc3)c3cc(-c4ccccc4)cc4c3-c3ccccc3C43c4ccccc4-c4c3ccc3ccccc43)cc21]
101
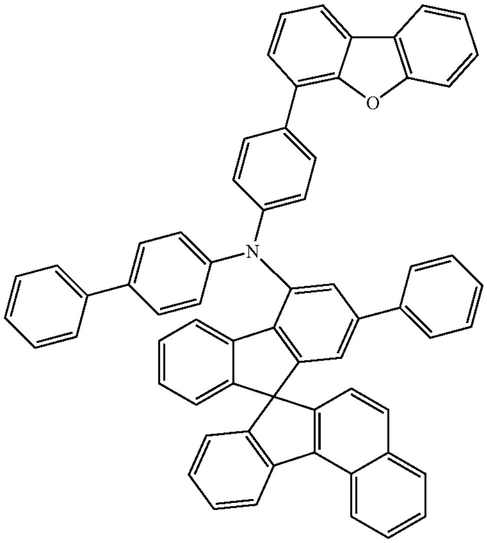 [SMILES: c1ccc(-c2ccc(N(c3ccc(-c4cccc5c4oc4ccccc45)cc3)c3cc(-c4ccccc4)cc4c3-c3ccccc3C43c4ccccc4-c4c3ccc3ccccc43)cc2)cc1]
102
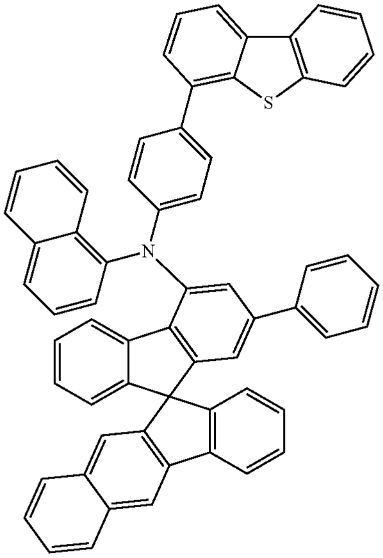 [SMILES: c1ccc(-c2cc(N(c3ccc(-c4cccc5c4sc4ccccc45)cc3)c3cccc4ccccc34)c3c(c2)C2(c4ccccc4-c4cc5ccccc5cc42)c2ccccc2-3)cc1]

-continued
103
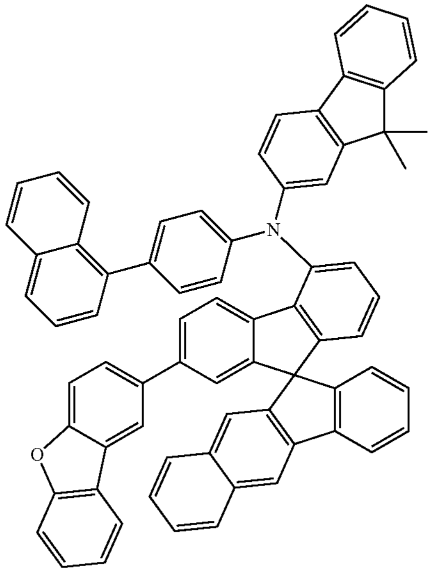 [SMILES: CC1(C)c2ccccc2-c2ccc(N(c3ccc(-c4cccc5ccccc45)cc3)c3cccc4c3-c3ccc(-c5ccc6oc7ccccc7c6c5)cc3C43c4ccccc4-c4cc5ccccc5cc43)cc21]
104
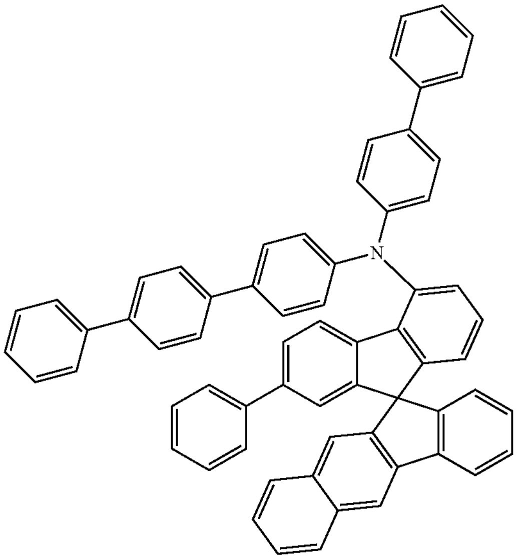 [SMILES: c1ccc(-c2ccc(-c3ccc(N(c4ccc(-c5ccccc5)cc4)c4cccc5c4-c4ccc(-c6ccccc6)cc4C54c5ccccc5-c5cc6ccccc6cc54)cc3)cc2)cc1]

-continued
105
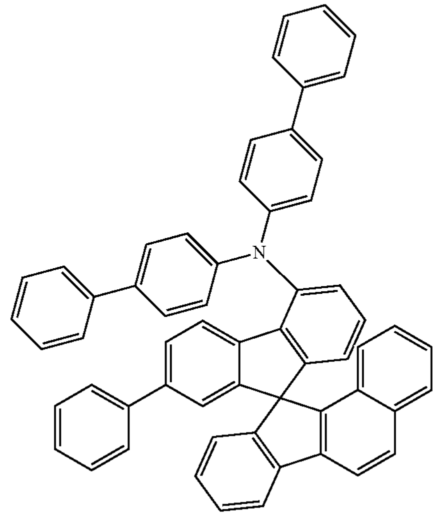 [SMILES: c1ccc(-c2ccc(N(c3ccc(-c4ccccc4)cc3)c3cccc4c3-c3ccc(-c5ccccc5)cc3C43c4ccccc4-c4ccc5ccccc5c43)cc2)cc1]
The compounds according to the invention can be prepared by synthetic steps known to the person skilled in the art, such as, for example, bromination, borylation, Ullmann arylation, Hartwig-Buchwald coupling, Suzuki-coupling as depicted in Scheme 1 below.
Scheme 1
Step 1)
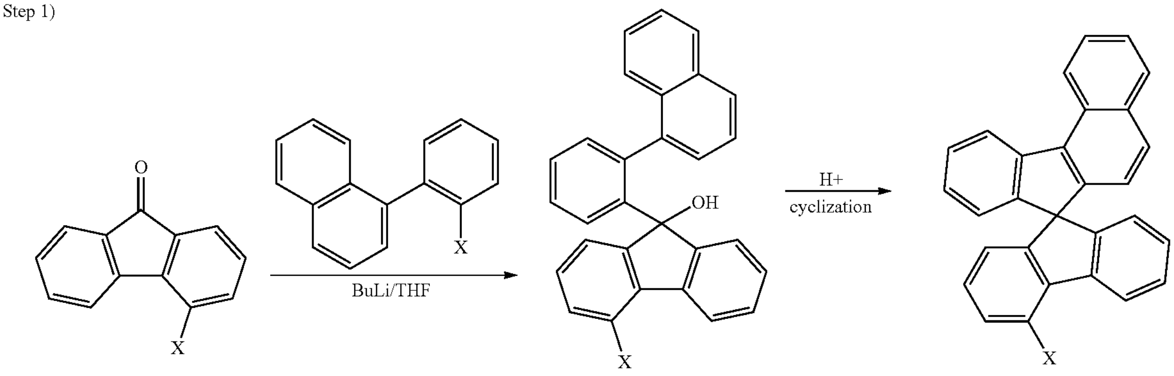

-continued

The step 1 is followed by step 2a orr step 2b:

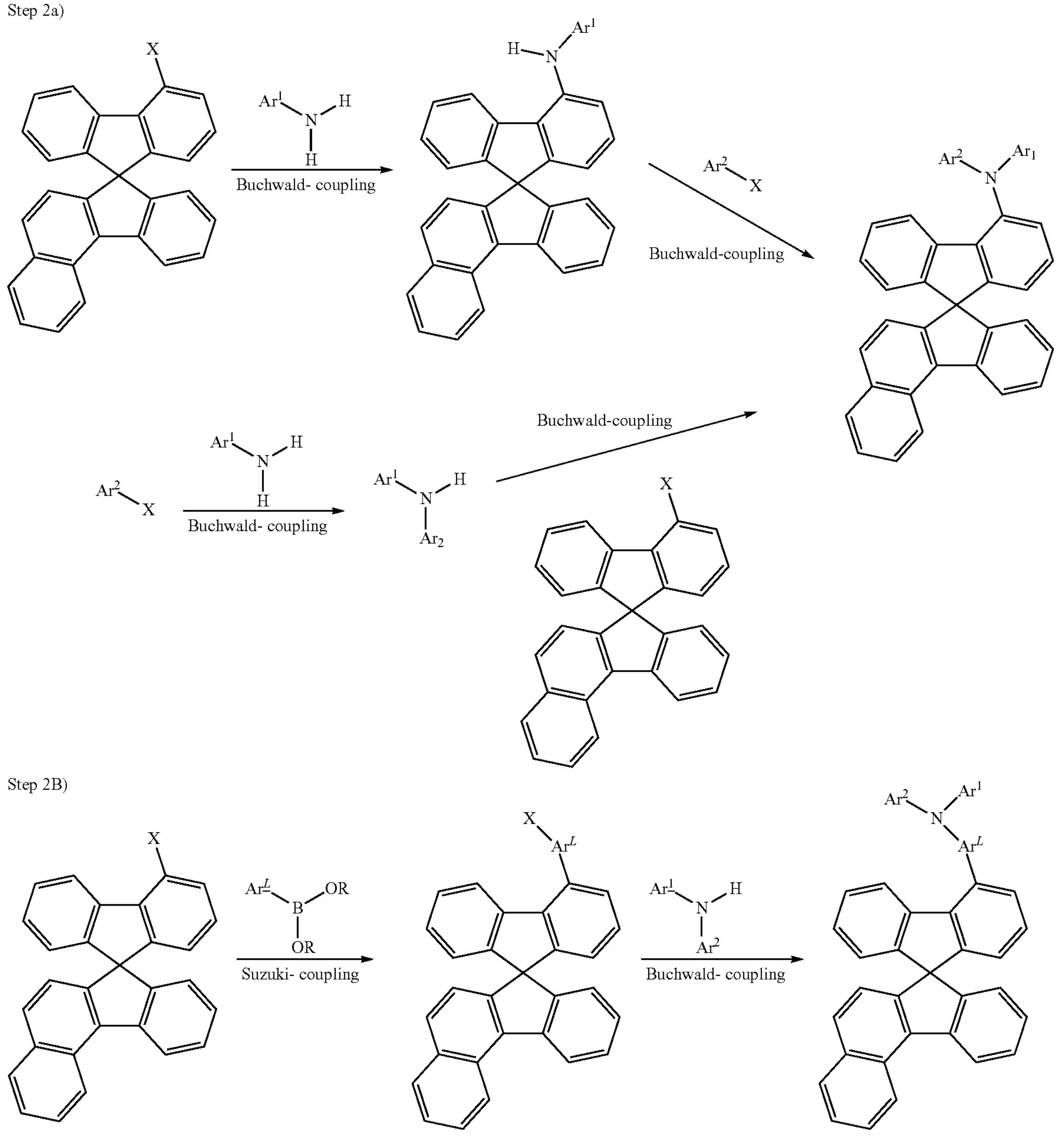

X is a halogen or another leaving group $Ar^1$, $Ar^2$ are aromatic or heteroaromatic ring systems The present invention therefore furthermore relates to a process for the preparation of a compound of the formula (1), characterised in that a diarylamino group is introduced by a C—N coupling reaction between a 1- or 3- or 4-halogenated spirobifluorene and a diarylamine.

The compounds according to the invention described above, in particular compounds which are substituted by reactive leaving groups, such as chlorine, bromine, iodine, tosylate, triflate, boronic acid or boronic acid ester, can be used as monomers for the preparation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (1), where the bond(s) to the polymer, oligomer or dendrimer may be localised at any desired positions in formula (1) substituted by R. Depending on the linking of the compound of the formula (1), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (1) may, for example, be linked via a trivalent or polyvalent group, for example via a trivalent or polyvalent aromatic or heteroaromatic group, to give a branched or dendritic oligomer or polymer. The same preferences as described above for compounds of the formula (1) apply to the recurring units of the formula (1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The polymers, oligomers and dendrimers usually also contain further units, for example emitting (fluorescent or phosphorescent) units, such as, for example, vinyltriarylamines (for example in accordance with WO 07/068325) or phosphorescent metal complexes (for example in accordance with WO 06/003000), and/or charge-transport units, in particular those based on triarylamines.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 02/067343 A1 and WO 2005/026144 A1.

The compounds according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds according to the invention in an electronic device, in particular in an organic electroluminescent device.

The present invention still furthermore relates to an electronic device comprising at least one compound according to the invention. The preferences stated above likewise apply to the electronic devices.

The electronic device is preferably selected from the group consisting of organic electroluminescent devices (organic light-emitting diodes, OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells (ODSSCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), but preferably organic electroluminescent devices (OLEDs), particularly preferably phosphorescent OLEDs.

The organic electroluminescent devices and the light-emitting electrochemical cells can be employed for various applications, for example for mono-chromatic or polychromatic displays, for lighting applications or for medical and/or cosmetic applications, for example in phototherapy.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present.

The organic electroluminescent device here may comprise one emitting layer or a plurality of emitting layers. If a plurality of emission layers is present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed here in different layers, depending on the precise structure. Preference is given to an organic electroluminescent device comprising a compound of the formula (1) or the preferred embodiments as hole-transport material in a hole-transport or hole-injection or exciton-blocking layer or as matrix material for fluorescent or phosphorescent emitters, in particular for phosphorescent emitters. The preferred embodiments indicated above also apply to the use of the materials in organic electronic devices.

In a preferred embodiment of the invention, the compound of the formula (1) or the preferred embodiments is employed as hole-transport or hole-injection material in a hole-transport or hole-injection layer. The emitting layer here can be fluorescent or phosphorescent. A hole-injection layer in the sense of the present invention is a layer which is directly adjacent to the anode. A hole-transport layer in the sense of the present invention is a layer which is located between a hole-injection layer and an emitting layer.

In still a further preferred embodiment of the invention, the compound of the formula (1) or the preferred embodiments is employed in an exciton-blocking layer. An exciton-blocking layer is taken to mean a layer which is directly adjacent to an emitting layer on the anode side.

The compound of the formula (1) or the preferred embodiments is particularly preferably employed in a hole-transport or exciton-blocking layer.

If the compound of the formula (1) is employed as a hole-transport material in a hole-transport layer, a hole-injection layer or an exciton-blocking layer, then the compound of formula (1) can be used in such a layer as a single material, i.e. in a proportion of 100%, or the compound of formula (1) can be used in combination with one or more of the further compounds (HT-1 to HT-22) in such a layer:

HT-1

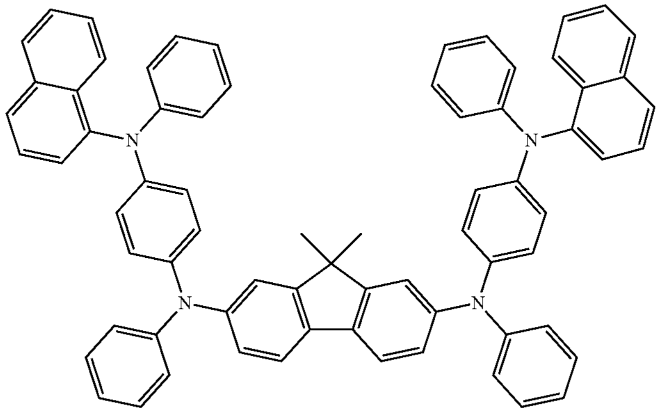

HT-2

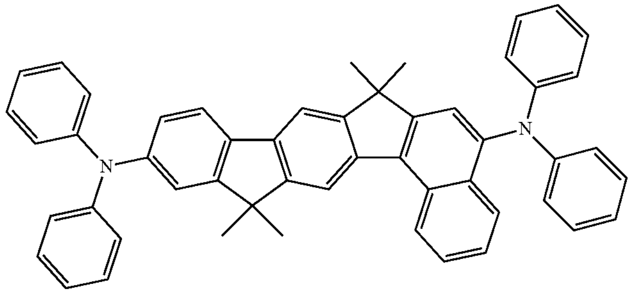

HT-3

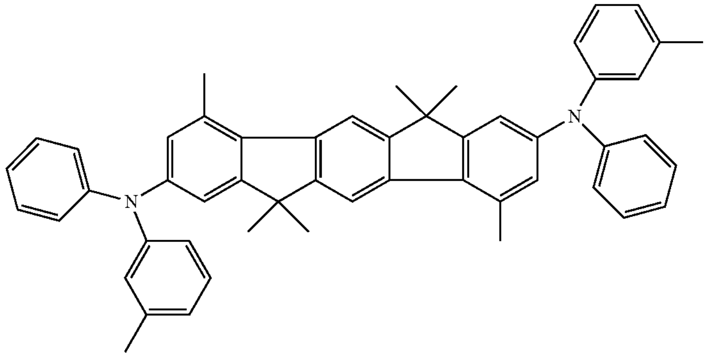

-continued
HT-4
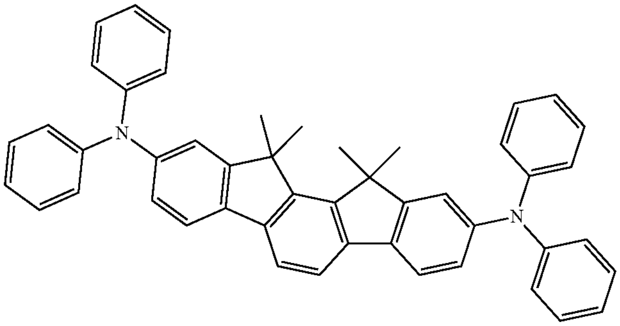
HT-5
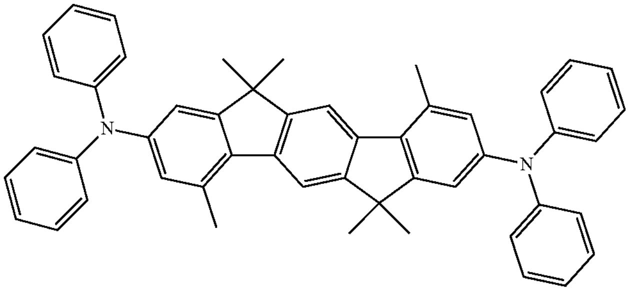
HT-6
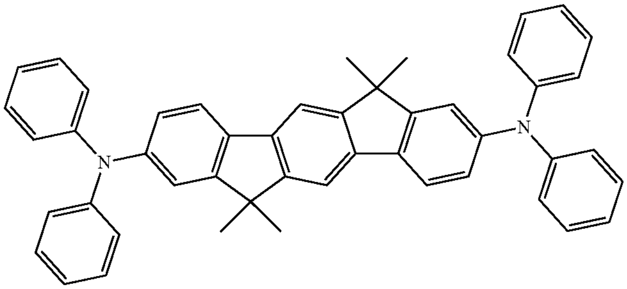
HT-7
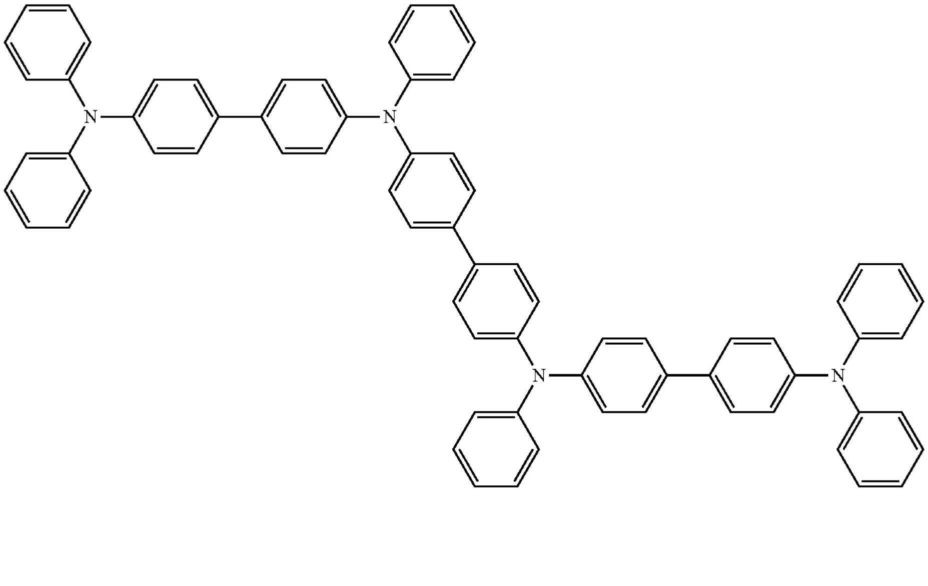

-continued
HT-8
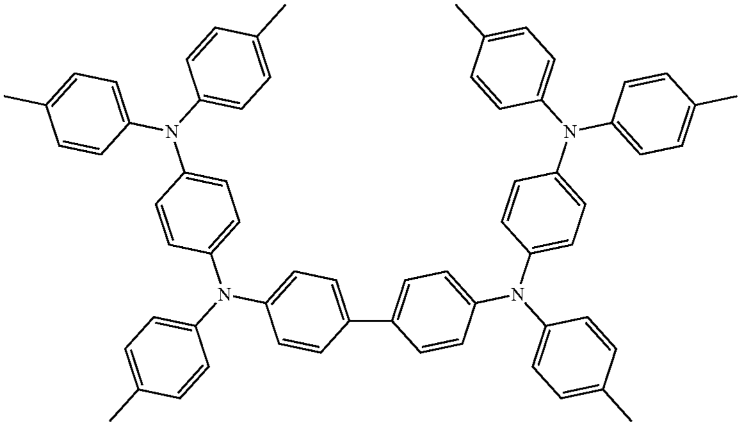
HT-9
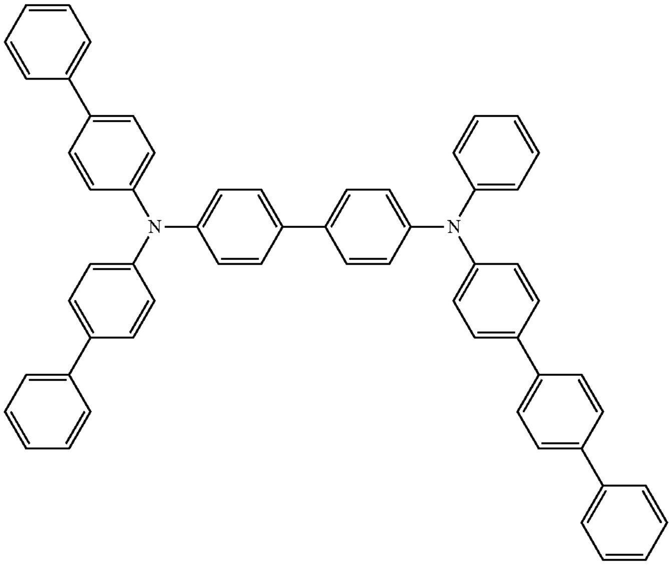
HT-10
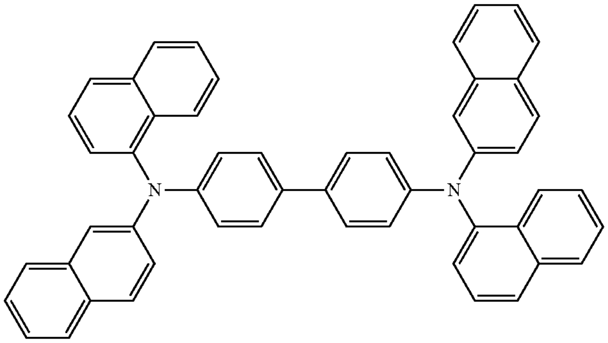
HT-11
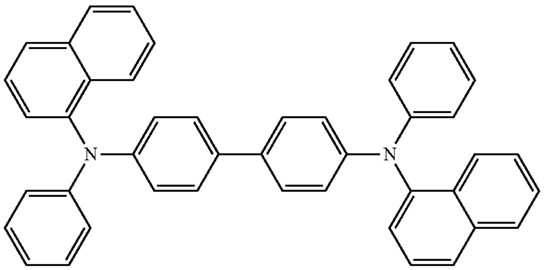

-continued
HT-12
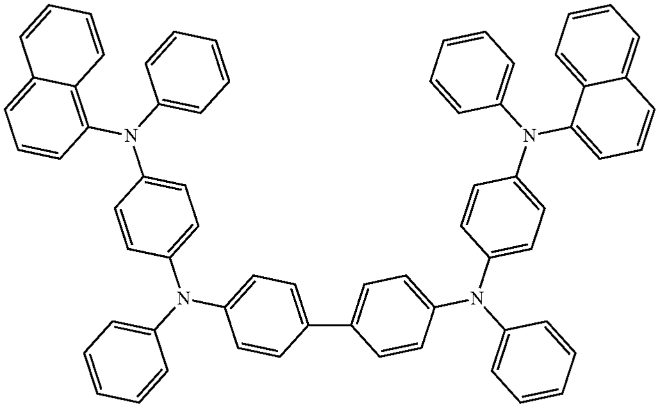
HT-13
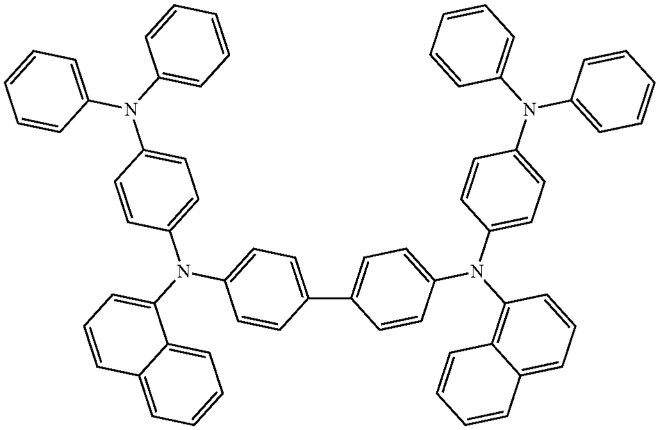
HT-14
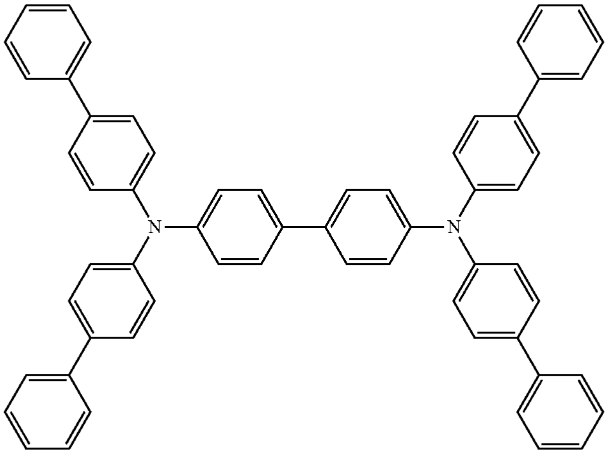
HT-15
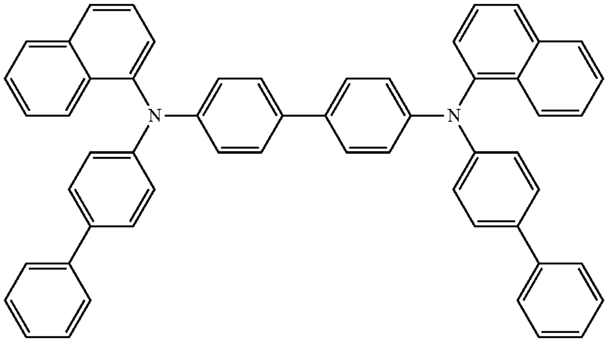

-continued
HT-16
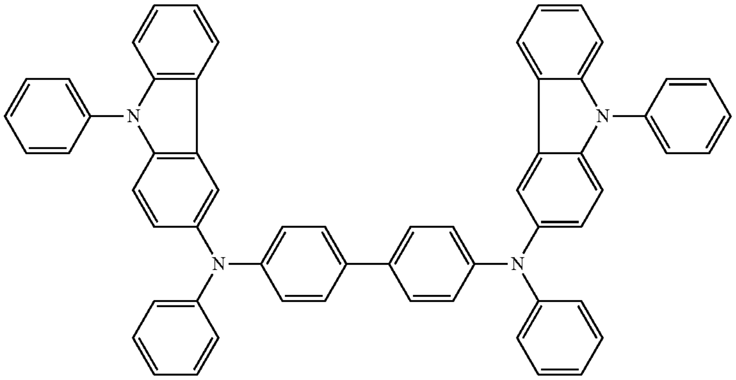
HT-17
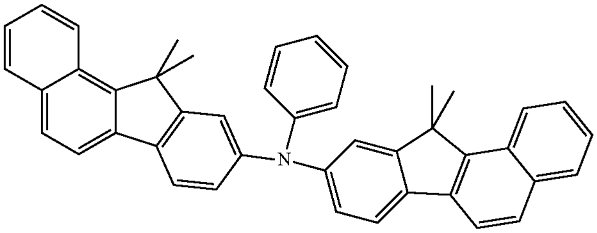
HT-18
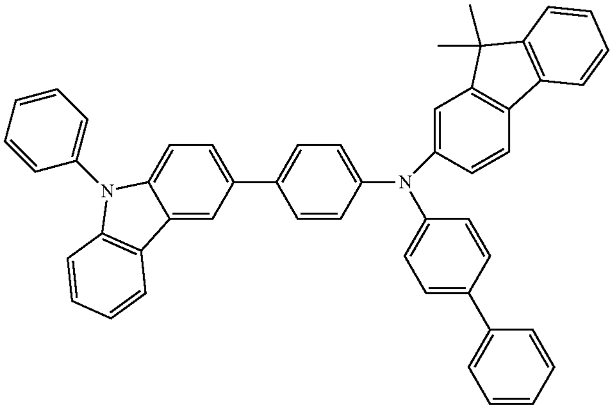
HT-19
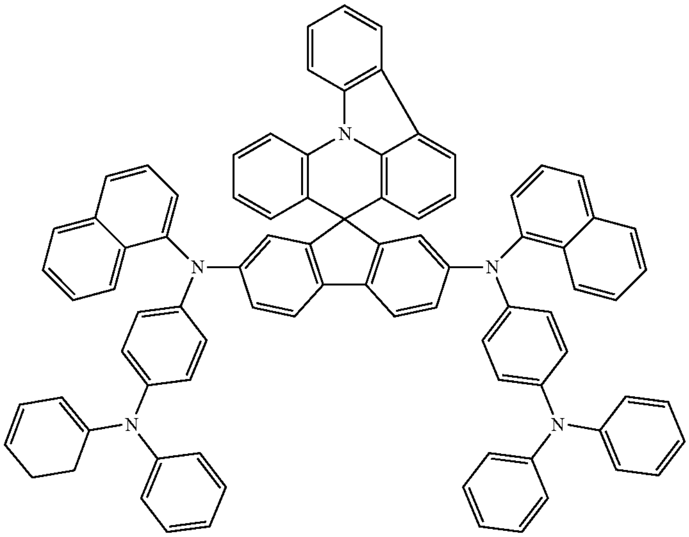

-continued

HT-20

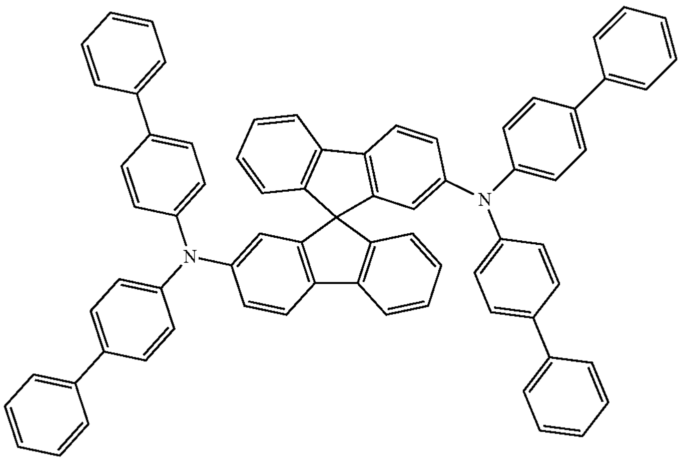

HT-21

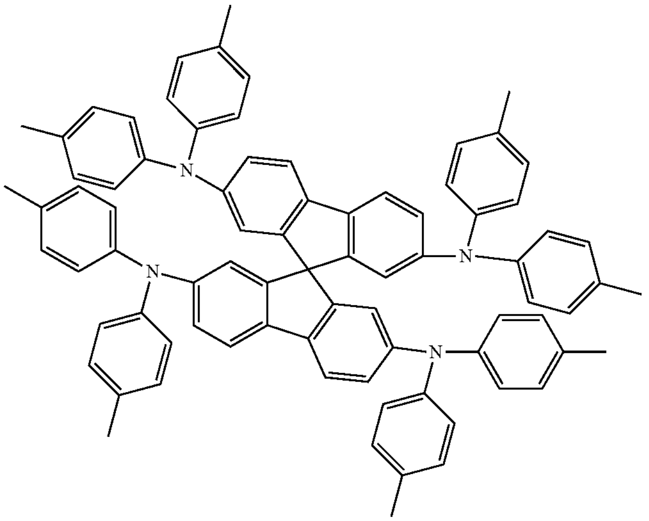

HT-22

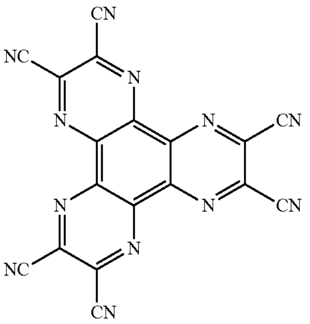

According to a preferred embodiment, the organic layer comprising the compound of formula (1) additionally comprises one or more p-dopants. Preferred p-dopant for the present invention are organic compounds that can accept electrons (electron acceptors) and can oxidize one or more of the other compounds present in the mixture.

Particularly preferred embodiments of p-dopants are described in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred as p-dopants are quinodimethane compounds, azaindenofluorendione, azaphenalene, azatriphenylene, $I_2$, metal halides, preferably transition metal halides, metal oxides, preferably metal oxides containing at least one transition metal or a metal of the 3rd main group and transition metal complexes, preferably complexes of Cu, Co, Ni, Pd and Pt with ligands containing at least one oxygen atom as binding site. Also preferred are transition metal oxides as dopants, preferably oxides of rhenium, molybdenum and tungsten, particularly preferably $Re_2O_7$, $MoO_3$, $WO_3$ and $ReO_3$.

The p-dopants are preferably distributed substantially uniformly in the p-doped layers. This can be achieved for example by co-evaporation of the p-dopant and of the hole-transport material matrix.
Particularly preferred p-dopants are selected from the compounds (D-1) to (D-13):
(D-1)
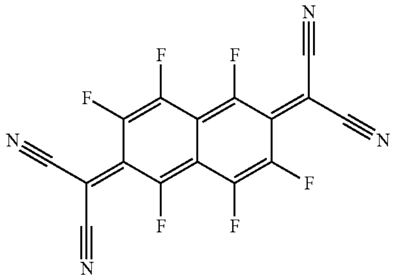
(D-2)
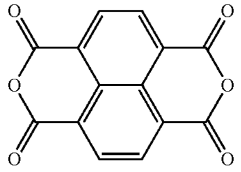
(D-3)
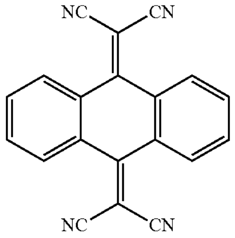
(D-4)
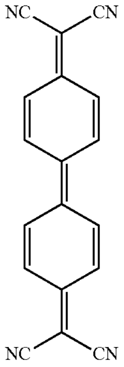
(D-5)
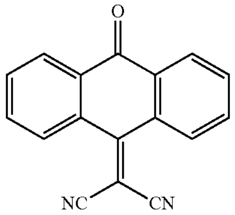
(D-6)
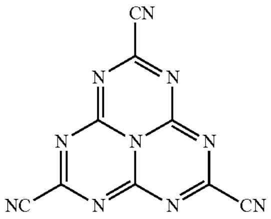
-continued
(D-7)
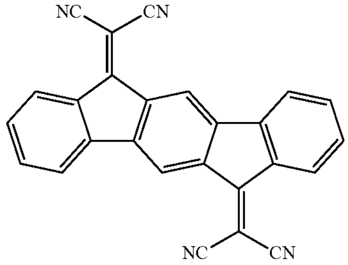
(D-8)
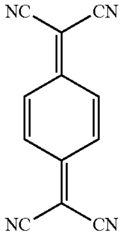
(D-9)
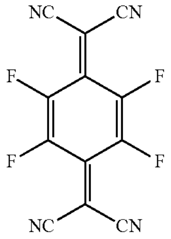
(D-10)
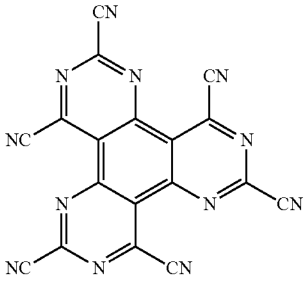
(D-11)
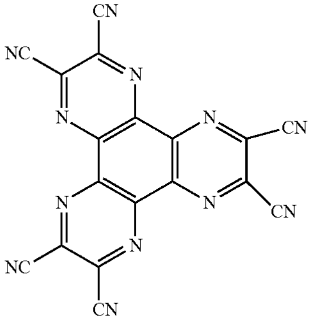

-continued (D-12)

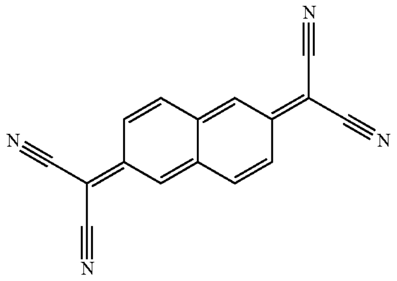

(D-13)

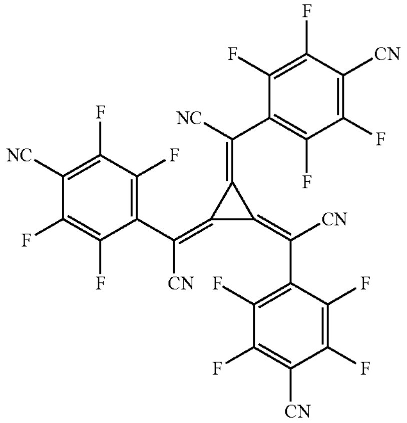

In an embodiment of the invention, the compound of the formula (1) or the preferred embodiments is used in a hole-transport or -injection layer in combination with a layer which comprises a hexaazatriphenylene derivative, in particular hexacyanohexaazatriphenylene (for example in accordance with EP 1175470). Thus, for example, preference is given to a combination which looks as follows: anode—hexaazatriphenylene derivative—hole-transport layer, where the hole-transport layer comprises one or more compounds of the formula (1) or the preferred embodiments. It is likewise possible in this structure to use a plurality of successive hole-transport layers, where at least one hole-transport layer comprises at least one compound of the formula (1) or the preferred embodiments. A further preferred combination looks as follows: anode—hole-transport layer—hexaazatriphenylene derivative—hole-transport layer, where at least one of the two hole-transport layers comprises one or more compounds of the formula (1) or the preferred embodiments. It is likewise possible in this structure to use a plurality of successive hole-transport layers instead of one hole-transport layer, where at least one hole-transport layer comprises at least one compound of the formula (1) or the preferred embodiments.

In a further preferred embodiment of the invention, the compound of the formula (1) or the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

Typical fluorescent compounds used in the emitting layers are depicted in the following Table:

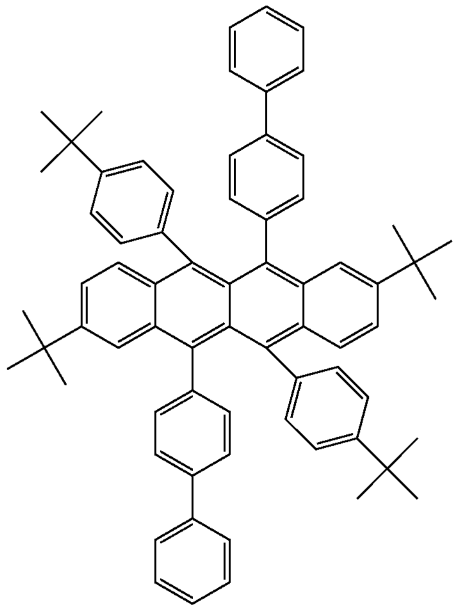 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

-continued
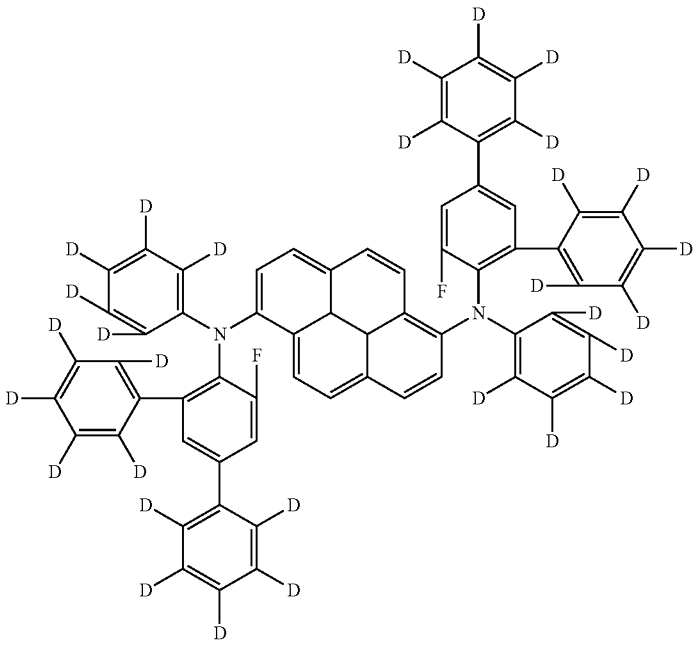 [SMILES: [2H]c1c([2H])c([2H])c(-c2cc(F)c(N(C3=CC=C4C=CC5=C(N(c6c(F)cc(-c7c([2H])c([2H])c([2H])c([2H])c7[2H])cc6-c6c([2H])c([2H])c([2H])c([2H])c6[2H])c6c([2H])c([2H])c([2H])c([2H])c6[2H])C=CC6=CC=C3C4C65)c3c([2H])c([2H])c([2H])c([2H])c3[2H])c(-c3c([2H])c([2H])c([2H])c([2H])c3[2H])c2)c([2H])c1[2H]]
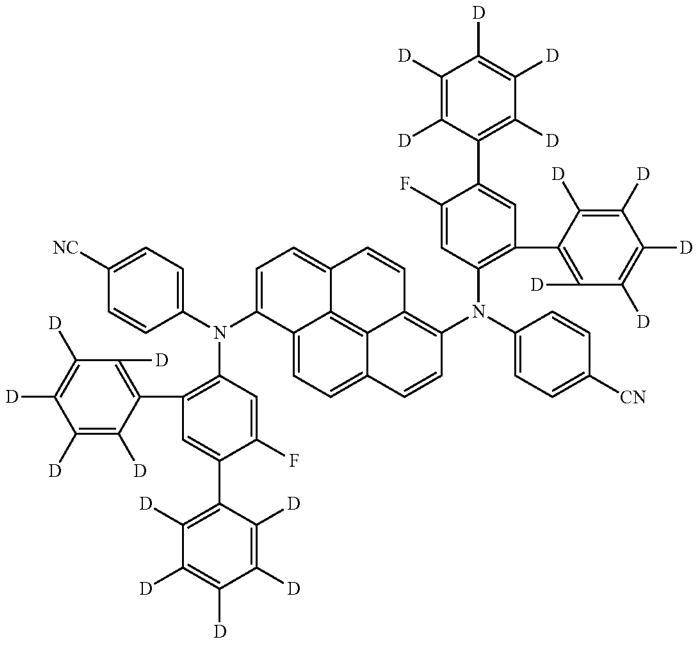 [SMILES: [2H]c1c([2H])c([2H])c(-c2cc(-c3c([2H])c([2H])c([2H])c([2H])c3[2H])c(N(c3ccc(C#N)cc3)c3ccc4ccc5c(N(c6ccc(C#N)cc6)c6cc(F)c(-c7c([2H])c([2H])c([2H])c([2H])c7[2H])cc6-c6c([2H])c([2H])c([2H])c([2H])c6[2H])ccc6ccc3c4c65)cc2F)c([2H])c1[2H]]

-continued
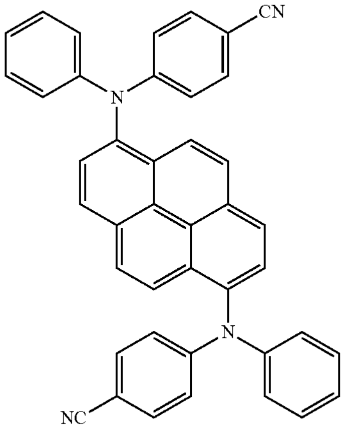 [SMILES: N#Cc1ccc(N(c2ccccc2)c2ccc3ccc4c(N(c5ccccc5)c5ccc(C#N)cc5)ccc5ccc2c3c54)cc1]
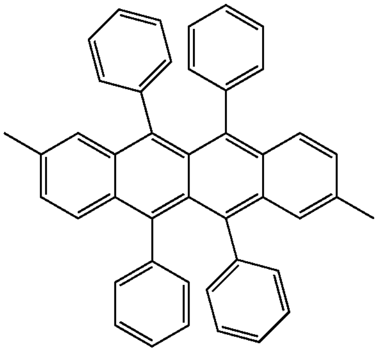
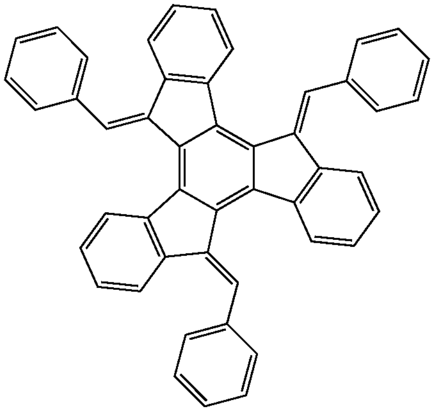 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]
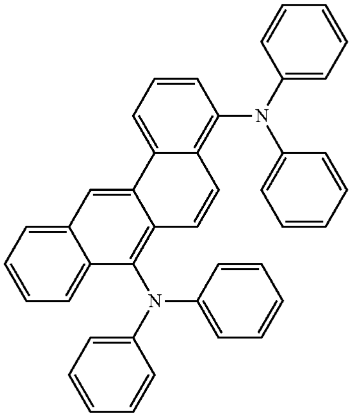 [SMILES: c1ccc(N(c2ccccc2)c2cccc3c2ccc2c(N(c4ccccc4)c4ccccc4)c4ccccc4cc23)cc1]

-continued
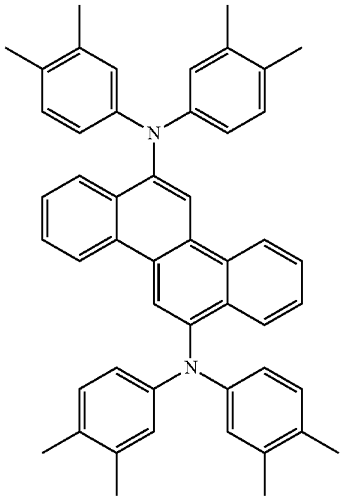
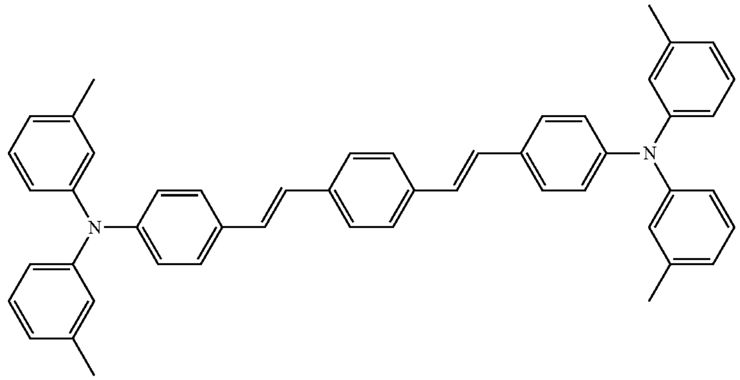 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]
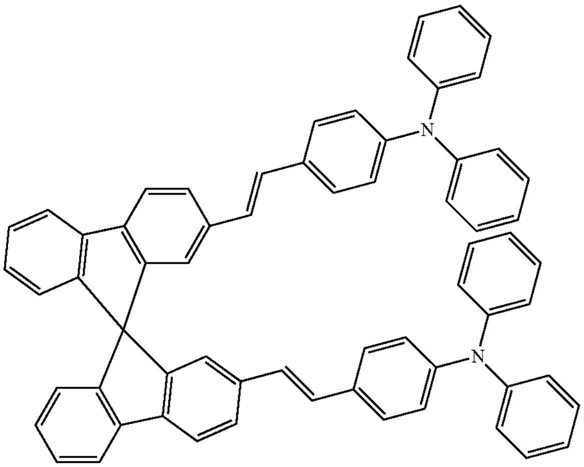 [SMILES: C(=C\c1ccc2c(c1)C1(c3ccccc3-2)c2ccccc2-c2ccc(/C=C/c3ccc(N(c4ccccc4)c4ccccc4)cc3)cc21)/c1ccc(N(c2ccccc2)c2ccccc2)cc1]

-continued
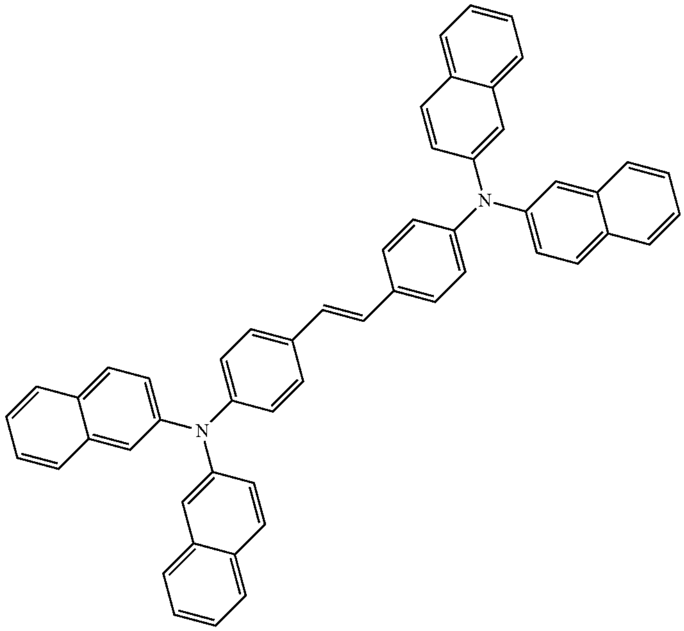 [SMILES: C(=C\c1ccc(N(c2ccc3ccccc3c2)c2ccc3ccccc3c2)cc1)/c1ccc(N(c2ccc3ccccc3c2)c2ccc3ccccc3c2)cc1]
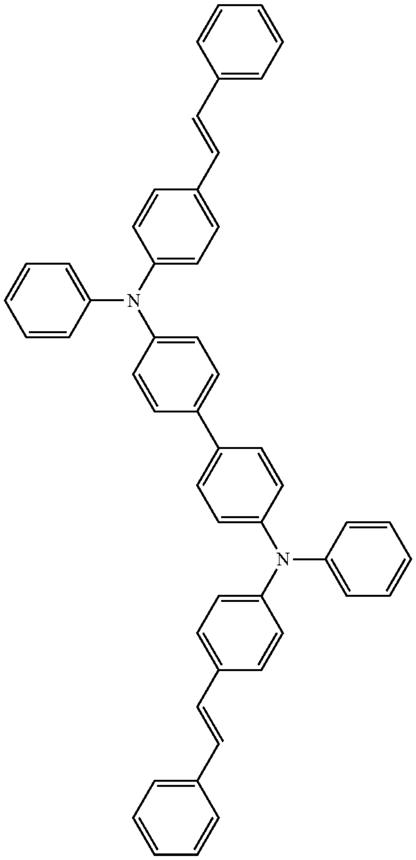 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]

-continued
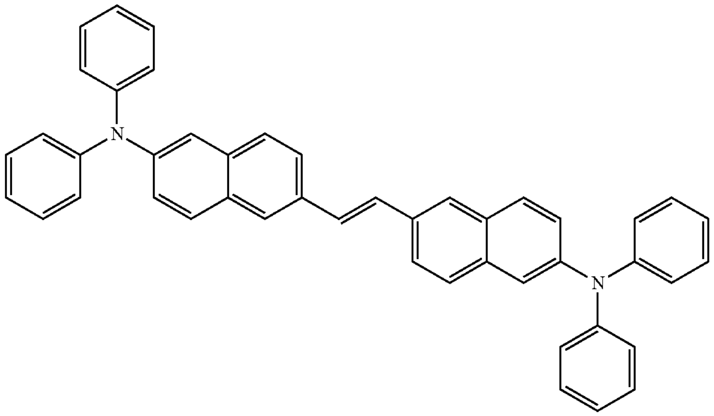 [SMILES: C(=C\c1ccc2cc(N(c3ccccc3)c3ccccc3)ccc2c1)/c1ccc2cc(N(c3ccccc3)c3ccccc3)ccc2c1]
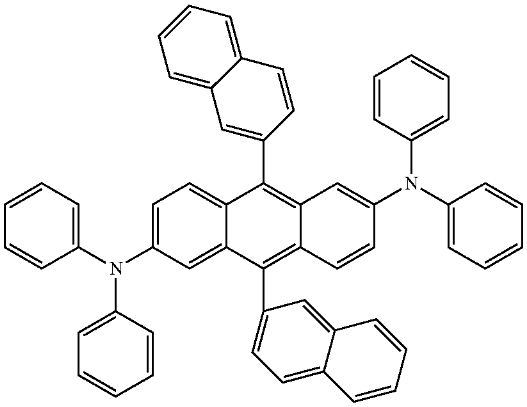 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
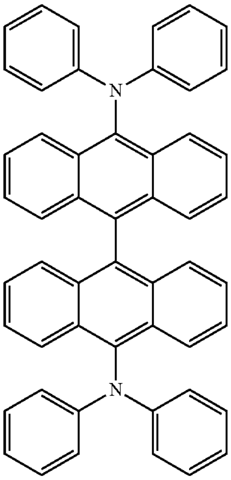 [SMILES: c1ccc(N(c2ccccc2)c2c3ccccc3c(-c3c4ccccc4c(N(c4ccccc4)c4ccccc4)c4ccccc34)c3ccccc23)cc1]

-continued
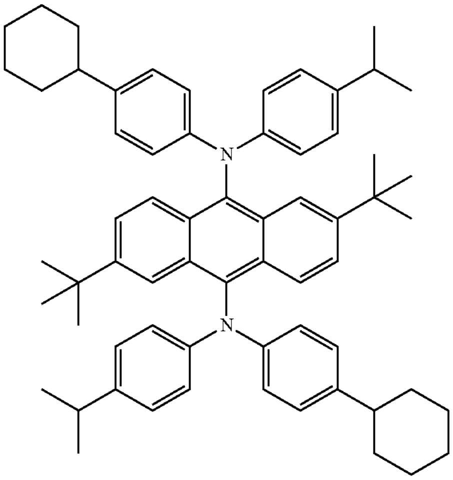 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
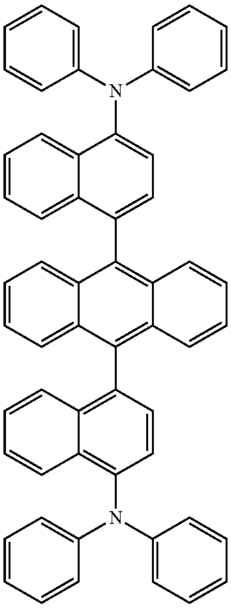 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]
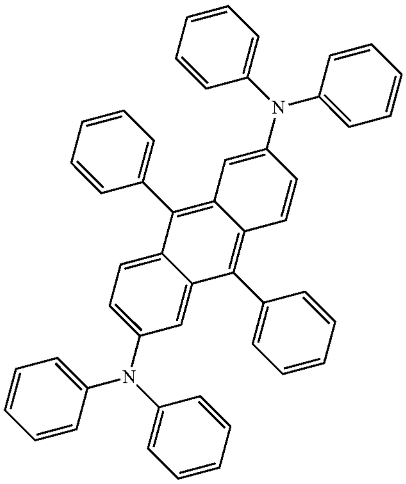 [SMILES: c1ccc(-c2c3ccc(N(c4ccccc4)c4ccccc4)cc3c(-c3ccccc3)c3ccc(N(c4ccccc4)c4ccccc4)cc23)cc1]

-continued
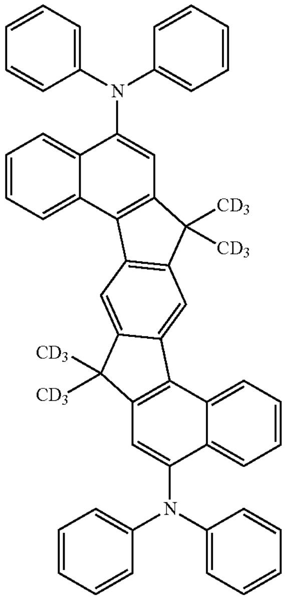 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]
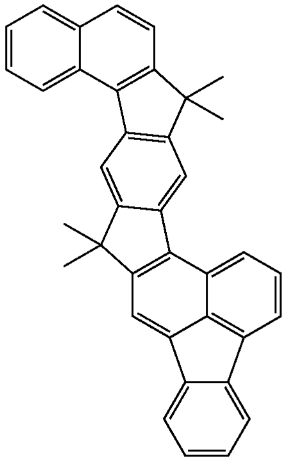 [SMILES: CC1(C)c2cc3c(cc2-c2c1ccc1ccccc21)C(C)(C)c1cc2c4c(cccc4c1-3)-c1ccccc1-2]
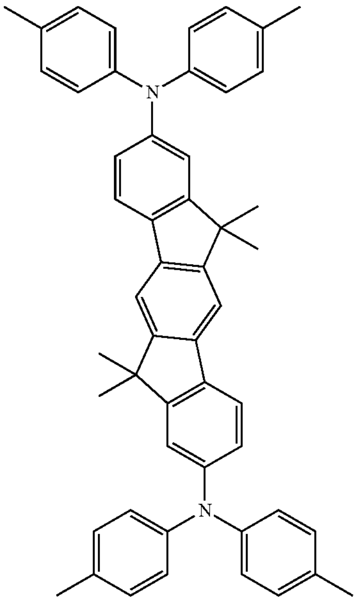

-continued
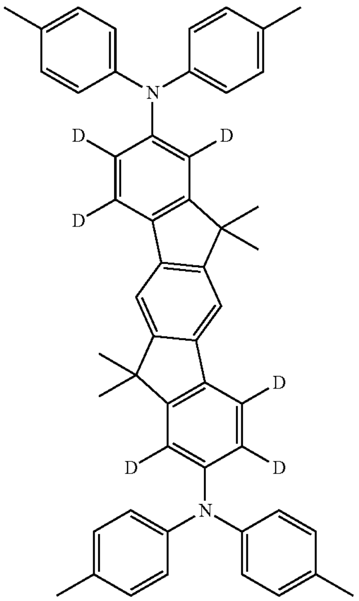
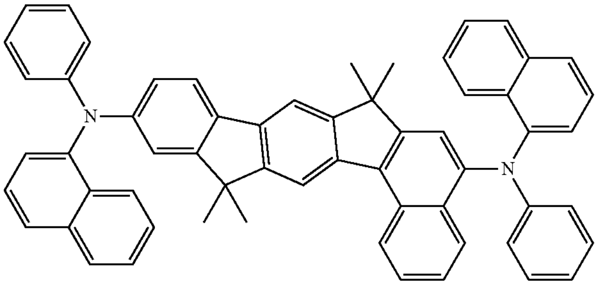 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
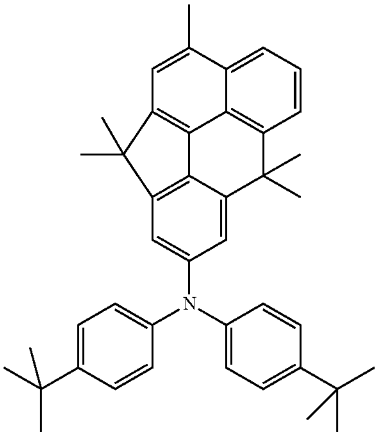 [SMILES: Cc1cc2c3c4c(cccc14)C(C)(C)c1cc(N(c4ccc(C(C)(C)C)cc4)c4ccc(C(C)(C)C)cc4)cc(c1-3)C2(C)C]

-continued
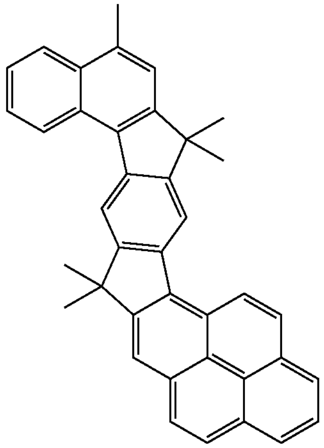 [SMILES: Cc1cc2c(c3ccccc13)-c1cc3c(cc1C2(C)C)-c1c(cc2ccc4cccc5ccc1c2c45)C3(C)C]
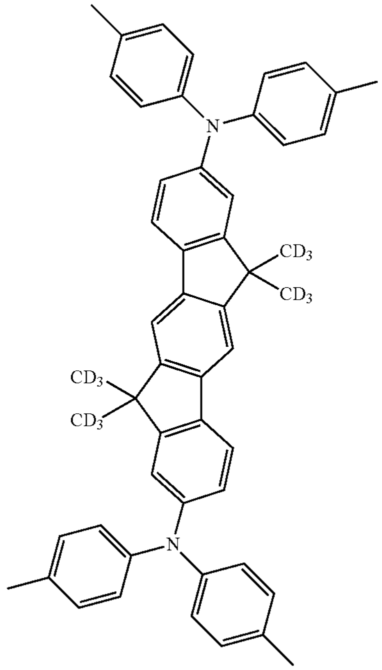
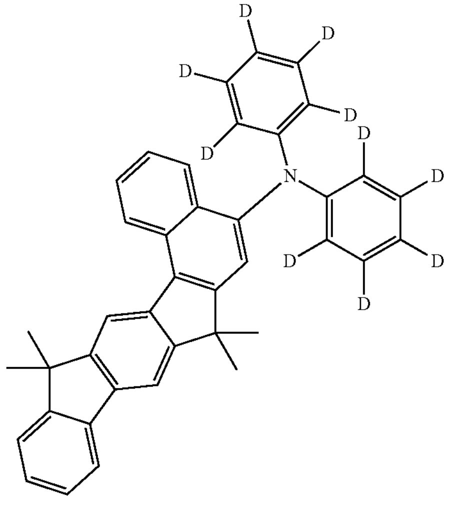 [SMILES: [2H]c1c([2H])c([2H])c(N(c2c([2H])c([2H])c([2H])c([2H])c2[2H])c2cc3c(c4ccccc24)-c2cc4c(cc2C3(C)C)-c2ccccc2C4(C)C)c([2H])c1[2H]]

-continued
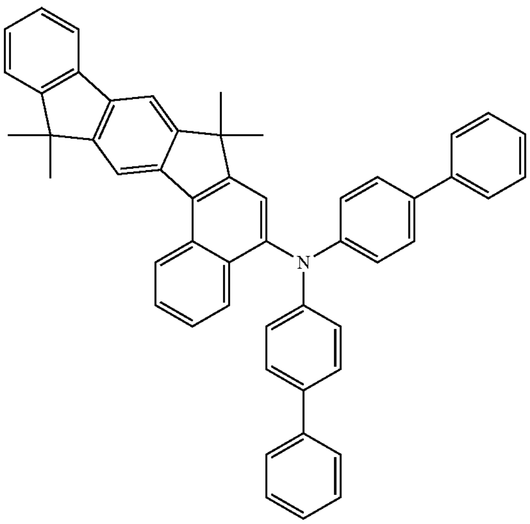 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]
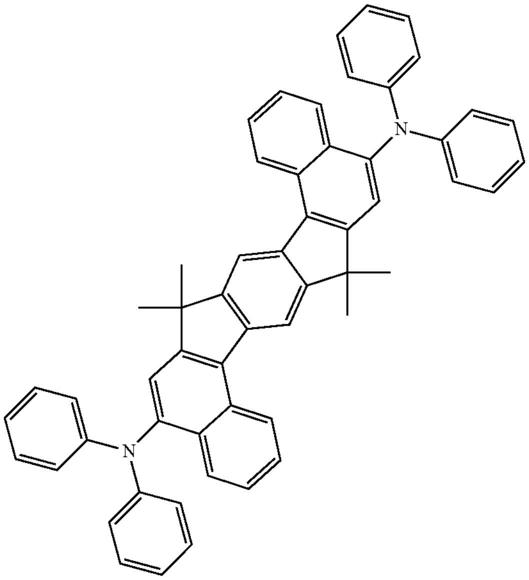 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]
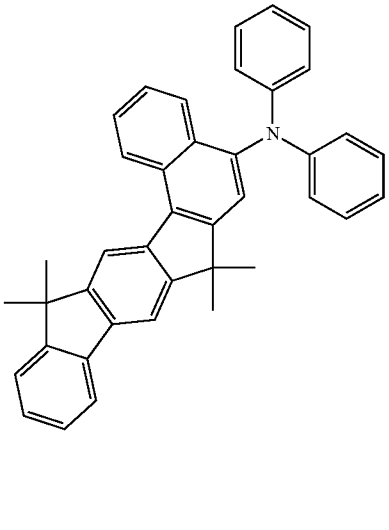 [SMILES: CC1(C)c2ccccc2-c2cc3c(cc21)-c1c(cc(N(c2ccccc2)c2ccccc2)c2ccccc12)C3(C)C]

-continued
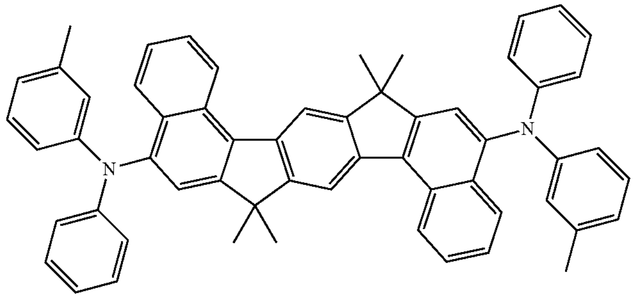 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
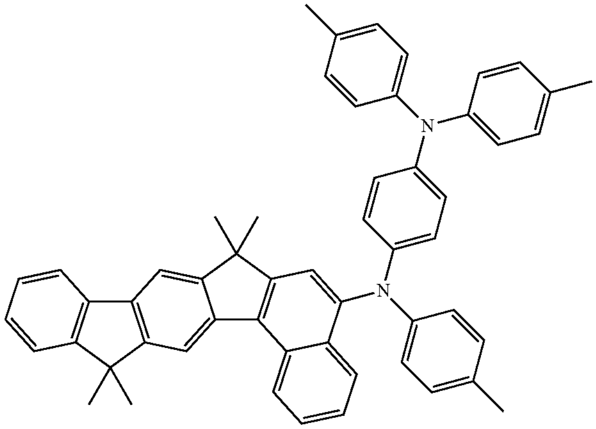 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
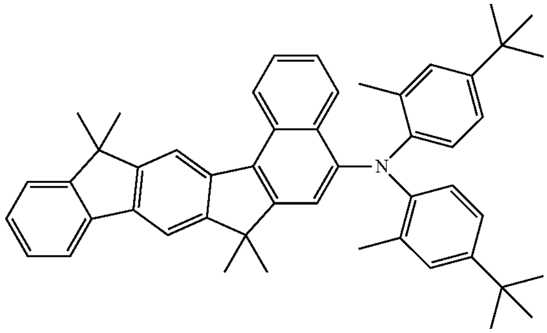 [SMILES: Cc1cc(C(C)(C)C)ccc1N(c1ccc(C(C)(C)C)cc1C)c1cc2c(c3ccccc13)-c1cc3c(cc1C2(C)C)-c1ccccc1C3(C)C]
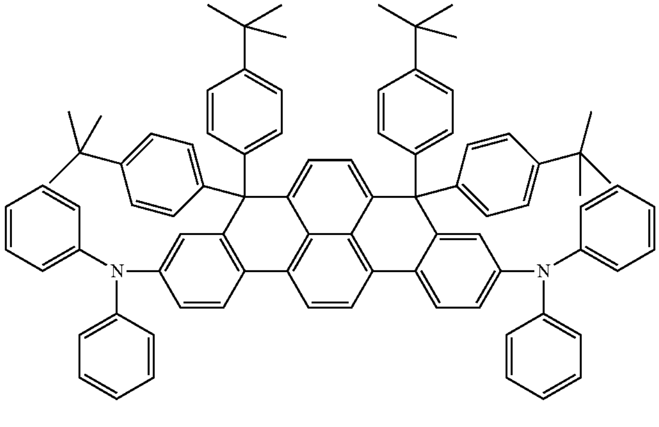 [SMILES: CC(C)(C)c1ccc(C2(c3ccc(C(C)(C)C)cc3)c3cc(N(c4ccccc4)c4ccccc4)ccc3-c3ccc4c5c(ccc2c35)C(c2ccc(C(C)(C)C)cc2)(c2ccc(C(C)(C)C)cc2)c2cc(N(c3ccccc3)c3ccccc3)ccc2-4)cc1]

-continued
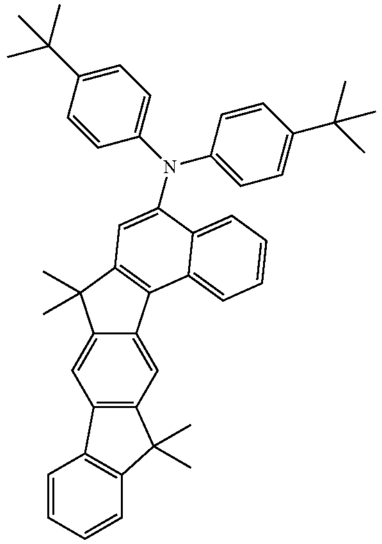 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
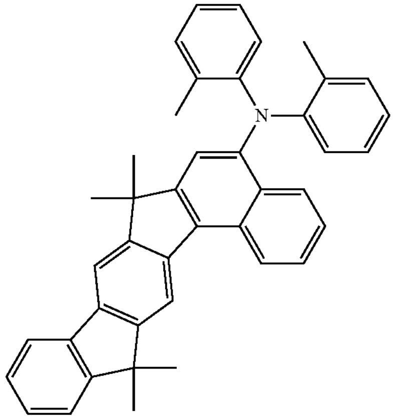 [SMILES: Cc1ccccc1N(c1ccccc1C)c1cc2c(c3ccccc13)-c1cc3c(cc1C2(C)C)-c1ccccc1C3(C)C]
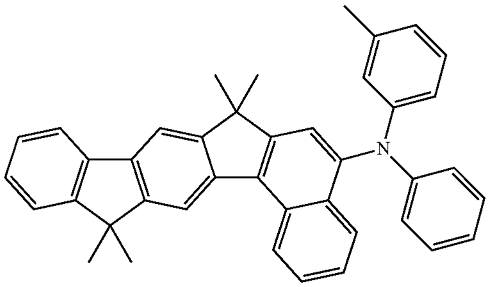 [SMILES: Cc1cccc(N(c2ccccc2)c2cc3c(c4ccccc24)-c2cc4c(cc2C3(C)C)-c2ccccc2C4(C)C)c1]
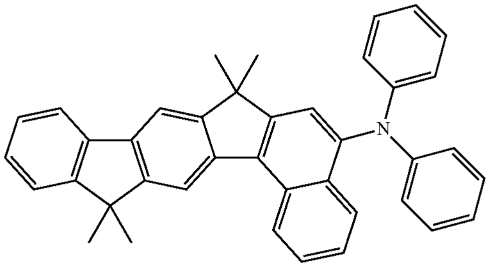 [SMILES: CC1(C)c2ccccc2-c2cc3c(cc21)-c1c(cc(N(c2ccccc2)c2ccccc2)c2ccccc12)C3(C)C]

-continued
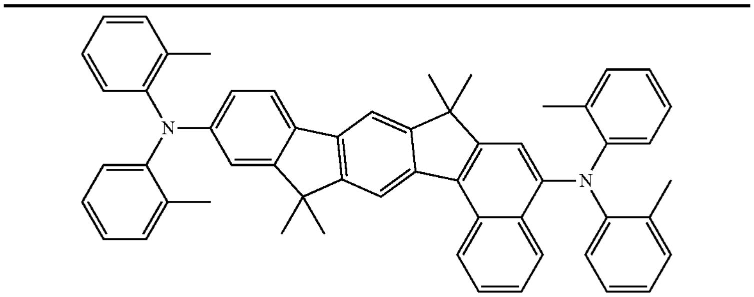
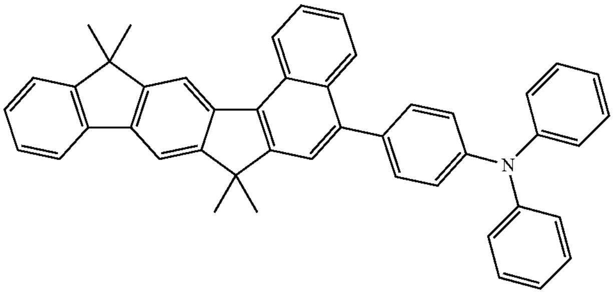 [SMILES: CC1(C)c2ccccc2-c2cc3c(cc21)-c1c(cc(-c2ccc(N(c4ccccc4)c4ccccc4)cc2)c2ccccc12)C3(C)C]
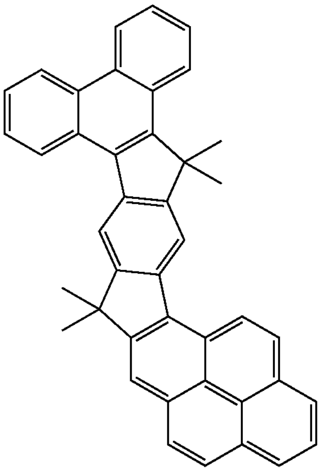 [SMILES: CC1(C)c2cc3c(cc2-c2c1cc1ccc4cccc5ccc2c1c45)C(C)(C)c1c-3c2ccccc2c2ccccc12]
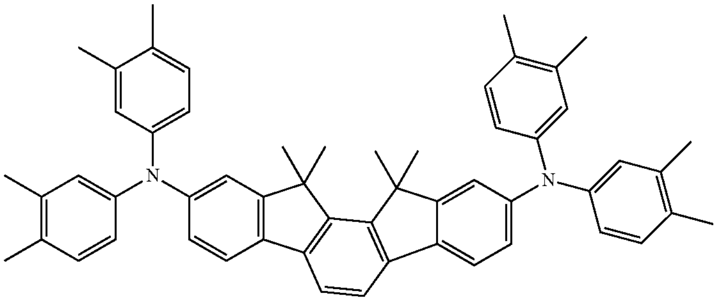
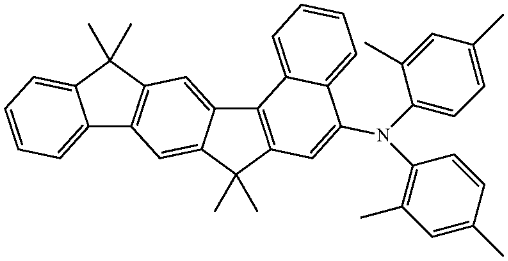 [SMILES: Cc1ccc(N(c2ccc(C)cc2C)c2cc3c(c4ccccc24)-c2cc4c(cc2C3(C)C)-c2ccccc2C4(C)C)c(C)c1]

-continued
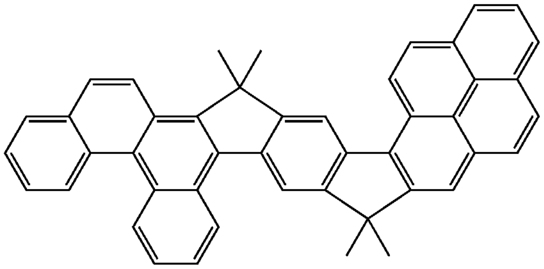 [SMILES: CC1(C)c2cc3c(cc2-c2c1cc1ccc4cccc5ccc2c1c45)C(C)(C)c1c-3c2ccccc2c2c1ccc1ccccc12]
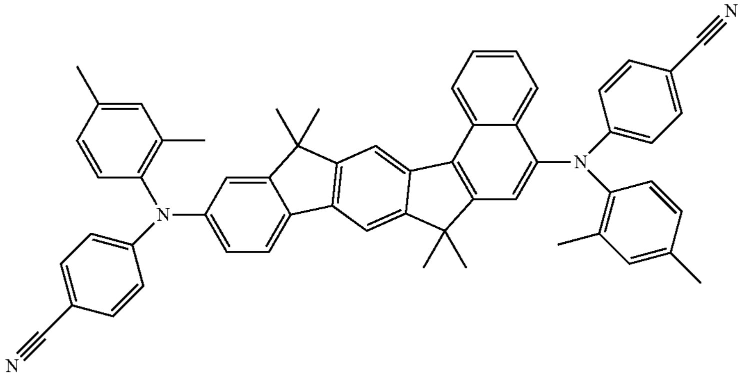 [SMILES: Cc1ccc(N(c2ccc(C#N)cc2)c2ccc3c(c2)C(C)(C)c2cc4c(cc2-3)C(C)(C)c2cc(N(c3ccc(C#N)cc3)c3ccc(C)cc3C)c3ccccc3c2-4)c(C)c1]
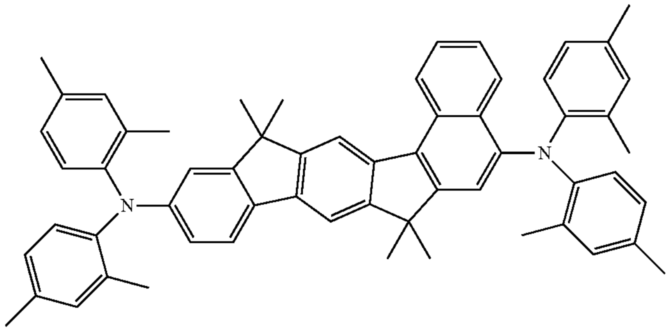
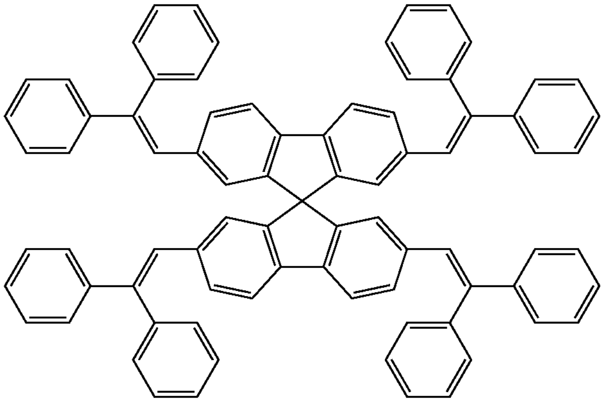 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]

-continued
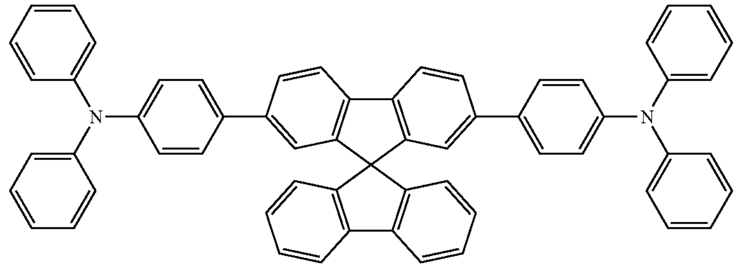 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]
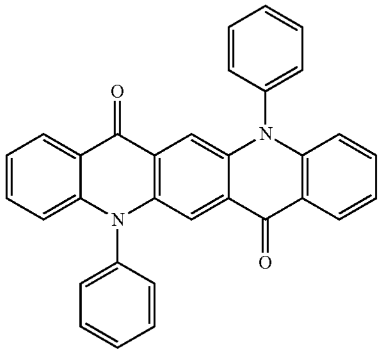 [SMILES: O=c1c2ccccc2n(-c2ccccc2)c2cc3c(=O)c4ccccc4n(-c4ccccc4)c3cc12]
Typical phosphorescent compounds used in the emitting layers are depicted in the following Table:
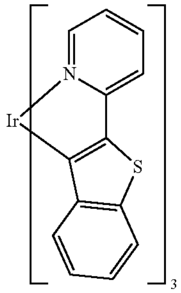
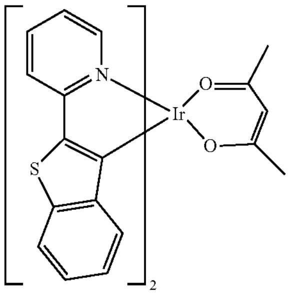
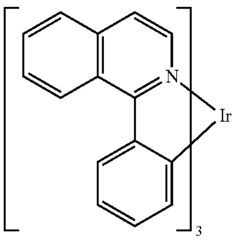
-continued
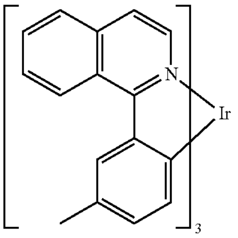
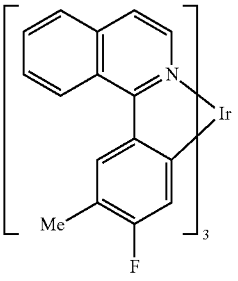
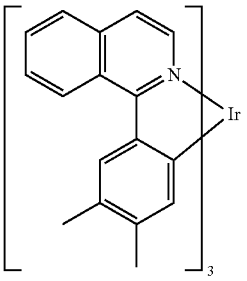

-continued
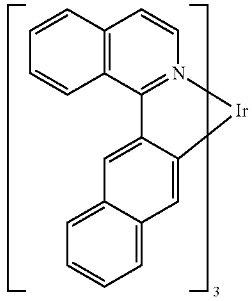
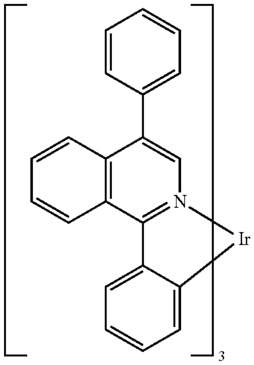
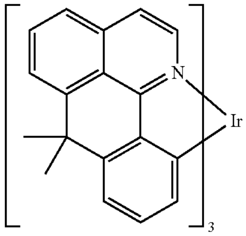
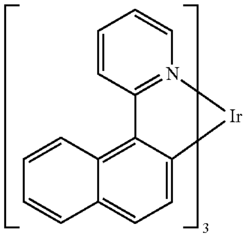
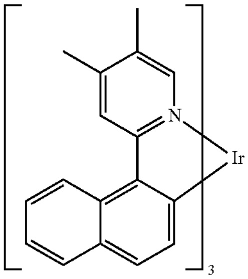
-continued
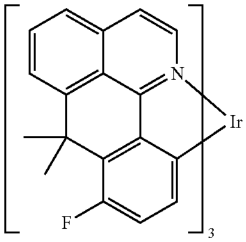
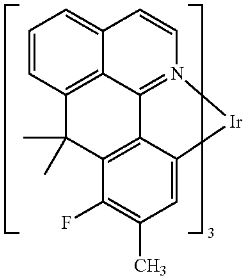
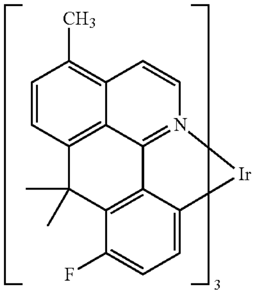
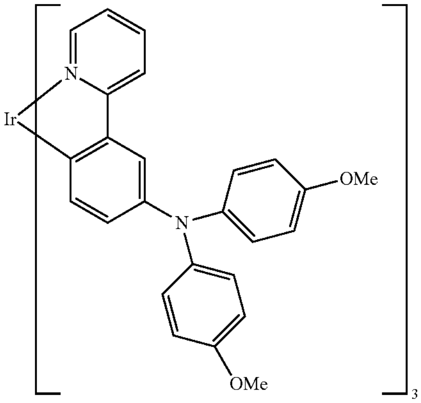
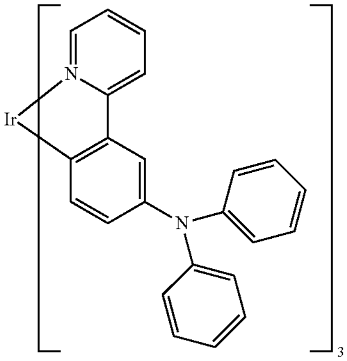

-continued
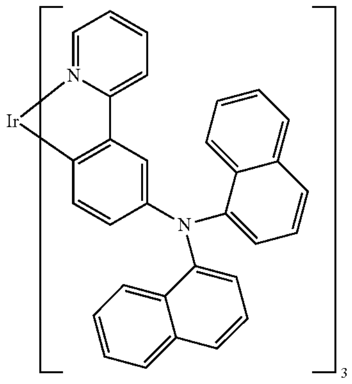
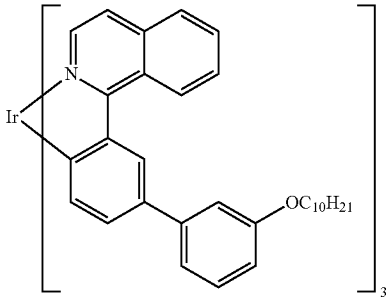
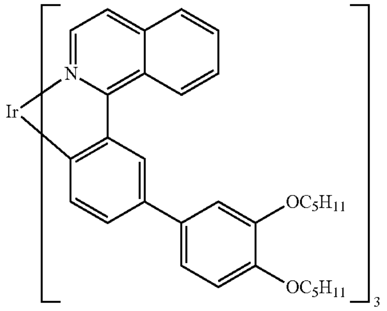
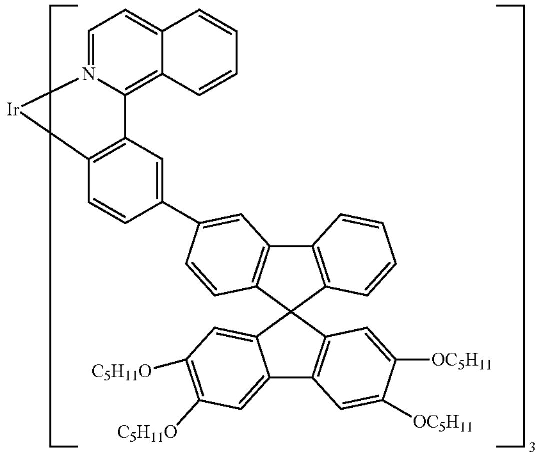
-continued
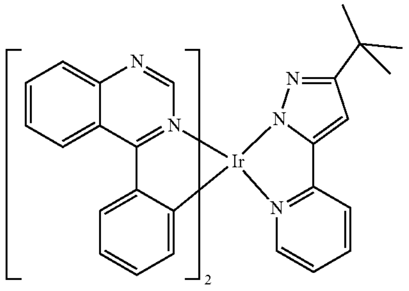
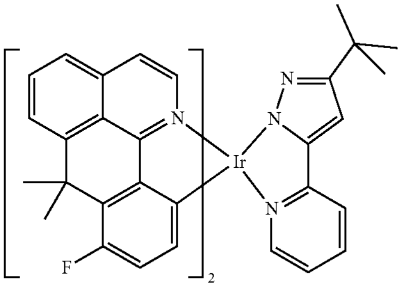
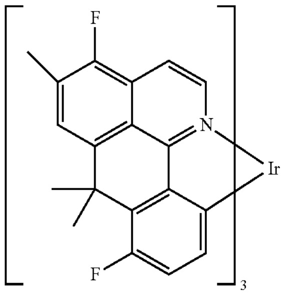
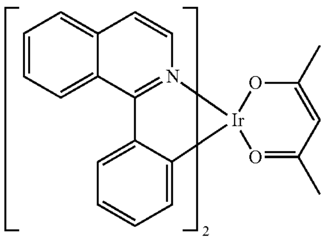
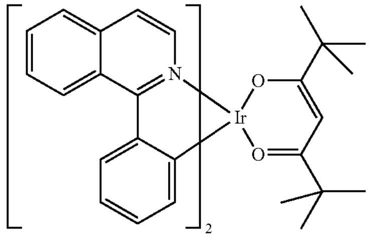
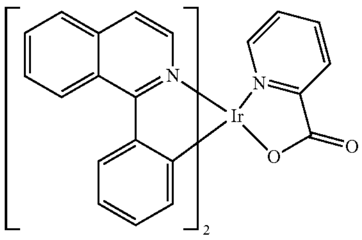

-continued
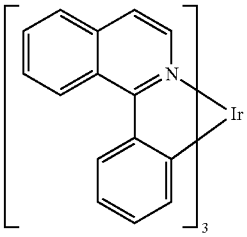
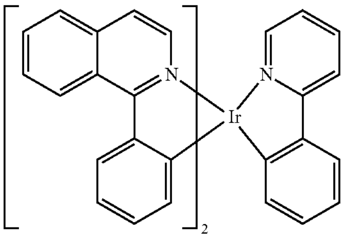
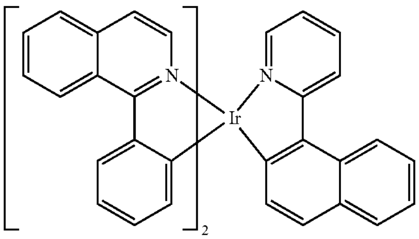
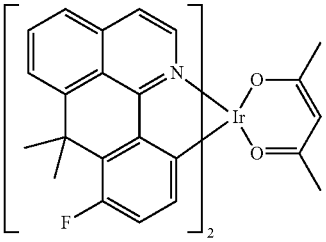
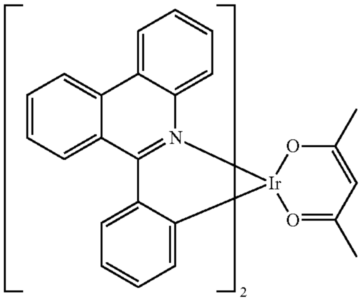
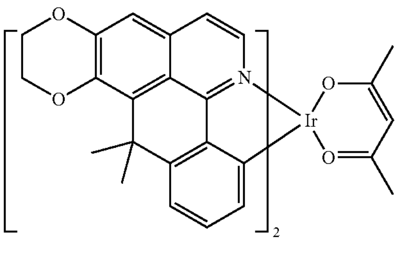
-continued
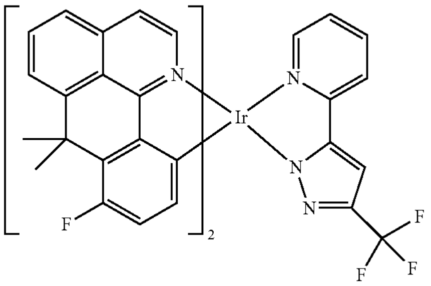
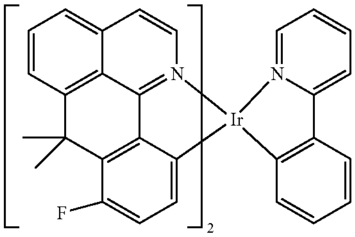
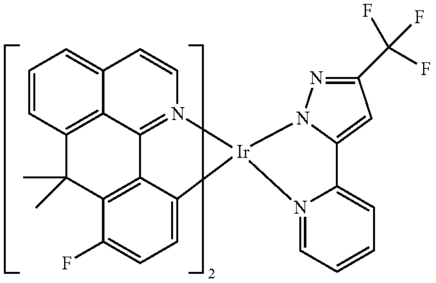
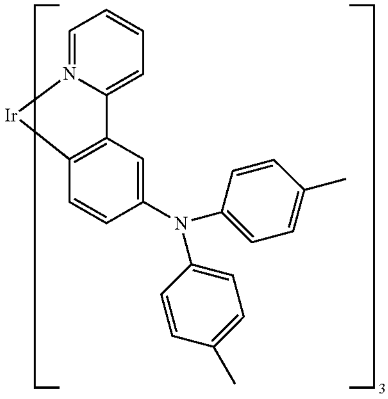
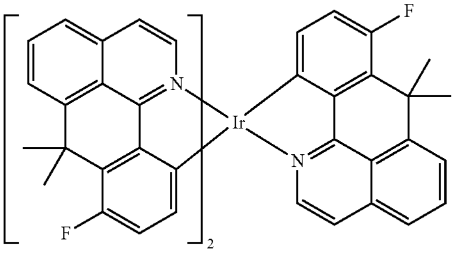

-continued
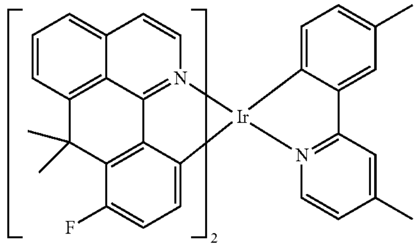
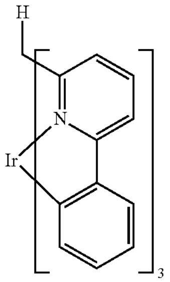
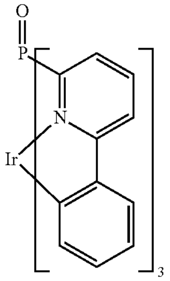
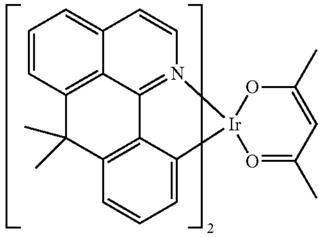
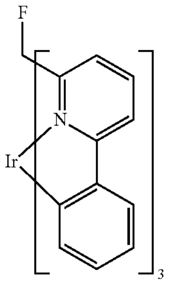
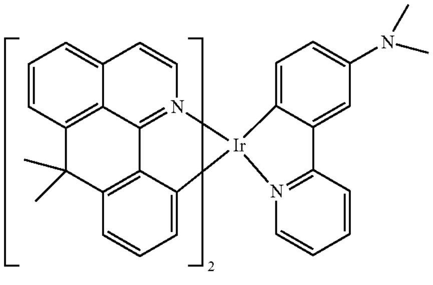
-continued
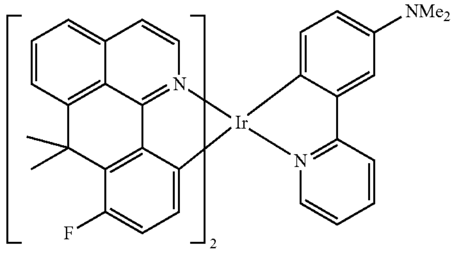
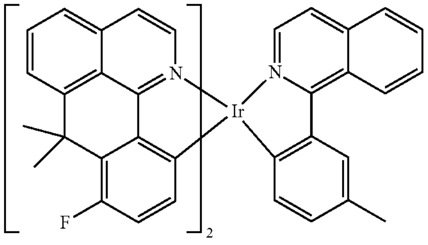
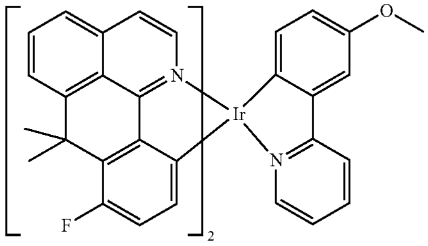
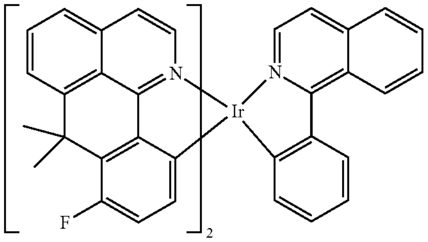
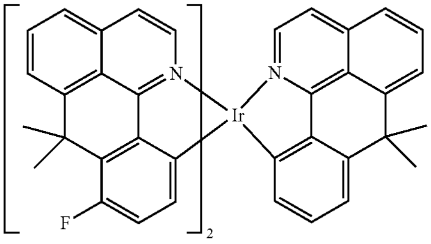

-continued
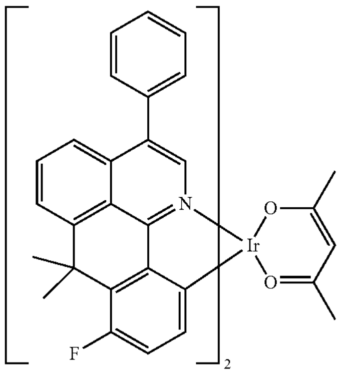
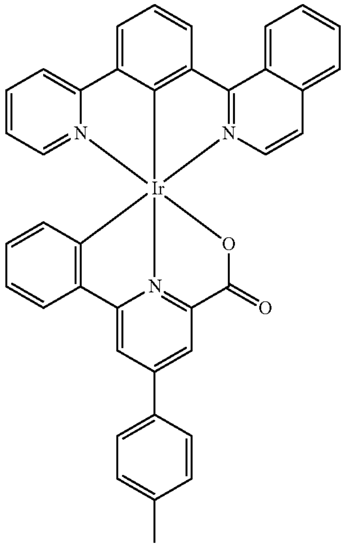
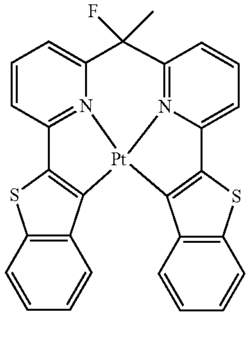
-continued
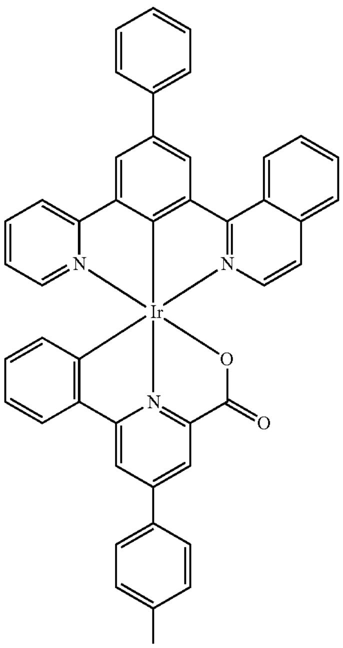
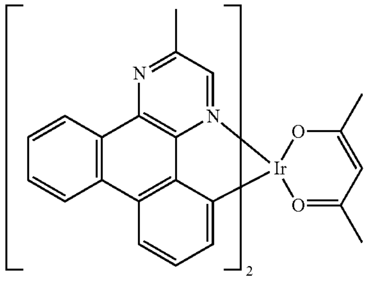
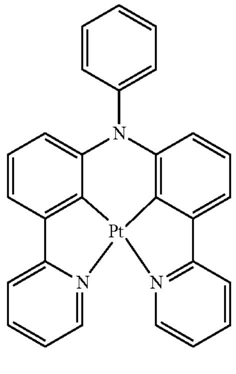
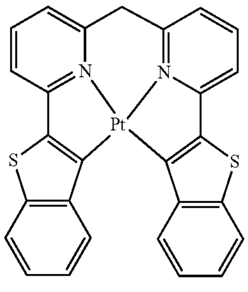

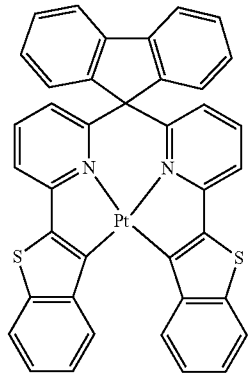
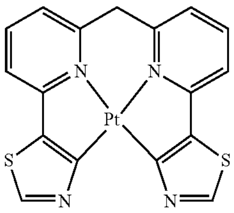
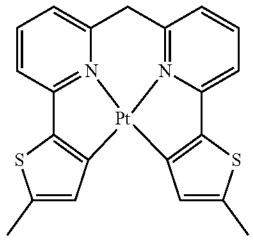
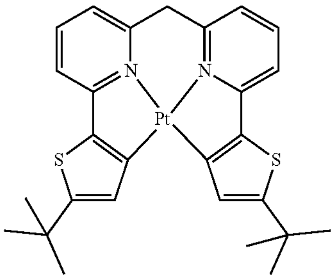
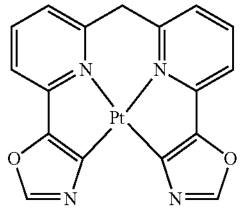
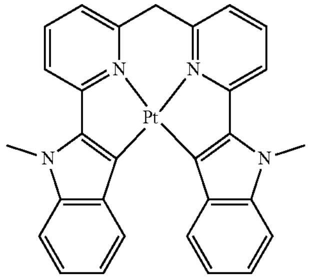
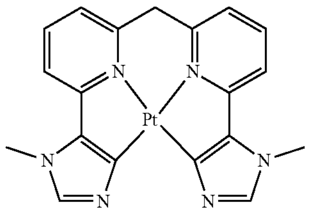
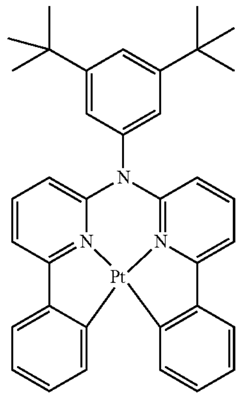
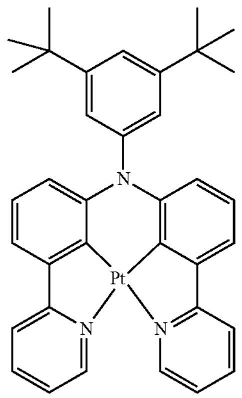
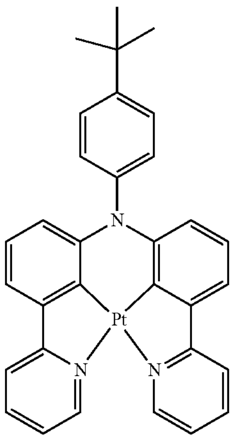

-continued
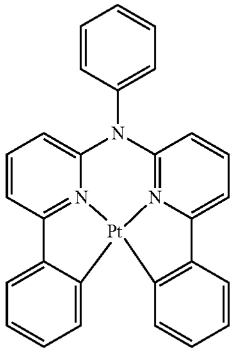
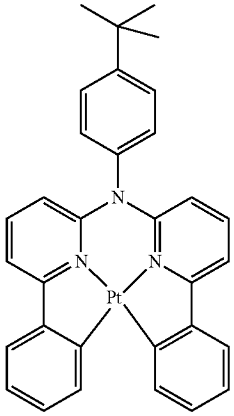
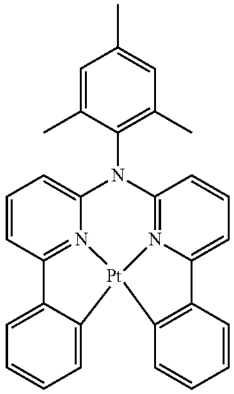
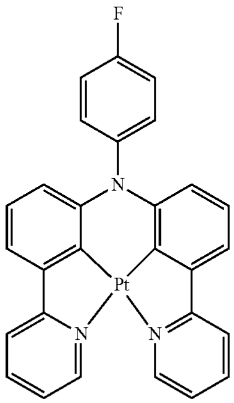
-continued
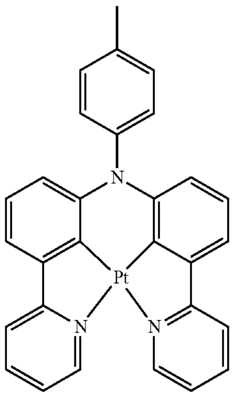
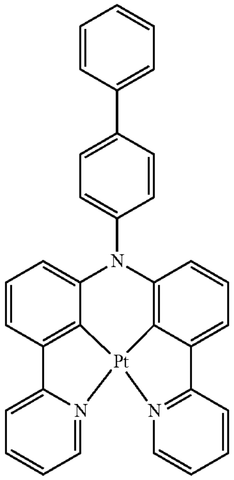
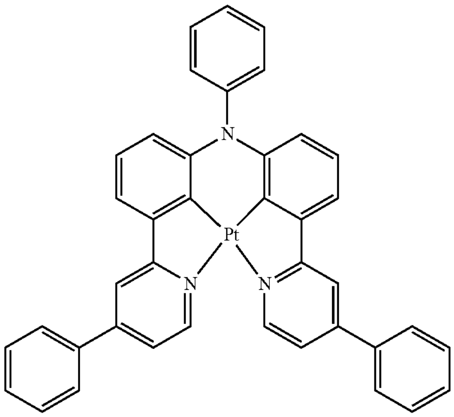

-continued
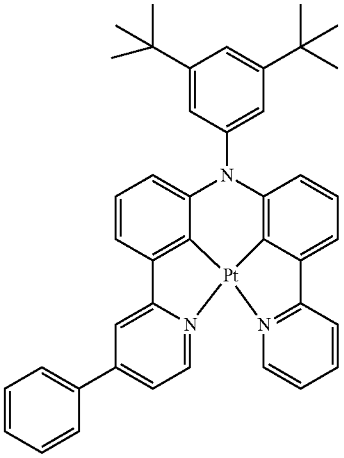
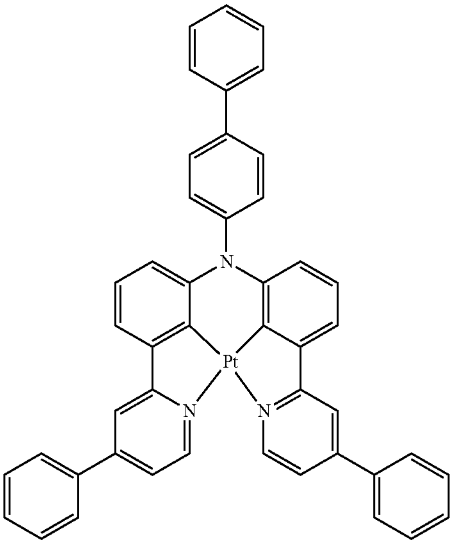
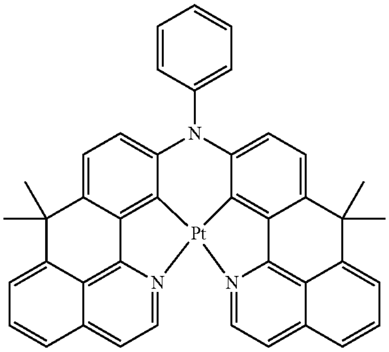
-continued
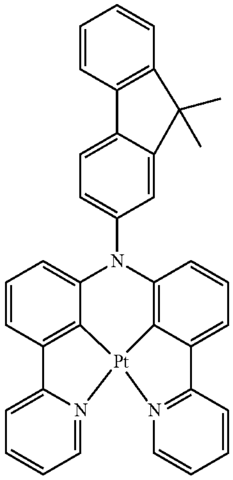
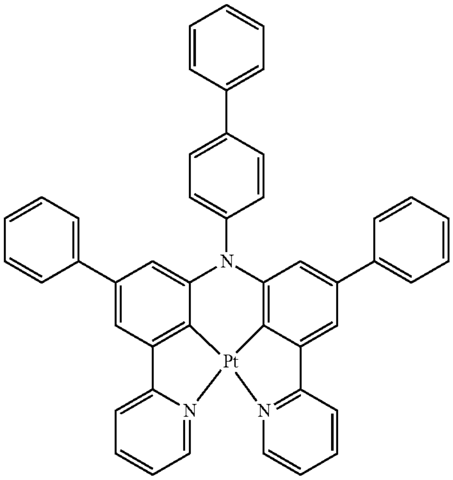
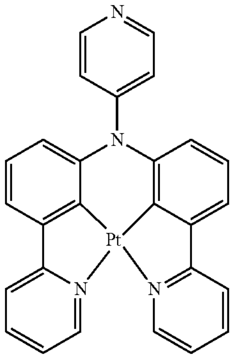

-continued
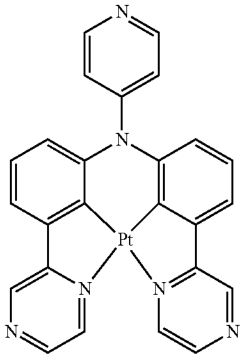
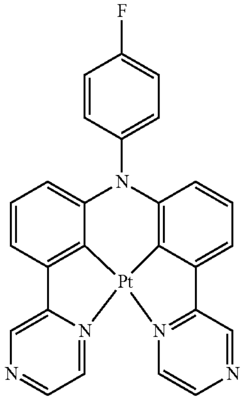
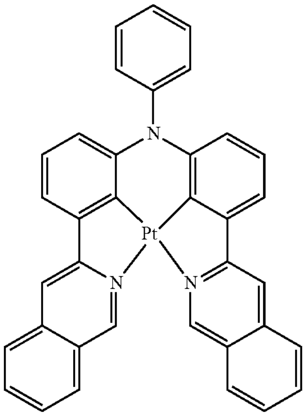
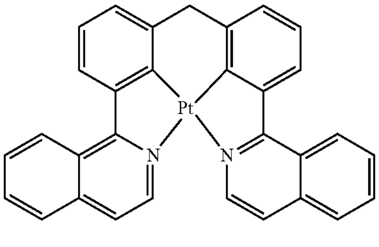
-continued
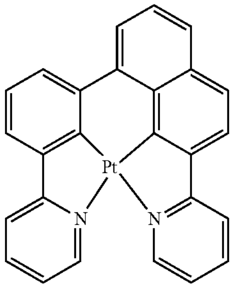
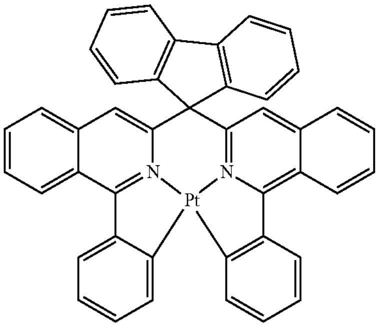
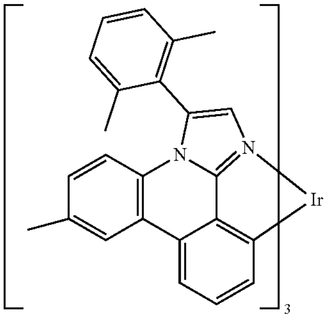
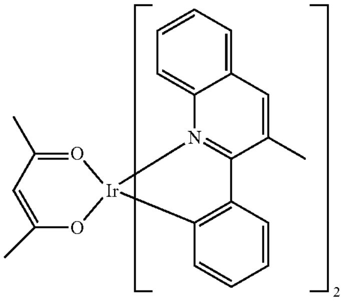
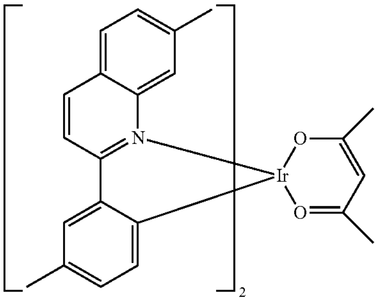

-continued
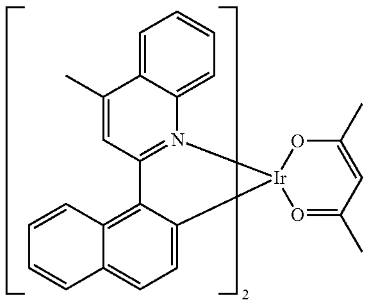
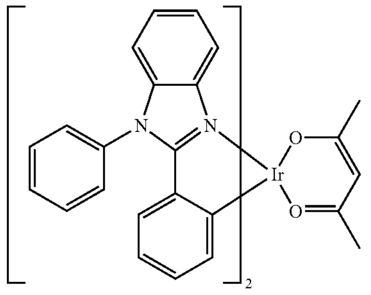
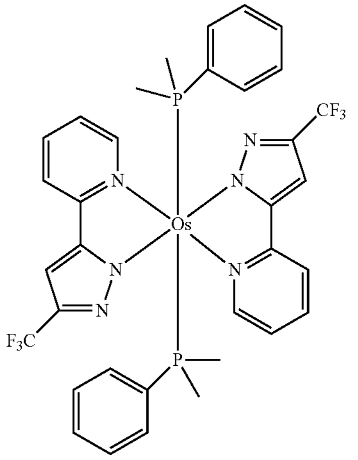
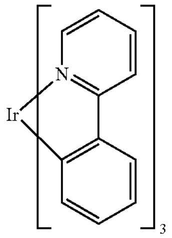
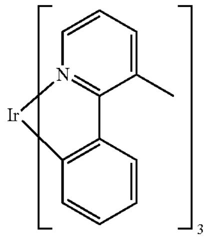
-continued
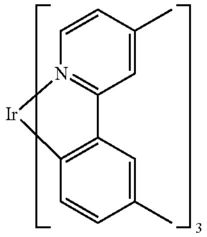
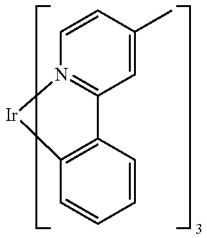
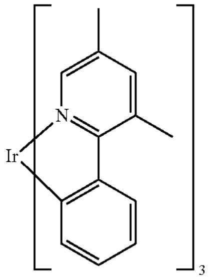
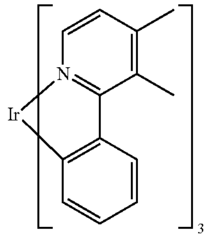
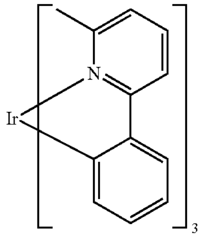
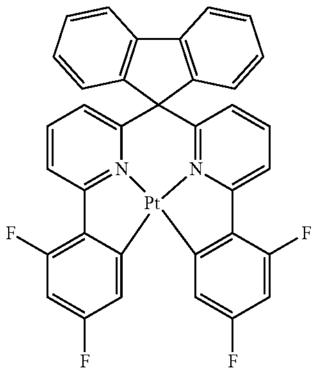

-continued
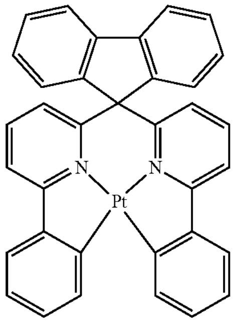
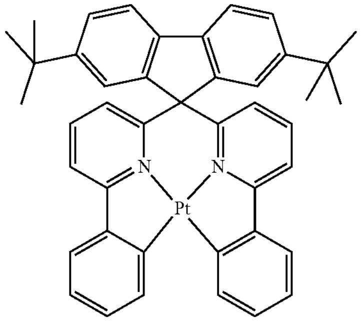
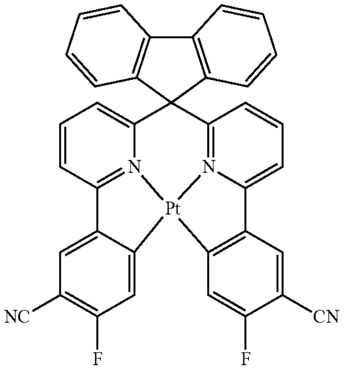
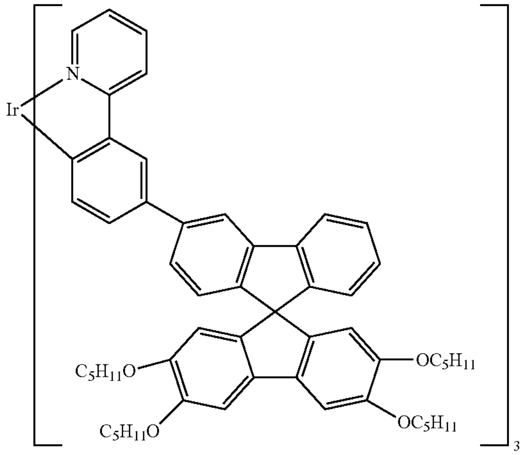
-continued
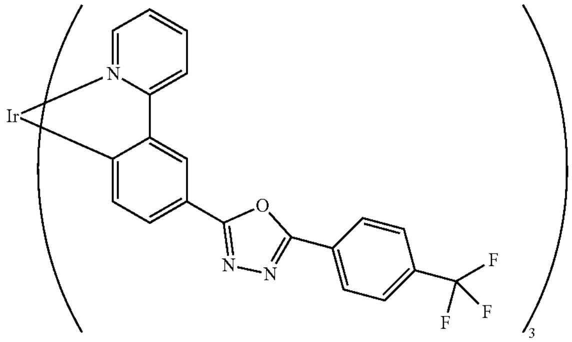
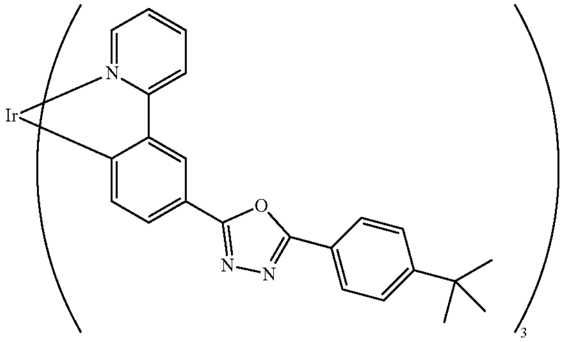
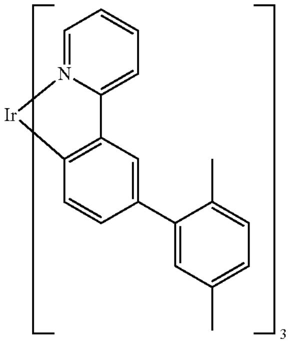
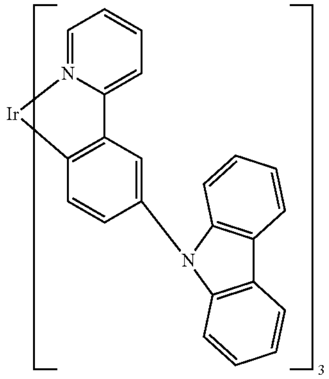

-continued
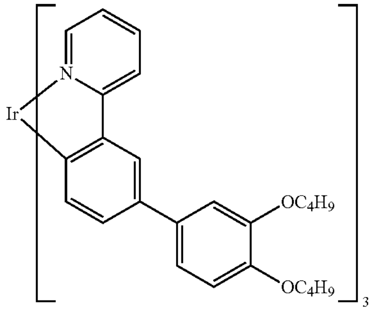
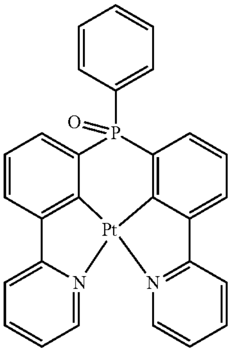
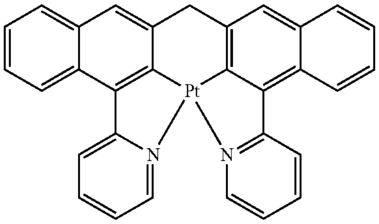
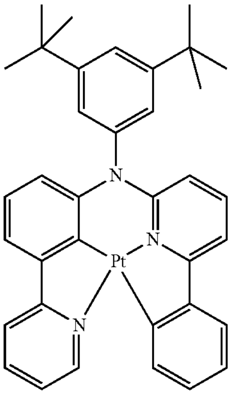
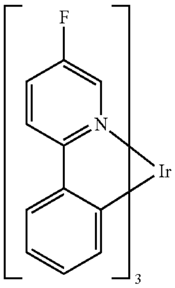
-continued
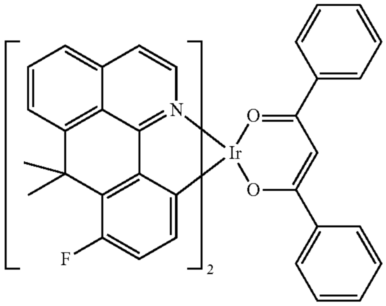
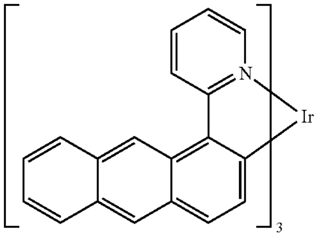
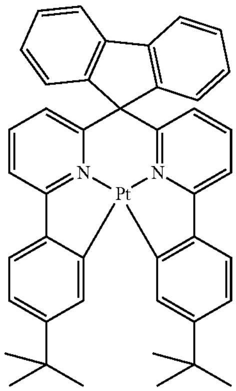
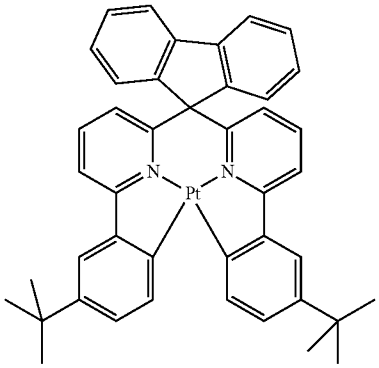

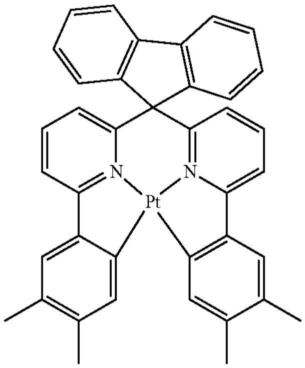
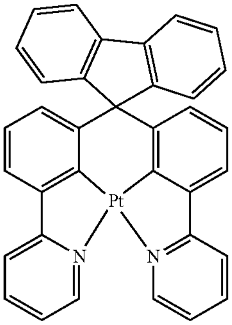
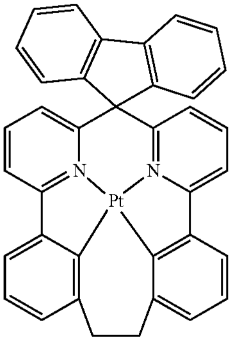
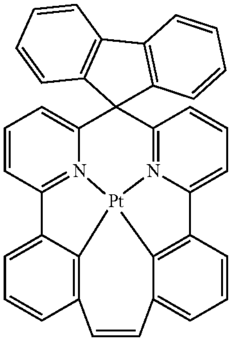
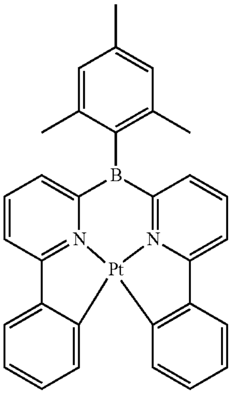
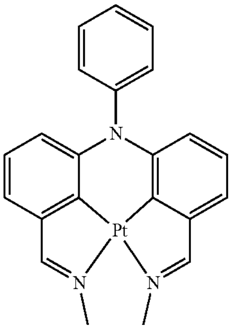
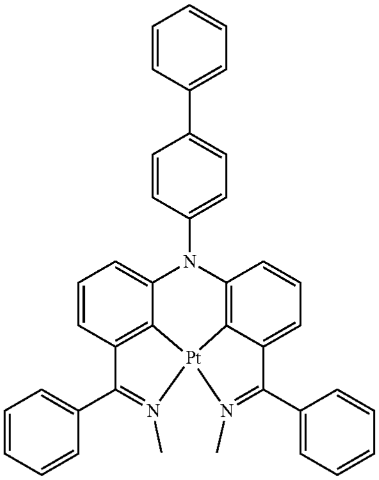
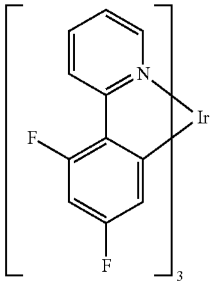

-continued
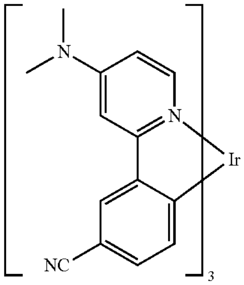
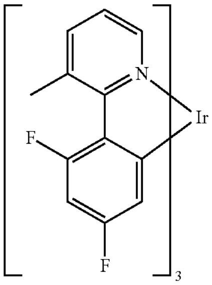
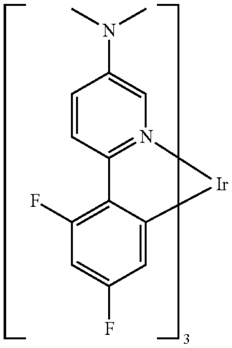
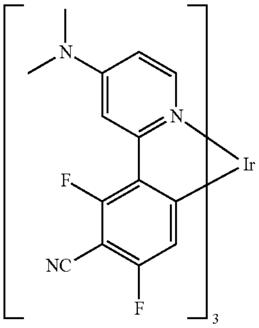
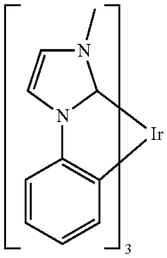
-continued
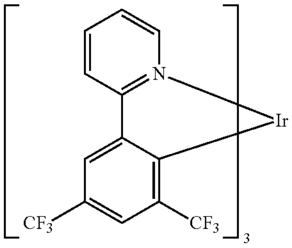
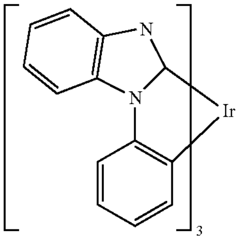
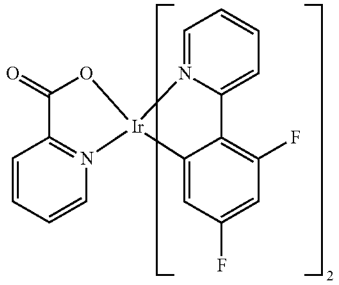
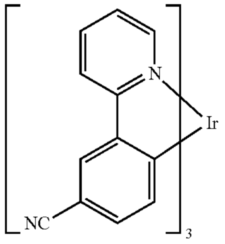
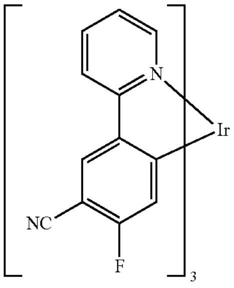
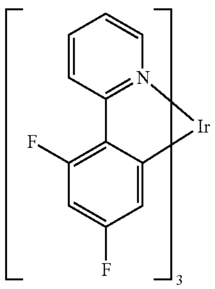

-continued
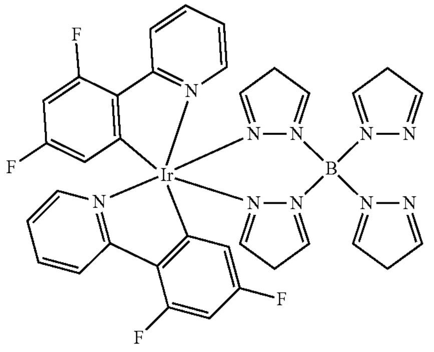
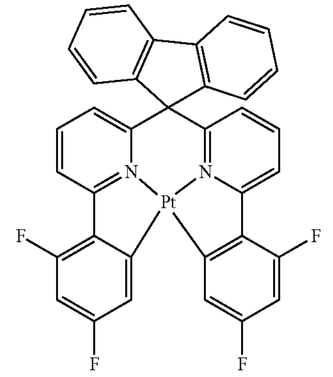
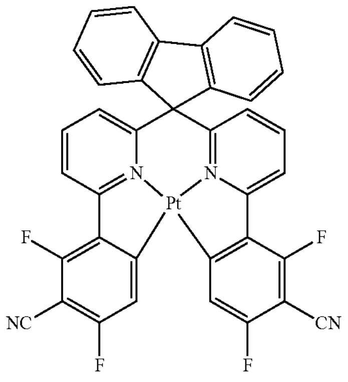
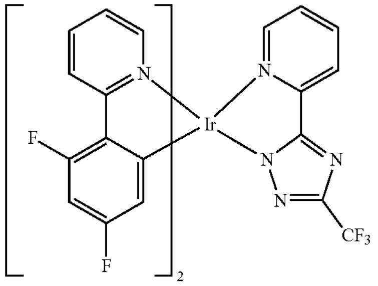
-continued
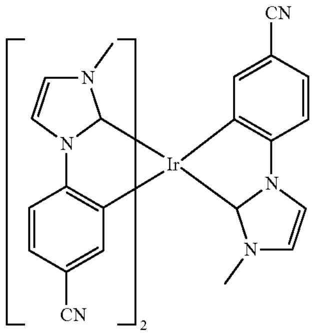
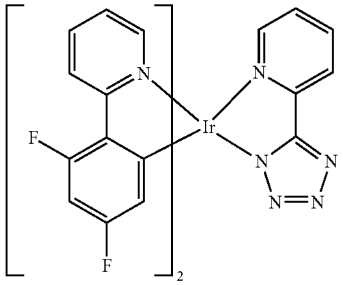
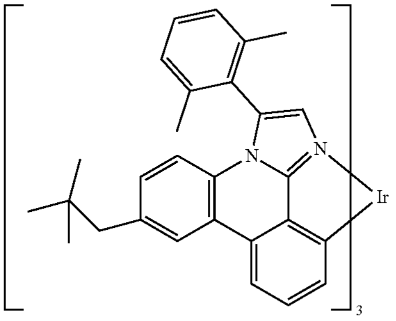
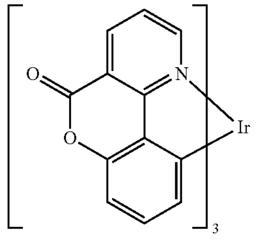
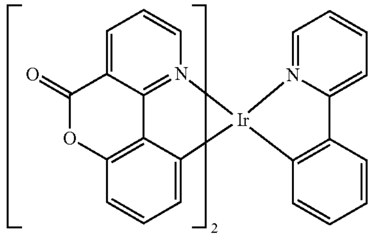

-continued

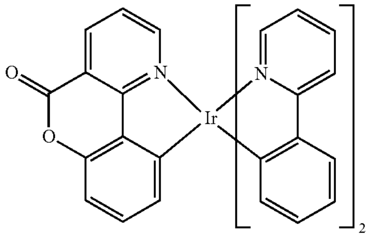

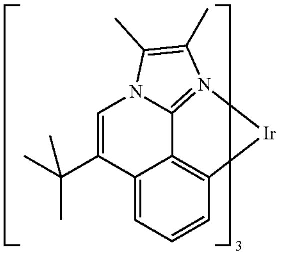

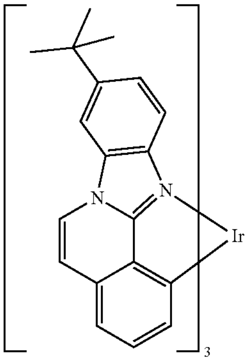

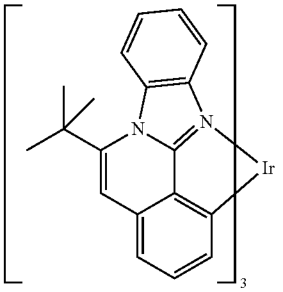

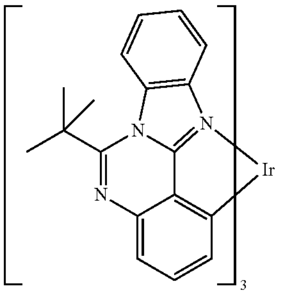

-continued

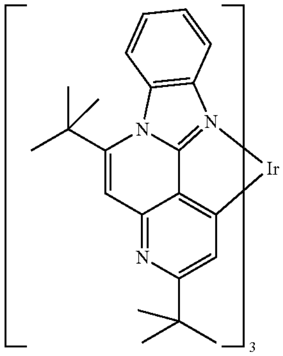

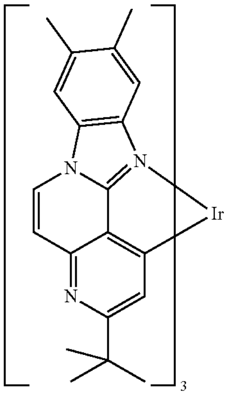

If the compound of the formula (1) or the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having a spin multiplicity>1, in particular from an excited triplet state. For the purposes of this application, all luminescent complexes containing transition metals or lanthanoids, in particular all luminescent iridium, platinum and copper complexes, are to be regarded as phosphorescent compounds.

The mixture comprising the matrix material, which comprises the compound of the formula (1) or the preferred embodiments, and the emitting compound comprises between 99.9 and 1% by weight, preferably between 99 and 10% by weight, particularly preferably between 97 and 60% by weight, in particular between 95 and 80% by weight, of the matrix material, based on the entire mixture comprising emitter and matrix material. Correspondingly, the mixture comprises between 0.1 and 99% by weight, preferably between 1 and 90% by weight, particularly preferably between 3 and 40% by weight, in particular between 5 and 20% by weight, of the emitter, based on the entire mixture comprising emitter and matrix material. The limits indicated above apply, in particular, if the layer is applied from solution. If the layer is applied by vacuum evaporation, the same numerical values apply, with the percentage in this case being indicated in % by vol. in each case.

A particularly preferred embodiment of the present invention is the use of the compound of the formula (1) or the preferred embodiments as matrix material for a phosphorescent emitter in combination with a further matrix material. Particularly suitable matrix materials which can be employed in combination with the compounds of the formula (1) or the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 or WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 08/056746, zinc complexes, for example in accordance with EP 652273 or WO 2009/062578, fluorene derivatives, for example in accordance with WO 2009/124627, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779, WO 2010/050778, WO 2011/042107 or WO 2011/088877. It is furthermore possible to use an electronically neutral co-host which has neither hole-transporting nor electron-transporting properties, as described, for example, in WO 2010/108579.

It is likewise possible to use two or more phosphorescent emitters in the mixture. In this case, the emitter which emits at shorter wavelength acts as co-host in the mixture.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 2000/70655, WO 2001/41512, WO 2002/02714, WO 2002/15645, EP 1191613, EP 1191612, EP 1191614, WO 2005/033244, WO 2005/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/157339 or WO 2012/007086. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to use the compound of the formula (1) or the preferred embodiments both in a hole-transport layer or exciton-blocking layer and as matrix in an emitting layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) according to the invention or the preferred embodiments.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, LITI (light induced thermal imaging, thermal transfer printing), ink-jet printing, screen printing, flexographic printing, offset printing or nozzle printing. Soluble compounds, which are obtained, for example, by suitable substitution, are necessary for this purpose. These processes are also particularly suitable for the compounds according to the invention, since these generally have very good solubility in organic solvents.

Also possible are hybrid processes, in which, for example, one or more layers are applied from solution and one or more further layers are applied by vapour deposition. Thus, for example, the emitting layer can be applied from solution and the electron-transport layer by vapour deposition.

These processes are generally known to the person skilled in the art and can be applied by him without inventive step to organic electroluminescent devices comprising the compounds according to the invention.

The processing of the compounds according to the invention from the liquid phase, for example by spin coating or by printing processes, requires formulations of the compounds according to the invention. These formulations can be, for example, solutions, dispersions or mini-emulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, dispersion or mini-emulsion, comprising at least one compound of the formula (1) or the preferred embodiments indicated above and at least one solvent, in particular an organic solvent. The way in which solutions of this type can be prepared is known to the person skilled in the art and is described, for example, in WO 2002/072714, WO 2003/019694 and the literature cited therein.

The present invention furthermore relates to mixtures comprising at least one compound of the formula (1) or the preferred embodiments indicated above and at least one further compound. The further compound can be, for example, a fluorescent or phosphorescent dopant if the compound according to the invention is used as matrix material. The mixture may then also additionally comprise a further material as additional matrix material.

The invention is explained in greater detail by the following examples, without wishing to restrict it thereby. On the basis of the descriptions, the person skilled in the art will be able to carry out the invention throughout the range disclosed and prepare further compounds according to the invention without inventive step and use them in electronic devices or use the process according to the invention.

EXAMPLES

A) Synthesis Examples

Example 1

Synthesis of bis-(fluorenyl-2-yl)-spiro-(7H-benzo[c]fluorene-7,9'-fluoren-4'-yl)-amine (1-1) and derivatives (1-2) bis (1-14)

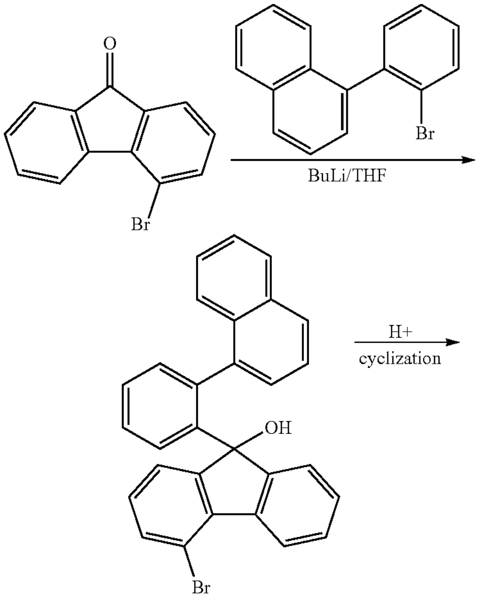

-continued

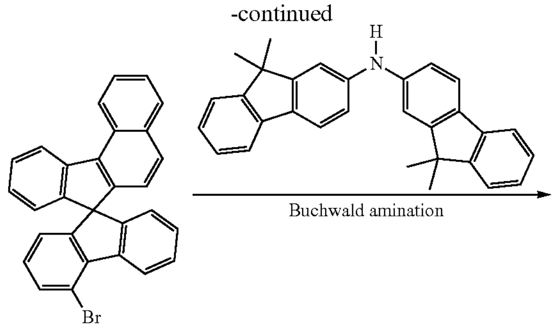

(I-1)

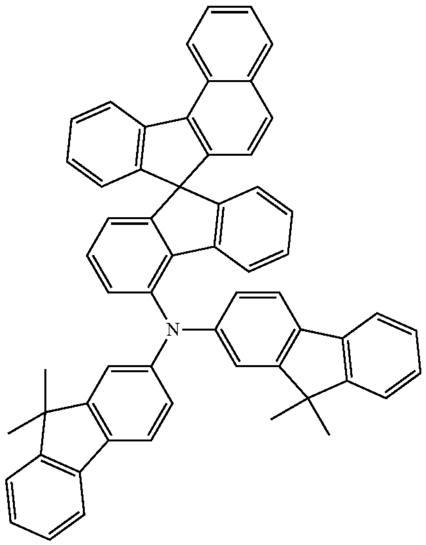

(1-1)

Synthesis of 4'-bromo-spiro-(7H-benzo[c]fluorene-7,9'-fluorene) (Intermediate I-1)

20.0 g (71 mmol) of 1-(2-Bromo-phenyl)-naphthalene (CAS-Nr.: 18937-27-3) was suspended in 500 mL of THF under Ar atmosphere then cooled at −78° C. 30 mL of (75 mmol/2.5 M in hexane) n-BuLi was added dropwise and the mixture was stirred for 1 h at this temperature. 18.3 g (71 mmol) of compound (II) was added portionwise at −78° C. and the mixture was stirred overnight at RT. After reaction completion, 200 mL of $H_2O$ was added. The organic phase was separated off and washed three times with 300 mL of water, dried over magnesium sulfate, filtered and subsequently evaporated to dryness. The residue was washed with 500 mL of heptane, filtered and used without further purification. The yield was 27.6 g (60 mmol), corresponding to 84% of theory. 25 g (54 mmol) of this compound was stirred vigorously under Ar atmosphere in a flask with 54.6 mL of HCl (540 mmol/36% aqueous solution) and 700 mL of acetic acid at 115° C. for 3 hr. The reaction mixture was cooled to RT and the resulting precipitate was washed with 100 mL of water and with 250 mL of EtOH for 2 hr in order to give a pale yellow powder. The yield was 15.8 g (35 mmol), corresponding to 66% of theory.

The following compounds are synthesized analogously:
| Ex. | Bromo-biphenyl | Aryl-fluorenone | Product | Overall yield |
|---|---|---|---|---|
| I-1 | 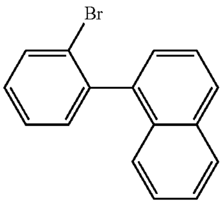 [SMILES: Brc1ccccc1-c1cccc2ccccc12] [18937-27-3] | 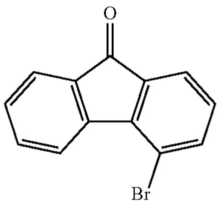 [SMILES: O=C1c2ccccc2-c2c(Br)cccc21] [4269-17-4] | 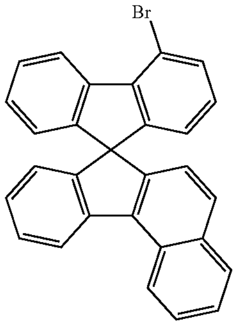 [SMILES: Brc1cccc2c1-c1ccccc1C21c2ccccc2-c2c1ccc1ccccc21] | 56% |
| I-2 | 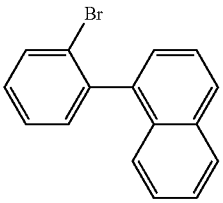 [SMILES: Brc1ccccc1-c1cccc2ccccc12] [18937-27-3] | 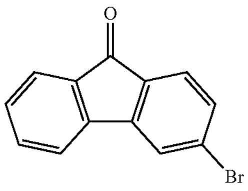 [SMILES: O=C1c2ccccc2-c2cc(Br)ccc21] [2041-19-2] | 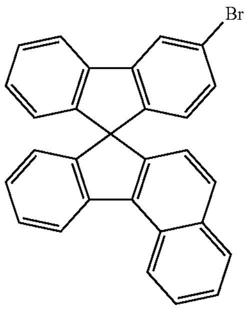 [SMILES: Brc1ccc2c(c1)-c1ccccc1C21c2ccccc2-c2c1ccc1ccccc21] | 65% |
| I-3 | 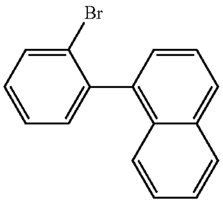 [SMILES: Brc1ccccc1-c1cccc2ccccc12] [18937-27-3] | 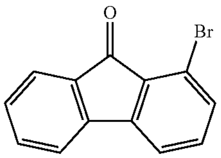 [SMILES: O=C1c2ccccc2-c2cccc(Br)c21] [36804-63-4] | 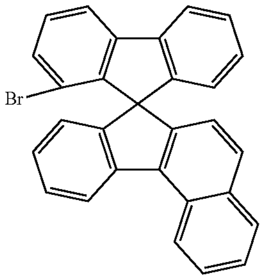 [SMILES: Brc1cccc2c1C1(c3ccccc3-2)c2ccccc2-c2c1ccc1ccccc21] | 51% |
| I-4 | 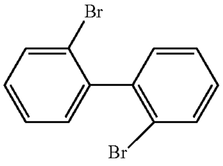 [SMILES: Brc1ccccc1-c1ccccc1Br] [13029-09-9] | 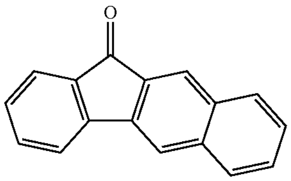 [SMILES: O=C1c2ccccc2-c2cc3ccccc3cc21] [3074-03-1] | 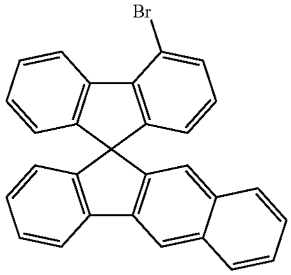 [SMILES: Brc1cccc2c1-c1ccccc1C21c2ccccc2-c2cc3ccccc3cc21] | 70% |

-continued

| Ex. | Bromo-biphenyl | Aryl-fluorenone | Product | Overall yield |
|---|---|---|---|---|
| I-5 | 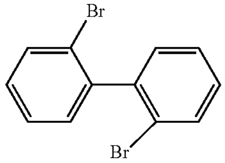 [SMILES: Brc1ccccc1-c1ccccc1Br] [13029-09-9] | 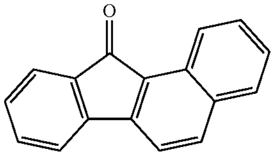 [SMILES: O=C1c2ccccc2-c2ccc3ccccc3c21] [479-79-8] | 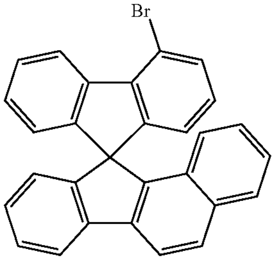 [SMILES: Brc1cccc2c1-c1ccccc1C21c2ccccc2-c2ccc3ccccc3c21] | 75% |

Synthesis of bis-(fluorenyl-2-yl)-spiro-(7H-benzo[c] fluorene-7,9'-fluoren-4'-yl) (1-1)

42 g (94 mmol) of intermediate (I-1) and 39.8 g (99 mmol) of bis-fluoren-2-yl-amine were suspended in 960 mL of toluene under Ar atmosphere. 3.8 mL (3.8 mmol) of tri-tert-butyl-phosphine was added to the flask and stirred under Ar atmosphere. 1.7 g (1.8 mmol) of $Pd_2(dba)_3$ was added to the flask and stirred under Ar atmosphere then 13.6 g (141 mmol) of sodium tert-butoxide was added to the flask. The reaction mixture was stirred under reflux for 15 hr. The reaction mixture was cooled to RT, the organic phase was separated off, washed three times with 200 mL of water, dried over magnesium sulfate, filtered and subsequently evaporated to dryness. The residue was purified by column chromatography on silica gel using a mixture of DCM/heptane (1:5) and by sublimation in vacuo. The yield was 36.3 g (47.4 mmol), corresponding to 50% of theory.

The following compounds are obtained analogously:

| Ex. | Halogenated-spirobifluorene | Amine | Product | Yield |
|---|---|---|---|---|
| 1-1 | 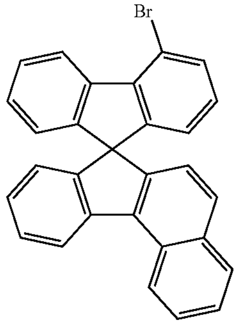 [SMILES: Brc1cccc2c1-c1ccccc1C21c2ccccc2-c2c1ccc1ccccc21] | 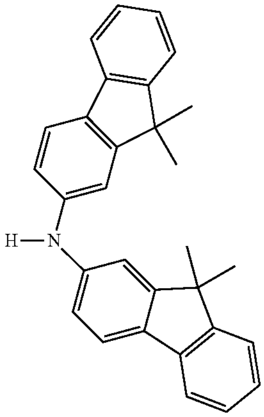 [SMILES: CC1(C)c2ccccc2-c2ccc(Nc3ccc4c(c3)C(C)(C)c3ccccc3-4)cc21] [500717-23-7] | 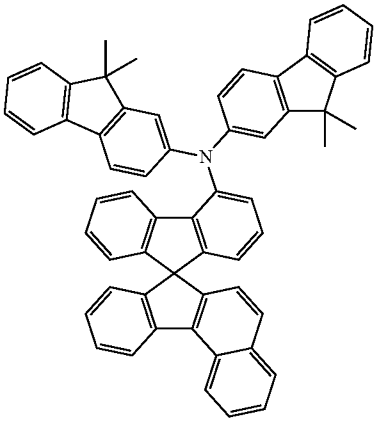 [SMILES: CC1(C)c2ccccc2-c2ccc(N(c3ccc4c(c3)C(C)(C)c3ccccc3-4)c3cccc4c3-c3ccccc3C43c4ccccc4-c4c3ccc3ccccc43)cc21] | 50% |

-continued
| Ex. | Halogenated-spirobifluorene | Amine | Product | Yield |
|---|---|---|---|---|
| 1-2 | 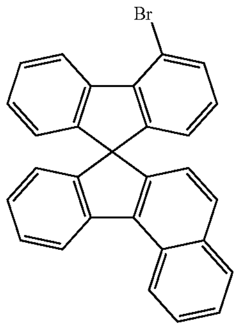 [SMILES: Brc1cccc2c1-c1ccccc1C21c2ccccc2-c2c1ccc1ccccc21] | 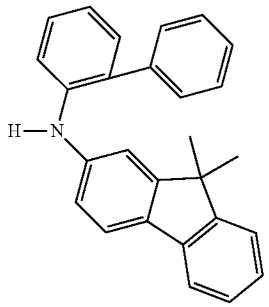 [SMILES: CC1(C)c2ccccc2-c2ccc(Nc3ccccc3-c3ccccc3)cc21] [1198395-24-2] | 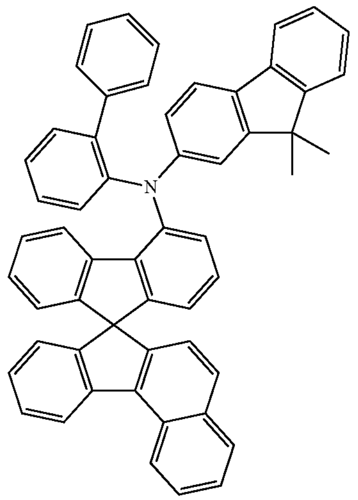 [SMILES: CC1(C)c2ccccc2-c2ccc(N(c3ccccc3-c3ccccc3)c3cccc4c3-c3ccccc3C43c4ccccc4-c4c3ccc3ccccc43)cc21] | 75% |
| 1-3 | 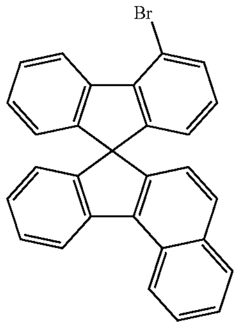 [SMILES: Brc1cccc2c1-c1ccccc1C21c2ccccc2-c2c1ccc1ccccc21] | 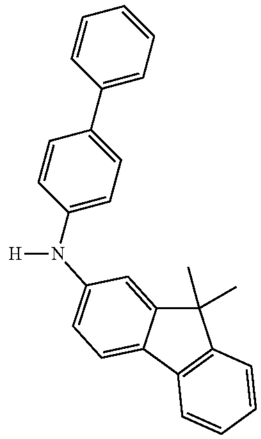 [SMILES: CC1(C)c2ccccc2-c2ccc(Nc3ccc(-c4ccccc4)cc3)cc21] [897671-69-1] | 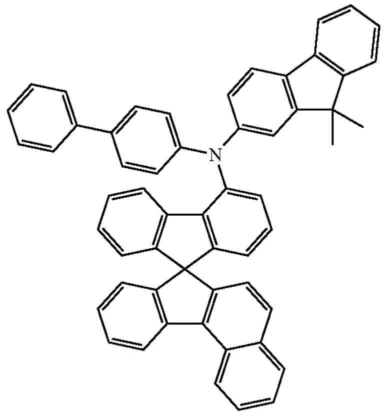 [SMILES: CC1(C)c2ccccc2-c2ccc(N(c3ccc(-c4ccccc4)cc3)c3cccc4c3-c3ccccc3C43c4ccccc4-c4c3ccc3ccccc43)cc21] | 55% |
| 1-4 | 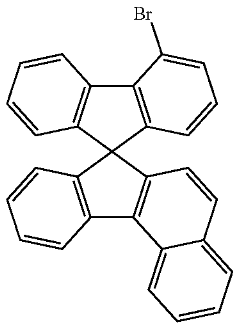 [SMILES: Brc1cccc2c1-c1ccccc1C21c2ccccc2-c2c1ccc1ccccc21] | 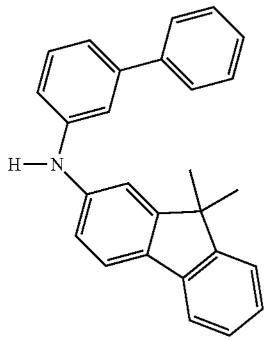 [SMILES: CC1(C)c2ccccc2-c2ccc(Nc3cccc(-c4ccccc4)c3)cc21] [1372778-66-9] | 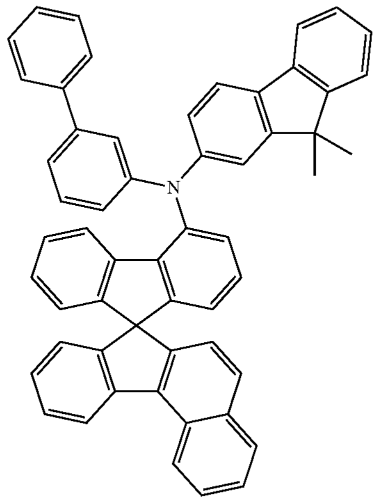 [SMILES: CC1(C)c2ccccc2-c2ccc(N(c3cccc(-c4ccccc4)c3)c3cccc4c3-c3ccccc3C43c4ccccc4-c4c3ccc3ccccc43)cc21] | 70% |

-continued
| Ex. | Halogenated-spirobifluorene | Amine | Product | Yield |
| --- | --- | --- | --- | --- |
| 1-5 | 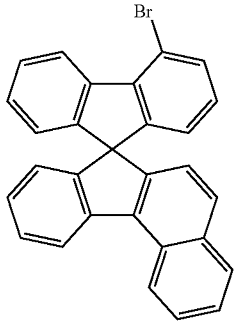 [SMILES: Brc1cccc2c1-c1ccccc1C21c2ccccc2-c2c1ccc1ccccc21] | 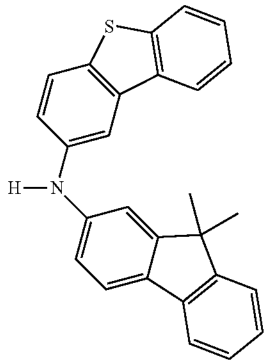 [SMILES: CC1(C)c2ccccc2-c2ccc(Nc3ccc4sc5ccccc5c4c3)cc21] [1429508-81] | 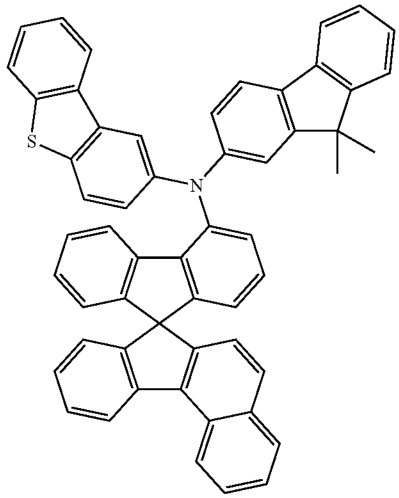 [SMILES: CC1(C)c2ccccc2-c2ccc(N(c3ccc4sc5ccccc5c4c3)c3cccc4c3-c3ccccc3C43c4ccccc4-c4c3ccc3ccccc43)cc21] | 66% |
| 1-6 | 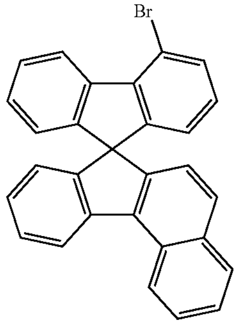 [SMILES: Brc1cccc2c1-c1ccccc1C21c2ccccc2-c2c1ccc1ccccc21] | 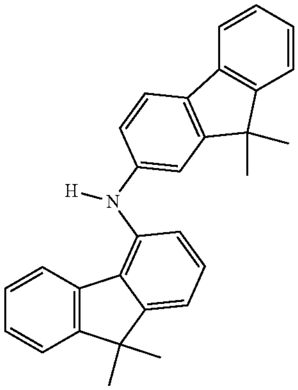 [SMILES: CC1(C)c2ccccc2-c2ccc(Nc3cccc4c3-c3ccccc3C4(C)C)cc21] [1644054-07-8] | 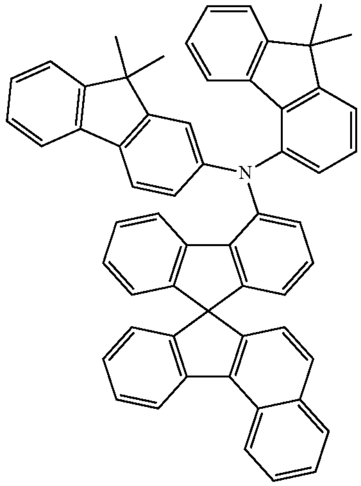 [SMILES: CC1(C)c2ccccc2-c2ccc(N(c3cccc4c3-c3ccccc3C4(C)C)c3cccc4c3-c3ccccc3C43c4ccccc4-c4c3ccc3ccccc43)cc21] | 65% |
| 1-7 | 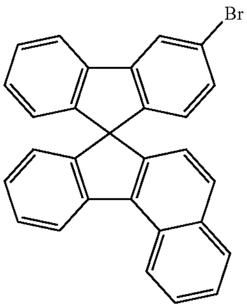 [SMILES: Brc1ccc2c(c1)-c1ccccc1C21c2ccccc2-c2c1ccc1ccccc21] | 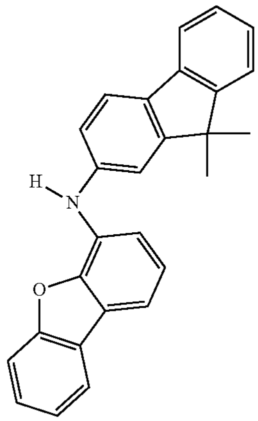 [SMILES: CC1(C)c2ccccc2-c2ccc(Nc3cccc4c3oc3ccccc34)cc21] [1426933-82-5] | 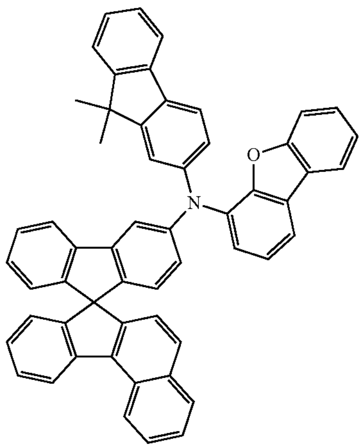 [SMILES: CC1(C)c2ccccc2-c2ccc(N(c3ccc4c(c3)-c3ccccc3C43c4ccccc4-c4c3ccc3ccccc43)c3cccc4c3oc3ccccc34)cc21] | 72% |

-continued
| Ex. | Halogenated-spirobifluorene | Amine | Product | Yield |
|---|---|---|---|---|
| 1-8 | 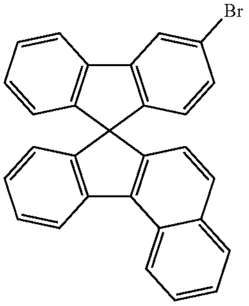 [SMILES: Brc1ccc2c(c1)-c1ccccc1C21c2ccccc2-c2c1ccc1ccccc21] | 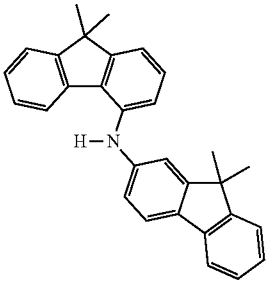 [SMILES: CC1(C)c2ccccc2-c2ccc(Nc3cccc4c3-c3ccccc3C4(C)C)cc21] [1644054-07-8] | 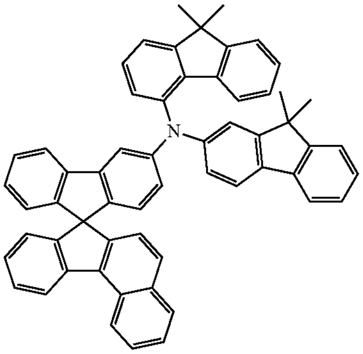 [SMILES: CC1(C)c2ccccc2-c2ccc(N(c3ccc4c(c3)-c3ccccc3C43c4ccccc4-c4c3ccc3ccccc43)c3cccc4c3-c3ccccc3C4(C)C)cc21] | 68% |
| 1-9 | 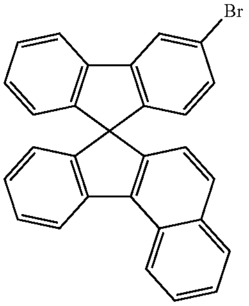 [SMILES: Brc1ccc2c(c1)-c1ccccc1C21c2ccccc2-c2c1ccc1ccccc21] | 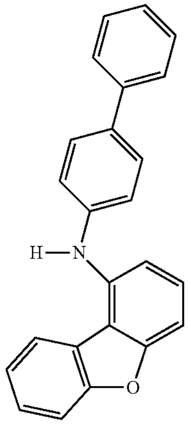 [SMILES: c1ccc(-c2ccc(Nc3cccc4oc5ccccc5c34)cc2)cc1] | 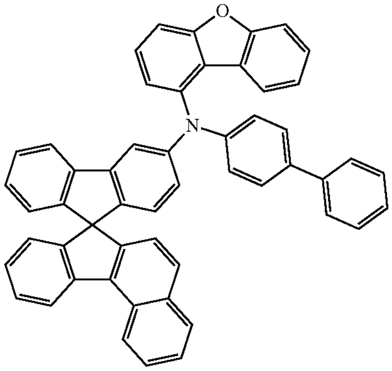 [SMILES: c1ccc(-c2ccc(N(c3ccc4c(c3)-c3ccccc3C43c4ccccc4-c4c3ccc3ccccc43)c3cccc4oc5ccccc5c34)cc2)cc1] | 68% |
| 1-10 | 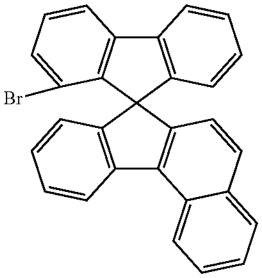 [SMILES: Brc1cccc2c1C1(c3ccccc3-2)c2ccccc2-c2c1ccc1ccccc21] | 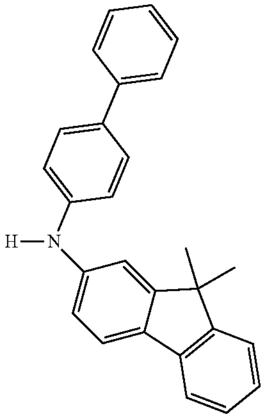 [SMILES: CC1(C)c2ccccc2-c2ccc(Nc3ccc(-c4ccccc4)cc3)cc21] [897671-69-1] | 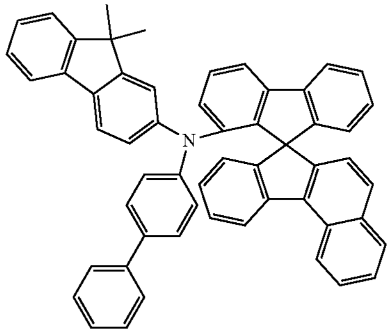 [SMILES: CC1(C)c2ccccc2-c2ccc(N(c3ccc(-c4ccccc4)cc3)c3cccc4c3C3(c5ccccc5-4)c4ccccc4-c4c3ccc3ccccc43)cc21] | 25% |

-continued
| Ex. | Halogenated-spirobifluorene | Amine | Product | Yield |
| --- | --- | --- | --- | --- |
| 1-11 | 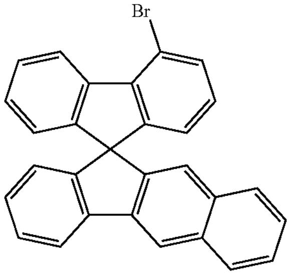 [SMILES: Brc1cccc2c1-c1ccccc1C21c2ccccc2-c2cc3ccccc3cc21] | 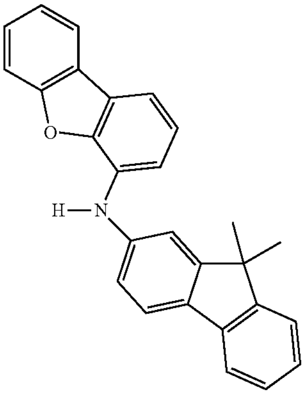 [SMILES: CC1(C)c2ccccc2-c2ccc(Nc3cccc4c3oc3ccccc34)cc21] [1426933-82-5] | 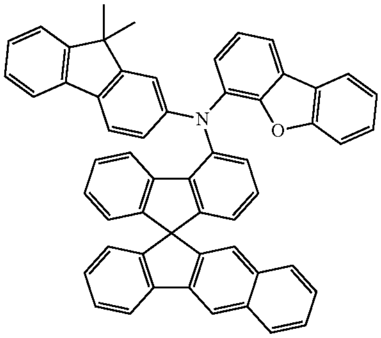 [SMILES: CC1(C)c2ccccc2-c2ccc(N(c3cccc4c3-c3ccccc3C43c4ccccc4-c4cc5ccccc5cc43)c3cccc4c3oc3ccccc34)cc21] | 73% |
| 1-12 | 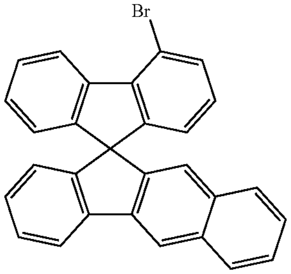 [SMILES: Brc1cccc2c1-c1ccccc1C21c2ccccc2-c2cc3ccccc3cc21] | 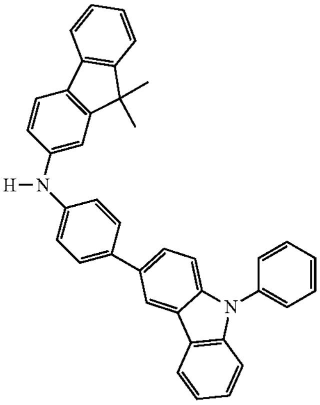 [SMILES: CC1(C)c2ccccc2-c2ccc(Nc3ccc(-c4ccc5c(c4)c4ccccc4n5-c4ccccc4)cc3)cc21] [1354653-33-0] | 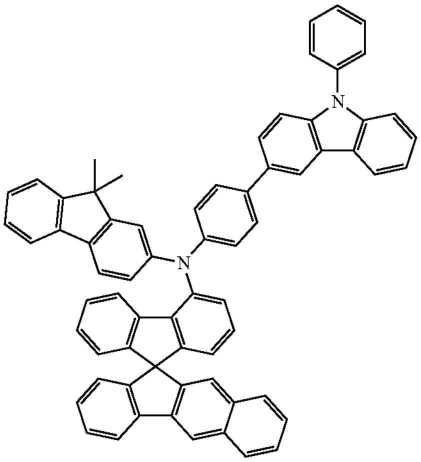 [SMILES: CC1(C)c2ccccc2-c2ccc(N(c3ccc(-c4ccc5c(c4)c4ccccc4n5-c4ccccc4)cc3)c3cccc4c3-c3ccccc3C43c4ccccc4-c4cc5ccccc5cc43)cc21] | 50% |
| 1-13 | 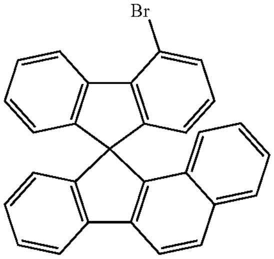 [SMILES: Brc1cccc2c1-c1ccccc1C21c2ccccc2-c2ccc3ccccc3c21] | 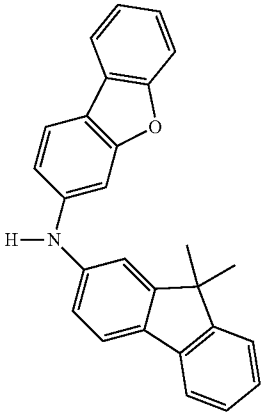 [SMILES: CC1(C)c2ccccc2-c2ccc(Nc3ccc4c(c3)oc3ccccc34)cc21] [1359833-89-8] | 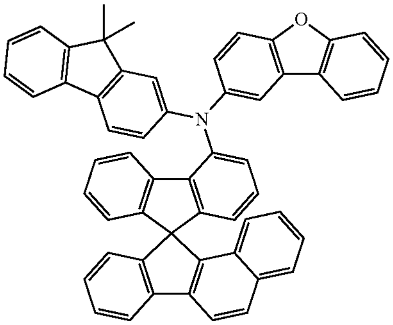 [SMILES: CC1(C)c2ccccc2-c2ccc(N(c3ccc4oc5ccccc5c4c3)c3cccc4c3-c3ccccc3C43c4ccccc4-c4ccc5ccccc5c43)cc21] | 67% |

-continued

| Ex. | Halogenated-spirobifluorene | Amine | Product | Yield |
|---|---|---|---|---|
| 1-14 | 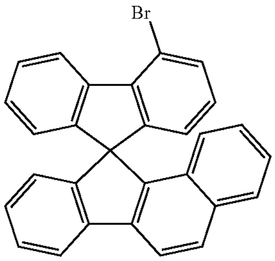 [SMILES: Brc1cccc2c1-c1ccccc1C21c2ccccc2-c2ccc3ccccc3c21] | 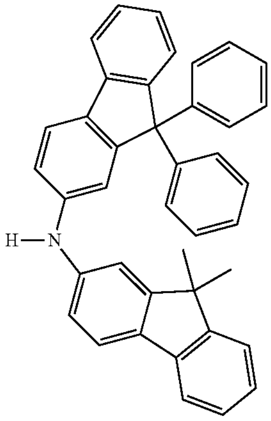 [SMILES: CC1(C)c2ccccc2-c2ccc(Nc3ccc4c(c3)C(c3ccccc3)(c3ccccc3)c3ccccc3-4)cc21] [1456702-56-9] | 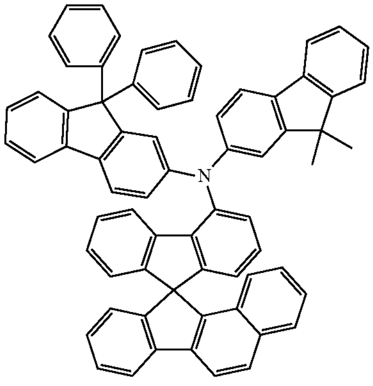 [SMILES: CC1(C)c2ccccc2-c2ccc(N(c3ccc4c(c3)C(c3ccccc3)(c3ccccc3)c3ccccc3-4)c3cccc4c3-c3ccccc3C43c4ccccc4-c4ccc5ccccc5c43)cc21] | 66% |

Example 2—Synthesis of Biphenyl-4-yl-(fluoren-2-yl)-spiro-(7H-benzo[c]fluorene-7,9'-fluoren-4'-yl)-4-phenyl-amine-(2-1) and Derivatives (2-2) to (2-4)

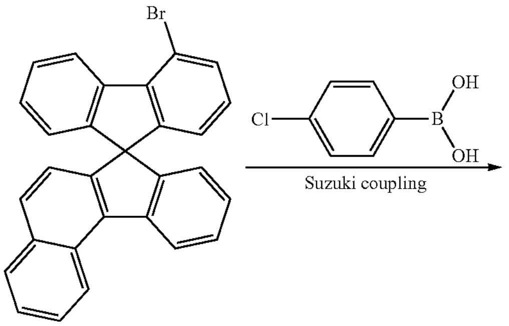

(I-1)

-continued

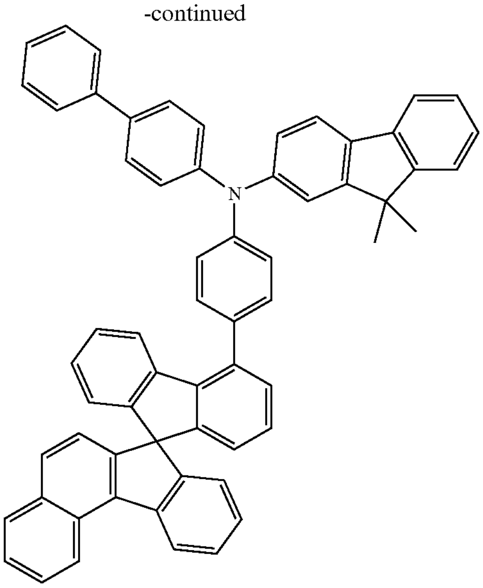

(2-1)

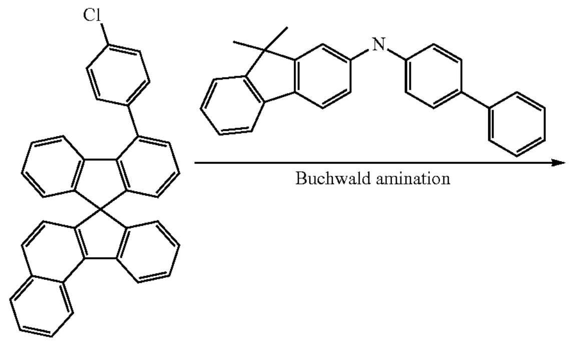

(II-1)

Synthesis of 4-chlorophenyl-spiro-(7H-benzo[c]fluorene-7,9'-fluoren-4'-yl (Intermediate II-1)

30 g (67 mmol) of compound (I-1), 11.1 g (71 mmol) of 4-chlorophenyl boronic acid and 14.3 g (135 mmol) of sodium carbonate were suspended in 500 mL of EtOH, 500 mL of $H_2O$ and 200 mL of toluene and stirred under Ar atmosphere. 2.3 g (2 mmol) of tetrakis(triphenylphosphine)-palladium was added to the flask. The reaction mixture was stirred under reflux overnight. The reaction mixture was cooled to RT, the reaction mixture was quenched. The organic phase was separated, washed three times with 200 mL of water, dried over magnesium sulfate, filtered and subsequently evaporated to dryness. The residue was purified by column chromatography on silica gel using a mixture of DCM/heptane (1:10). The yield was 24.3 g (51 mmol), corresponding to 75.6% of theory.

The following compounds are obtained analogously:
| | Educt 1 | Educt 2 | Product | Yield |
|---|---|---|---|---|
| II-1 | 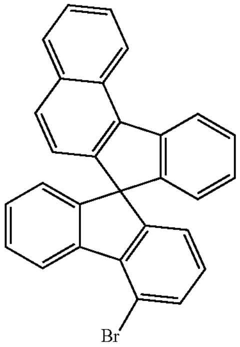 [SMILES: Brc1cccc2c1-c1ccccc1C21c2ccccc2-c2c1ccc1ccccc21] | 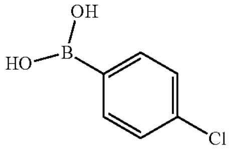 [1679-18-1] | 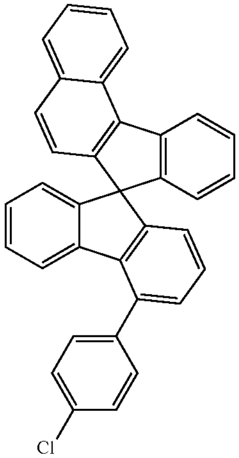 [SMILES: Clc1ccc(-c2cccc3c2-c2ccccc2C32c3ccccc3-c3c2ccc2ccccc32)cc1] | 76% |
| II-2 | 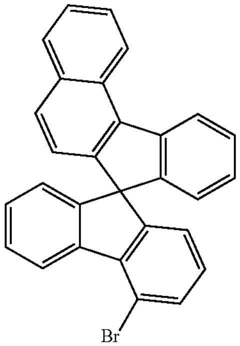 [SMILES: Brc1cccc2c1-c1ccccc1C21c2ccccc2-c2c1ccc1ccccc21] | 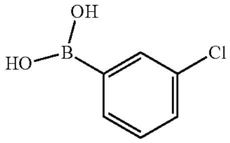 [63503-60-6] | 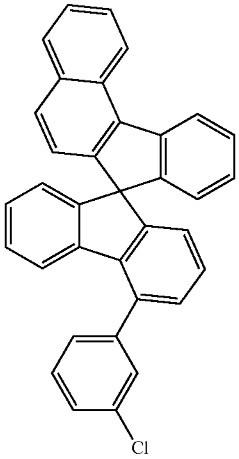 [SMILES: Clc1cccc(-c2cccc3c2-c2ccccc2C32c3ccccc3-c3c2ccc2ccccc32)c1] | 84% |
| II-3 | 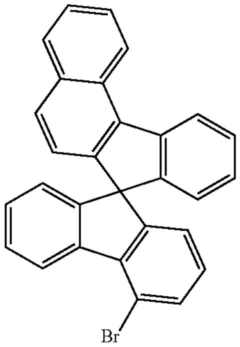 [SMILES: Brc1cccc2c1-c1ccccc1C21c2ccccc2-c2c1ccc1ccccc21] | 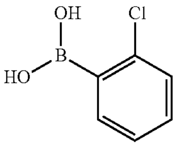 [3900-89-8] | 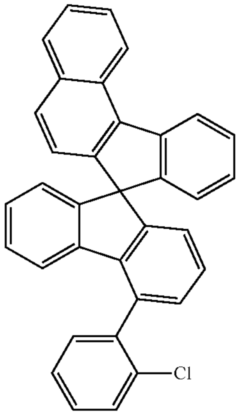 [SMILES: Clc1ccccc1-c1cccc2c1-c1ccccc1C21c2ccccc2-c2c1ccc1ccccc21] | 89% |

-continued

| | Educt 1 | Educt 2 | Product | Yield |
|---|---|---|---|---|
| II-4 | 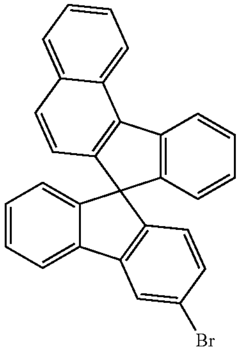 [SMILES: Brc1ccc2c(c1)-c1ccccc1C21c2ccccc2-c2c1ccc1ccccc21] | 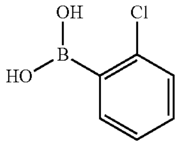 [3900-89-8] | 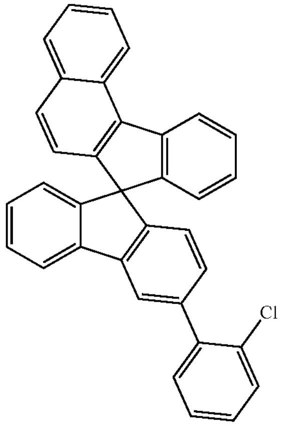 [SMILES: Clc1ccccc1-c1ccc2c(c1)-c1ccccc1C21c2ccccc2-c2c1ccc1ccccc21] | 88% |
| II-5 | 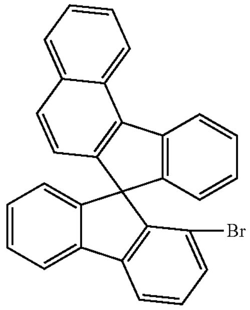 [SMILES: Brc1cccc2c1C1(c3ccccc3-2)c2ccccc2-c2c1ccc1ccccc21] | 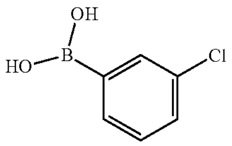 [63503-60-6] | 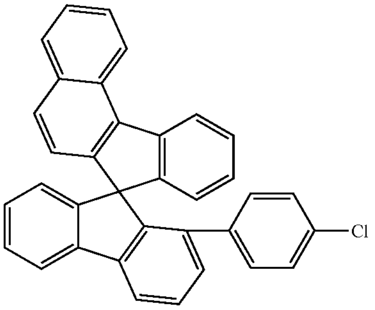 [SMILES: Clc1ccc(-c2cccc3c2C2(c4ccccc4-3)c3ccccc3-c3c2ccc2ccccc32)cc1] | 85% |

10 g (22 mmol) of compound (II-1) and 8.3 g (23 mmol) of biphenyl-4-yl-2-(9,9'-dimethylfluorenyl)-amine were suspended in 250 mL of toluene under Ar atmosphere. 0.90 mL (0.9 mmol) of tri-tert-butyl-phosphine was added to the flask and stirred under Ar atmosphere. 0.41 g (0.45 mmol) of $Pd_2(dba)_3$ was added to the flask and stirred under Ar atmosphere then 3.22 g (33 mmol) of sodium tert-butoxide was added to the flask. The reaction mixture was stirred under reflux overnight. The reaction mixture was cooled to RT, the organic phase was separated off, washed three times with 100 mL of water, dried over magnesium sulfate, filtered and subsequently evaporated to dryness. The residue was purified by column chromatography on silica gel using a mixture of DCM/heptane (1:5). The yield was 12.9 g (16 mmol), corresponding to 72.9% of theory. The compound was sublimated in vacuo.

The following compounds are obtained analogously:
| | Educt 1 | Educt 2 | Product | Yield |
|---|---|---|---|---|
| 2-1 | 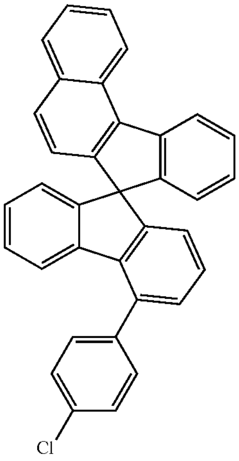 [SMILES: Clc1ccc(-c2cccc3c2-c2ccccc2C32c3ccccc3-c3c2ccc2ccccc32)cc1] | 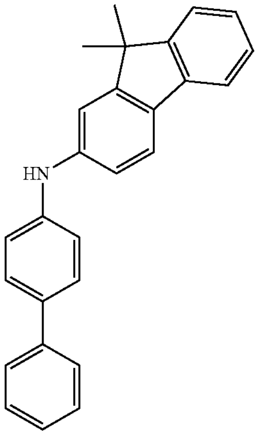 [SMILES: CC1(C)c2ccccc2-c2ccc(Nc3ccc(-c4ccccc4)cc3)cc21] [897671-69-1] | 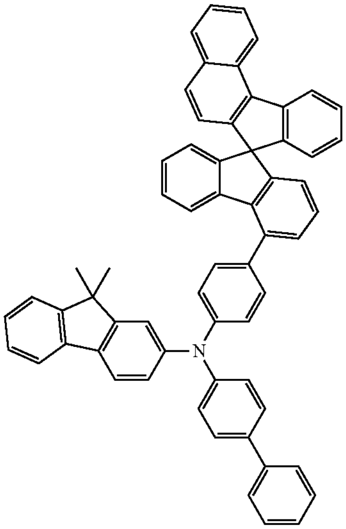 [SMILES: CC1(C)c2ccccc2-c2ccc(N(c3ccc(-c4ccccc4)cc3)c3ccc(-c4cccc5c4-c4ccccc4C54c5ccccc5-c5c4ccc4ccccc54)cc3)cc21] | 73% |
| 2-2 | 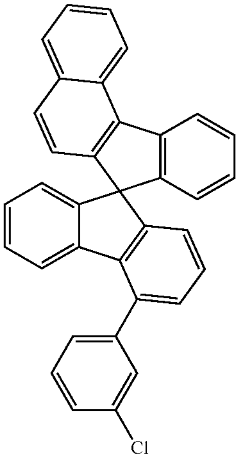 [SMILES: Clc1cccc(-c2cccc3c2-c2ccccc2C32c3ccccc3-c3c2ccc2ccccc32)c1] | 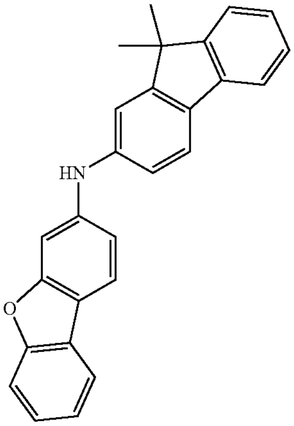 [SMILES: CC1(C)c2ccccc2-c2ccc(Nc3ccc4c(c3)oc3ccccc34)cc21] [1427556-50-0] | 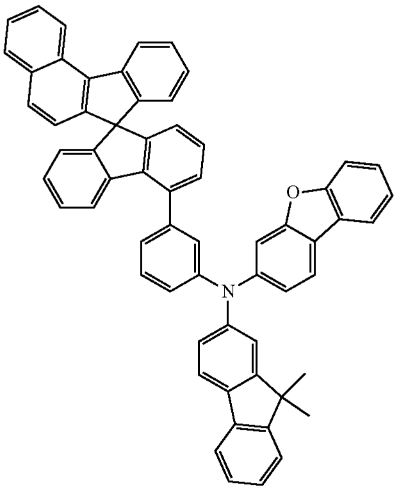 [SMILES: CC1(C)c2ccccc2-c2ccc(N(c3cccc(-c4cccc5c4-c4ccccc4C54c5ccccc5-c5c4ccc4ccccc54)c3)c3ccc4c(c3)oc3ccccc34)cc21] | 44% |
| 2-3 | 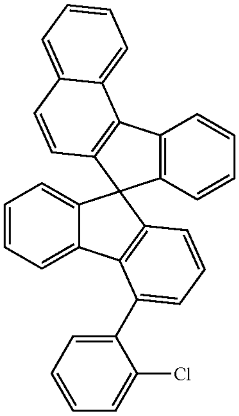 [SMILES: Clc1ccccc1-c1cccc2c1-c1ccccc1C21c2ccccc2-c2c1ccc1ccccc21] | 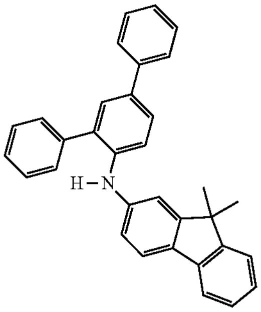 [SMILES: CC1(C)c2ccccc2-c2ccc(Nc3ccc(-c4ccccc4)cc3-c3ccccc3)cc21] [1609484-31-2] | 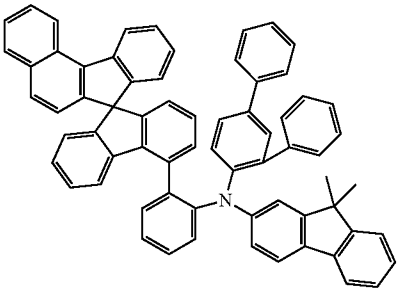 [SMILES: CC1(C)c2ccccc2-c2ccc(N(c3ccc(-c4ccccc4)cc3-c3ccccc3)c3ccccc3-c3cccc4c3-c3ccccc3C43c4ccccc4-c4c3ccc3ccccc43)cc21] | 57% |

-continued

| | Educt 1 | Educt 2 | Product | Yield |
|---|---|---|---|---|
| 2-4 | 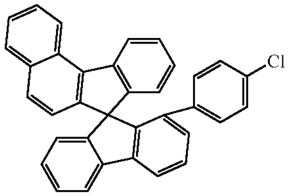 [SMILES: Clc1ccc(-c2cccc3c2C2(c4ccccc4-3)c3ccccc3-c3c2ccc2ccccc32)cc1] | 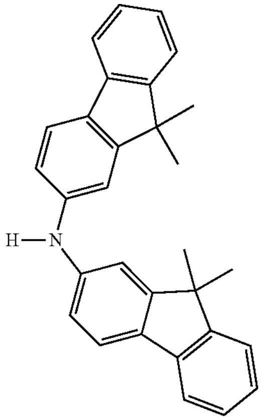 [SMILES: CC1(C)c2ccccc2-c2ccc(Nc3ccc4c(c3)C(C)(C)c3ccccc3-4)cc21] [500717-23-7] | 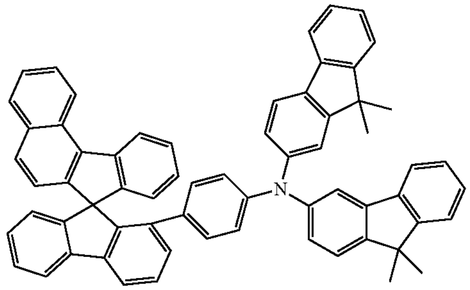 [SMILES: CC1(C)c2ccccc2-c2cc(N(c3ccc(-c4cccc5c4C4(c6ccccc6-5)c5ccccc5-c5c4ccc4ccccc54)cc3)c3ccc4c(c3)C(C)(C)c3ccccc3-4)ccc21] | 50% |

B) Devices Examples

OLEDs according to the invention and OLEDs in accordance with the prior art are produced by a general process in accordance with WO 2004/058911, which is adapted to the circumstances described here (layer-thickness variation, materials).

The data for various OLEDs are presented in Examples E1 to E4 below (see Tables 1 to 3). The substrates used are glass plates coated with structured ITO (indium tin oxide) in a thickness of 50 nm. The OLEDs basically have the following layer structure: substrate/hole-injection layer (HIL)/hole-transport layer (HTL)/hole-injection layer (HTL2)/electron-blocking layer (EBL)/emission layer (EML)/electron-transport layer (ETL)/electron-injection layer (EIL) and finally a cathode. The cathode is formed by an aluminium layer with a thickness of 100 nm.

The precise structure of the OLEDs is shown in table 1.

The materials required for the production of the OLEDs are shown in table 3.

All materials are evaporated by thermal vapour deposition in a vacuum chamber. The emission layer always consists of minimum one matrix material (host material) and an emitting dopant (emitter), which is admixed with the matrix material or matrix materials in a certain proportion by volume by co-evaporation. An expression such as H1:SEB (5%) denotes that material H1 is present in the layer in a proportion by volume of 95% and SEB is present in the layer in a proportion of 5%. Analogously, other layers may also consist of a mixture of two or more materials.

The OLEDs are characterised by standard methods. For this purpose, the electroluminescence spectra and the external quantum efficiency (EQE, measured in percent) as a function of the luminous density, calculated from current/voltage/luminous density characteristic lines (IUL characteristic lines) assuming Lambertian emission characteristics, and the lifetime are determined. The expression EQE @ 10 $mA/cm^2$ denotes the external quantum efficiency at an operating current density of 10 $mA/cm^2$. LT80 @ 60 $mA/cm^2$ is the lifetime until the OLED has dropped from its initial luminance of i.e. 5000 $cd/m^2$ to 80% of the initial intensity, i.e. to 4000 $cd/m^2$ without using any acceleration factor. The data for the various OLEDs containing inventive and comparative materials are summarised in table 2.

Use of Compounds According to the Invention as Hole-Transport Materials in Fluorescent OLEDs In particular, compounds according to the invention are suitable as HIL, HTL, EBL or matrix material in the EML in OLEDs. They are suitable as a single layer, but also as mixed component as HIL, HTL, EBL or within the EML. Compared with components from prior art (V1 and V2), the samples comprising the compounds according to the invention exhibit both higher efficiencies and also improved lifetimes in singlet blue.

TABLE 1

| Structure of the OLEDs | | | | | | | |
|---|---|---|---|---|---|---|---|
| Ex. | HIL Thickness/nm | HTL Thickness/nm | HTL2 Thickness/nm | EBL Thickness/nm | EML Thickness/nm | ETL Thickness/nm | EIL Thickness/nm |
| E1 | HIM:F4TCNQ (5%) 20 nm | HIM 160 nm | HTM1:F4TCNQ (5%) 20 nm | HTM1 10 nm | H1:SEB (5%) 20 nm | ETM:LiQ (50%) 30 nm | LiQ 1 nm |
| E2 | HIM:F4TCNQ (5%) 20 nm | HIM 160 nm | HTM2:F4TCNQ (5%) 20 nm | HTM2 10 nm | H1:SEB (5%) 20 nm | ETM:LiQ (50%) 30 nm | LiQ 1 nm |
| E3 | HIM:F4TCNQ (5%) 20 nm | HIM 160 nm | HTM3:F4TCNQ (5%) 20 nm | HTM3 10 nm | H1:SEB (5%) 20 nm | ETM:LiQ (50%) 30 nm | LiQ 1 nm |

TABLE 1-continued

| Structure of the OLEDs | | | | | | | |
|---|---|---|---|---|---|---|---|
| Ex. | HIL Thickness/nm | HTL Thickness/nm | HTL2 Thickness/nm | EBL Thickness/nm | EML Thickness/nm | ETL Thickness/nm | EIL Thickness/nm |
| E4 | HIM:F4TCNQ (5%) 20 nm | HIM 160 nm | HTM4:F4TCNQ (5%) 20 nm | HTM4 10 nm | H1:SEB (5%) 20 nm | ETM:LiQ (50%) 30 nm | LiQ 1 nm |
| V1 | HIM:F4TCNQ (5%) 20 nm | HIM 160 nm | HTMv1:F4TCNQ (5%) 20 nm | HTMv1 10 nm | H1:SEB (5%) 20 nm | ETM:LiQ (50%) 30 nm | LiQ 1 nm |
| V2 | HIM:F4TCNQ (5%) 20 nm | HIM 160 nm | HTMv2:F4TCNQ (5%) 20 nm | HTMv2 10 nm | H1:SEB (5%) 20 nm | ETM:LiQ (50%) 30 nm | LiQ 1 nm |

TABLE 2

| Data for the OLEDs | | |
|---|---|---|
| Ex. | EQE @ 10 mA/cm$^2$ % | LT80 @ 60 mA/cm$^2$ [h] |
| E1 | 8.0 | 320 |
| E2 | 7.9 | 330 |
| E3 | 7.8 | 310 |
| E4 | 7.7 | 310 |
| V1 | 7.2 | 290 |
| V2 | 7.4 | 280 |

TABLE 3

Structures of the materials used

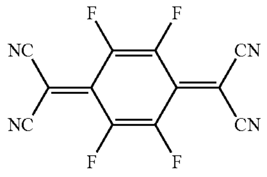 [SMILES: N#CC(C#N)=c1c(F)c(F)c(=C(C#N)C#N)c(F)c1F]

F4TCNQ

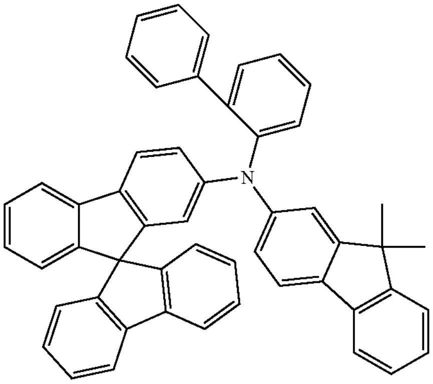 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

HIM

TABLE 3-continued

Structures of the materials used

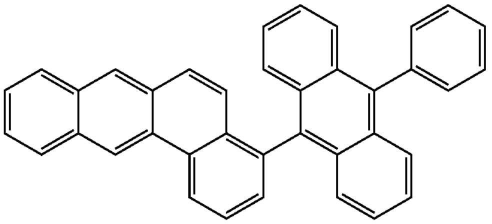 [SMILES: c1ccc(-c2c3ccccc3c(-c3cccc4c3ccc3cc5ccccc5cc34)c3ccccc23)cc1]

H1

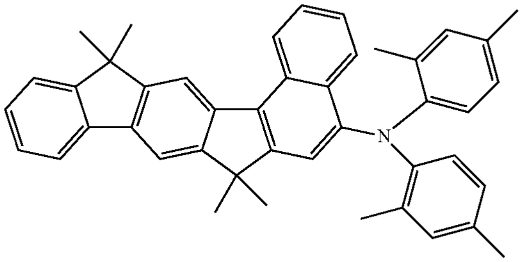 [SMILES: Cc1ccc(N(c2ccc(C)cc2C)c2cc3c(c4ccccc24)-c2cc4c(cc2C3(C)C)-c2ccccc2C4(C)C)c(C)c1]

SEB

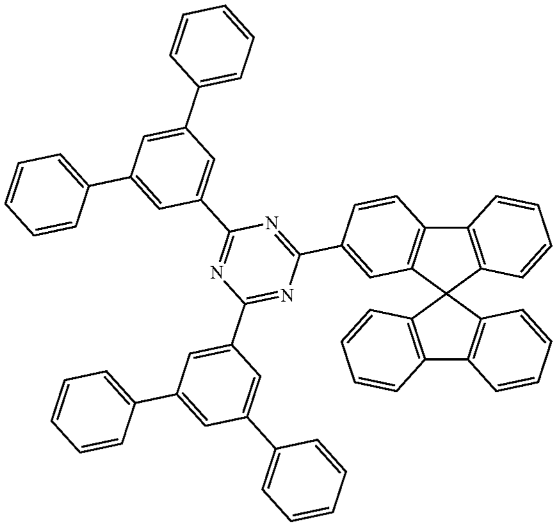 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

ETM

TABLE 3-continued
Structures of the materials used
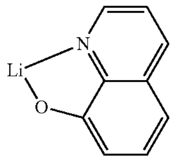
LiQ
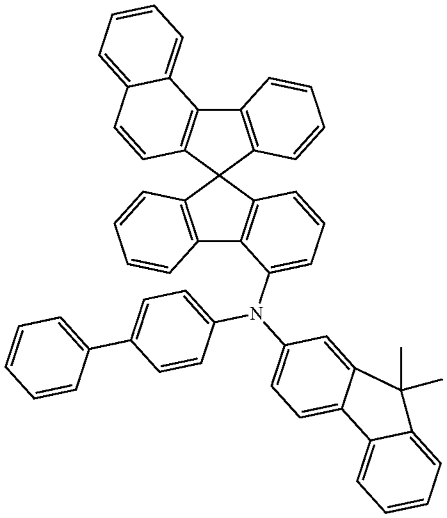 [SMILES: CC1(C)c2ccccc2-c2ccc(N(c3ccc(-c4ccccc4)cc3)c3cccc4c3-c3ccccc3C43c4ccccc4-c4c3ccc3ccccc43)cc21]
HTM1
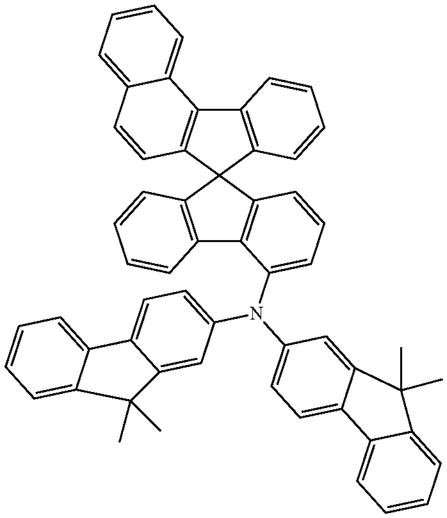 [SMILES: CC1(C)c2ccccc2-c2ccc(N(c3ccc4c(c3)C(C)(C)c3ccccc3-4)c3cccc4c3-c3ccccc3C43c4ccccc4-c4c3ccc3ccccc43)cc21]
HTM2
TABLE 3-continued
Structures of the materials used
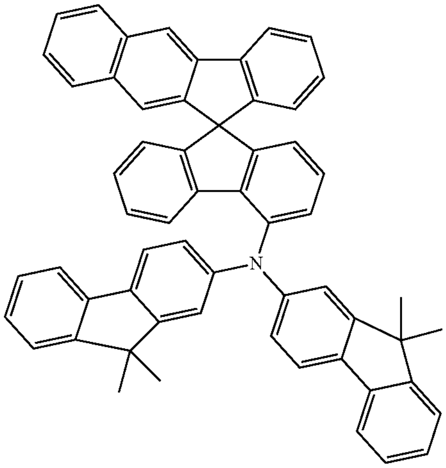 [SMILES: CC1(C)c2ccccc2-c2ccc(N(c3ccc4c(c3)C(C)(C)c3ccccc3-4)c3cccc4c3-c3ccccc3C43c4ccccc4-c4cc5ccccc5cc43)cc21]
HTM3
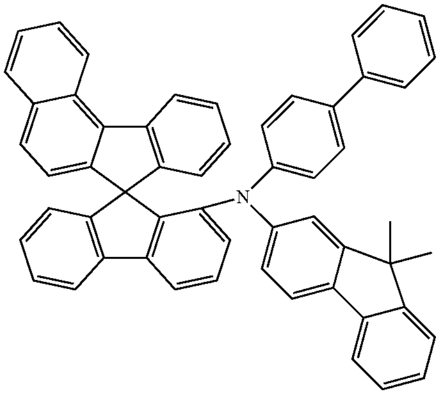 [SMILES: CC1(C)c2ccccc2-c2ccc(N(c3ccc(-c4ccccc4)cc3)c3cccc4c3C3(c5ccccc5-4)c4ccccc4-c4c3ccc3ccccc43)cc21]
HTM4
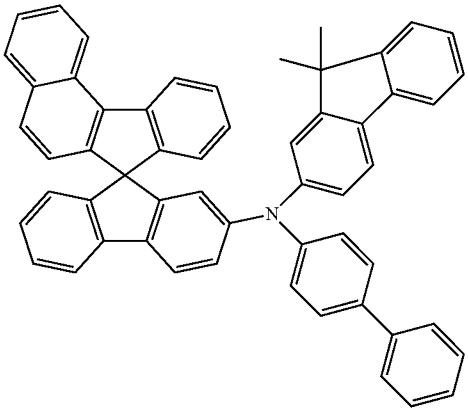 [SMILES: CC1(C)c2ccccc2-c2ccc(N(c3ccc(-c4ccccc4)cc3)c3ccc4c(c3)C3(c5ccccc5-4)c4ccccc4-c4c3ccc3ccccc43)cc21]
HTMv1

TABLE 3-continued

| Structures of the materials used |
| --- |
| 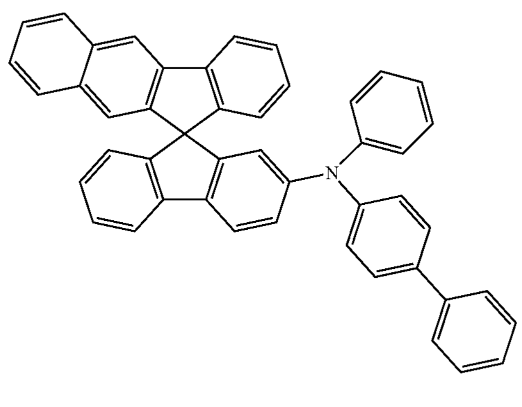 [SMILES: c1ccc(-c2ccc(N(c3ccccc3)c3ccc4c(c3)C3(c5ccccc5-4)c4ccccc4-c4cc5ccccc5cc43)cc2)cc1] |
| HTMv2 |

Example 1

OLED devices with the structures shown in table 1 are produced. Table 2 shows the performance data of the examples described. The device is a singlet blue device with comparison of HTM1, HTM2, HTM3, HTM4, HTMv1 and HTMv2 as material in the electron blocking layer (EBL). It can be shown, that the external quantum efficiency of the device @ 10 mA/cm$^2$ with inventive materials is at least 0.3% or more higher than both of the comparative examples. Even in lifetime the inventive examples E1 to E4 are much better than the references. The device with HTM2 has a lifetime down to 80% of its initial brightness @ 60 mA/cm$^2$ constant driving current density of 330 h. The two comparative examples achieve 290 h and 280 h respectively. Also the other three inventive examples do show higher lifetimes than the references with 320 h and twice 310 h.

The invention claimed is:

1. An organic electroluminescent device comprising a cathode, an anode, one or more hole-injection layers, one or more hole-transport layers, one or more exciton-blocking layers and at least one emitting layer, where the compound of formula (1A-1) is employed as a hole-transport material in an exciton-blocking layer, which is directly adjacent to an emitting layer on the anode side;

formula (1A-1)

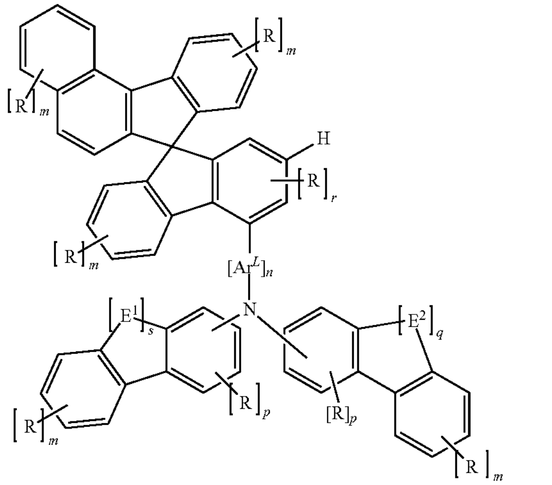

wherein $E^1$, $E^2$ are identically or differently on each occurrence, selected from $C(R^0)_2$, R, $R^0$ stand on each occurrence, identically or differently, for H, D, F, Cl, Br, I, CHO, CN, $C(=O)Ar^3$, $P(=O)(Ar^3)_2$, $S(=O)Ar^3$, $S(=O)_2Ar^3$, $N(Ar^3)_2$, $NO_2$, $Si(R^1)_3$, $B(OR^1)_2$, $OSO_2R^1$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^1$, where in each case one or more non-adjacent $CH_2$ groups may be replaced by $R^1C{=}CR^1$, C≡C, $Si(R^1)_2$, $Ge(R^1)_2$, $Sn(R^1)_2$, C=O, C=S, C=Se, $P(=O)(R^1)$, SO, $SO_2$, O, S or $CONR^1$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^1$, or an aryloxy groups having 5 to 40 aromatic ring atoms, which may be substituted by one or more radicals $R^1$ where two adjacent substituents R do not form a mono- or polycyclic, aliphatic ring system or aromatic ring system, which may be substituted by one or more radicals $R^1$ and two adjacent substituents $R^0$ do not form a mono- or polycyclic, aliphatic ring system or aromatic ring system, which may be substituted by one or more radicals $R^1$, $R^1$ stands on each occurrence, identically or differently, for H, D, F, Cl, Br, I, CHO, CN, $C(=O)Ar^3$, $P(=O)(Ar^3)_2$, $S(=O)Ar^3$, $S(=O)_2Ar^3$, $N(Ar^3)_2$, $NO_2$, $Si(R^2)_3$, $B(OR^2)_2$, $OSO_2R^2$, a straight-chain alkyl, alkoxy or thioalkyl groups having 1 to 40 C atoms or branched or cyclic alkyl, alkoxy or thioalkyl groups having 3 to 40 C atoms, each of which may be substituted by one or more radicals $R^2$, where in each case one or more non-adjacent $CH_2$ groups may be replaced by $R^2C{=}CR^2$, C≡C, $Si(R^2)_2$, $Ge(R^2)_2$, $Sn(R^2)_2$, C=O, C=S, C=Se, $P(=O)(R^2)$, SO, $SO_2$, O, S or $CONR^2$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^2$, or an aryloxy group having 5 to 60 aromatic ring atoms, which may be substituted by one or more radicals $R^2$, $R^2$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 C atoms;

$Ar^3$ is an aromatic or heteroaromatic ring system having 5 to 24 aromatic ring atoms, which may in each case also be substituted by one or more radicals $R^3$;

n is 0;

m is on each occurrence, identically or differently, 0, 1, 2, 3 or 4;

p is on each occurrence, identically or differently, 0, 1, 2 or 3;

q=1 and s=1;

r is on each occurrence, identically or differently, 0, 1 or 2.

2. The device according to claim 1, wherein $R^0$ stands on each occurrence, identically or differently, for H, D, F, CN, $Si(R^1)_3$, a straight-chain alkyl groups having 1 to 10 C atoms or a branched or cyclic alkyl groups having 3 to 10 C atoms, each of which may be substituted by one or more radicals $R^1$, where in each case one or more H atoms may be replaced by F, or an aryl or heteroaryl groups having 5 to 40 aromatic ring atoms, which may in each case be substituted by one or more radicals $R^1$.

3. The device according to claim 1, wherein R stands on each occurrence, identically or differently, for H, D, F, CN, a straight-chain alkyl or alkoxy group having 1 to 10 C atoms or a branched or cyclic alkyl or alkoxy group having 3 to 10 C atoms, each of which may be substituted by one or more radicals $R^1$, where one or more non-adjacent $CH_2$ groups may be replaced by O and where one or more H atoms may be replaced by F, or an aromatic or heteroaromatic ring systems having 5 to 24 aromatic ring atoms, which may in each case be substituted by one or more radicals $R^1$.

* * * * *